US012104149B2

(12) United States Patent　　　(10) Patent No.:　　US 12,104,149 B2
Allbritton et al.　　　(45) Date of Patent:　　Oct. 1, 2024

(54) DEVICES, SYSTEMS AND APPARATUSES FOR GENERATING SELF-SUSTAINING HYPOXIC CONDITIONS AND GASEOUS AND NON-GASEOUS CHEMICAL GRADIENTS FOR IN VITRO CELL CULTURE

(71) Applicant: The University of North Carolina at Chapel Hill, Chapel Hill, NC (US)

(72) Inventors: Nancy L. Allbritton, Seattle, WA (US); Yuli Wang, Lynnwood, WA (US); Raehyun Kim, Chapel Hill, NC (US); Peter Joseph Attayek, Durham, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 811 days.

(21) Appl. No.: 17/044,083

(22) PCT Filed: May 15, 2019

(86) PCT No.: PCT/US2019/032393
§ 371 (c)(1),
(2) Date: Sep. 30, 2020

(87) PCT Pub. No.: WO2019/222333
PCT Pub. Date: Nov. 21, 2019

(65) Prior Publication Data
US 2021/0087515 A1　　Mar. 25, 2021

Related U.S. Application Data

(60) Provisional application No. 62/671,661, filed on May 15, 2018.

(51) Int. Cl.
*C12M 1/34*　　(2006.01)
*C12M 1/00*　　(2006.01)
(Continued)

(52) U.S. Cl.
CPC ............ *C12M 41/34* (2013.01); *C12M 21/08* (2013.01); *C12M 23/34* (2013.01); *C12M 25/02* (2013.01);
(Continued)

(58) Field of Classification Search
None
See application file for complete search history.

(56) References Cited

U.S. PATENT DOCUMENTS 8,946,305 B2　2/2015　Liao et al.
9,040,665 B2　5/2015　Wnek et al.
(Continued)

FOREIGN PATENT DOCUMENTS

JP　　2008513159 A　　5/2008
JP　　2011523355 A　　8/2011
(Continued)

OTHER PUBLICATIONS

Sadabad et al., "A simple coculture system shows mutualism between anaerobic faecalibacteria and epithelial Caco-2 cells", Scientific Reports 5, Article No. 17906 (2016) (Year: 2016).*
(Continued)

*Primary Examiner* — Samuel P Siefke
*Assistant Examiner* — Henry H Nguyen
(74) *Attorney, Agent, or Firm* — KDW FIRM PLLC

(57) ABSTRACT

Disclosed herein are devices, apparatuses and methods for generating self-sustaining gaseous and non-gaseous gradients across a cell support structure and for culturing one or more cells or tissues under hypoxic conditions. Methods of generating one or more gas gradients across a cell support structure include providing a luminal container having a bottom wall that is a gas permeable membrane, positioning a cell support structure above the bottom wall, positioning one or more cells or tissues on the cell support structure, and (Continued)

generating one or more gas gradients between the bottom wall, across the cell support structure and into a luminal reservoir. An apparatus to produce hypoxic conditions for cell cultures includes a luminal container having a bottom wall, a cell support structure on the bottom wall, and a cover that sealably closes the open top, such that a hypoxic condition can be generated in the luminal reservoir.

11 Claims, 48 Drawing Sheets

(51) Int. Cl.
    *C12M 1/12*         (2006.01)
    *C12M 3/00*         (2006.01)
    *C12N 5/071*        (2010.01)

(52) U.S. Cl.
    CPC .......... *C12M 41/46* (2013.01); *C12N 5/0679* (2013.01); *C12N 2500/02* (2013.01)

(56) References Cited

U.S. PATENT DOCUMENTS

| | | | |
|---|---|---|---|
| 9,132,208 | B2 | 9/2015 | Chen et al. |
| 9,200,676 | B2 | 12/2015 | Yamaguchi |
| 9,205,172 | B2 | 12/2015 | Leonard Neethling et al. |
| 9,211,362 | B2 | 12/2015 | Hwang et al. |
| 9,272,004 | B2 | 3/2016 | Nataraj et al. |
| 9,283,301 | B1 | 3/2016 | Simionescu et al. |
| 11,193,110 | B2 | 12/2021 | Allbritton et al. |
| 2003/0017142 | A1 | 1/2003 | Toner et al. |
| 2005/0106717 | A1 | 5/2005 | Wilson et al. |
| 2006/0019389 | A1 | 1/2006 | Yayon et al. |
| 2006/0121609 | A1 | 6/2006 | Yannas et al. |
| 2007/0134790 | A1 | 7/2007 | Gould et al. |
| 2010/0047853 | A1 | 2/2010 | Kuo |
| 2010/0075293 | A1* | 3/2010 | Chang .............. C12M 29/10 435/284.1 |
| 2012/0015003 | A1 | 1/2012 | Gleeson et al. |
| 2012/0089238 | A1 | 4/2012 | Kang et al. |
| 2014/0093478 | A1 | 4/2014 | Turnbaugh et al. |
| 2017/0059555 | A1 | 3/2017 | Iyer et al. |
| 2017/0306278 | A1 | 10/2017 | Nguyen et al. |
| 2018/0002672 | A1 | 1/2018 | Allbritton et al. |
| 2019/0211296 | A1 | 7/2019 | Allbritton |
| 2019/0382703 | A1* | 12/2019 | Katayama ............ C12M 23/12 |
| 2021/0395661 | A1 | 12/2021 | Allbritton et al. |

FOREIGN PATENT DOCUMENTS

| | | |
|---|---|---|
| JP | 2012500371 A | 1/2012 |
| JP | 2013510179 A | 3/2013 |
| JP | 2014514942 A | 6/2014 |
| JP | 6920203 B2 | 7/2021 |
| JP | 7042252 | 3/2022 |
| WO | WO/2005/072419 | 8/2005 |
| WO | 2005104755 A2 | 11/2005 |
| WO | WO/2009/132196 A2 | 10/2009 |
| WO | WO/2012/136701 A1 | 10/2012 |
| WO | 2014021778 A1 | 6/2014 |
| WO | WO/2014/186430 A1 | 11/2014 |
| WO | WO 2015/020614 A1 | 2/2015 |
| WO | WO/2016/123474 A1 | 8/2016 |
| WO | WO 2017/131839 A2 | 8/2017 |
| WO | WO/2018/022548 A1 | 2/2018 |
| WO | 2018175861 A1 | 9/2018 |
| WO | WO 2019/141824 A1 | 7/2019 |
| WO | WO 2019/227012 A1 | 11/2019 |
| WO | WO2020/102682 A1 | 5/2020 |

OTHER PUBLICATIONS

Canadian Office Action for Application No. 3052250 dated May 12, 2023.
Japanese Office Action for Application No. 2022560193 dated Apr. 25, 2023.
Japanese Office Action for Application No. 2020565308 dated Apr. 18, 2023.
Canadian Office Action for Application No. 3093581 dated Aug. 23, 2023.
Canadian Office Action for Application No. 3093585 dated Aug. 28, 2023.
Canadian Office Action for Application No. 3112220 dated Sep. 1, 2023.
Canadian Office Action for Application No. 3170294 dated Sep. 11, 2023.
Japanese Office Action for Application No. 2021517604 dated Aug. 21, 2023.
Japanese Decision to Grant for Application No. 2020560193 dated Sep. 19, 2023.
European Office Action for Application No. 16744178 dated Oct. 10, 2023.
Non-Final Office Action for U.S. Appl. No. 18/371,636 dated Nov. 6, 2023.
Advisory Action and Interview Summary corresponding to U.S. Appl. No. 15/545,456 dated Apr. 10, 2019.
Advisory Action corresponding to U.S. Appl. No. 16/316,139 dated Apr. 4, 2022.
A. DeWard, J. Cramer, and E. Lagasse, Cellular heterogeneity in the mouse esophagus implicates the 30 presence of a nonquiescent epithelial stem cell population, Cell. Rep. 9(2), 701-711 (Oct. 23, 2014).
A. Gracz et al., CD24 and CD44 Mark Human Intestinal Epithelial Cell Populations with Characteristics of Active and Facultative Stem Cells, Stem Cells 31(9), 2024-30 (2013).
A. L. Paguirigan and D. J. Beebe, "Protocol for the fabrication of enzymatically crosslinked gelatin microchannels for microfluidic cell culture", Nat Protoc, 2007, 2, 1782-1788.
Alipour et al. Measurement of Vocal Folds Elastic Properties for Continuum Modeling. Journal of Voice (2012), 26(6), 816.e21-816. e29. (Year: 2012).
A. Quaroni. Short-term primary culture of epithelial cells from human colon. Gastroenterology, 1989, 96, 535-536.
Bartsch et al. "Establishment of a Long-Term Culture System for Rat Colon Epithelial Cells," In Vitro Cell. Dev. Biol.—Animal, 2004, vol. 40, pp. 278-284 (Year: 2004).
Belchior. Gustavo Gross et al. Stem cells and biopharmaceuticals: Vital roles in the growth of tissue-engineered small intestine, Seminars in. Pediatric Surgery, 23(3):141-149 (2014).
Bishop et al. Regulation of Caco-2 cell proliferation by basolateral membrane epidermal growth factor receptors. Am J. Physiol (1994), v267(5 Pt. 1), G892-900. (Year: 1994).
Boccellato et al., "Polarised epithelial monolayers of the gastric mucosa reveal insights into mucosal homeostasis and defence against infection," Gut, vol. 68, pp. 400-413 (2019).
Bo Liu et al. Chemistry of Periodate-Mediated Cross-Linking of 3.4-Dihydroxylphenylalanine (DOPA)-Containing Molecules to Proteins, J Am Chem Soc. 2006; 29:15228-15235, p. 8.
C. Booth, S. Patel, G. R. Bennion and C. S. Patten. The isolation and culture of adult mouse colonic epithelium. Epithelial Cell Biol., 1995, 4, 76-86.
C. Kosinski, et al., Gene expression patterns of human colon tops and basal crypts and BMP antagonists as intestinal stem cell niche factors, Proc. Natl. Acad. Sci. U S. A., 2007, 104, 15418-15423.
C. Moon, K. L. VanDussen, H. Miyoshi and T. S. Stappenbeck. Development of a primary mouse intestinal epithelial cell monolayer culture system to evaluate factors that modulate IgA transcytosis. Mucosal Immunol, 2014, 7, 818-828.
C. R. Yang, "Enhance physiocochemical properties of collagen by using EDC/NHS-crosslinking", Bull. Mat. Sci, 2012, 35, 913-918.
Canadian Office Action Corresponding to Canadian Application No. 3,009,153 dated Feb. 2, 2022.
Cell Culture Inserts, 0.4um, Falcon®. MG Scientific, internet article (2014). (Year: 2014).
Corrected Notice of Allowance corresponding to U.S. Appl. No. 15/545,456 dated Aug. 2, 2021.

(56) References Cited

OTHER PUBLICATIONS

Costello et al., "Synthetic Small Intestinal Scaffolds for Improved Studies of Intestinal Differentiation," Biotechnology and Bioengineering, vol. 111, No. 6, Jun. 2014. pp. 1222-1232.
Cummings et al. "Properties of engineered vascular constructs made from collagen, fibrin, and collagen-fibrin mixtures," Biomaterials 25, 3699-3706 (2003).
D.R. Donohoe, N. Garge, X. X. Zhang, W. Sun, T. M. O'Connell, M. K. Bunger and S. J. Bultman, The Microbiome and ButyrateRegulat Energy Metabolism and Autophagy in the Mammalian Colon, Cell Metabolism, 2011, 13, 517-526.
Donohoe et al., "The Warburg Effect Dictates the Mechanism of Butyrate-Mediated Histone Acetylation and Cell Proliferation," Supplemental Information, Molecular Cell, vol. 48, 612-626 (2012).
Deveney et al. Establishment of Human Colonic Epithelial Cells in Long-Term Culture. Journal of Surgical Research (1996), 64, 161.
Fuchs et al. "A matter of life and death: self-renewal in stem cells," Embo Reports, vol. 14, No. 1, pp. 39-48 (2013).
E. J. Formeister, A. L. Sionas, D. K. Lorance, C. L. Barkley, G. H. Lee and S. T. Magness, "Distinct SOX9 levels differentially mark stem/progenitor populations and enteroendocrine cells of the smal intestine epithelium", Am. J Physiol.—Gastroint. Liver Physiol., 2009, 296, G 1108-G1118.
Song et al. "Collagen scaffolds derived from a marine source and their biocompatibility," Biomaterials, 27, 2951-2961 (2006).
Elamin et al., "Effects of Ethanol and Acetaldehyde on Tight Junction Integrity: In Vitro Study in a Three Dimensional Intestinal Epithelial Cell Culture Model." PLoS One, vol. 7, Article ID e35008 (2012).
Extended European Search Report corresponding to European Application No. 16744178.1, dated Jul. 2, 2018, 7 pages.
Extended European Search Report corresponding to European Patent Application No. 17835084.9 dated Mar. 5, 2020.
Extended European Search Report corresponding to European Application No. 19806626.8-1132 dated Feb. 4, 2022.
Extended European Search Report corresponding to European Application No. 19804471.1-1132 dated Feb. 28, 2022.
F. Wang et al., Isolation and Characterization of Intestinal Stem Cells Based on Surface Marker Combinations and Colony-Formation Assay Gastroenterology 145(2), 383-95 (2013a).
Ferruzza et al. A protocol for differentiation of human intestinal Caco-2 cells in asymmetricserum-containing medium. Toxicology in Vitro (2012), v26, p. 1252-1255. (Year: 2012).
Frantz et al., "The extracellular matrix at a glance", Journal of Cell Science (2010), 123, 4195-4200. (Year: 2010).
Gaudier et al., "Butyrate specifically modulates MUC gene expression in intestinal epithelial goblet cells deprived of glucose," Am J. Physiol Gastrointest Liver Physiol., vol. 287: G1168-G1174 (2004).
G. L. Eastwood and J. S. Trier. "Organ culture of human rectal mucosa", Gastroenterology, 1973, 64(3), 375-382.
Gracz et al., "Identification, Isolation, and Culture of Intestinal Epithelial Stem Cells from Murine Intestine," Methods Mol Biol. ,;vol. 879, pp. 89-107, 23 page author manuscript. (Year: 2012).
Gonzalez S et al. A 3D Culture System Enhances the Ability of Human Bone Marrow Stromal Cells to Support the Growth of Limbal Stem/Progenitor Cells, Stem Cell Res. 2016, 16(2):358-364, p. 2,3.
H. Autrup, L. A. Barrett, F. E. Jackson, M. L. Jesudason, G. Stoner, P. Phelps, B. F. Trump and C. C. Harris. Explant culture of human colon. Gastroenterology, 1978, 74, 1248-1257.
Sundararaghavan et al. "Genipin-induced changes in collagen gels: Correlation of mechanical properties to fluorescence," Journal of Biomedical Materials Research Part A, 87A, 308-320 (2008).
Yoo et al. "Effects of Schisandra Lignans on P-Glycoprotein-Mediated Drug Efflux in Human Intestinal Caco-2 Cells," Planta Med., 73, 444-450 (2007).
H. J. Kim, D. Huh, G. Hamilton and D. E. Ingber. Human gut-on-a-chip inhabited by microbial flora that experiences intestinal peristalsis-like motions and flow. Lab Chip, 2012, 12, 2165-2174.
Hai-Long Li et al. The Effect of Amino Density on the Attachment, Migration, and Differentiation of Rat Neural Stem Cells In Vitro, Mol Cells. 2013; 35:436-443. pp. 436, 437, 441.
Hass et al. Lack of Butyrate Is Associated With Induction of Bax and Subsequent Apoptosis in the Proximal Colon of Guinea Pig. Gastroenterology (1997), 112:875-881. (Year: 1997).
International Preliminary Report on Patentability corresponding to International Application No. PCT/US2016/015631 dated Aug. 1, 2017.
International Preliminary Report on Patentability corresponding to International Application No. PCT/US2017/043601 dated Jan. 29, 2019.
International Preliminary Report on Patentability corresponding to International Application No. PCT/US2019/032393 dated Nov. 17, 2020.
International Preliminary Report on Patentability corresponding to International Application No. PCT/US2019/033955 dated Dec. 1, 2020.
International Preliminary Report on Patentability corresponding to International Application No. PCT/US2019/061743 dated May 18, 2021.
International Search Report corresponding to International Application No. PCT/US2016/015631 dated May 26, 2016.
International Search Report corresponding to International Application No. PCT/US2017/043601 dated Nov. 16, 2017.
International Search Report corresponding to International Application No. PCT/US2019/032393 dated Jul. 23, 2019.
International Search Report corresponding to International Application No. PCT/US2019/033955 dated Aug. 15, 2019.
International Search Report corresponding to International Application No. PCT/US2019/061743 dated Feb. 11, 2020.
Interview Summary corresponding to U.S. Appl. No. 15/545,456 dated Mar. 15, 2019.
J. B. Seidelin, T. Horn and 0. H. Nielsen. Simple and efficient method for isolation and cultivation of endoscopically obtained human colonocytes. Am. J. Physiol.—Gastroint. Liver Physiol., 2003, 285, G1122-G1128.
J. H. Sung, J. J. Yu, D. Luo, M. L. Shuler and J. C. March. Microscale 3-D hydrogel scaffold for biomimetic gastrointestinal (GI) tract model. Lab Chip, 2011, 11, 389-392.
J. H. Sung, M. B. Esch, J. M. Prat, C. J. Long, A. Smith, J. J. Hickman and M. L. Shuler, Microfabricated mammalian organ systems and their integration into models of whole animals and humans. Lab Chip, 2013, 13(7), 1201-1212.
Orban et al. "Crosslinking of collagen gels by transglutaminase," Journal of Biomedical Materials Research Part A, 68A, 756-762 (2004).
J. Mills and R. Shivdasani, Gastric epithelial stem cells, Gastroenterology 140(2), 412-424 (Feb. 2011).
J. R. Davie, "Inhibition of Histone Deacetylase Activity by Butyrate", American Society for Nutritional Sciences, 2003, 133, 2485S-2493S.
Jones, S. P. et al. Inhibition of Histone Deacetylase Activity by ButyrateEcotoxicology 23, 802-808 (2014).
VanDussen et al. "Development of an enhanced human gastrointestinal epithelial culture system to facilitate patient-based assays," Gut, vol. 64, pp. 911-920 (2015).
Kaminsky et al. "Small Intestinal Cytochromes P450," Critical Reviews in Toxicology 21, 407-422 (1992).
Kharkar et al., "Designing degradable hydrogels for orthogonal control of cell microenvironments," Chem. Soc. Rev., vol. 42, pp. 7335-7372. (Year: 2013).
Damink et al. "Glutaraldehyde as a crosslinking agent for collagen-based biomaterials," Journal of Materials Science: Materials in Medicine, 6, 460-472 (1995).
Lancaster, M. A. et al. "Organogenesis in a dish: Modeling development and disease using organoid technologies", Science, 345(6194):283 (2014).
Levenberg S, et al. Differentiation of human embryonic stem cells on three-dimensional polymer scaffolds, PNAS. 2003, 100(22): 12741-12746, p. 12741.
M. A. Cayo, A. K. Cayo, S. M. Jarjour and H. Chen, "Sodium butyrate activates Notch1 signaling, reduces tumor markers, and

(56) References Cited

OTHER PUBLICATIONS induces cell cycle arrest and apoptosis in pheochromocytoma", American Journal of Translational Research, 2009, 1, 178-183.
M. Brittan and N. A. Wright, "Stem Cell in Gastrointestinal Structure and Neoplastic Development", Gut, 2004, 53, 899-910.
M. Hovakimyan, R. F. Guthoff and O. Stachs, "Collagen Cross-Linking: Current Status and Future Directions", Journal of Ophthalmology, 2012, 2012, Article ID 406850.
M. Stelzner, M. Helmrath, J. C. Y. Dunn, S. J. Henning, C. W. Houchen, C. Kuo, J. Lynch, L. H. Li, S. T. Magness, M. G. Martin, M. H. Wong, J. Yu and N. I. H. I. S. C. Consortiu,Am. J Physiol.—Gastroint. Liver Physiol., 2012, 302, G1359-G1363.
Maenosono et al. "A Transparent Polyimide Film as a Biological Cell Culture Sheet with Microstructures,". Journal of Biomaterials and Nanobiotechnology, vol. 5, pp. 17-23.(Year: 2014).
Maina JN. Structure, function and evolution of the gas exchangers: comparative perspectives, J Anat. 2002, 201:281-304, p. 300.
Martignoni et al., Abstract of "An in vivo and in vitro comparison of CYP induction in rat liver and intestine using slices and quantitative RT-PCR," Chemico-Biological Interactions, vol. 151, Iss. 1, pp. 1-11 (2004), 19 pages.
Martignoni "Species and strain differences in drug metabolism in liver and intestine," University of Groningen/UMCG, 1-136 (2006).
Matsuzawa A et al. Construction of three-dimensional liver tissue models by cell accumulation technique and maintaining their metabolic functions for long-term culture without medium change, J Biomed Mater Res Part A. 2014, p. 1, Apr. 2015:103(4):1554-64.
Muñoz-Pinto et al. Lamina Propria Cellularity and Collagen Composition: An Integrated Assessment of Structure in Humans. Annals of Otology, Rhinology, and Laryngology (2009), 118(4), 299-306. (Year: 2009).
Barker, M. van de Wetering and H. Clevers, "The intestinal stem cell", Genes & Development, 2008, 22, 1856-1864.
Vrana et al. "EDC/NHS cross-linked collagen foams as scaffolds for artificial corneal stroma," Journal of Biomaterials Science—Polymer Edition, vol. 18, No. 12, pp. 1527-1545 (2007).
N. Seyedhassantehrani, Y. Li and L. Yao, "Dynamic behaviours of astrocytes in chemically modified fibrin and collagen hydrogels" Integrative Biology, vol. 8, pp. 624-634 (2016).
Notice of Allowance corresponding to U.S. Appl. No. 15/545,456 dated Jul. 21, 2021.
Notice of Publication corresponding to European Patent Application No. 17835084.9-1120 dated May 8, 2019.
Notice of Publication corresponding to European Patent Application No. 19804471.1 dated Feb. 24, 2021.
Notice of Publication corresponding to European Patent Application No. 19806626.8-1111 dated Mar. 17, 2021.
Notice of Publication corresponding to European Patent Application No. 19884975.4-1132 dated Aug. 25, 2021.
Notice of Allowance corresponding to Japanese Patent Application No. 2019-504019 dated Mar. 8, 2022.
Office Action (Restriction Requirement) corresponding to U.S. Appl. No. 15/545,456 dated Jul. 5, 2018.
Office Action corresponding to U.S. Appl. No. 15/545,456 dated Aug. 28, 2018.
Office Action corresponding to European Patent Application No. 16744178.1 dated Nov. 11, 2020.
Office Action corresponding to Japanese Patent Application No. 2017540628 dated Nov. 4, 2020.
Office Action corresponding to Japanese Patent Application No. 2017540628 dated Jan. 7, 2020.
Decision to Grant corresponding to Japanese Patent Application No. 2019504019 dated Feb. 28, 2022.
Office Action corresponding to U.S. Appl. No. 15/545,456 dated Jan. 29, 2019.
Office Action corresponding to U.S. Appl. No. 15/545,456 dated Dec. 16, 2019.
Office Action corresponding to U.S. Appl. No. 15/545,456 dated Mar. 13, 2020.
Office Action corresponding to U.S. Appl. No. 15/545,456 dated Oct. 19, 2020.
Office Action (Restriction Requirement) corresponding to U.S. Appl. No. 16/316,139 dated Feb. 4, 2021.
Office Action corresponding to U.S. Appl. No. 16/316,139 dated Apr. 28, 2021.
Office Action corresponding to U.S. Appl. No. 16/316,139 dated Jan. 26, 2022.
P. Jung, T. Sato, A. Merlos-Suarez, F. M. Barriga, M. Iglesias, D. Rossell, H. Auer, M. Gallardo, M. A. Blasco, E. Sancho, H. Clevers and E. Batlle. Isolation and in vitro expansion of human colic stem cells. Nature Medicine, 2011, 17, 1225-1227.
Shah et al. "Role of Caco-2 cell monolayers in prediction of intestinal drug absorption," Biotechnol. Prog. 22: 186-198 (2006).
Szpak, "Fish bone chemistry and ultrastructure: implications for taphonomy and stable isotope analysis," J. Archaeol. Sci, 38, 3358-3372 (2011).
Paine et al. "Cytochrome P-450 1A1 Expression in Human Small Bowel: Interindividual Variation and Inhibition by Ketoconazole," Drug Metabolism and Disposition, vol. 27, No. 3, pp. 360-364 (1999).
Park YB et al. Alterations of proliferative and differentiation potentials of human embryonic stem cells during long-term culture, Exp Mol Med. 2008, 40(1):98-108, p. 1.
Pedron S. et al. Microfluidic approaches for the fabrication of gradient crosslinked networks based on poly(ethylene glycol) and hyperbranched polymers for manipulation of cell interactions, J Biomed Mat Res. 2011; 96(1):196-203.
Petersen et al. Generation of L Cells in Mouse and Human Small Intestine Organoids. Diabetes, 63(2), pp. 410-420.
Q. Ramadan, H. Jafarpoorchekab, C. B. Huang, P. Silacci, S. Carrara, G. Koklu, J. Ghaye, J. Ramsden, C. Ruffert, G. Vergeres and M. A. M. Gijs. NutriChip: nutrition analysis meets microfliudics. Lab Chip, 2013, 13, 196-203.
R. H. Whitehead, A. Brown and P. S. Bhathal. A method for the isolation and culture of human colonic crypts in collagen gels. In Vitro Cellular & Developmental Biology, 1987, vol. 23, No. 6, pp. 436-442.
Ramanujan et al. Diffusion and Convection in Collagen Gels: Implications for Transport in the Tumor Interstitium. Biophysical Journal (2002), 83, 1650-1660.
Roeder et al. "Compliance, elastic modulus, and burst pressure of small-intestine submucosa (SIS), small-diameter vascular grafts," J Biomed Mater Res. 47, 65-70 (1999).
Rodriguez-Serrano et al., "Differentiation of Intestinal Epithelial Cells Mediated by Cell Confluence and/or Exogenous Nucleoside Supplementation." Cell Tissues Organs, vol. 191, pp. 478-488 (2010).
Rosa ACP et al. Interaction of *Escherichia coli* strains of non-EPEC serogroups that carry eae and lack the EAF and stx gene sequences with undifferentiated and differentiated intestinal human Caco-2 cells, FEMS Microbiology Letters. 2001, 200: 117-122, p. 118.
S. Umar, Intestinal Stem Cells, Curr. Gastroenterol Rep. 12(5), 340-348 (Oct. 2010).
S. Yui, T. Nakamura, T. Sato, Y. Nemoto, T. Mizutani, X. Zheng, S. Ichinose, T. Nagaishi, R. Okamoto, K. Tsuchiya, H. Clevers and M. Watanabe. Functional engraftment of colon epithelium expanded in vitro from a single adult Lgr5+ stem cell. Nature Medicine, 2012, 18, 618-623.
Seo JB et al. Epithelial monolayer culture system for real-time single-cell analyses, Phys Rep. 2014, 2(4):e12002, p. 1-3.
Simon AK et al. Polymer-Based Mesh as Supports for Multi-layered 3D Cell Culture and Assays, Biomaterials. 2014; 35(1):1-21, abstract.
Soofi, S.S. et al., "The elastic modulus of Matrigel™ as determined by atomic force microscopy", Journal of Structural Biology 167, 216-219 (2009).
Speer et al., "Molecular transport through primary human small intestinal monolayers by culture on a collagen scaffold with a gradient of chemical cross-linking", Journal of Biological Engineering (Apr. 27, 2019).
Spence, Jason el al. "Directed differentiation of human pluripotent stem cells into intestinal tissue in vitro", Nature, 470(7332):105-109 (2011).

(56) References Cited

OTHER PUBLICATIONS

Szymanski P et al. Adaptation of High-Throughput Screening in Drug Discovery—Toxicological Screening Tests, Int J Mol Sci. 2012, 13:427-452, abstract.
Sträter et al. Rapid Onset of Apoptosis In Vitro Follows Disruption of beta 1-Integrin/Matrix Interactions in Human Colonic Crypt Cells. Gastroenterology (1996), 110, 1776-1784. (Year: 1996).
T. Sato, D. E. Stange, M. Ferrante, R. G. Vries, J. H. Van Es, S. Van den Brink, W. J. Van Houdt, A. Pronk, J. Van Gorp, P. D. Siersema and H. Clevers. Long-term expansion of epithelial organoids from human colon, adenoma, adenocarcinoma, and Barrett's epitheiuum. Gastroenterology, 2011, 141, 1762-1772.
Sato, et. al. "Paneth Cells constitute the niche for Lgr5 stem cells in intestinal crypts," Nature, 469(7330), pp. 415-418 (2011).
T. Sato, R. G. Vries, H. J. Snippert, M. van de Wetering, N. Barker, D. E. Stange, J. H. van Es, A. Abo, P. Kujala, P. J. Peters and H. Clevers. Single Lgr5 stem cells build crypt-villus structures in vitro without a mesenchymal niche. Nature, 2009, 459, 262-U147.
T. Yen and N. Wright, The gastrointestinal tract stem cell niche, Stem Cell Rev. 2(3), 203-212 (2006).
Tang et al. Utilization of a Human Intestinal Epithelial Cell Culture System (Caco-2) for Evaluating Cytoprotective Agents. Pharm Res (1993), v10(11), p. 1620-1626. (Year: 1993).
Transwell® permeable supports (2007), 8 pages. (Year: 2007).
Wang et al., "Formation of Human Colonic Crypt Array by Application of Chemical Gradients Across a Shaped Epithelial Monolayer", Cellular and Molecular Gastroenterology and Hepatology. vol. 5, No. 2, pp. 113-130 (2018).
Wang et al. Influence of micro-well biomimetic topography on intestinal epithelial Caco-2 cell phenotype. Biomaterials (2009), v30, p. 6825-6834. (Year: 2009).
Wang et al., "Synergic effects of crypt-like topography and ECM proteins on intestinal cell behavior in collagen based membranes," Biomaterials, vol. 31, Iss. 29, pp. 7586-7598 (2010).
Wang, Yuli et al. "A microengineered collagen scaffold for generating a polarized crypt-vilus architecture of human small intestinal epithelium", Biomaterials, 128:44-45 (2017).
Wang et al., "Building a Thick Mucus Hydrogel Layer to Improve the Physiological Relevance of In Vitro Primary Colonic Epithelial Models," Cellular and Molecular Gastroenterology and Hepatology, Jul. 26, 2019 (Jul. 26, 2019), vol. 8, Iss. 4, pp. 653-655.
Watson, Carey et al. "An in vivo model of human small intestine using pluripotent stem cells", Nature Medicine, 20(11)1310-1314 (2014).
Written Opinion corresponding to International Application No. PCT/US2016/015631 dated May 26, 2016.
Written Opinion and International Search Report corresponding to International Application No. PCT/US2017/043601 dated Nov. 16, 2017.
Written Opinion of the International Searching Authority corresponding to International Application No. PCT/US2019/032393 dated Jul. 23, 2019.
Written Opinion of the International Searching Authority corresponding to International Application No. PCT/US2019/033955 dated Aug. 15, 2019.
Written Opinion of the International Searching Authority corresponding to International Application No. PCT/US2019/061743 dated Feb. 11, 2020.
Yeste et al., "Engineering and monitoring cellular barrier models," Journal of Biological Engineering, Sep. 12, 2018 (Sep. 12, 2018), vol. 12, No. 18, pp. 1-19.
X. Yin, H. F. Farin, J. H. van Es, H. Clevers, R. Langer and J. M. Karp. Niche-independent high-purity cultures of Lgr5+ intestinal stem cells and their progeny. Nature Methods, 2014, 11, 106-112.
Di et al. "Collagen stabilization and modification using a polyepoxide, triglycidyl isocyanurate," Polymer Degradation and Stability, 94, 1684-1692 (2009).
Y. L. Wang, A. A. Ahmad, C. E. Sims, S. T. Magness and N. L. Allbritton. In vitro generation of colonic epithelium from primary cells guided by microstructures. Lab Chip, 2014, 14, 1622-1631.

Y. W. Liu, L. H. Gan, D. J. Carlsson, P. Fagerholm, N. Lagali, M. A. Watsky, R. Munger, W. G. Hodge, D. Priest and M. Griffith, "A Simple, Cross-linked Collagen Tissue Substitute for Corneal Implantation", Invest. Ophthalmol. Vis. Sci., 2006, 47, 1869-1875.
Anonye, B. O. et al. Probing host-anaerobe interactions in innovative human gut cellular models. bioRxiv, doi:10.1101/269035, 43 pages (2018).
Anonye et al. Probing Clostridium difficule infection in innovative human gut cellular models, bioRxiv, 269035, 28 pages (2018).
Bertout, J. A., Patel, S. A. & Simon, M. C. The impact of O2 availability on human cancer. Nature reviews. Cancer 8, 967, 22 pages (2008).
Blouin, J. M. et al. Butyrate elicits a metabolic switch in human colon cancer cells by targeting the pyruvate dehydrogenase complex. International journal of cancer 128, 2591-2601 (2011).
Boccellato et al. "Polarised epithelial monolayers of the gastric mucosa reveal insights into mucosa! homeostasis and defence against infection," Gut, Feb. 7, 2018 (Feb. 7, 2018), vol. 68, pp. 400-413.
Brennan, M. D., Rexius-Hall, M. L. & Eddington, D. T. A 3D-printed oxygen control insert for a 24-well plate. PloS one 10, e0137631, 9 pages (2015).
Buchwald, P. FEM-based oxygen consumption and cell viability models for avascular pancreatic islets. Theoretical Biology and Medical Modelling 6, 5, 13 pages (2009).
Byrne, M. B., Leslie, M. T., Gaskins, H. R. & Kenis, P. J. "Methods to study the tumor microenvironment under controlled oxygen conditions," Author manuscript, 19 pages, published in final edited form as: Trends in biotechnology 32, 556-563 (2014).
Cani, P. D. "Gut microbiota-at the intersection of everything?" Abstract of Nature Reviews Gastroenterology & Hepatology 14, 321-322 (2017) [6 pages].
Chen, Y. et al. "Robust bioengineered 3D functional human intestinal epithelium," Scientific reports 5, 13708, 11 pages (2015).
Chen, Y.-A. et al. "Generation of oxygen gradients in microfluidic devices for cell culture using spatially confined chemical reactions," Abstract of Lab on a Chip 11, 3626-3633, 6 pages (2011).
Colgan, S. P. & Taylor, C. T. "Hypoxia: an alarm signal during intestinal inflammation," Author Manuscript, published in final edited form as: Nature Reviews Gastroenterology and Hepatology 7, 281-287 (2010) [16 pages].
Colgan, S.P., Dzus, A.L. & Parkos, C.A. "Epithelial exposure to hypoxia modulates neutrophil transepithelial migration," Journal of Experimental Medicine 184, 1003-1015 (1996).
Eveillard, M. et al. "Identification and characterization of adhesive factors of Clostridium difficile involved in adhesion to human colonic enterocyte-like Caco-2 and mucus-secreting HT29 cells in culture," Molecular microbiology 7, pp. 371-381 (1993).
Gersemann, M. et al. "Differences in goblet cell differentiation between Crohn's disease and ulcerative colitis," Abstract of Differentiation 77, pp. 84-94 (2009)[3 pages].
Gibson et al. "Isolation of Colonic Crypts That Maintain Structural and Metabolic Viability In Vitro," Gastroenterology, 1989, vol. 96, pp. 283-291 (Year: 1989).
Gross, M. W., Karbach, U., Groebe, K., Franko, A. J. & Mueller-Klieser, W. "Calibration of misonidazole labeling by simultaneous measurement of oxygen tension and labeling density in multicellular spheroids," International journal of cancer 61, 567-573 (1995).
Huang, Y., Zitta, K., Bein, B., Steinfath, M. & Albrecht, M. An insert-based enzymatic cell culture system to rapidly and reversibly induce hypoxia: investigations of hypoxia-induced cell damage, protein expression and phosphorylation in neuronal IMR-32 cells. Disease models & mechanisms 6, 1507-1514 (2013).
Hubbi, M.E. & Semenza, G.L. Regulation of cell proliferation by hypoxia-inducible factors. American Journal of Physiology-Cell Physiology 309, C775-C782 (2015).
Ivanovic, Z. Hypoxia or in situ normoxia: The stem cell paradigm. Journal of cellular physiology 219, 271-275 (2009).
JanssenDuijghuijsen, L.M. et al. Mitochondrial ATP Depletion Disrupts Caco-2 Monolayer Integrity and Internalizes Claudin 7. Frontiers in Physiology 8 (2017).

(56) References Cited

OTHER PUBLICATIONS

Janvilisri, T., Scaria, J. & Chang, Y.-F. Transcriptional profiling of Clostridium difficile and Caco-2 cells during infection. The Journal of infectious diseases 202, 282-290 (2010).

Kaidi, A., Williams, A.C. & Paraskeva, C. Interaction between β-catenin and HIF-1 promotes cellular adaptation to hypoxia. Nature cell biology 9, 210-217 (2007).

Kaiko, G. E. & Stappenbeck, T. S. Host-microbe interactions shaping the gastrointestinal environment. Trends in immunology 35, 538-548 (2014).

Kelly, C.J. et al. Fundamental role for HIF-1α in constitutive expression of human β defensin-1. Mucosal Immunology 6, 1110 (2013).

Kim, H. J., Li, H., Collins, J. J. & Ingber, D. E. Contributions of microbiome and mechanical deformation to intestinal bacterial overgrowth and inflammation in a human gut-on-a-chip. Proceedings of the National Academy of Sciences 113, E7-E15 (2016).

Kim, Y.-G. et al. Neonatal acquisition of *Clostridia* species protects against colonization by bacterial pathogens. Science 356, 315-319, doi:10.1126/science.aag2029 (2017).

Koh, M. Y. & Powis, G. Passing the baton: the HIF switch. Trends in biochemical sciences 37, 364-372 (2012).

Lamberti, A., Marasso, S. L. & Cocuzza, M. PDMS membranes with tunable gas permeability for microfluidic applications. Rsc Advances 4, 61415-61419 (2014).

LeBlanc, J. G. et al. Bacteria as vitamin suppliers to their host: a gut microbiota perspective. Current opinion in biotechnology 24, 160-168 (2013).

Leffler, D.A. & Lamont, J.T. Clostridium difficile Infection. New England Journal of Medicine 372, 1539-1548 (2015).

Lynch, S.V. & Pedersen, O. The Human Intestinal Microbiome in Health and Disease. N Engl J Med 375, 2369-2379 (2016).

Markov, D. A., Lillie, E. M., Garbett, S. P. & McCawley, L. J. Variation in diffusion of gases through PDMS due to plasma surface treatment and storage conditions. Biomedical microdevices 16, 91-96 (2014).

Marzorati, M. et al. The HMI™ module: a new tool to study the Host-Microbiota Interaction in the human gastrointestinal tract in vitro. BMC microbiology 14, 133 (2014).

Nagpal, R., Yadav, H. & Marotta, F. Gut microbiota: the next-gen frontier in preventive and therapeutic medicine? Frontiers in medicine 1 (2014).

Oppegard, S. C. & Eddington, D. T. A microfabricated platform for establishing oxygen gradients in 3-D constructs. Biomedical microdevices 15, 407-414 (2013).

Oppegard, S. C., Blake, A. J., Williams, J. C. & Eddington, D. T. Precise control over the oxygen conditions within the Boyden chamber using a microfabricated insert. Lab on a chip 10, 2366-2373 (2010).

Oppegard, S. C., Nam, K.-H., Carr, J. R., Skaalure, S. C. & Eddington, D. T. Modulating temporal and spatial oxygenation over adherent cellular cultures. PloS one 4, e6891 (2009).

Peery, A.F. et al. Burden of gastrointestinal disease in the United States: 2012 update. Gastroenterology 143, 1179-1187. e1173 (2012).

Quaroni et al. "Epithelioid Cell Cultures From Rat Small Intestine," J. Cell Biology, 1979, vol. 80, pp. 248-265 (Year: 1979).

Ex Parte Quayle Action and Interview Summary corresponding to U.S. Appl. No. 15/545,456 dated Mar. 16, 2021.

Rexius-Hall, M. L., Mauleon, G., Malik, A. B., Rehman, J. & Eddington, D. T. Microfluidic platform generates oxygen landscapes for localized hypoxic activation. Lab on a chip 14, 4688-4695 (2014).

Sampson, T. R. et al. Gut microbiota regulate motor deficits and neuroinflammation in a model of Parkinson's disease. Cell 167, 1469-1480. e1412 (2016).

Schneeberger, K., Roth, S., Nieuwenhuis, E.E. & Middendorp, S. Intestinal epithelial cell polarity defects in disease: lessons from microvillus inclusion disease. Disease models & mechanisms 11, dmm031088 (2018).

Schuijers, J. & Clevers, H. Adult mammalian stem cells: the role of Wnt, Lgr5 and R-spondins. The EMBO journal 31, 2685-2696 (2012).

Shah, P. et al. A microfluidics-based in vitro model of the gastrointestinal human-microbe interface. Nature communications 7 (2016).

Shimamura, S. et al. Relationship Between Oxygen Sensitivity and Oxygen Metabolism of *Bifidobacterium* Species. Journal of Dairy Science 75, 3296-3306 (1992).

Simon, M. C. & Keith, B. The role of oxygen availability in embryonic development and stem cell function. Nature reviews. Molecular cell biology 9, 285 (2008).

Skolimowski, M. et al. Microfluidic dissolved oxygen gradient generator biochip as a useful tool in bacterial biofilm studies. Lab on a Chip 10, 2162-2169 (2010).

Sommer, F., Anderson, J.M., Bharti, R., Raes, J. & Rosenstiel, P. The resilience of the intestinal microbiota influences health and disease. Nat Rev Microbiol 15, 630-638 (2017).

Tsujii, M. et al. Colonic mucosal hemodynamics and tissue oxygenation in patients with ulcerative colitis: Investigation by organ reflectance spectrophotometry. Journal of Gastroenterology 30, 183-188 (1995).

Uchida, H., Sato, A., Miyayama, A. & Tsukada, K. Generation of an oxygen gradient in a microfluidic device and cellular analysis in hypoxia. Advanced Biomedical Engineering 2, 143-149 (2013).

Ulluwishewa, D. et al. Live Faecalibacterium prausnitzii in an apical anaerobic model of the intestinal epithelial barrier. Cellular microbiology 17, 226-240 (2015).

Varia, M.A. et al. Pimonidazole: a novel hypoxia marker for complementary study of tumor hypoxia and cell proliferation in cervical carcinoma. Gynecologic oncology 71, 270-277 (1998).

Wagner, B.A., Venkataraman, S. & Buettner, G.R. The rate of oxygen utilization by cells. Free radical biology & medicine 51, 700-712 (2011).

Waligora, A.J., Barc, M.C., Bourlioux, P., Collignon, A. & Karjalainen, T. Clostridium difficile cell attachment is modified by environmental factors. Applied and environmental microbiology 65, 4234-4238 (1999).

Walsh III, D. I. et al. Emulation of Colonic Oxygen Gradients in a Microdevice. SLAS Technology: Translating Life Sciences Innovation, 2472630317743425 (2017).

Wang, Y. et al. Bioengineered Systems and Designer Matrices That Recapitulate the Intestinal Stem Cell Niche. Cell Mol Gastroenterol Hepatol 5, 440-453 e441 (2018).

Wang, Y. et al. Self-renewing monolayer of primary colonic or rectal epithelial cells. Cellular and Molecular Gastroenterology and Hepatology (2017).

Wang et al. "Capture and 3D culture of colonic crypts and colonoids in a microarray platform," Lab Chip, The Royal Society of Chemistry, vol. 13, pp. 4625-4634 (2013b).

Ward, J. B., Keely, S. J. & Keely, S. J. "Oxygen in the regulation of intestinal epithelial transport," The Journal of physiology 592, pp. 2473-2489 (2014).

Wiegand, P.N. et al. Clinical and economic burden of Clostridium difficile infection in Europe: a systematic review of healthcare-facility-acquired infection. Journal of Hospital Infection 81, 1-14 (2012).

Zeitouni, N. E., Chotikatum, S., von Köckritz-Blickwede, M. & Naim, H. Y. The impact of hypoxia on intestinal epithelial cell functions: consequences for invasion by bacterial pathogens. Molecular and cellular pediatrics 3, 14 (2016).

Zheng, L., Kelly, C. J. & Colgan, S. P. "Physiologic hypoxia and oxygen homeostasis in the healthy intestine. A review in the theme: cellular responses to hypoxia," American Journal of Physiol Cell Physiol 309, pp. C350-C360 (2015).

Zhou, W. et al. Multifunctional bioreactor system for human intestine tissues. ACS biomaterials science & engineering 4, 231-239 (2017).

Barkla et al. "The fate of epithelial cells in the human large intestine." Pathology vol. 31, pp. 230-238, (1999).

Bartfeld, "Modeling infectious diseases and host-microbe interactions in gastrointestinal organoids." Developmental biology, vol. 420, pp. 262-270, (2016).

(56) References Cited

OTHER PUBLICATIONS

Basak et al., "Induced quiescence of Lgr5+ stem cells in intestinal organoids enables differentiation of hormone-producing enteroendocrine cells." Cell Stem Cell, vol. 20, pp. 177-190 e4, (2017).
Dekkers et al., "A functional CFTR assay using primary cystic fibrosis intestinal organoids." Nature medicine, vol. 19, pp. 939, (2013).
Finkbeiner et al., "Stem cell-derived human intestinal organoids as an infection model for rotaviruses." MBio vol. 3, e00159-12, (2012).
Gamet et al., "Effects of short-chain fatty acids on growth and differentiation of the human colon-cancer cell line HT29." International Journal of Cancer vol. 52, pp. 286-289, (1992).
Gattazzo et al., "Extracellular matrix: a dynamic microenvironment for stem cell niche." Biochimica et Biophysica Acta (BBA)—General Subjects, vol. 1840, pp. 2506-2519, (2014).
Hall et al., "Human genetic variation and the gut microbiome in disease." Nature Reviews Genetics vol. 18, pp. 690, (2017).
In et al., "Enterohemorrhagic *Escherichia coli* reduces mucus and intermicrovillar bridges in human stem cell-derived colonoids." Cellular and molecular gastroenterology and hepatology vol. 2, pp. 48-62 e3, (2016).
Ito et al., "Metabolism and the control of cell fate decisions and stem cell renewal." Annual review of cell and developmental biology. vol. 32, pp. 399-409, (2016).
Kaiko et al., "The colonic crypt protects stem cells from microbiota-derived metabolites." Cell vol. 165, pp. 1708-1720, (2016).
Karve et al., "Intestinal organoids model human responses to infection by commensal and Shiga toxin producing *Escherichia coli.*" PloS one vol. 12, e0178966, (2017).
Kozuka et al., "Development and Characterization of a Human and Mouse Intestinal Epithelial Cell Monolayer Platform." Stem cell reports vol. 9, pp. 1976-1990, (2017).
Li et al., "Role of mechanical factors in fate decisions of stem cells." Regenerative medicine vol. 6, pp. 229-240, (2011).
Semrau et al., "Studying lineage decision-making in vitro; emerging concepts and novel tools." Annual review of cell and developmental biology vol. 31, pp. 317-345, (2016).
Shreiner et al., "The gut microbiome in health and in disease." Current opinion in gastroenterology vol. 31, pp. 69, (2015).
Terryn et al., "Recent advances in lineage differentiation from stem cells: hurdles and opportunities?" F1000Resarch vol. 7, (2018).
Tong et al., "Towards a defined ECM and small molecule based monolayer culture system for the expansion of mouse and human intestinal stem cells." Biomaterials vol. 154, pp. 60-73, (2018).
Tremlett et al., "The gut microbiome in human neurological disease: a review." Annals of Neurology, (2017).
Tsubouchi, "Kinetic analysis of epithelial cell migration in the mouse descending colon." Developmental Dynamics, vol. 161, pp. 239-246, (1981).
Van Es et al., "Dll1+ secretory progenitor cells revert to stem cells upon crypt damage." Nature cell biology vol. 14, p. 1099, (2012).
Wang et al., "In vitro Generation of Mouse Colon Crypts." ACS biomaterials science & engineering vol. 3, pp. 2502-2513, (2017).
Whitehead et al., "Effects of short-chain fatty acids on a new human colon carcinoma cell line (LIM1215)." Gut, vol. 27, pp. 1457-1463, (1986).
Young, "The role of the microbiome in human health and disease: an introduction for clinicians." BMJ vol. 356, j831, (2017).
Xu et al., "Butyrate induces apoptosis by activating PDC and inhibiting complex I through SIRT3 inactivation." Signal Transduction and Targeted Therapy, vol. 2, pp. e16035, (2017).
Fung et al., "Butyrate-Induced Apoptosis in HCT116 Colorectal Cancer Cells Includes Induction of a Cell Stress Response." Journal of Proteome Research, vol. 10, pp. 1860-1869 (2011).
Ruemmele et al., "Butyrate induced Caco-2 cell apoptosis is mediated via the mitochondrial pathway." Gut, vol. 52, pp. 94-100, (2003).
Koh et al., "From Dietary Fiber to Host Physiology: Short-Chain Fatty Acids as Key Bacterial Metabolites." Cell, vol. 165, pp. 1332-1345, (2016).
Barker, "Adult intestinal stem cells: critical drivers of epithelial homeostasis and regeneration." Nature Reviews Molecular Cell Biology, vol. 15, pp. 19-33 (2014).
Sternini et al., "Enteroendocrine cells: a site of 'taste' in gastrointestinal chemosensing." Current Opinion in Endocrinology, Diabetes, and Obesity, vol. 15, pp. 73, (2008).
Birchenough et al., "A sentinel goblet cell guards the colonic crypt by triggering Nlrp6-dependent Muc2 secretion." Science, vol. 352, pp. 1535-1542, (2016).
Valenta et al., "The many faces and functions of β-catenin." The EMBO Journal, vol. 31, pp. 2714-2736, (2012).
Provenzano and Keely, "Mechanical signaling through the cytoskeleton regulates cell proliferation by coordinated focal adhesion and Rho GTPase signaling",J. Cell Sci, vol. 124, pp. 1195-1205, (2011).
Yim and Sheetz, "Force-dependent cell signaling in stem cell differentiation." Stem Cell Research & Therapy, vol. 3, pp. 41, (2012).
Lü et al., "Differential regulation of morphology and stemness of mouse embryonic stem cells by substrate stiffness and topography," Biomaterials, vol. 35, pp. 3945-3955, (2014).
Chowdhury et al., "Soft Substrates Promote Homogeneous Self-Renewal of Embryonic Stem Cells via Downregulating Cell-Matrix Tractions." PloS one, vol. 5, e15655, (2010).
Janshoff et al., "Cell Adhesion to Ordered Pores: Consequences for Cellular Elasticity." Journal of Adhesion Science and Technology, vol. 24, pp. 2287-2300, (2010).
Rother et al., "Cytoskeleton remodelling of confluent epithelial cells cultured on porous substrates." Journal of the Royal Society Interface, vol. 12, 20141057, (2015).
Hayman et al., "Growth of human stem cell-derived neurons on solid three-dimensional polymers." Journal of Biochemical and Biophysical Methods, vol. 62, pp. 231-240, (2005).
Peyton et al., "Marrow-Derived Stem Cell Motility in 3D Synthetic Scaffold Is Governed by Geometry Along With Adhesivity and Stiffness." Biotechnology and Bioengineering, vol. 108, pp. 1181-1193, (2011).
Ahmad et al., "Optimizing Wnt-3a and R-spondin1 concentrations for stem cell renewal and differentiation in intestinal organoids using a gradient-forming microdevice." RSC Advances, vol. 5, pp. 74881-74891 (2015).
Franck et al., "Three-Dimensional Traction Force Microscopy: A New Tool for Quantifying Cell-Matrix Interactions." PloS one, vol. 6, e17833, (2011).
Qu et al., "Maturation State and Matrix Microstructure Regulate Interstitial Cell Migration in Dense Connective Tissues." Scientific Reports, vol. 8, 3295, (2018).
Vallo et al., "Elastic Modulus and Yield Stress of Epoxy Networks in the Glassy State." Polymer Gels and Networks, vol. 1, pp. 257-266, (1993).
Engelberg and Tesoro, "Mechanical and Thermal Properties of Epoxy Resins With Reversible Crosslinks," Polymer Engineering & Science, vol. 30, pp. 303-307, (1990).
Faul et al., "G*Power 3: A flexible statistical power analysis program for the social, behavioral, and biomedical sciences," Behavior Research Methods, vol. 39, pp. 175-191, (2007).
Schindelin et al., "Fiji—an Open Source platform for biological image analysis." Nature Methods, vol. 9, pp. 676, (2012).
Pai et al., "Photoresist with Low Fluorescence for Bioanalytical Applications," Analytical Chemistry, vol. 79, pp. 8774-8780, (2007).
Allen et al., "Adherent and soluble Mucus in the Stomach and Duodenum." Digestive Diseases and Sciences vol. 30, 55S-62S, (1985).
Pelaseyed et al., "The mucus and mucins of the goblet cells and enterocytes provide the first defense line of the gastrointestinal tract and interact with the immune system." Immunological reviews vol. 260, pp. 8-20, (2014).
Murgia et al., "The role of mucus on drug transport and its potential to affect therapeutic outcomes." Adv Drug Deliv Rev vol. 124, pp. 82-97, (2018).

(56) References Cited

OTHER PUBLICATIONS

Lehr et al., "An estimate of turnover time of intestinal mucus gel layer in the rat in situ loop." International Journal of Pharmaceutics vol. 70 pp. 235-240, (1991).
Wei et al., "Fatty Acid Synthase Modulates Intestinal Barrier Function through Palmitoylation of Mucin 2." Cell Host & Microbe vol. 11, pp. 140-152, (2012).
Johansson et al., "The inner of the two Muc2 mucin-dependent mucus layers in colon is devoid of bacteria." Proceedings of the National Academy of Sciences of the United States of America, vol. 105, pp. 15064-15069, (2008).
Hansson, "Role of mucus layers in gut infection and inflammation." Current Opinion in Microbiology vol. 15, pp. 57-62, (2012).
Carlson et al., "Engineering the Mucus Barrier." Annual Review of Biomedical Engineering vol. 20, pp. 197-220, (2018).
Werlang et al., "Engineering mucus to study and influence the microbiome." Nature Reviews Materials vol. 4, pp. 134-145, (2019).
Rogier et al., "Secretory IgA is Concentrated in the Outer Layer of Colonic Mucus along with Gut Bacteria." Pathogens vol. 3, pp. 390-403, (2014).
Gunasekara et al., "A Monolayer of Primary Colonic Epithelium Generated on a Scaffold with a Gradient of Stiffness for Drug Transport Studies." Analytical Chemistry vol. 90, pp. 13331-13340, (2018).
Quigley, "Gut bacteria in health and disease." Gastroenterology & hepatology vol. 9, pp. 560-569, (2013).
Gagnon et al., "Comparison of the Caco-2, HT-29 and the mucus-secreting HT29-MTX intestinal cell models to investigate *Salmonella* adhesion and invasion," Journal of Microbiological Methods, vol. 94, pp. 274-279 (2013).
Lesuffleur et al., "Growth adaptation to methotrexate of HT-29 human colon carcinoma cells is associated with their ability to differentiate into columnar absorptive and mucus-secreting cells." Cancer Research vol. 50, pp. 6334-6343, (1990).
Nusrat et al., "Clostridium difficile Toxins Disrupt Epithelial Barrier Function by Altering Membrane Microdomain Localization of Tight Junction Proteins." Infection and Immunity vol. 69, pp. 1329-1336, (2001).
Date et al., "Mini-Gut Organoids: Reconstitution of Stem Cell Niche." Annual Review of Cell and Developmental Biology vol. 31, pp. 269-289, (2015).
Sato et al., "Long-term Expansion of Epithelial Organoids From Human Colon, Adenoma, Adenocarcinoma, and Barrett's Epithelium." Gastroenterology vol. 141, pp. 1762-1772, (2011).
Fatehullah et al., "Cell and tissue polarity in the intestinal tract during tumourigenesis: cells still know the right way up, but tissue organization is lost." Philosophical Transactions of the Royal Society B—Biological Sciences vol. 368, 20130014, (2013).
Noel et al., "A primary human macrophage-enteroid co-culture model to investigate mucosal gut physiology and host pathogen interactions." Scientific Reports vol. 7, pp. 45270, (2017).
Puzan et al., "Enteric Nervous System Regulation of Intestinal Stem Cell Differentiation and Epithelial Monolayer Function." Scientific Reports vol. 8, pp. 6313, (2018).
Wang et al., "Analysis of Interleukin 8 Secretion by a Stem-Cell-Derived Human-Intestinal-Epithelial-Monolayer Platform." Analytical Chemistry vol. 90, pp. 11523-11530, (2018).
Whitcutt et al., "A biphasic chamber system for maintaining polarity of differentiation of cultured respiratory tract epithelial cells." In Vitro Cellular & Developmental Biology, vol. 24, pp. 420-428, (1988).
Gray et al., "Mucociliary differentiation of serially passaged normal human tracheobronchial epithelial cells," American Journal of Respiratory Cell and Molecular Biology, vol. 14, pp. 104-112 (1996).
Raredon et al., "A Rotating Bioreactor for Scalable Culture and Differentiation of Respiratory Epithelium." Cell Medicine vol. 7, pp. 109-121, (2012).
O'Boyle et al., "Temporal dynamics of ovine airway epithelial cell differentiation at an air-liquid interface." Plos One vol. 12, e0181583, (2017).

Ootani et al., "An air-liquid interface promotes the differentiation of gastric surface mucous cells (GSM06) in culture." Biochemical and Biophysical Research Communications vol. 271, pp. 741-746, (2000).
Yokoyama et al., "Differentiation of gastric surface mucous cells (GSM06) induced by air-liquid interface is regulated partly through mitogen-activated protein kinase pathway." Journal of Gastroenterology and Hepatology, vol. 22, pp. 2310-2315, (2007).
Navabi et al., "Gastrointestinal Cell Lines Form Polarized Epithelia with an Adherent Mucus Layer when Cultured in Semi-Wet Interfaces with Mechanical Stimulation." Plos One vol. 8, e68761, (2013).
Elkins et al., "Mechanisms and applications of hypertonic saline." Journal of the Royal Society of Medicine, vol. 104, pp. S2-S5, (2011).
Tu et al., "Effect of osmotic response element binding protein on mucus secretion with hypertonicity in human airway epithelial cells," Zhonghua Yi Xue Za Zhi, vol. 91, pp. 549-553, (2011) [English Abstract].
Lüdeking et al., "Osmotic changes and ethanol modify TFF gene expression in gastrointestinal cell lines." Febs Letters vol. 439, pp. 180-184, (1998).
Shields et al., "Absorption and secretion of water and electrolytes by the intact colon in a patient with primary aldosteronism." British Medical Journal vol. 1, pp. 93-96, (1968).
Wapnir et al., "Regulation mechanisms of intestinal secretion: implications in nutrient absorption." The Journal of Nutritional Biochemistry vol. 13, pp. 190-199, (2002).
Koch et al., "Plasma vasoactive intestinal polypeptide concentration determination in patients with diarrhea." Gastroenterology vol. 100, pp. 99-106, (1991).
Schwartz et al., "Vasoactive intestinal peptide stimulation of adenylate cyclase and active electrolyte secretion in intestinal mucosa." Journal of Clinical Investigation vol. 54, pp. 536-544, (1974).
Wu et al., "Vasoactive Intestinal Polypeptide Promotes Intestinal Barrier Homeostasis and Protection Against Colitis in Mice." Plos One vol. 10, e0125225, (2015).
Johansson et al., "Bacteria penetrate the normally impenetrable inner colon mucus layer in both murine colitis models and patients with ulcerative colitis." Gut, vol. 63, pp. 281-291, (2014).
Lin et al., "Air-liquid interface (ALI) culture of human bronchial epithelial cell monolayers as an in vitro model for airway drug transport studies." Journal of Pharmaceutical Sciences vol. 96, pp. 341-350, (2007).
Bernstam et al., "Keratinocytes grown at the air-liquid interface." In Vitro Cellular & Developmental Biology vol. 22, pp. 695-705, (1986).
Ootani et al., "Sustained in vitro intestinal epithelial culture within a Wnt-dependent stem cell niche." Nature Medicine vol. 15, pp. 1-U140, (2009).
Voth et al., "Clostridium difficile toxins: mechanism of action and role in disease." Clinical microbiology reviews vol. 18, pp. 247-263, (2005).
He et al., "Clostridium difficile toxin A triggers human coloncyte IL-8 release via mitochondrial oxygen radical generation." Gastroenterology, vol. 122, pp. 1048-1057, (2002).
Mahida et al., "Effect of Clostridium difficile toxin A on human intestinal epithelial cells: induction of interleukin 8 production and apoptosis after cell detachment." Gut vol. 38, pp. 337-347, (1996).
Haller et al., "Non-pathogenic bacteria elicit a differential cytokine response by intestinal epithelial cell/leucocyte co-cultures." Gut vol. 47, pp. 79-87, (2000).
Parlesak et al., "Modulation of Cytokine Release by Differentiated CACO-2 Cells in a Compartmentalized Coculture Model with Mononuclear Leucocytes and Nonpathogenic Bacteria." Scandinavian Journal of Immunology vol. 60, pp. 477-485, (2004).
English Translation of Notice of Allowance corresponding to JP Patent Application No. JP 2017-540628 dated Jun. 29, 2021.
English Translation of First Office Action corresponding to JP Patent Application No. JP 2019-504019 dated May 25, 2021.
Japanese Office Action for Application No. 2021517604 dated Jan. 31, 2024.
Canadian Office Action for Application No. 3009153 dated Mar. 13, 2024.

(56) References Cited

OTHER PUBLICATIONS

Gunawardene Ashok R. et al., "Classification and functions of enteroendocrine cells of the lower gastrointestinal tract: Classification and functions of colorectal enteroendocrine cells," International Review of Experiemental Pathology, vol. 92, No. 4: 219-231 (Aug. 31, 2011).

Extended European Search Report for Application No. 21779789.3, dated Jun. 10, 2024, 13 pages.

Bhat et al., "The limiting role of mucus in drug absorption: drug permeation through mucus solution," International Journal of Pharmaceuticals, vol. 126: 179-187 (1995).

* cited by examiner

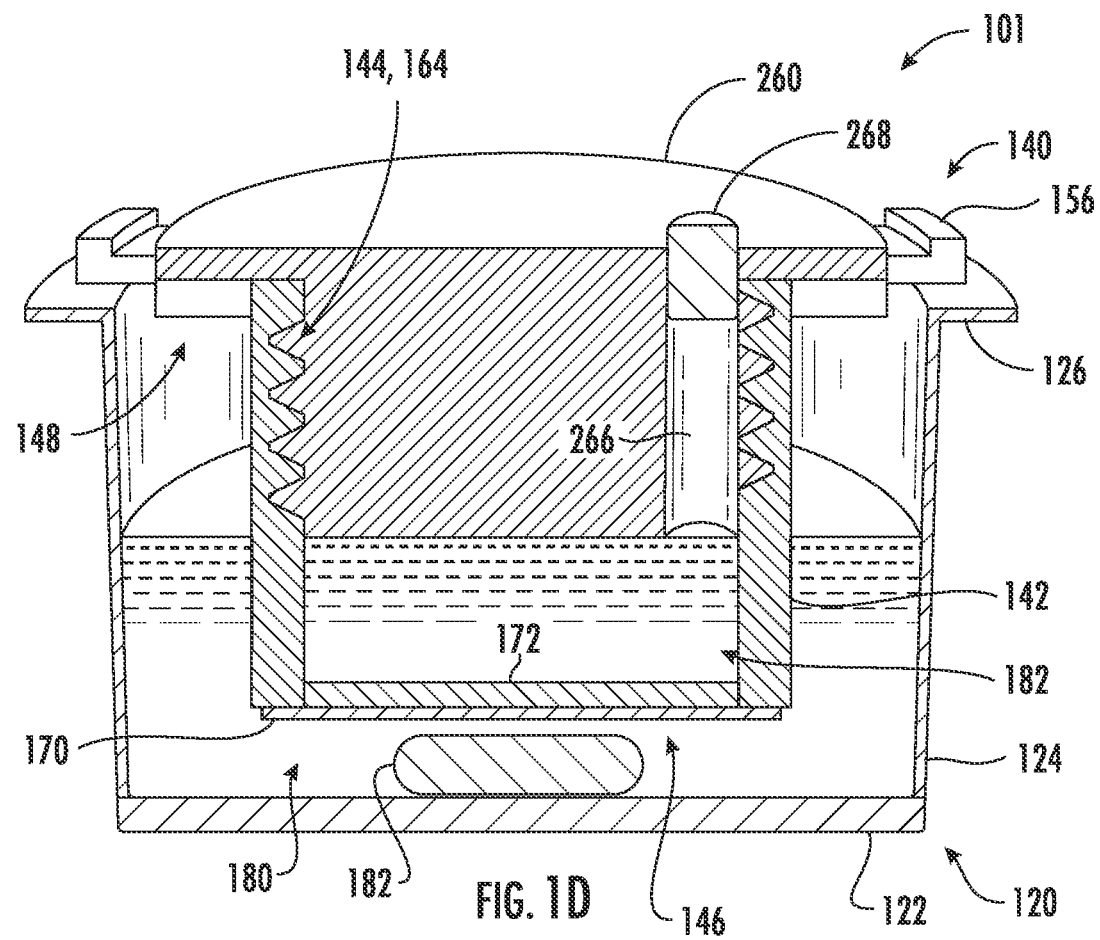

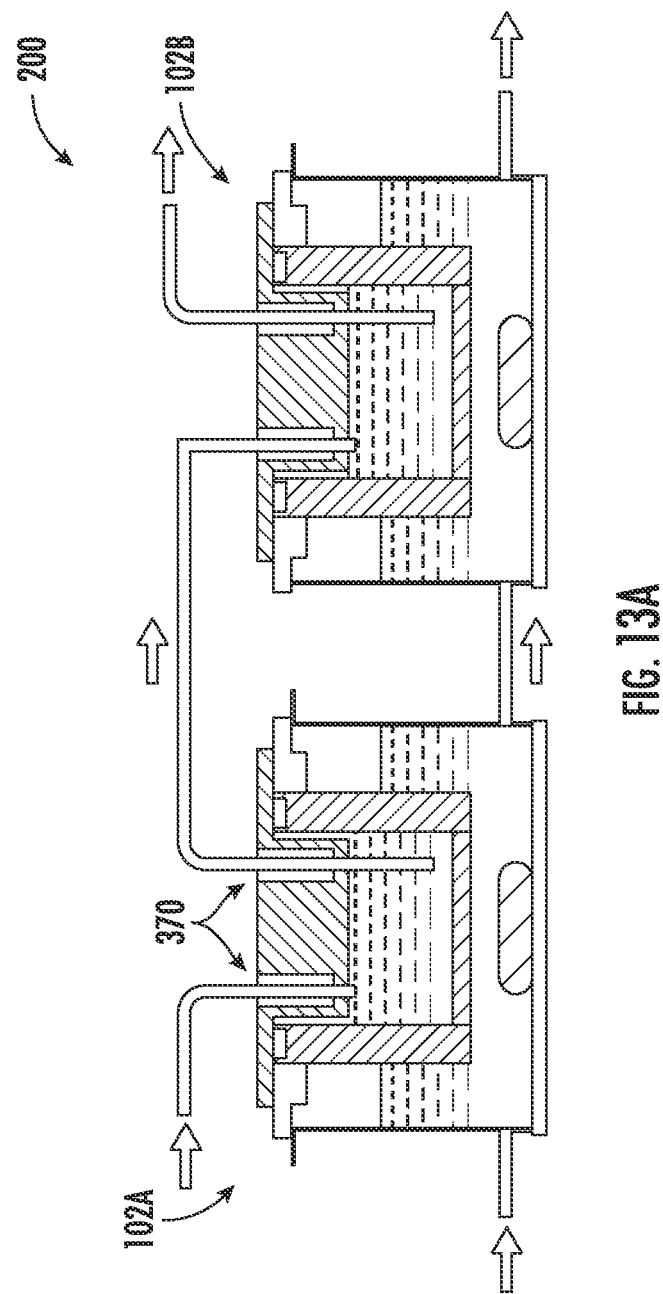

DEVICES, SYSTEMS AND APPARATUSES FOR GENERATING SELF-SUSTAINING HYPOXIC CONDITIONS AND GASEOUS AND NON-GASEOUS CHEMICAL GRADIENTS FOR IN VITRO CELL CULTURE

CROSS-REFERENCE TO RELATED APPLICATIONS

This application claims benefit of U.S. Provisional Patent Application Ser. No. 62/671,661, filed May 15, 2018, herein incorporated by reference in its entirety.

STATEMENT OF FEDERAL SUPPORT

This invention was made with government support under grant number DK 109559 awarded by National Institutes of Health. The government has certain rights to this invention.

TECHNICAL FIELD

The subject matter disclosed herein relates generally to generating self-sustaining hypoxic conditions and gaseous and non-gaseous chemical gradients for in vitro cell culture. More specifically, disclosed herein are apparatuses and methods for generating self-sustaining gaseous and non-gaseous chemical gradients in in vitro cell cultures.

BACKGROUND

Development of in vitro culture systems such as, for example, intestinal organoid cultures, intestinal self-renewing monolayers, and gut-on-a-chip type devices, offer useful in vitro platforms with advantages over the use of in vivo animal models. However, in vitro platforms currently available have either failed to replicate the particular gas distribution or gradient found in the natural environment of the system of interest or they require application of external gas mixtures.

The present disclosure overcomes previous shortcomings in the art by providing apparatus and methods for generating gaseous and non-gaseous chemical gradients in in vitro cell culture that more accurately recapitulate an in vivo ecosystem of interest (e.g., an in vivo intestinal system).

SUMMARY

This summary lists several embodiments of the presently disclosed subject matter, and in many cases lists variations and permutations of these embodiments. This summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently disclosed subject matter, whether listed in this summary or not. To avoid excessive repetition, this Summary does not list or suggest all possible combinations of such features.

In some embodiments, provided herein are methods of generating a gas gradient across a cell support structure. Such methods can in some embodiments comprise providing a luminal container comprising a bottom wall, at least one sidewall extending upwardly from the bottom wall, and a top opening defined by the at least one sidewall, wherein the bottom wall of the luminal container comprises a gas permeable membrane, positioning a cell support structure above the bottom wall, positioning one or more cells and/or tissues on the cell support structure, installing a cover on the luminal container to close the open top, wherein a luminal reservoir is defined between a bottom surface of the cover and the cell support structure and/or the one or more cells and/or tissue, and generating a gas gradient (higher to lower and/or lower to higher) between the bottom wall, across the cell support structure and into the luminal reservoir.

Alternatively, or in addition, in some embodiments, methods of culturing one or more cells and/or tissues under hypoxic conditions are provided. Such methods can comprise providing a luminal container comprising a bottom wall, at least one sidewall extending upwardly from the bottom wall, and a top opening defined by the at least one sidewall, positioning a cell support structure on the bottom wall, positioning one or more cells and/or tissues on the cell support structure, installing a cover on the luminal container to close the open top, wherein a luminal reservoir is defined between a bottom surface of the cover and the cell support structure and/or the one or more cells, and generating hypoxic conditions in the luminal reservoir, wherein the hypoxic conditions are generated by the one or more cells and/or tissue on the cell support structure in the luminal container with the cover in the installed position.

In any of the methods disclosed herein, including those above, the bottom wall of the luminal container can comprise a gas impermeable membrane. The bottom wall of the luminal container can also comprise a gas permeable membrane.

In some embodiments, such methods can further comprise generating a gas gradient between gas gradient (higher to lower or lower to higher) between the bottom wall through the one or more cells and/or tissue (e.g., across the cell support structure) and into the luminal reservoir. Moreover, in some aspects, such methods can further comprise providing a gas to the one or more cells and/or tissue through the gas permeable membrane of the bottom wall of the luminal container, and generating a gas gradient (higher to lower) between the gas permeable membrane of the bottom wall of the luminal container through the one or more cells and/or tissue (e.g., across the cell support structure) and into the luminal reservoir. The gas can be provided passively through the permeable membrane from the atmosphere (in which the luminal container is maintained (held)).

In any of the methods disclosed herein, including those above, the methods can further comprise providing a basal container comprising a bottom wall and at least one sidewall extending upwardly from the bottom wall, wherein the bottom wall and the at least one sidewall define a well, and wherein the luminal container is held within the well of the basal container, the bottom wall of the basal container is spaced apart from the bottom wall of the luminal container, a basal reservoir is defined between the bottom wall of the basal container and the bottom wall of the luminal container and/or between the at least one sidewall of the basal container and the at least one sidewall of the luminal container, and a basal medium positioned in the basal reservoir, wherein the basal medium provides the gas to the one or more cells and/or tissue through the gas permeable membrane of the bottom wall, thereby generating a gas gradient (higher to lower) between the basal medium and the luminal reservoir (perpendicularly through the one or more cells and/or tissue).

In some embodiments, the luminal container in these methods can be divided into at least two compartments by a second gas permeable membrane and the gas gradient is generated between the at least two compartments. In some aspects, the luminal container can comprise at least two luminal containers, including a first luminal container comprising a bottom wall, at least one sidewall extending upwardly from the bottom wall, and a top opening defined by the at least one sidewall, wherein the bottom wall of the first luminal container comprises a gas permeable membrane, and a second luminal container comprising a bottom wall, at least one sidewall extending upwardly from the bottom wall, and a top opening defined by the at least one sidewall, wherein the bottom wall of the second luminal container comprises a gas permeable membrane, wherein the first luminal container is held within the second luminal container, and a gas gradient is generated between the at least two luminal containers.

In any of the methods disclosed herein, including those above, the cover can comprise at least one port or channel (e.g., about 1, 2, 3, 4, 5, or more) extending from a top or a side surface of the cover to a bottom surface of the cover of the luminal container. Alternatively, or in addition, the luminal container can comprise at least one port or channel (e.g., about 1, 2, 3, 4, 5, or more) in the side wall or bottom wall. Alternatively, or in addition, the basal container comprises at least one port or channel (e.g., about 1, 2, 3, 4, 5, or more) in the side wall or bottom wall.

In any of the methods disclosed herein, including those above, such methods can further comprise introducing substances into or extracting substances from the luminal reservoir through the at least one port or channel. Likewise, such methods can further comprise introducing substances into or removing substances from the basal reservoir through the at least one port or channel.

In any of the methods disclosed herein, including those above, such methods can further comprise inserting at least one sensor and/or tubing into the at least one port or channel of the cover and/or the basal container. In some aspects, the at least one sensor is a gas sensor, a pH sensor, pressure sensor, flow sensor, temperature sensor, and/or a chemical/biological sensor. The methods can further comprise sealing the at least one port or channel.

In any of the methods disclosed herein, including those above, such methods can further comprise providing a gas or consuming a gas in the luminal container, luminal reservoir, basal reservoir and/or basal container. The luminal medium and/or the basal medium can comprise a dissolved gas. In some aspects, the basal medium can comprise oxygen generating materials.

In any of the methods disclosed herein, including those above, such methods can further comprise providing at least one gas to the luminal reservoir through the at least one port or channel of the cover, thereby generating a gas gradient across the cell support structure. Likewise, such methods can, in some embodiments, comprise providing at least one gas to the basal reservoir through the at least one port or channel of the basal container, thereby generating a gas gradient across the cell support structure. The at least one gas can be oxygen, nitrogen, hydrogen, methane, carbon dioxide, carbon monoxide, sulphide, skatole, indole, methanethiol, dimethyl sulfide, volatile amine, volatile sulfur compound (VSC) (e.g., disulfur monoxide, hydrogen sulfide), methyl mercaptan or methanethiol, dimethyl disulfide (DMDS), dimethyl trisulfide (DMTS), volatile fatty acid, and/or nitric oxide. In some aspects, the at least one gas is oxygen. In some embodiments, the at least one gas is oxygen and the oxygen concentration in the luminal reservoir is less than about 21%. In some embodiments, the at least one gas is oxygen and the oxygen concentration in the luminal reservoir is from about 0% to about 14%, optionally about 0% to about 5%. In some aspects, the at least one gas is oxygen and a stable hypoxia in the luminal reservoir generates an oxygen gradient between the luminal reservoir and the basal reservoir.

In some embodiments, the at least one gas is provided or consumed by a gas generating or gas consuming cell, tissue, or organism. In some embodiments, the gas generating or gas consuming cell, tissue, or organism is the same as the one or more cells or tissues positioned on the cell support structure. In some embodiments, the gas generating or gas consuming cell, tissue, or organism is a bacterium, an archaeon, a fungus, a virus, a helminth, an amoeba, a protozoan. In some embodiments, the at least one gas generating cell, tissue or organism is in the basal medium and provides the gas to the one or more cells and/or tissue through the gas permeable membrane of the bottom wall, thereby generating a gradient across the cell support structure between the basal medium and the luminal reservoir. In some embodiments, the at least one gas generating cell, tissue or organism is in a luminal medium positioned in the luminal reservoir and in direct contact with the cells, thereby providing the gas directly to the one or more cells and/or tissue and generating a gradient across the cell support structure between the luminal medium and the basal reservoir.

In any of the methods disclosed herein, including those above, such methods can further comprise generating a gradient of a non-gaseous chemical across the cell support structure. In some aspects, the one or more cells and/or tissue positioned on the cell support structure produce and/or consume the non-gaseous chemical, thereby generating the gradient across the cell support structure. In some embodiments, a non-gaseous chemical producing cell, tissue or organism is introduced into the basal medium or luminal medium, thereby generating the gradient across the cell support structure (perpendicularly through the one or more cells and/or tissue). In some embodiments, a non-gaseous chemical producing cell, tissue, or organism that is introduced is the same as the one or more cells or tissues positioned on the cell support structure. In some embodiments, the introduced non-gaseous chemical producing cell, tissue, or organism is a bacterium, an archaeon, a fungus, a virus, a helminth, an amoeba, a protozoan. In some embodiments, a non-gaseous chemical is introduced into the basal medium or into the luminal medium, thereby generating the gradient of the non-gaseous chemical across the cell support structure (perpendicularly through the one or more cells and/or tissue) from the luminal medium to the basal medium or from the basal medium to the luminal medium. The gas permeable membrane is permeable to the non-gaseous chemical. The non-gaseous chemical can be a protein, a fatty acid, a growth factor, a hormone, a metabolite, an ion, a carbohydrate, a peptide, a lipopeptide, an amino acid, and/or a test drug.

In any of the methods disclosed herein, including those above, the gas gradient is stable in about 30 minutes to about six hours. In some aspects, the gas gradient is self-sustaining.

In any of the methods disclosed herein, including those above, such methods can further comprise modulating the gradient by mixing the basal medium. In some embodiments, such methods further comprise modulating the gradient by selection of the cells or tissue positioned on the cell support structure. In some embodiments, such methods further comprise modulating the gas gradient by modifying the volume of the luminal reservoir, the volume of the basal reservoir, the gas permeability of the cell support structure, the gas permeability of the side wall of the luminal container, the gas permeability of the bottom wall of the luminal container, and/or the gas permeability of the cover. In some embodiments, such methods further comprise modulating the gas gradient by modifying the volume of the basal medium, the gas permeability of the side wall of the basal container, and/or the gas permeability of the bottom wall of the basal container. In some embodiments, such methods further comprise modulating the gas gradient by modifying the volume of the luminal medium. In some embodiments, the gas permeability of the side wall of the luminal container, the bottom wall of the luminal container, the cover, the side wall of the basal container, and/or the bottom wall of the basal container is modulated by selecting materials for construction based on gas permeability and thicknesses.

In any of the methods disclosed herein, including those above, the one or more cells comprises one or more cell types (e.g., 1, 2, 3, 4, 5, 6, 7, 8, 9, 10, or more). The one or more cells can be a eukaryotic cell line. In some aspects, the one or more cells can be primary cells. In some embodiments, the one or more cells can be mammalian cells. The one or more cells can be human cells. In some embodiments, the one or more cells can be fibroblasts, myofibroblasts, endothelial cells, adipocytes, muscle cells, bone cells, nervous cells, immune cells, stem cells (e.g., embryonic, induced pluripotent stem cells, mesenchymal stem cells, hematopoietic stem cells), digestive tract cells, reproductive tract cells, eye cells, kidney cells, brain cells, bone marrow cells, intestinal cells, epithelial cells and/or cancerous cells. The one or more cells can be gastrointestinal cells. The one or more cells can be primary colon epithelial cells. The primary colon epithelial cells can be human.

In any of the methods disclosed herein, including those above, the one or more cells can be in a two dimensional form or a three dimensional form. In some aspects, the one or more cells and/or tissue can be in a three dimensional culture format of an in vitro culture, an ex vivo culture, an entire organism, an entire organ, a partial organ, and/or an ex vivo tissue section. The in vitro culture or ex vivo culture can be embedded in a natural or artificial hydrogel. In some aspects, the one or more tissues can be one or more types of tissue (e.g., 1, 2, 3, 4, 5, 6, 7, 8, 9, 10 or more). The one or more tissues can be an entire organism, an entire organ, a part of an organ, an in vitro culture, an ex vivo culture, and/or an ex vivo tissue section. The one or more cells and/or tissue can be an in vitro colonic epithelial crypt, the crypt comprising a luminal side and a basal side above the cell support structure. The in vitro colonic epithelium crypt can be an in vitro human colonic epithelium crypt.

In any of the methods disclosed herein, including those above, such methods can further comprise adding at least one microorganism to the luminal reservoir, thereby providing the microorganism access to the luminal side of the crypt and/or the cell support side of the crypt.

Also provided herein are apparatuses to produce hypoxic conditions for in vitro and/or ex vivo cell culture. Such apparatuses can comprise a luminal container comprising a bottom wall, at least one sidewall extending upwardly from the bottom wall, and an open top defined by the at least one sidewall, a cell support structure on the bottom wall, and a cover that is configured to engage the luminal container and close the open top in an installed position, wherein a luminal reservoir is defined between a bottom surface of the cover and the cell support structure with the cover in the installed position, and wherein the apparatus is configured to generate a hypoxic condition in the luminal reservoir with the cover in the installed position. In some embodiments, one or more cells and/or tissue can be positioned on the cell support structure. In some aspects, the hypoxic conditions are self-sustaining.

In some embodiments, the cover can comprise a plug that is received through the open top and engages the luminal container in the installed position. Each of an inner surface of the at least one sidewall and an outer surface of the plug can comprise threads, wherein the plug can be threadingly engaged with the luminal container in the installed position.

In some embodiments, in any of the apparatuses and/or devices disclosed herein, including those above, can further comprise a channel extending from a top surface of the plug to the bottom surface of the plug, and a sensor that is configured to extend through the channel and into the luminal reservoir to measure an oxygen saturation level therein. In some aspects, the sensor can be a gas sensor, a pH sensor or a chemical sensor. In some aspects, the sensor can be an oxygen sensor, a nitrogen sensor, a hydrogen sensor, a methane sensor, a carbon dioxide sensor, carbon monoxide sensor, a sulphide sensor, skatole sensor, indole sensor, methanethiol sensor, dimethyl sulfide sensor, a volatile amine sensor, a volatile sulfur compounds (VSC), methyl mercaptan or methanethiol sensor, a dimethyl disulfide (DMDS) sensor, a dimethyl trisulfide (DMTS) sensor, a volatile fatty acid sensor, and/or a nitric oxide sensor.

In some embodiments, the channel is sealed around the sensor at the top surface of the plug. In some embodiments, the apparatus can comprise an annular gasket extending along at least a portion of a length of the channel, wherein the gasket is configured to receive the sensor therethrough and seal the channel. In some embodiments, the channel is a first channel, and at least one second channel extends from the top surface of the plug to the bottom surface of the plug. In some embodiments, the at least one second channel is for adding test drugs, adding test microbes, and/or exchanging medium in the luminal reservoir. In some aspects, the at least one second channel is configured to receive a sensor therethrough. In some embodiments, the at least one second channel is configured to receive a pH sensor and/or a chemical sensor therethrough. In some aspects, such an apparatus can further comprise at least one annular gasket extending along at least a portion of a length of the at least one second channel, wherein the at least one annular gasket is configured to receive the sensor therethrough and seal the at least one second channel. In some aspects, the at least one second channel is sealable.

In some embodiments, the plug comprises polydimethylsiloxane (PDMS). In some embodiments, the plug has the same diameter as the inner diameter of the luminal container. In some embodiments, the disclosed apparatuses can further comprise an annular gasket (e.g., an o-ring) that is disposed between the plug and the luminal container when the plug is in the installed position. In some embodiments, in the disclosed apparatuses, a seat is defined in the at least one sidewall of the luminal container, and the gasket rests on the seat. In some aspects, the gasket rests on an upper portion of the at least one sidewall of the luminal container.

In some embodiments, the apparatuses disclosed herein, including those above, are configured such that at least one of the luminal container and the plug comprises a locking mechanism configured to lockingly engage the luminal container and the plug. The plug can comprise a locking fin, and the at least one sidewall of the luminal container can comprise a recess configured to receive the locking fin when the plug is in the installed position.

In some embodiments, the apparatuses disclosed herein, including those above, further comprise a basal container comprising a bottom wall and at least one sidewall extending upwardly from the bottom wall, wherein the bottom wall and the at least one sidewall define a well, and wherein the luminal container is held within the well of the basal container, the bottom wall of the basal container is spaced apart from the bottom wall of the luminal container, and a basal reservoir is defined between the bottom wall of the basal container and the bottom wall of the luminal container and/or between the at least one sidewall of the basal container and the at least one sidewall of the luminal container. Such an apparatus can further comprise a basal medium in the basal reservoir that is configured to provide oxygen to the one or more cells and/or tissue. Such an apparatus can further comprise a stirring device (e.g., a magnetic stir bar) configured to stir the basal medium in the basal reservoir. In some aspects, the bottom wall of the luminal container can comprise a porous membrane. The bottom wall of the luminal container can comprise an oxygen permeable membrane.

In some aspects, the basal container can comprise a plurality of wells or a shared well, the apparatus can comprise a plurality of the luminal containers, and each of the luminal containers can be held in one of the basal wells or basal shared well. The luminal container can be a first luminal container, the basal container can be a first basal container, the cover can be a first cover, the luminal reservoir can be a first luminal reservoir, and the basal reservoir can be a first basal reservoir, where the apparatus can further comprise a second luminal container and a second cover that define a second luminal reservoir with the second cover in an installed position, a second basal container with the second luminal container received therein to define a second basal reservoir, a first tissue and/or one or more cells is received in the first basal reservoir, a second tissue and/or one or more cells is received in the second basal reservoir, the first and second luminal reservoirs are fluidly connected to one another, and the first and second basal reservoirs are fluidly connected to one another. Likewise, in some aspects such an apparatus can further comprise a third luminal container and a third cover that define a third luminal reservoir with the third cover in an installed position, the apparatus can further comprise a third basal container with the third luminal container received therein to define a third basal reservoir, a third tissue and/or one or more cells can be received in the third basal reservoir, the first, second, and third luminal reservoirs can be fluidly connected to one another, and the first, second, and third basal reservoirs can be fluidly connected to one another.

In some embodiments, the apparatuses disclosed herein, including those above, are configured such that the bottom wall of the luminal container comprises an oxygen impermeable or low permeability member. In some aspects, the cover can comprise a lid comprising a top wall and at least one sidewall extending downwardly from the top wall and that engages the at least one sidewall of the luminal container in the installed position. In some aspects, each of an outer surface of the at least one sidewall of the luminal container and an inner surface of the at least one sidewall of the lid comprises threads, and wherein the lid is threadingly engaged with the luminal container in the installed position. In some aspects, the bottom wall of the luminal container can comprise an oxygen permeable material.

In some embodiments, the apparatuses disclosed herein, including those above, are configured such that the cell support structure comprises a layer of an extracellular matrix protein (e.g., collagen, fibronectin, laminin, Matrigel and/or a synthetic polymer (e.g., poly-l-lysine) or a scaffold comprising an extracellular matrix (e.g., a collagen scaffold). The cell support structure can comprise two or three dimensional micropatterns or microstructures.

Also provided herein are methods of making a live cell and/or tissue construct under hypoxic conditions. Such methods can comprise using and/or providing an apparatus as disclosed herein, including hereinabove, and culturing the one or more cells and/or tissue positioned on the cell support structure, thereby producing hypoxic conditions under which the cells are grown, the hypoxic conditions are generated by the one or more cells and/or tissue on the cell support structure in the luminal container with the cover in the installed position.

Also provided herein are methods of culturing one or more cells and/or tissue under hypoxic conditions, the method comprising. Such methods can comprise using and/or providing an apparatus as disclosed herein, including hereinabove, and culturing the one or more cells and/or tissue positioned on the cell support structure, thereby producing hypoxic conditions under which the cells are grown, wherein the hypoxic conditions are generated by the one or more cells and/or tissue on the cell support structure in the luminal container with the cover in the installed position.

Also provided herein are methods of generating a gas gradient across a cell support structure. Such methods can comprise using and/or providing an apparatus as disclosed herein, including hereinabove, and culturing the one or more cells and/or tissue positioned on the cell support structure, and generating a gas gradient (higher to lower or lower to higher) across the cell support structure.

These and other objects are achieved in whole or in part by the presently disclosed subject matter. Further, objects of the presently disclosed subject matter having been stated above, other objects and advantages of the presently disclosed subject matter will become apparent to those skilled in the art after a study of the following description, drawings and examples.

BRIEF DESCRIPTION OF THE DRAWINGS

The presently disclosed subject matter can be better understood by referring to the following figures. The components in the figures are not necessarily to scale, emphasis instead being placed upon illustrating the principles of the presently disclosed subject matter (often schematically). In the figures, like reference numerals designate corresponding parts throughout the different views. A further understanding of the presently disclosed subject matter can be obtained by reference to an embodiment set forth in the illustrations of the accompanying drawings. Although the illustrated embodiment is merely exemplary of systems for carrying out the presently disclosed subject matter, both the organization and method of operation of the presently disclosed subject matter, in general, together with further objectives and advantages thereof, can be more easily understood by reference to the drawings and the following description. The drawings are not intended to limit the scope of this presently disclosed subject matter, which is set forth with particularity in the claims as appended or as subsequently amended, but merely to clarify and exemplify the presently disclosed subject matter.

Like numbers refer to like elements throughout. In the figures, the thickness of certain lines, layers, components, elements or features can be exaggerated for clarity. Where used, broken lines illustrate optional features or operations unless specified otherwise.

For a more complete understanding of the presently disclosed subject matter, reference is now made to the below drawings.

Figure 1A:
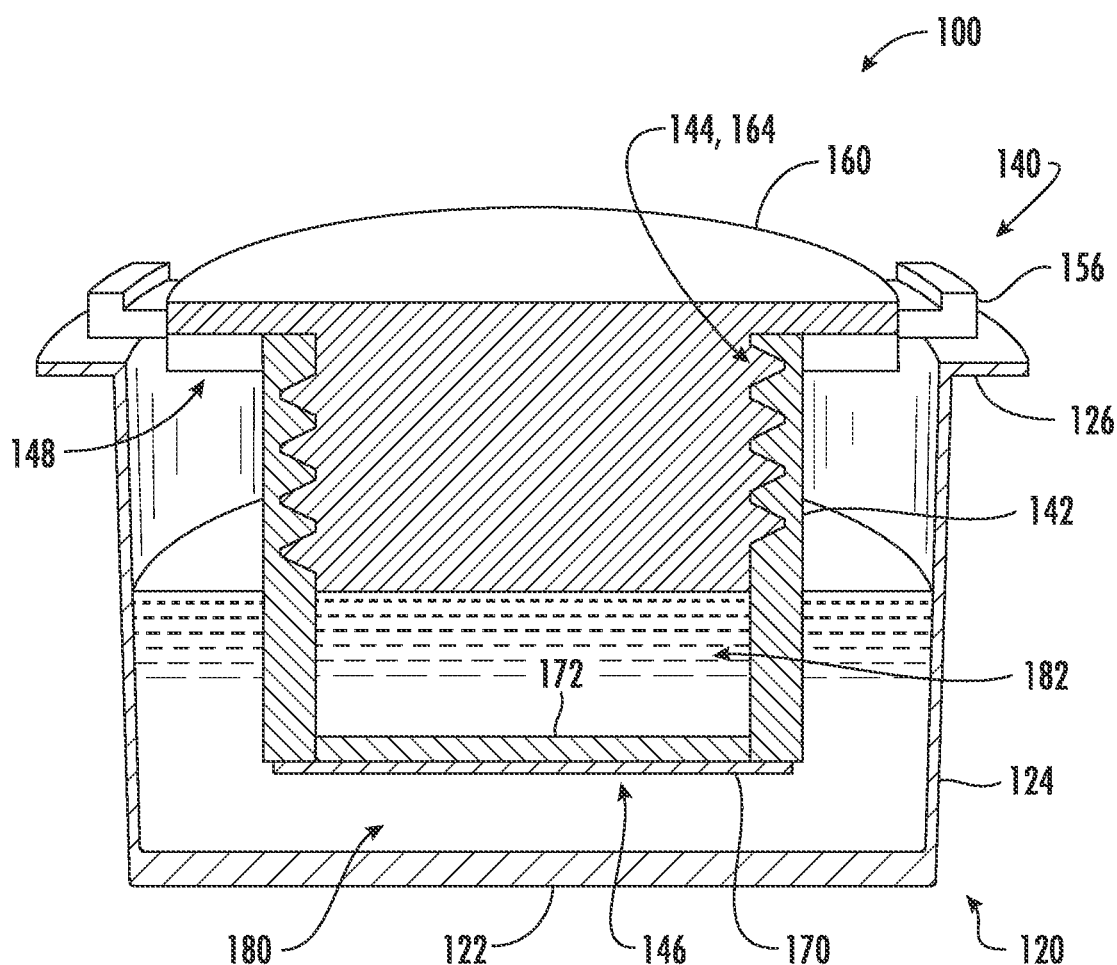

FIG. 1A is a cross-sectional view of an apparatus according to a first example embodiment disclosed herein.

Figure 1B:
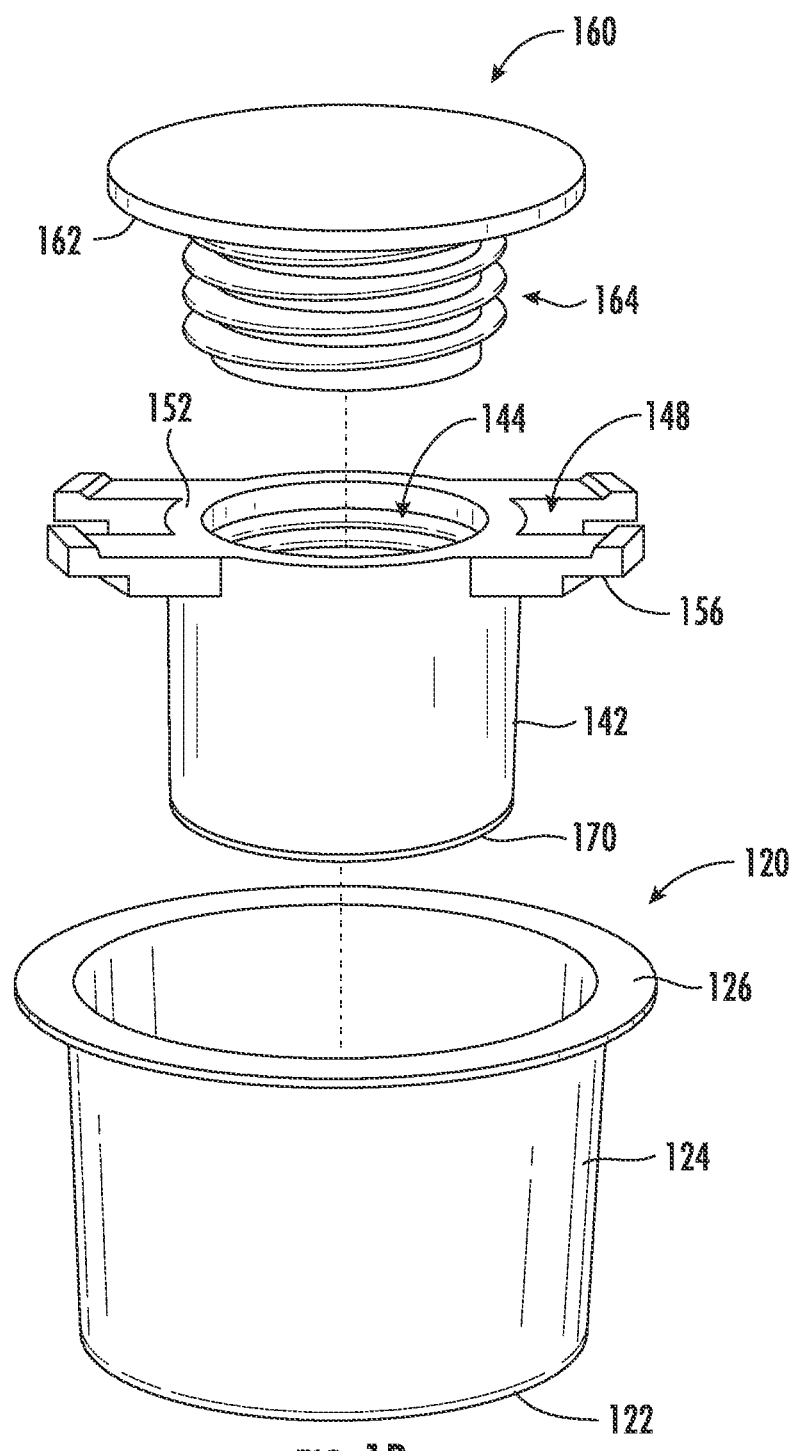

FIG. 1B is an exploded view of the apparatus according to FIG. 1A.

Figure 1C:
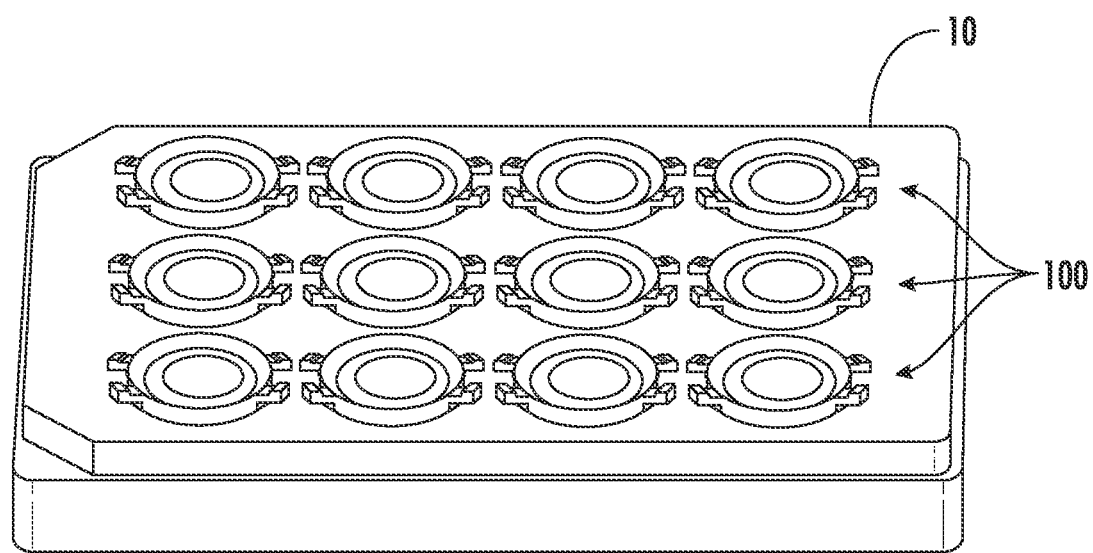

FIG. 1C is an example illustration of a plurality of apparatuses according to FIG. 1A, which are arranged in an array defined by, for example, a microtiter plate.

FIG. 1D is a cross-sectional view of an apparatus according to a second example embodiment disclosed herein.

Figure 1E:
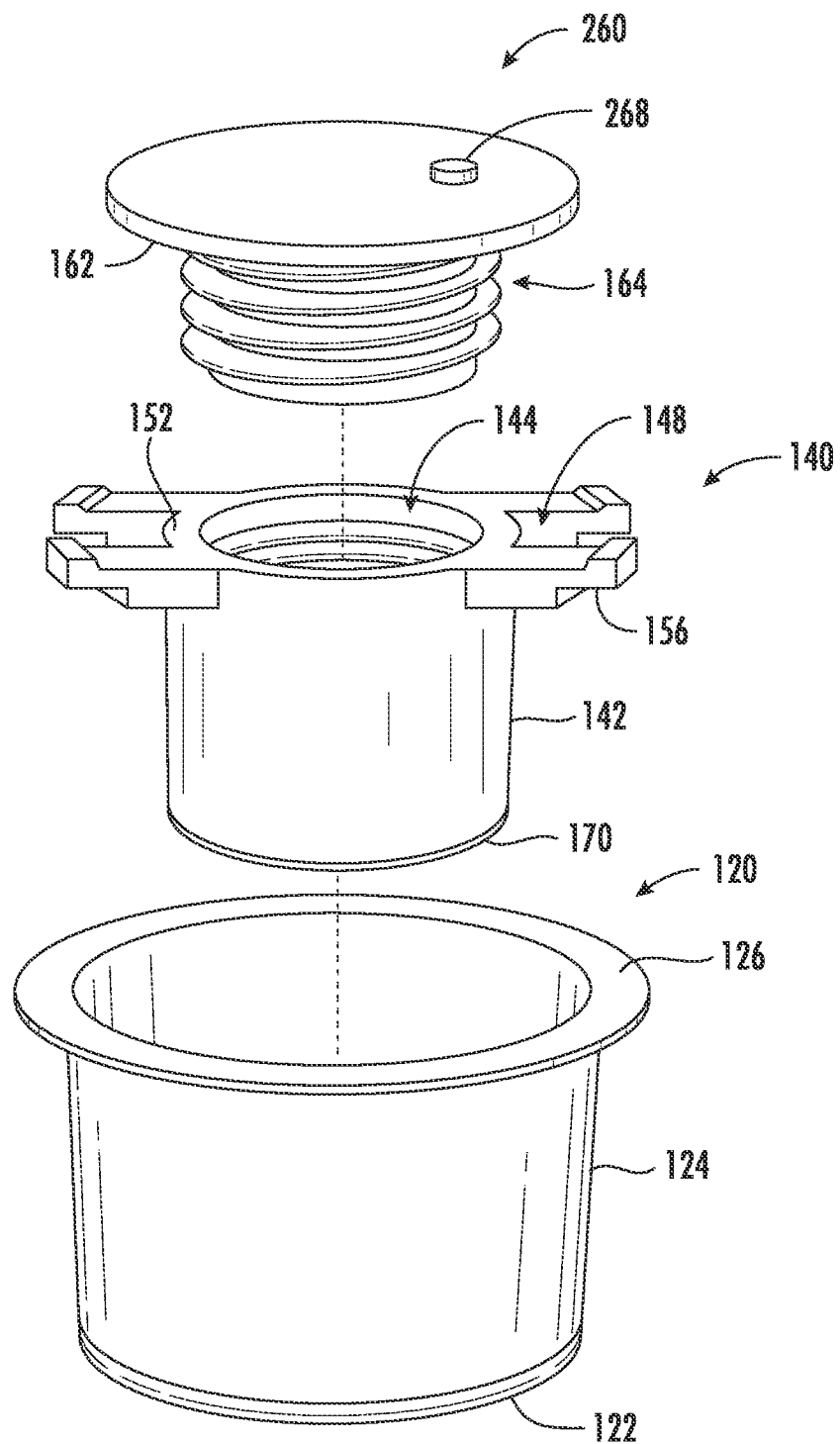

FIG. 1E is an exploded view of the apparatus according to FIG. 1D.

Figure 1F:
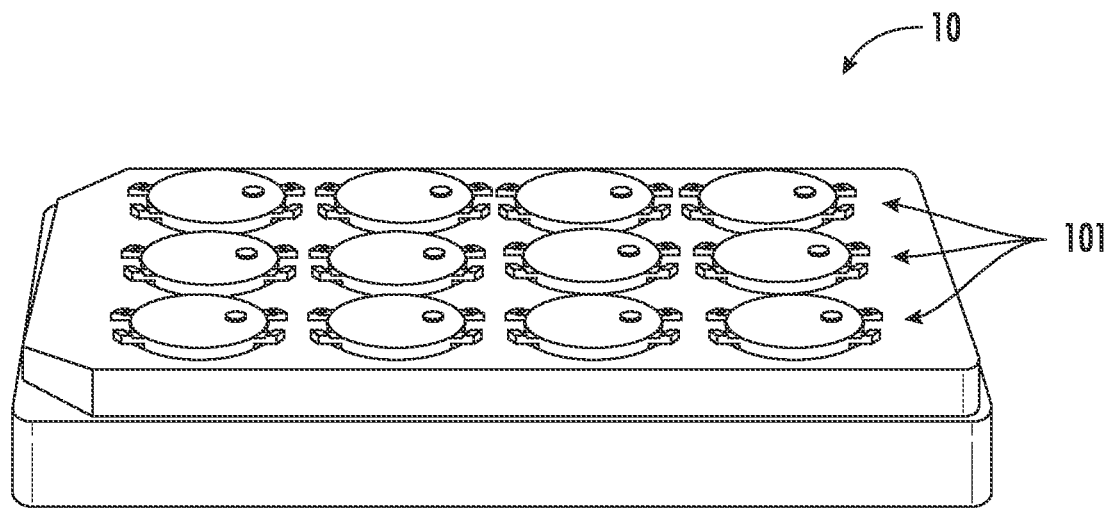

FIG. 1F is an example illustration of a plurality of apparatuses according to FIG. 1D, which are arranged in an array defined by, for example, a microtiter plate.

Figure 1G:
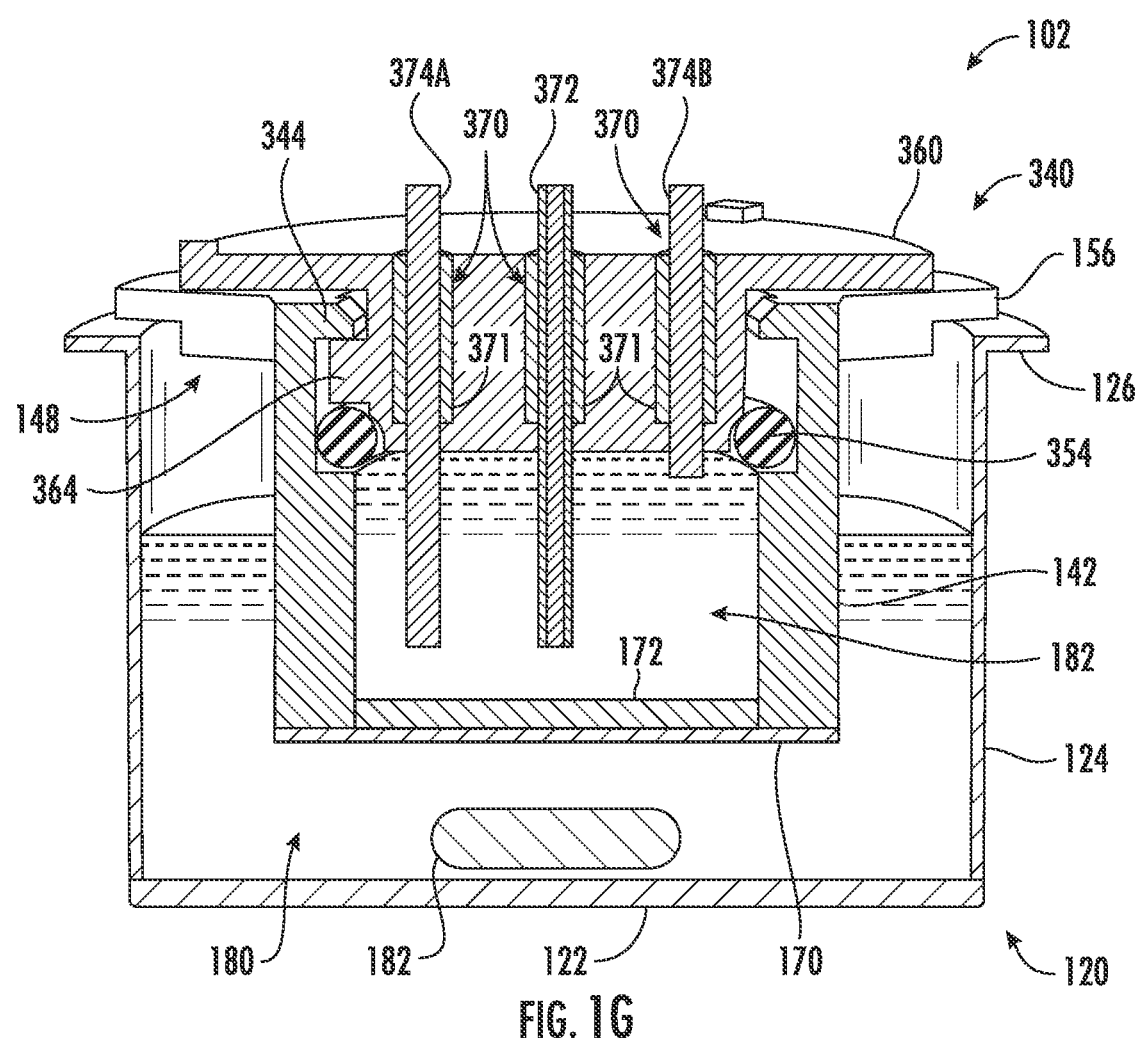

FIG. 1G is a cross-sectional view of an apparatus according to a third example embodiment disclosed herein.

Figure 1H:
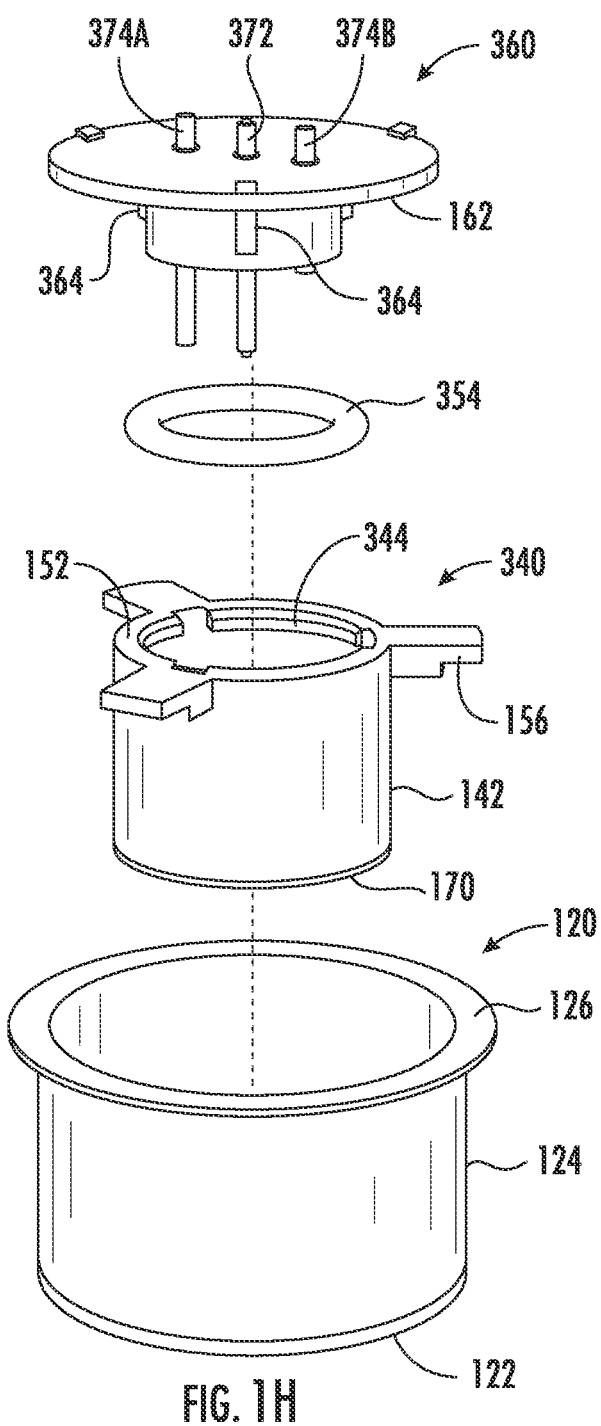

FIG. 1H is an exploded view of the apparatus according to FIG. 1G.

Figure 1J:
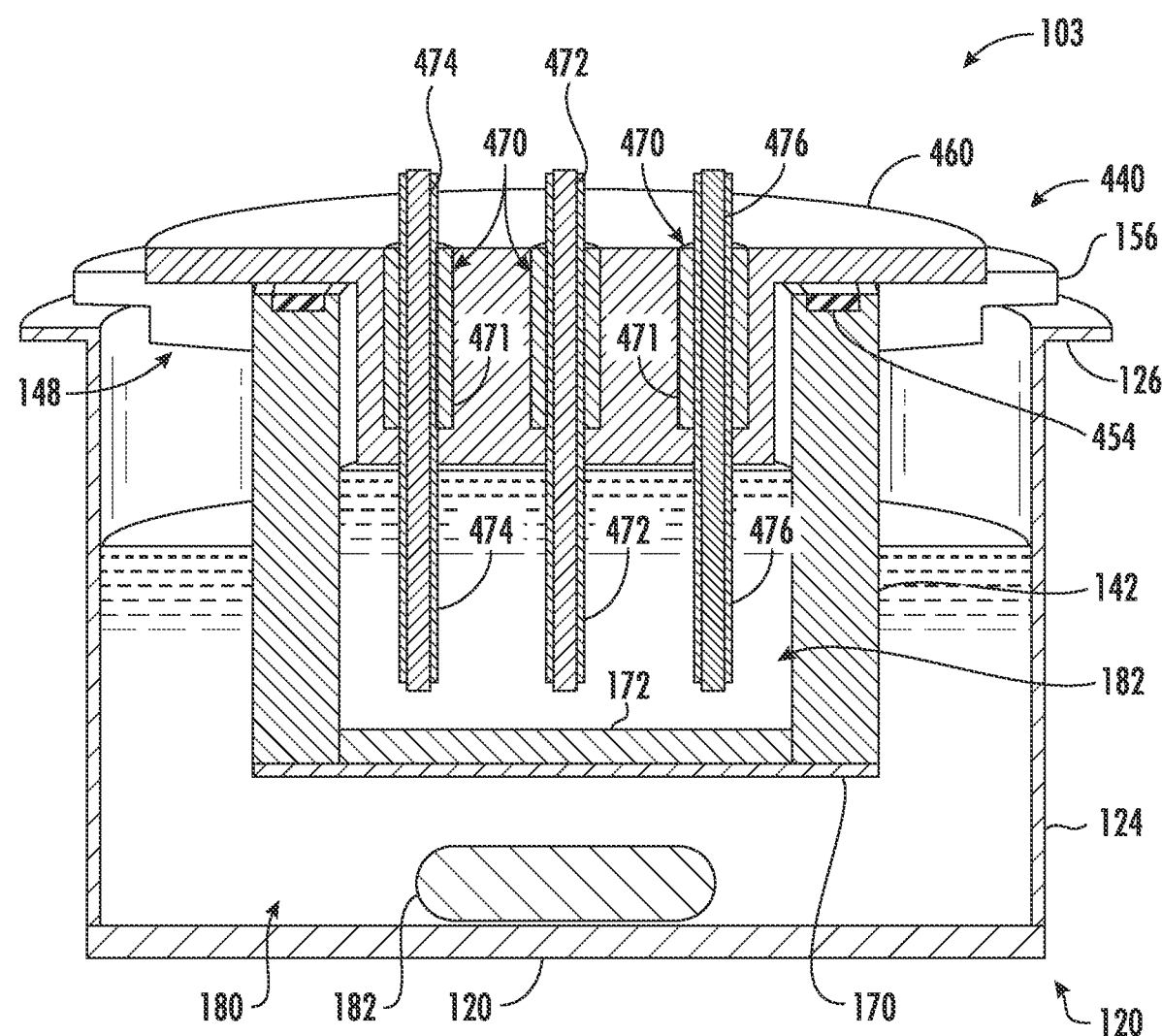

FIG. 1J is a cross-sectional view of an apparatus according to a fourth example embodiment disclosed herein.

Figure 1K:
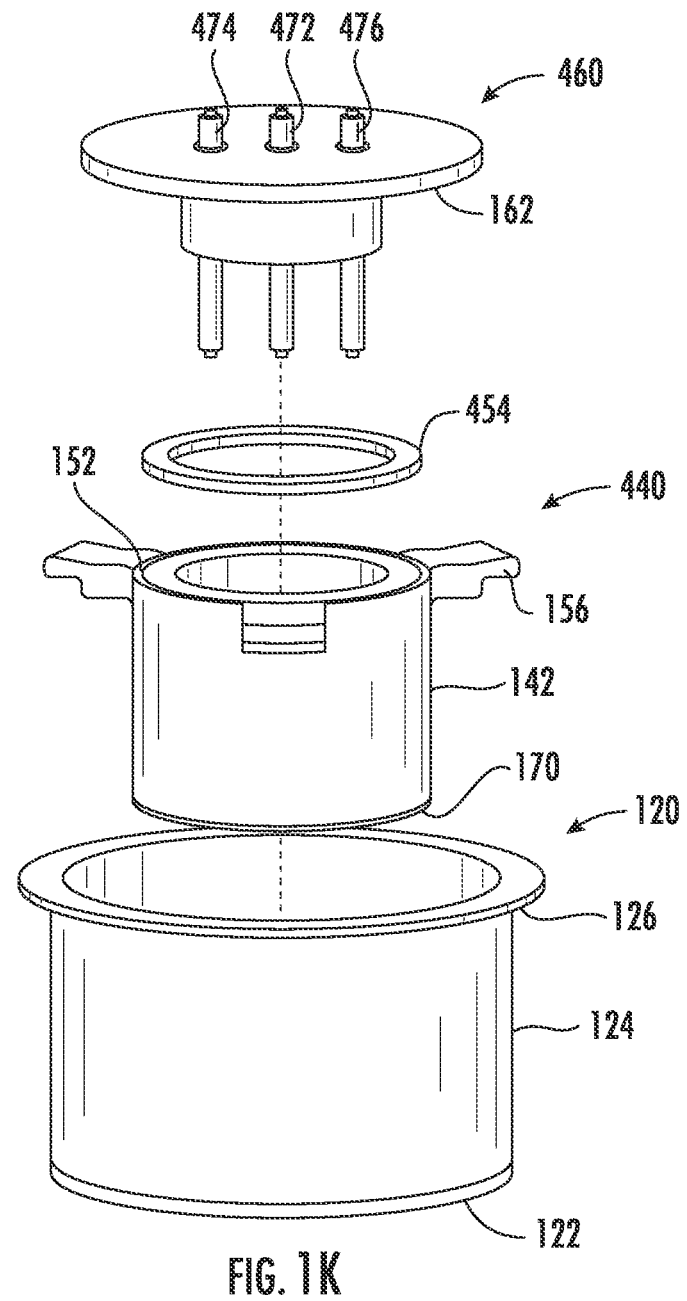

FIG. 1K is an exploded view of the apparatus according to FIG. 1J.

Figure 2A:
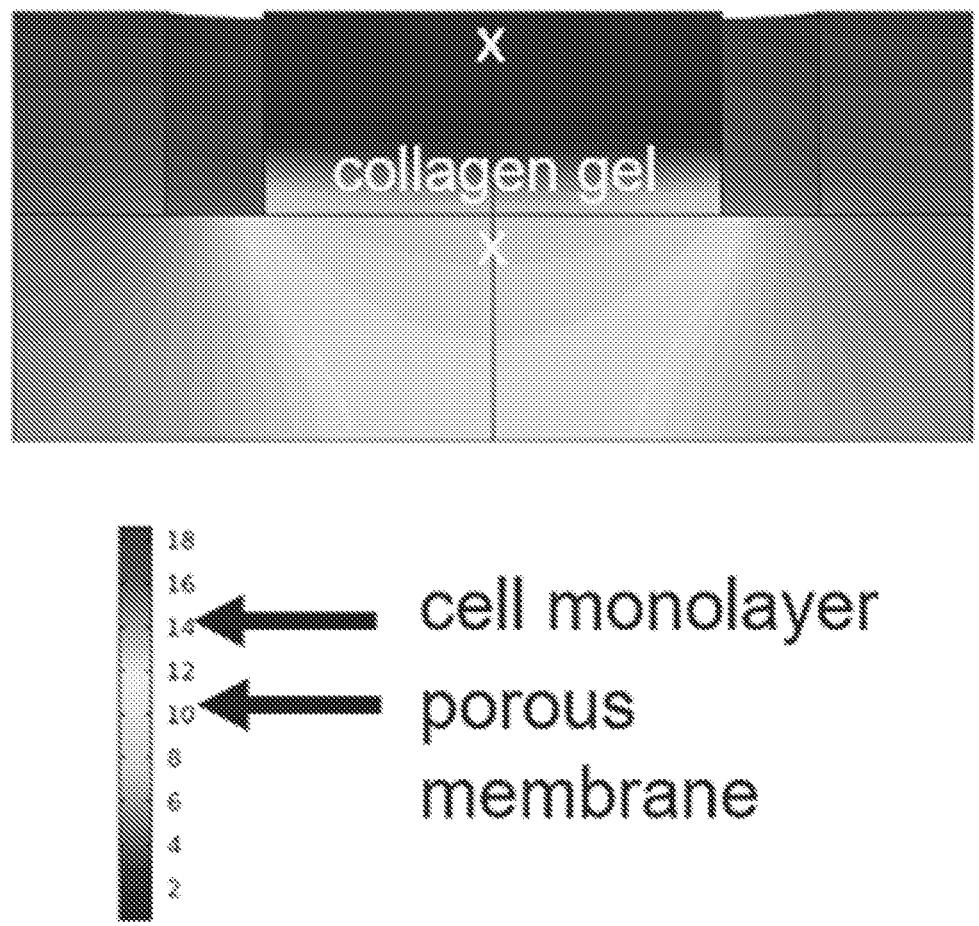
Figure 2B:
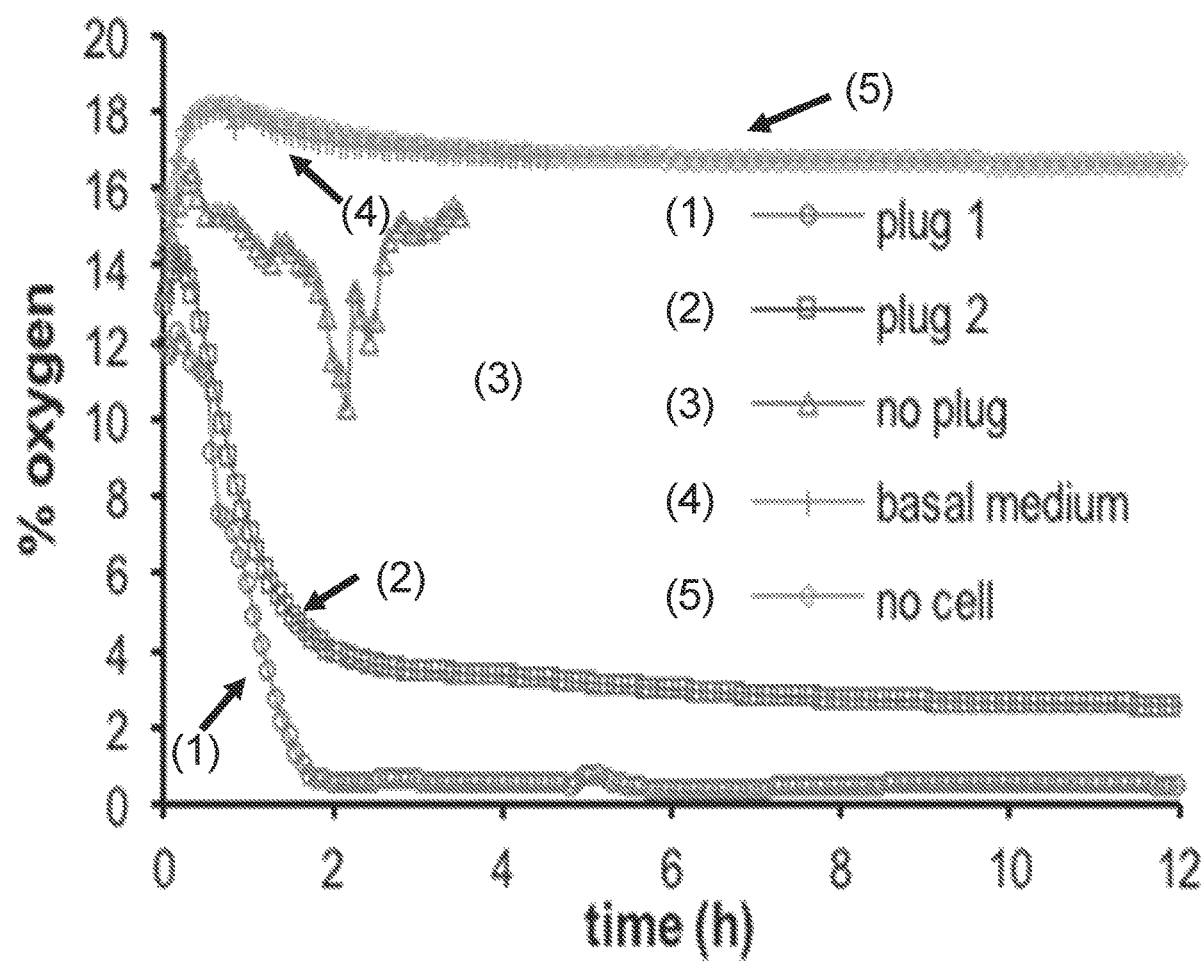

FIG. 2A illustrates computational results of oxygen saturation in a device or system as disclosed herein. FIG. 2B is a plot of data that illustrates the oxygen saturation level of the luminal media as measured with and without a human colon cell monolayer and with and without a plug. Plug 1 was 20 mm and cured at 95° C., and Plug 2 was 15 mm and cured at 70° C.

Figure 3A:
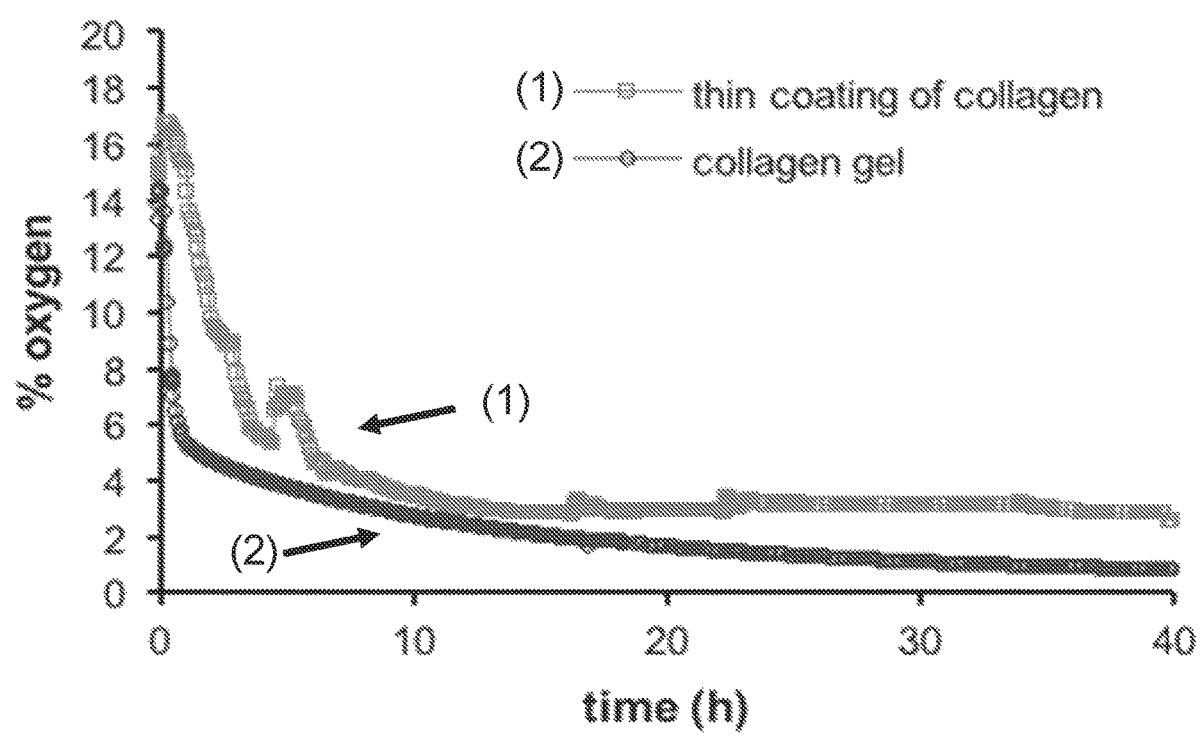
Figure 3B:
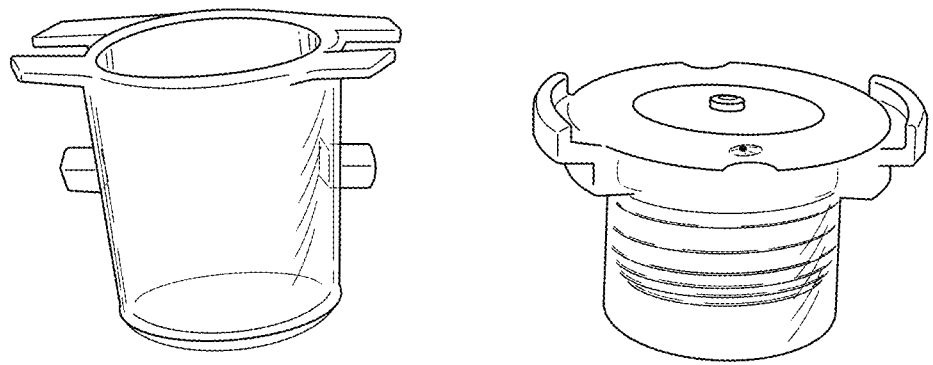
Figure 3C:
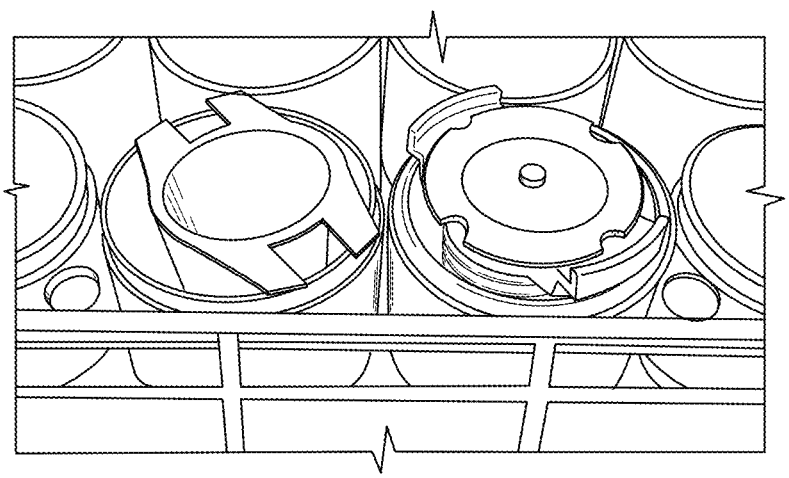
Figure 3D:
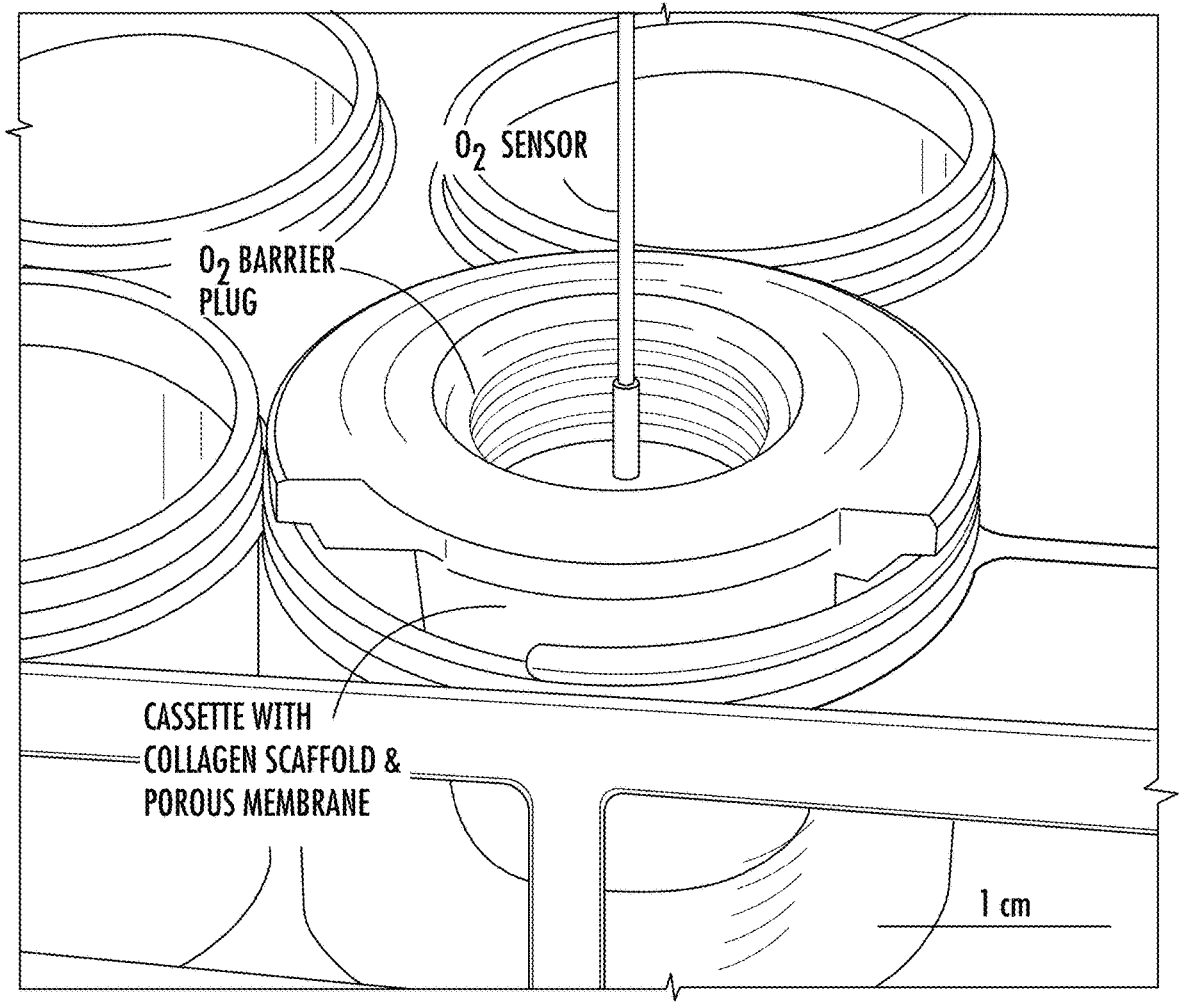
Figure 3E:
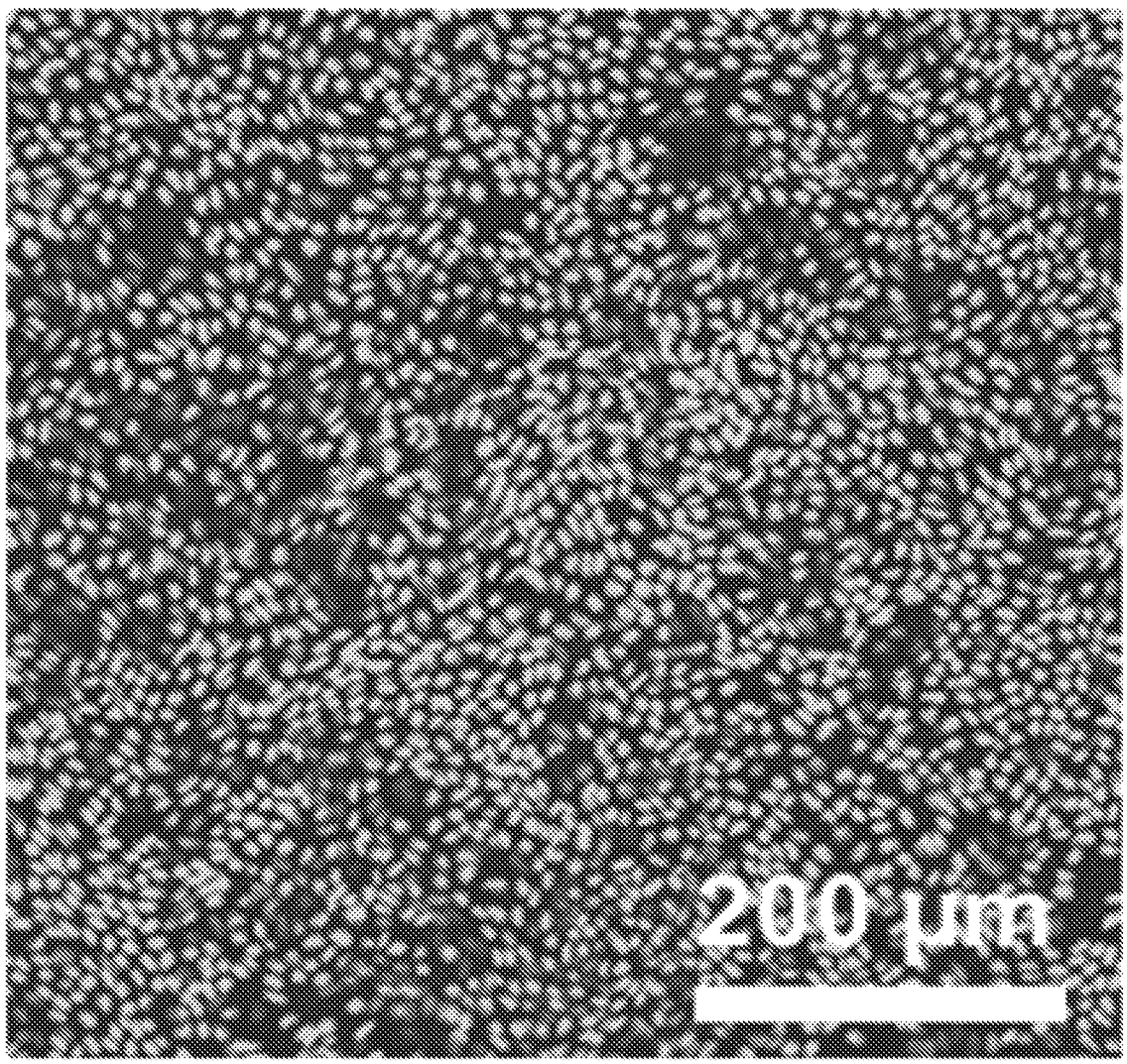
Figure 3F:
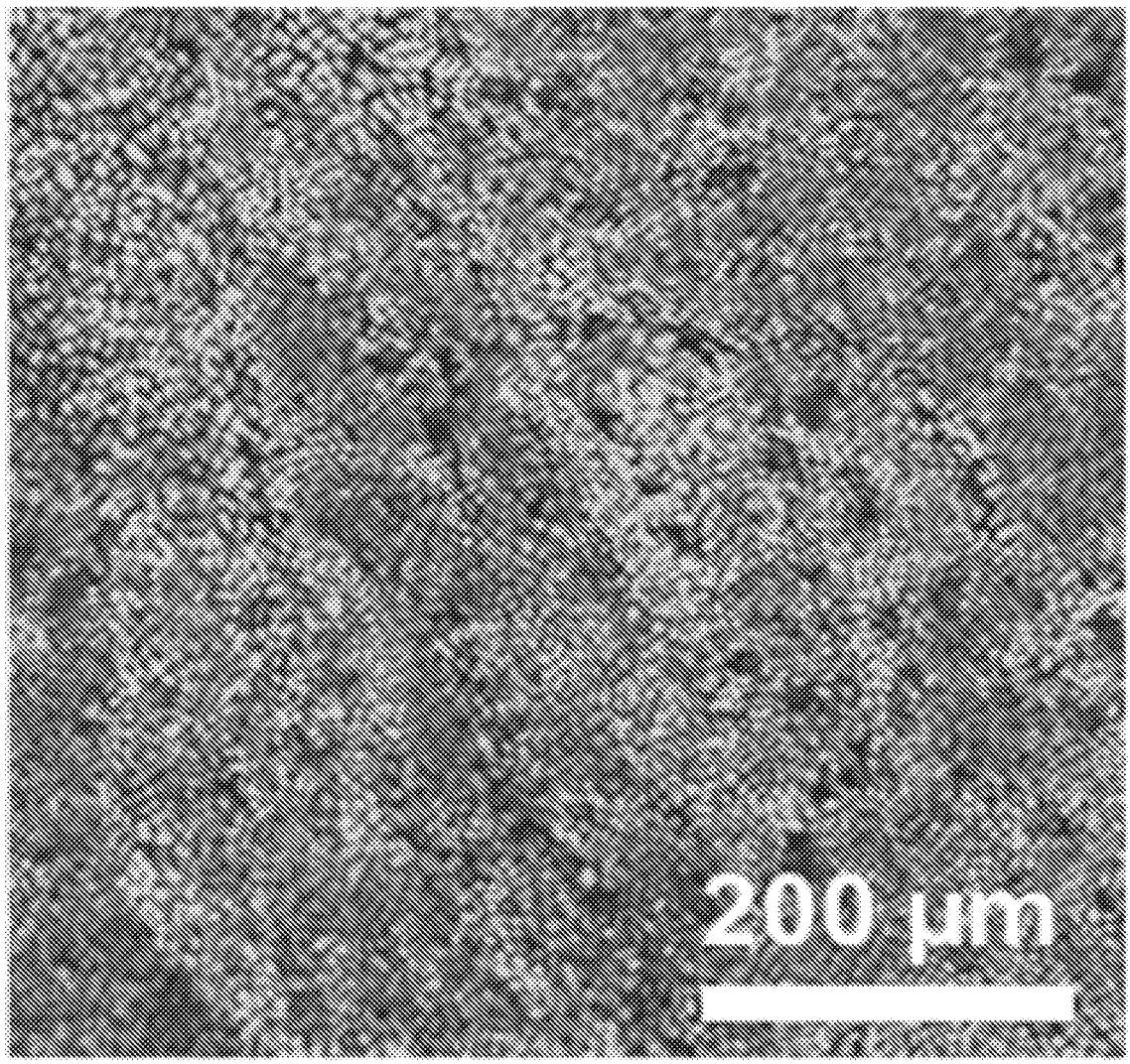

FIG. 3A is a plot of data illustrating oxygen saturation of the medium in the luminal side after sealing the insert with a plug. FIGS. 3B-3D are photographs of example cell chamber and devices as disclosed herein, with the plug in experimental setup. FIGS. 3E and 3F are images showing nuclear staining (Hoechst 33342) on the cells grown on thin collagen coating (FIG. 3E) and collagen gel (FIG. 3F) scaffold.

Figure 4A:
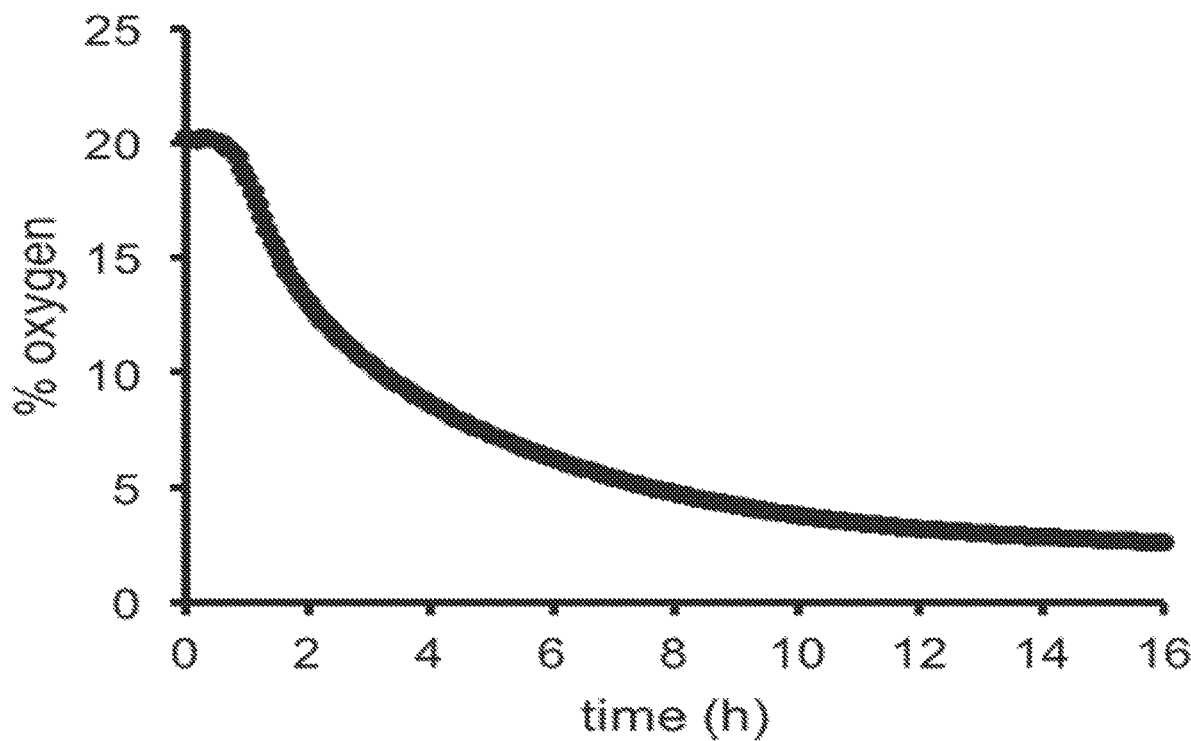
Figure 4B:
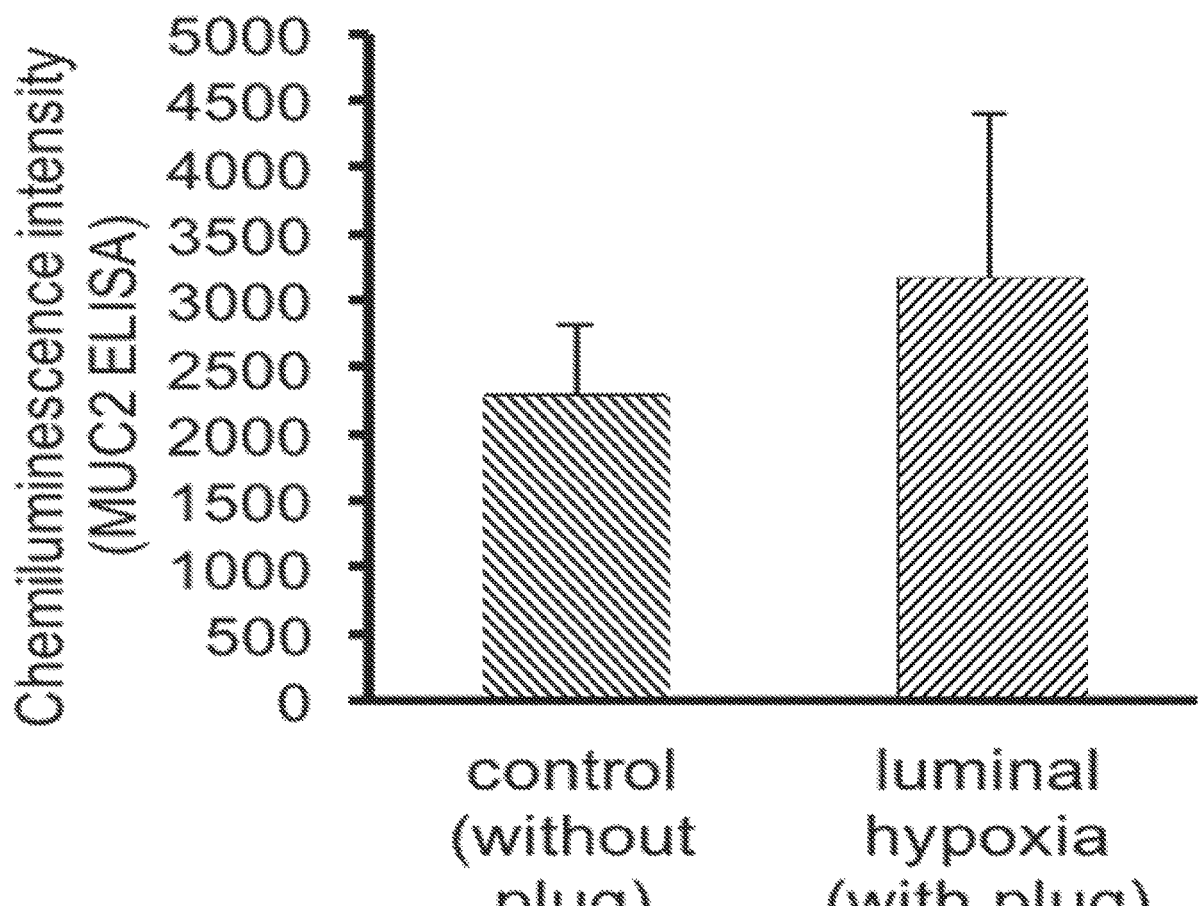

FIG. 4A shows oxygen saturation of the medium in the luminal side after sealing the insert with a plug in the presence of mouse primary colon epithelial cells, with FIG. 4B showing secretion of mucin-2 into luminal media in aerobic control without a plug and luminal hypoxia induced by a plug is a top view of the crypt-shaped scaffold array.

Figure 5A:
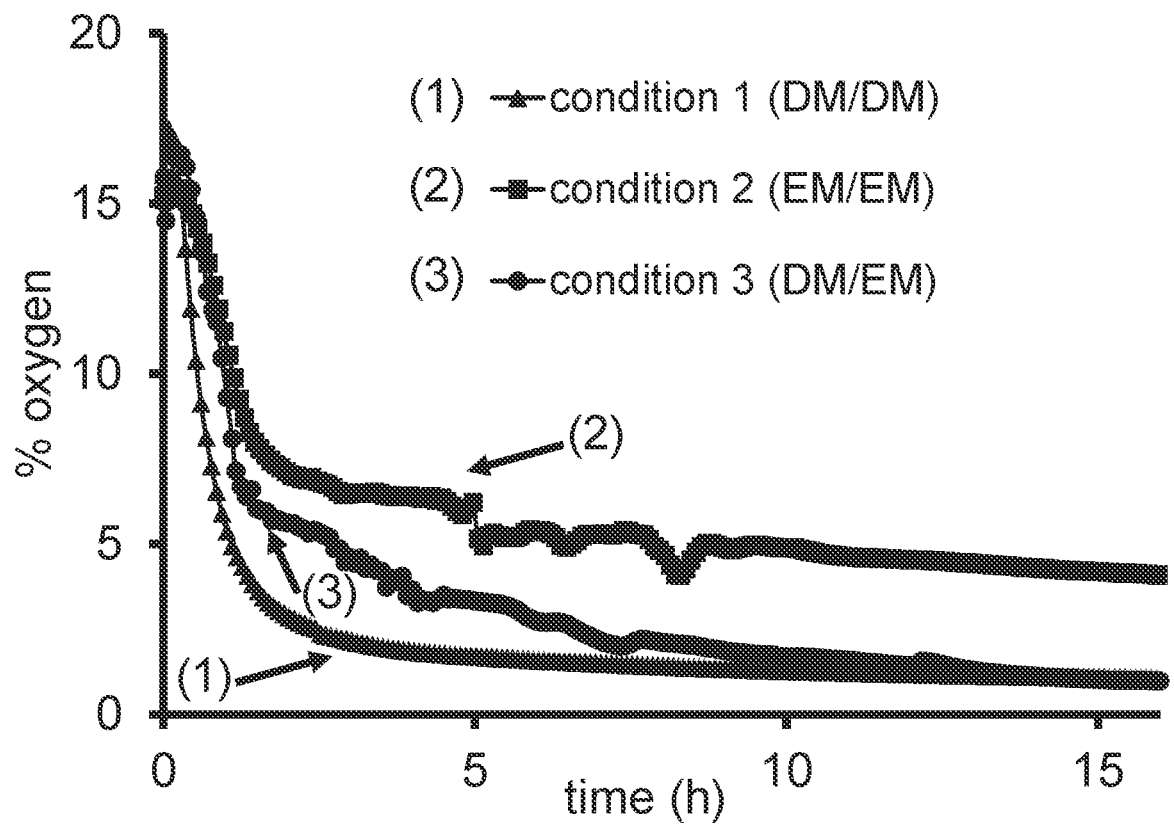
Figure 5B:
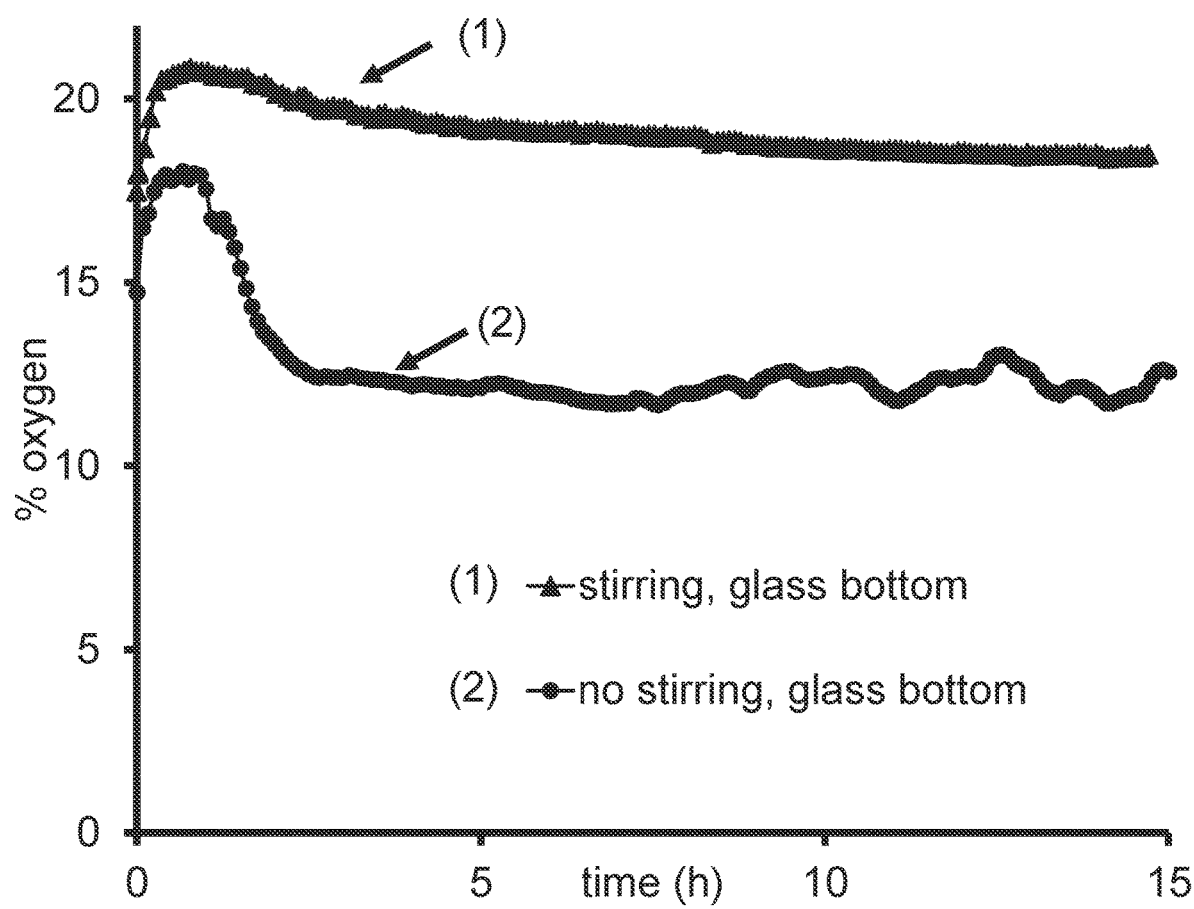

FIG. 5A illustrates oxygen saturation of the luminal media in the presence of human primary colon epithelial cells exposed in different luminal and basal media after sealing the insert with a plug, while FIG. 5B shows basal oxygen saturation in the presence of human primary colon epithelial cells exposed to differentiation media (DM/DM condition in FIG. 5A on both luminal and basal side) with and without mechanical stirring by magnetic stir bar on a stir plate.

Figure 6A:
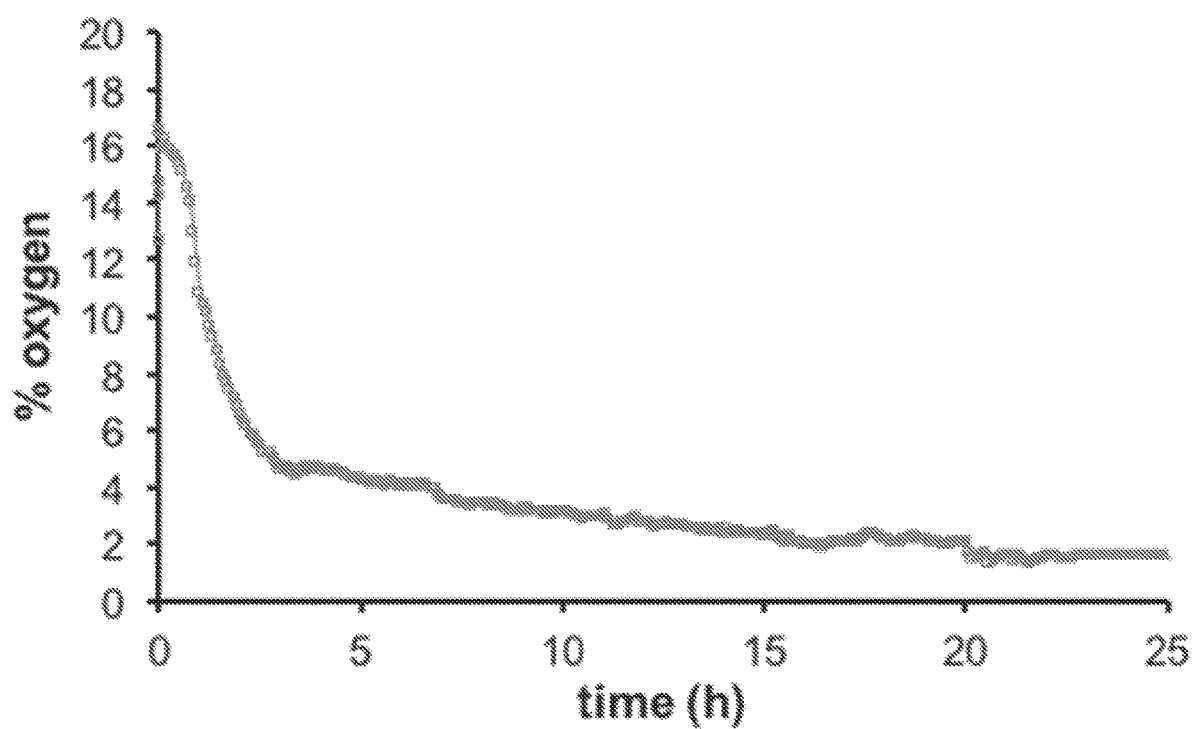
Figure 6B:
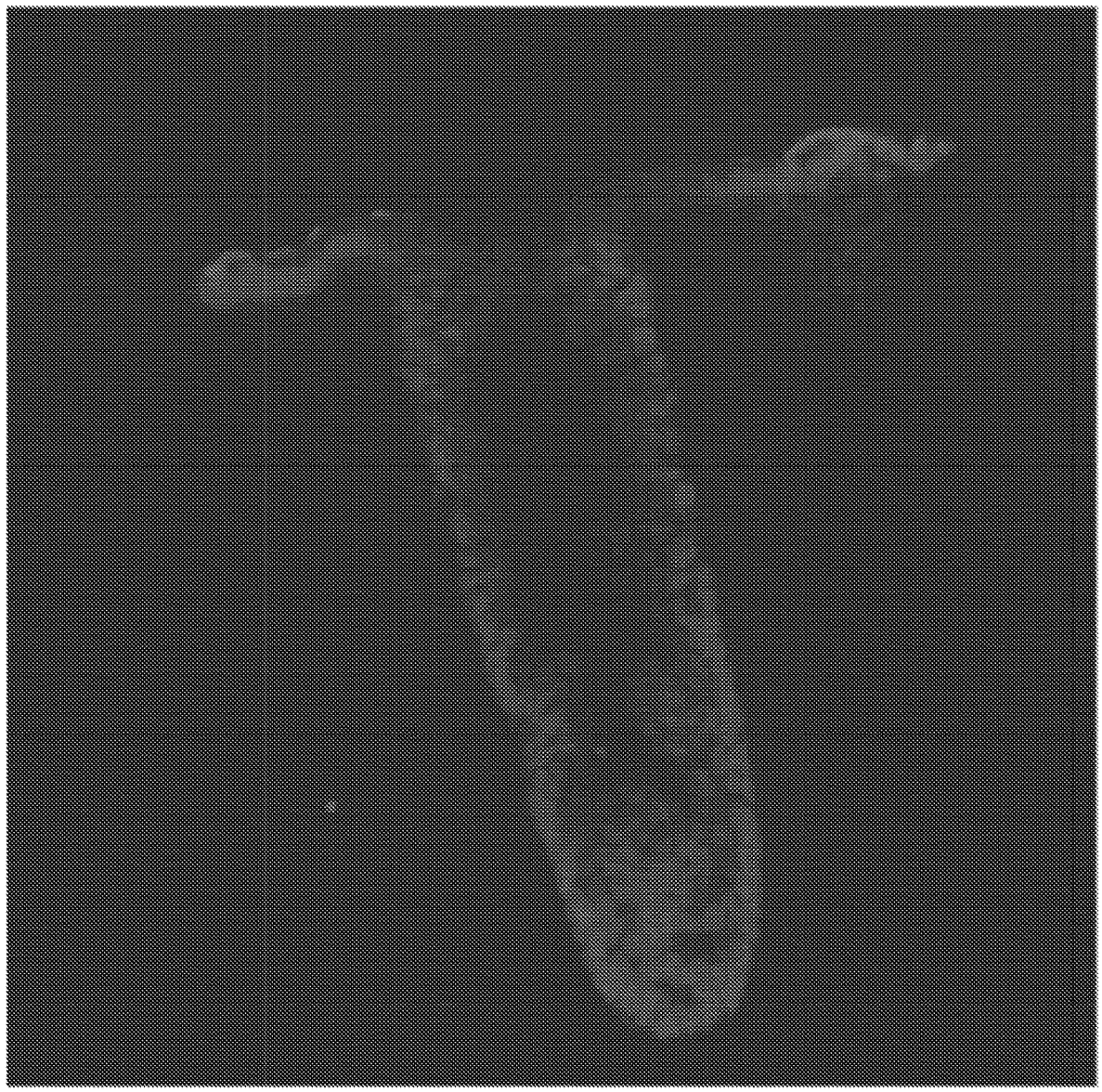

FIG. 6A shows the oxygen level in the luminal medium over time measured with a needle type oxygen probe. FIG. 6B illustrates pimonidazole staining and nuclei staining of in vitro crypt epithelium cultured using a device/apparatus as disclosed herein. The luminal side shows bright fluorescence signal marking the location of pimonidazole binding. The crypt was 430 microns long and approximately 125 microns wide.

Figure 7:
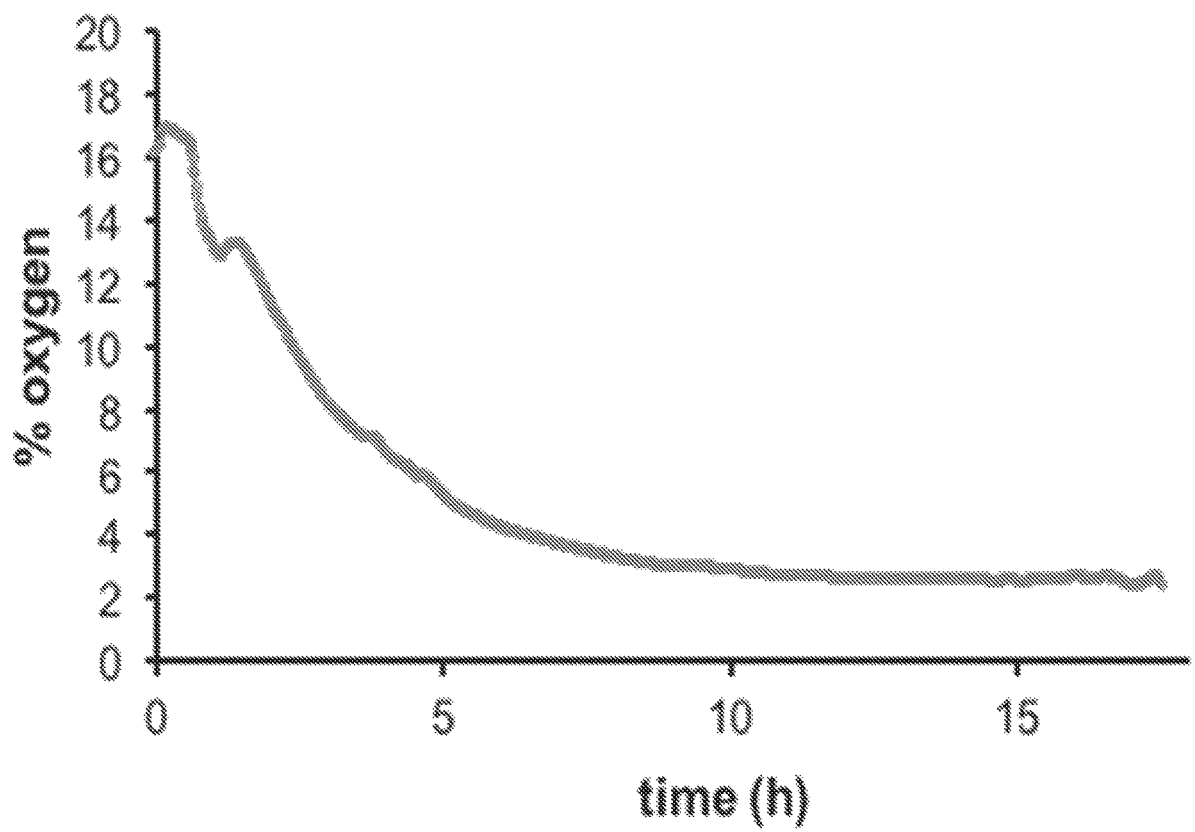

FIG. 7 shows oxygen saturation of a medium as measured over time with a needle type oxygen probe in a device/apparatus as disclosed herein.

Figure 8A:
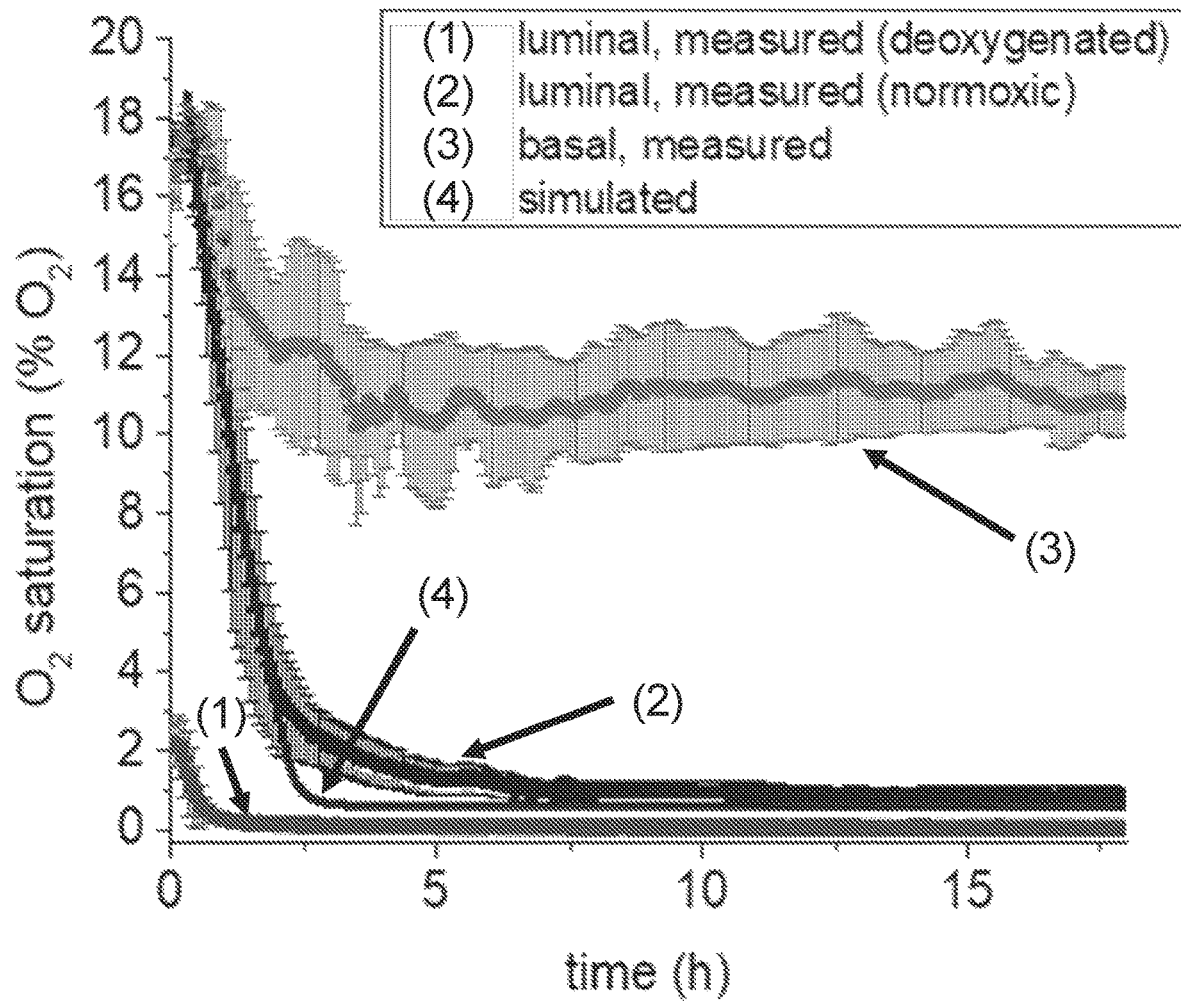
Figure 8B:
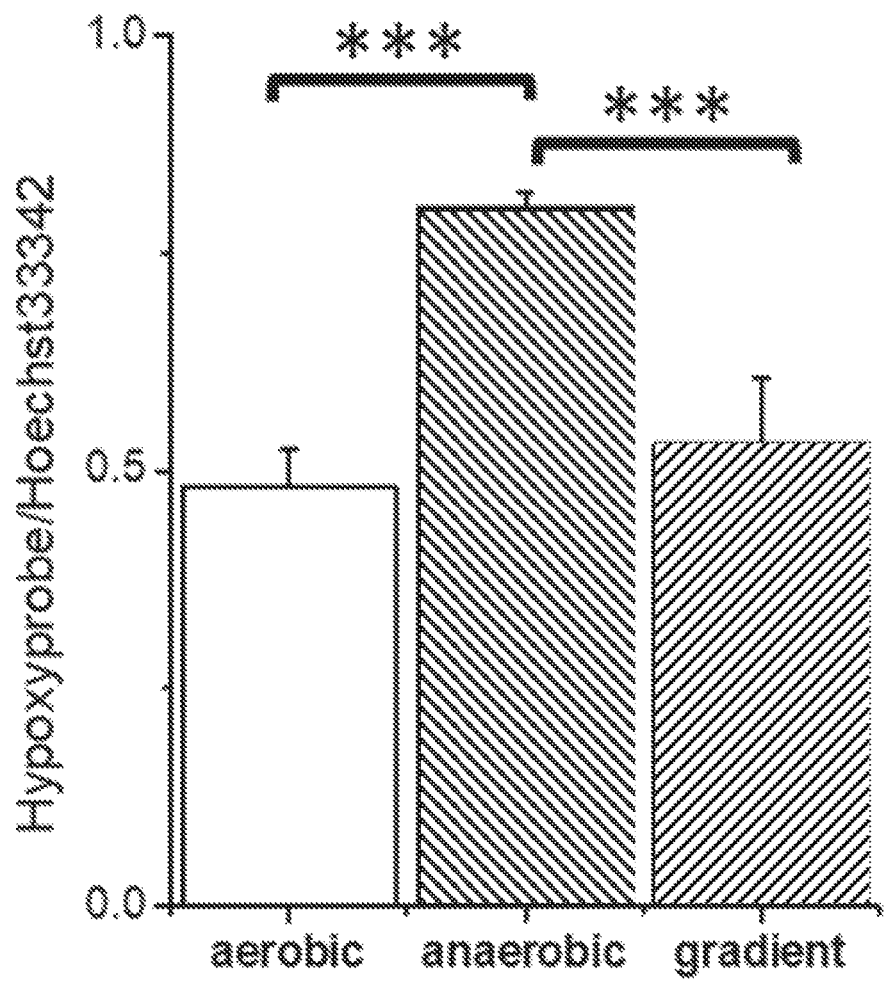
Figure 8C:
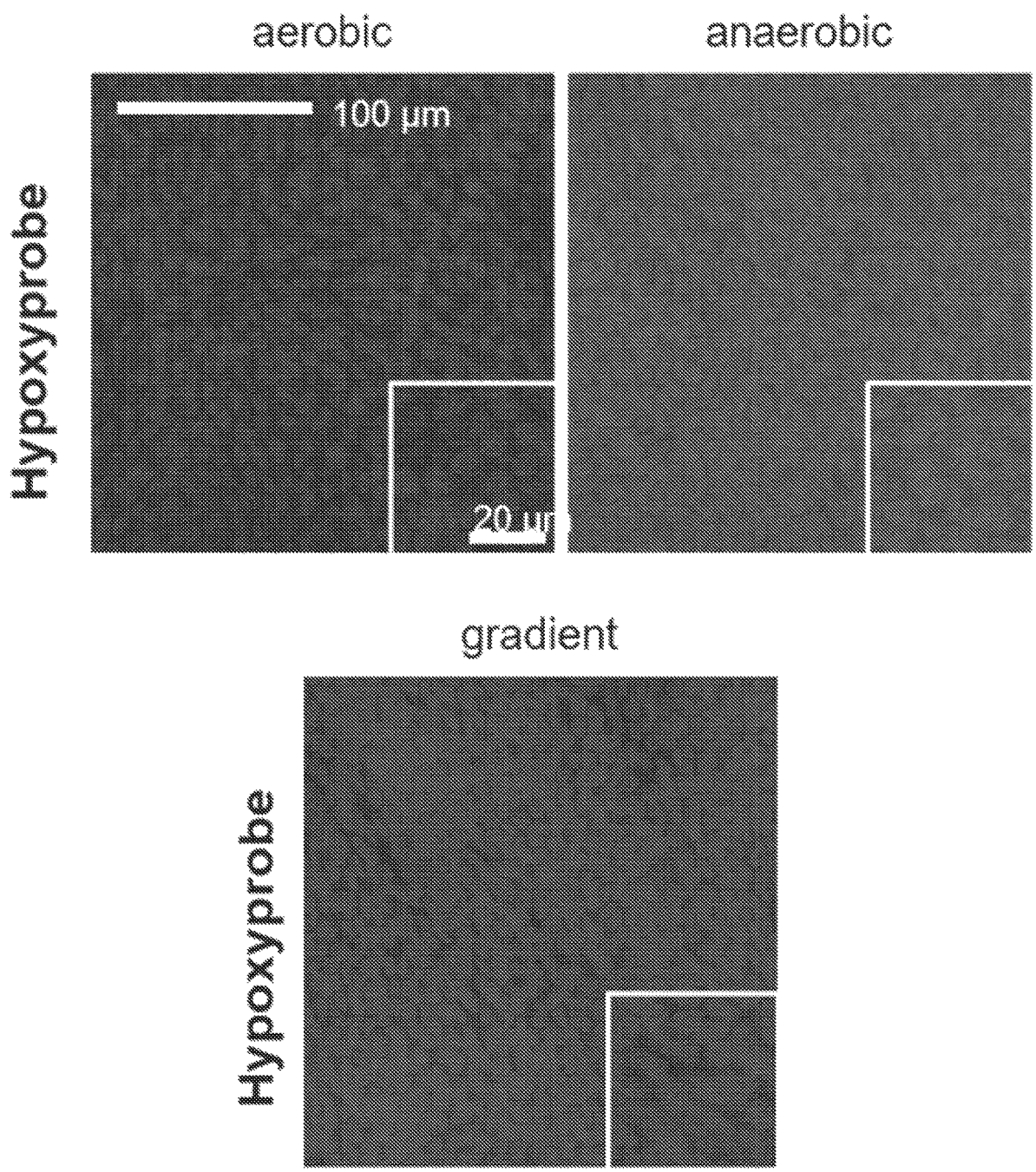

FIG. 8A shows the luminal and basal oxygen profiles over time experimentally measured in a device/apparatus as disclosed herein. Human colon epithelial cells were grown for 10 days as described herein and then oxygen level of the luminal (1 mm below the bottom of the plug) and basal media (just below the porous membrane of the cell chamber) was measured. The simulated luminal oxygen level was included for comparison (n=3 for all measurements). FIG. 8B shows the data comparing Hypoxyprobe retention detected by immunofluorescence (n=3;*and**indicate p<0.05 and p<0.01). FIG. 8C shows representative images of Hypoxyprobe stained human colonic epithelial cells in aerobic, anaerobic and under oxygen gradient.

Figure 9A:
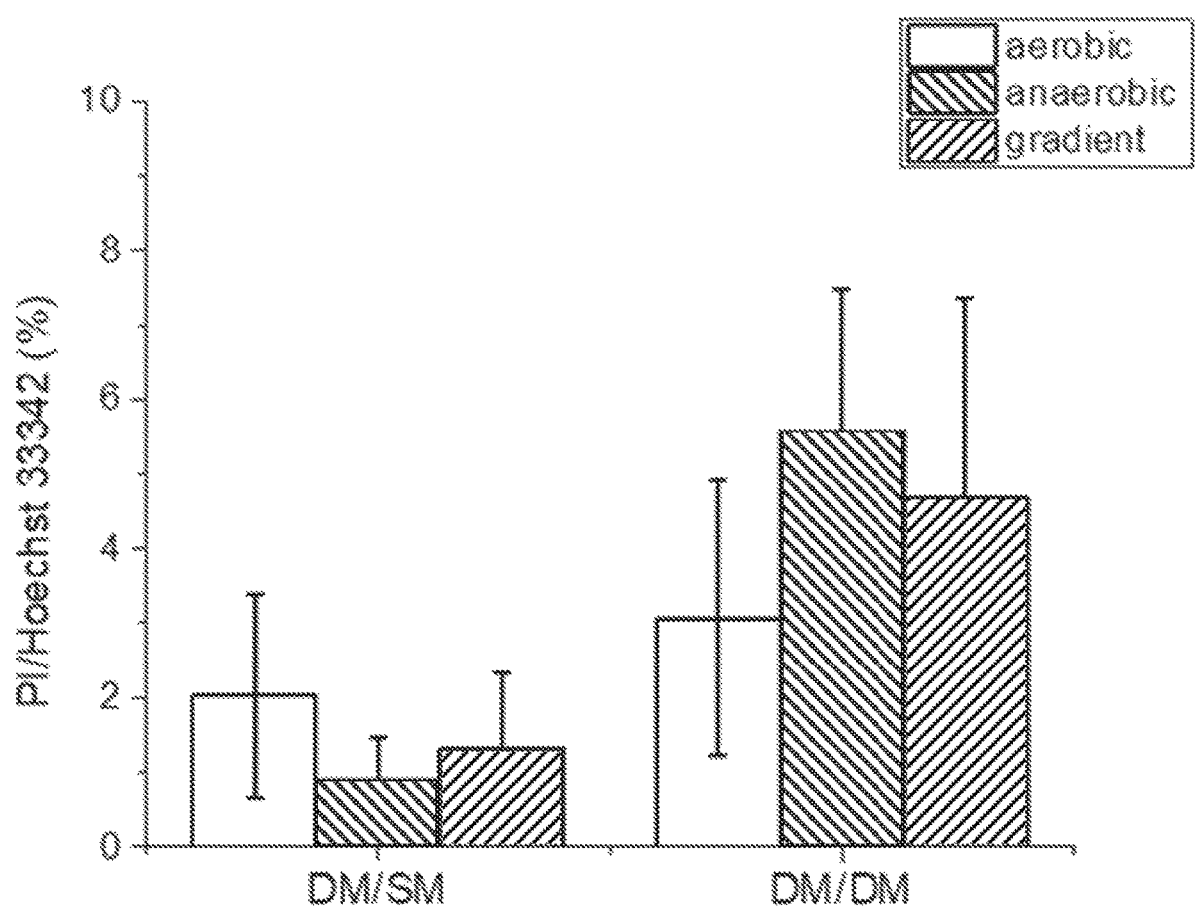
Figure 9B:
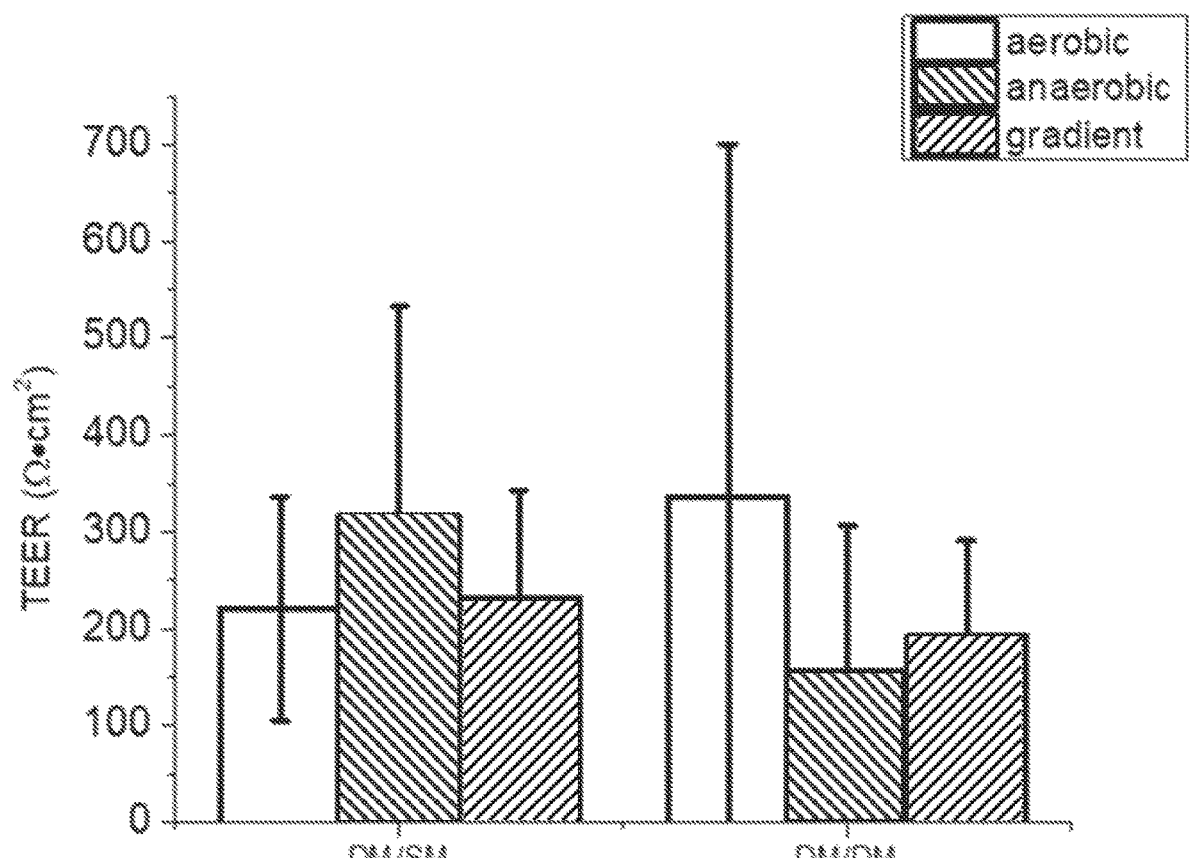
Figure 9C:
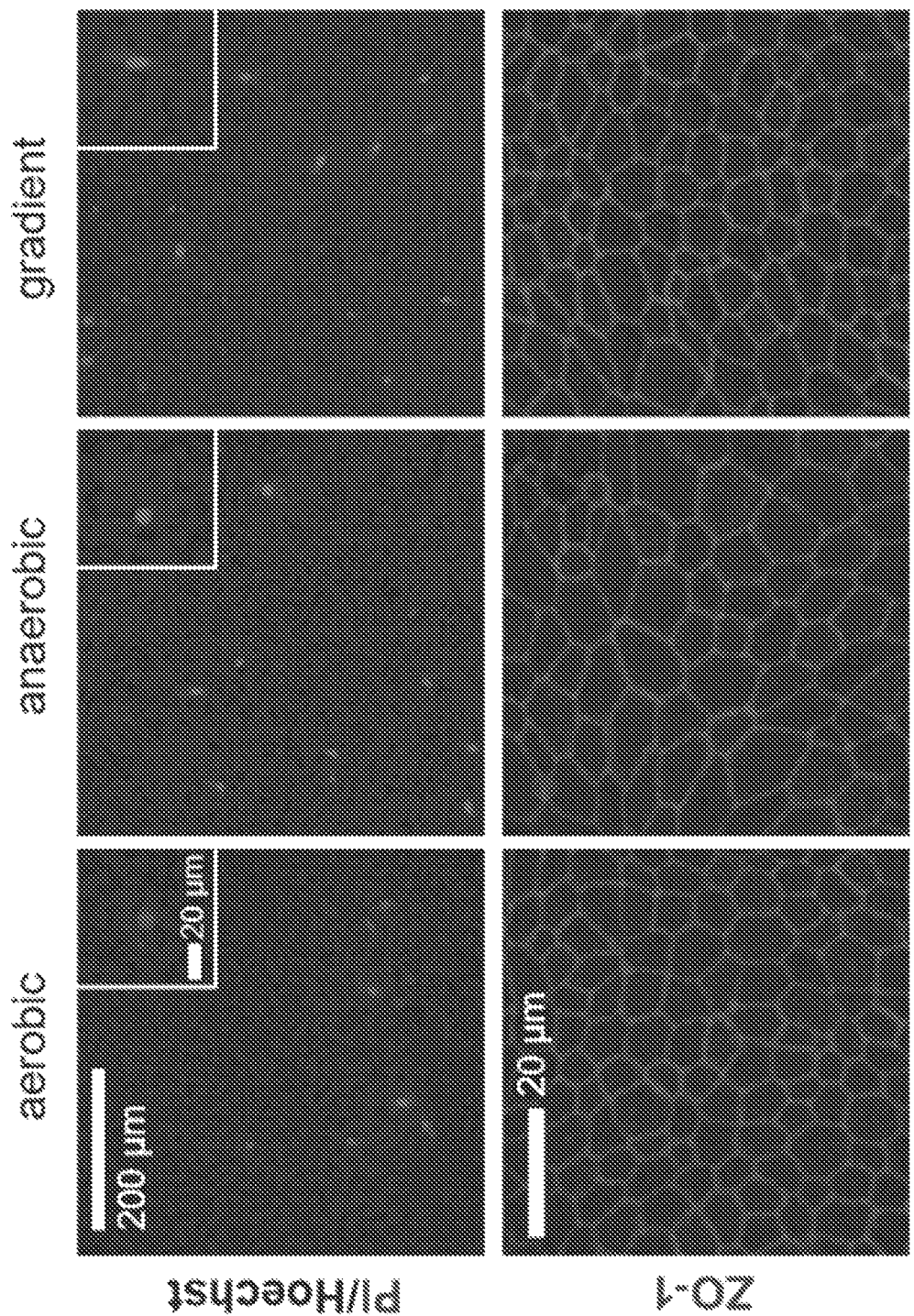
Figure 9D:
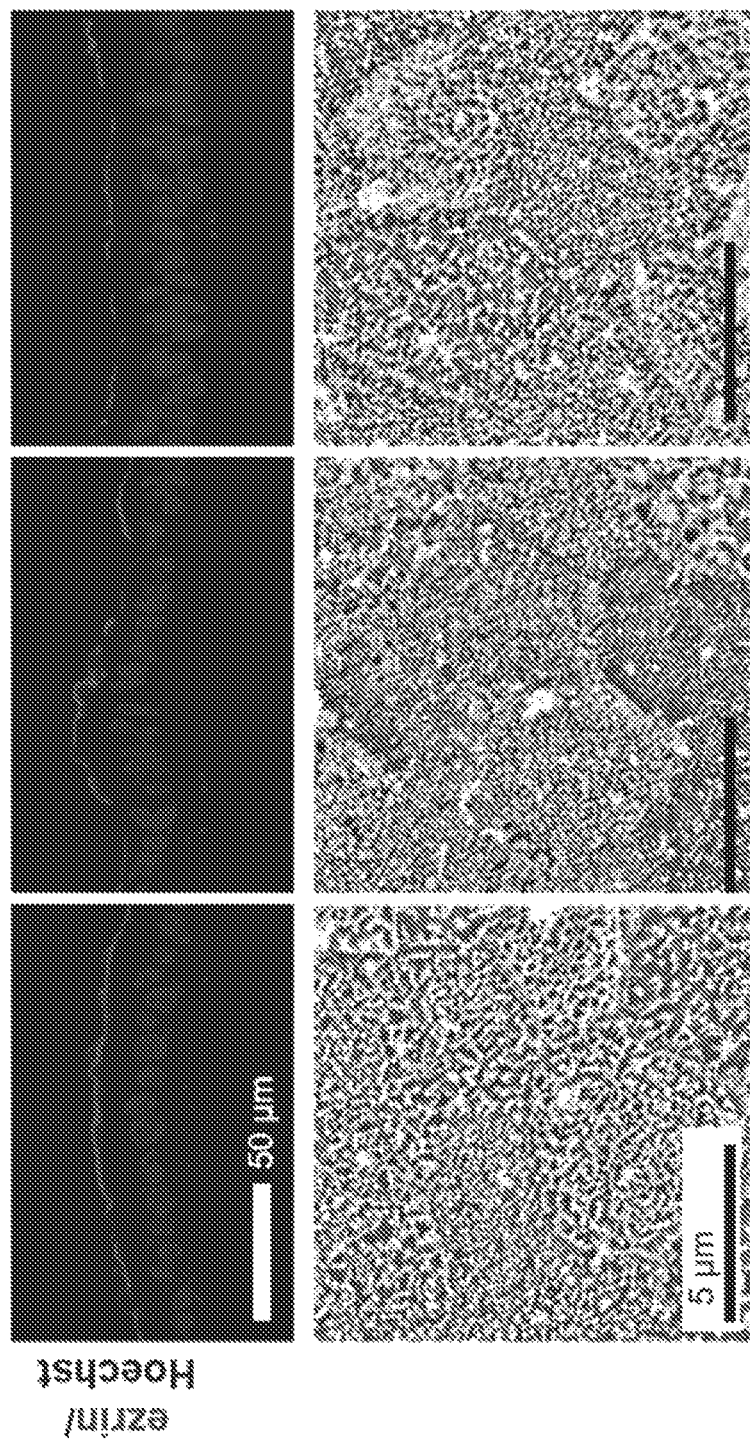

FIGS. 9A through 9D show the cell viability, polarization and barrier functions in different oxygen conditions. The cells were grown aerobically for 10 days as indicated herein and then exposed to different oxygen conditions, i.e. in aerobic, anaerobic, and oxygen gradient for 2 days and then assayed. FIG. 9A shows cell viability assessed by PI/Hoechst 33342 staining (n=3 except anaerobic in DM/DM (n=2). FIG. 9B shows transepithelial electrical resistance values of the cells exposed to different oxygen environments for 2 days in the presence (left) and absence (right) of the growth factors (n=21 for DM/SM aerobic, n=20 for DM/SM anaerobic and gradient, n=7 for DM/DM aerobic and gradient, n=6 for DM/DM anaerobic. FIGS. 9C and 9D are representative images of PI/Hoechst 33342 staining in different oxygen conditions in the presence or absence of growth factors in the basal side, representative images of the human colonic epithelial cells cryosectioned and stained for ezrin with or without the growth factors in the basal side, and representative images of ZO-1 in the human colonic epithelial cells in aerobic, anaerobic, and under oxygen gradient by immunofluorescence (DM/SM, DM/DM, respectively).

Figure 10A:
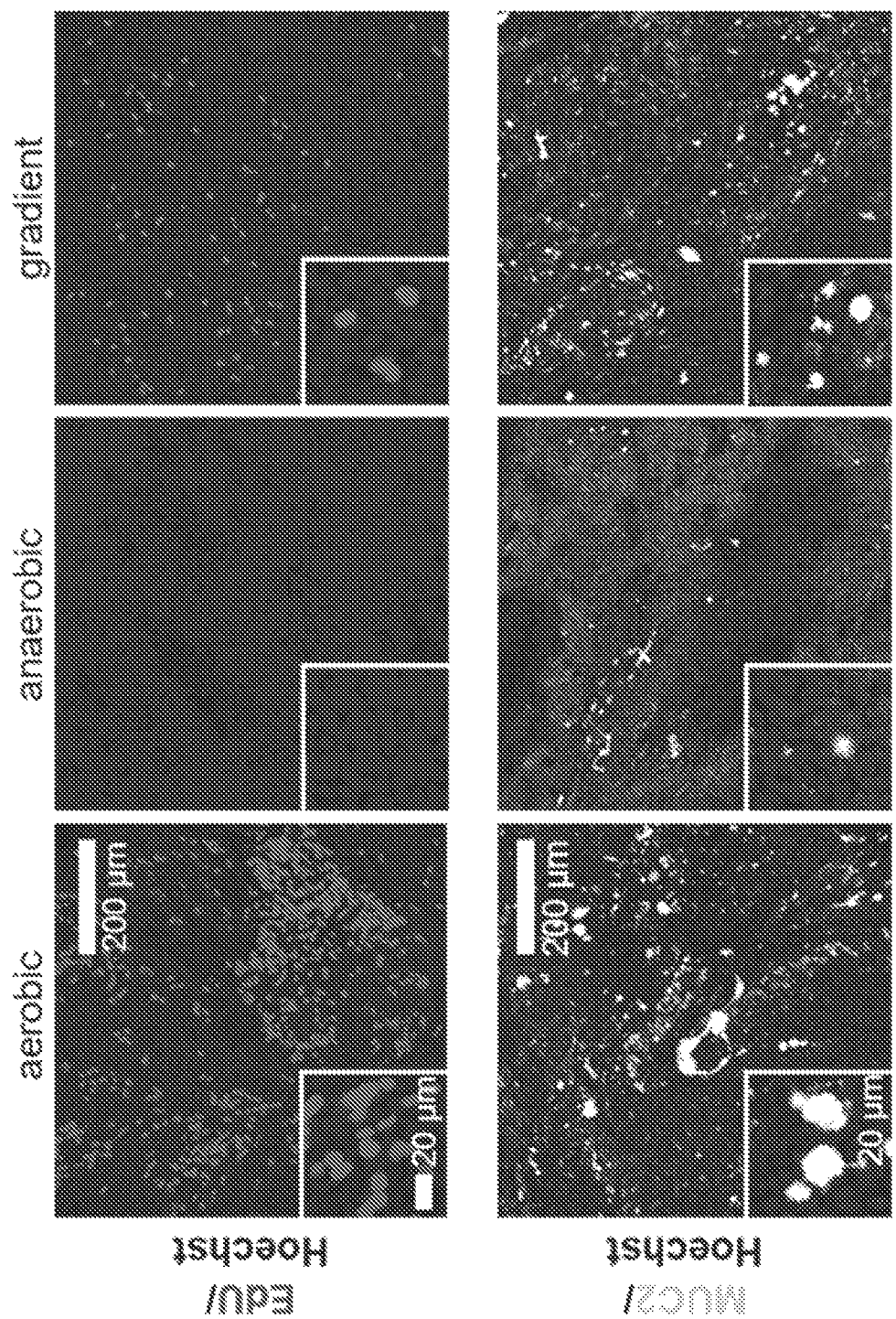
Figure 10B:
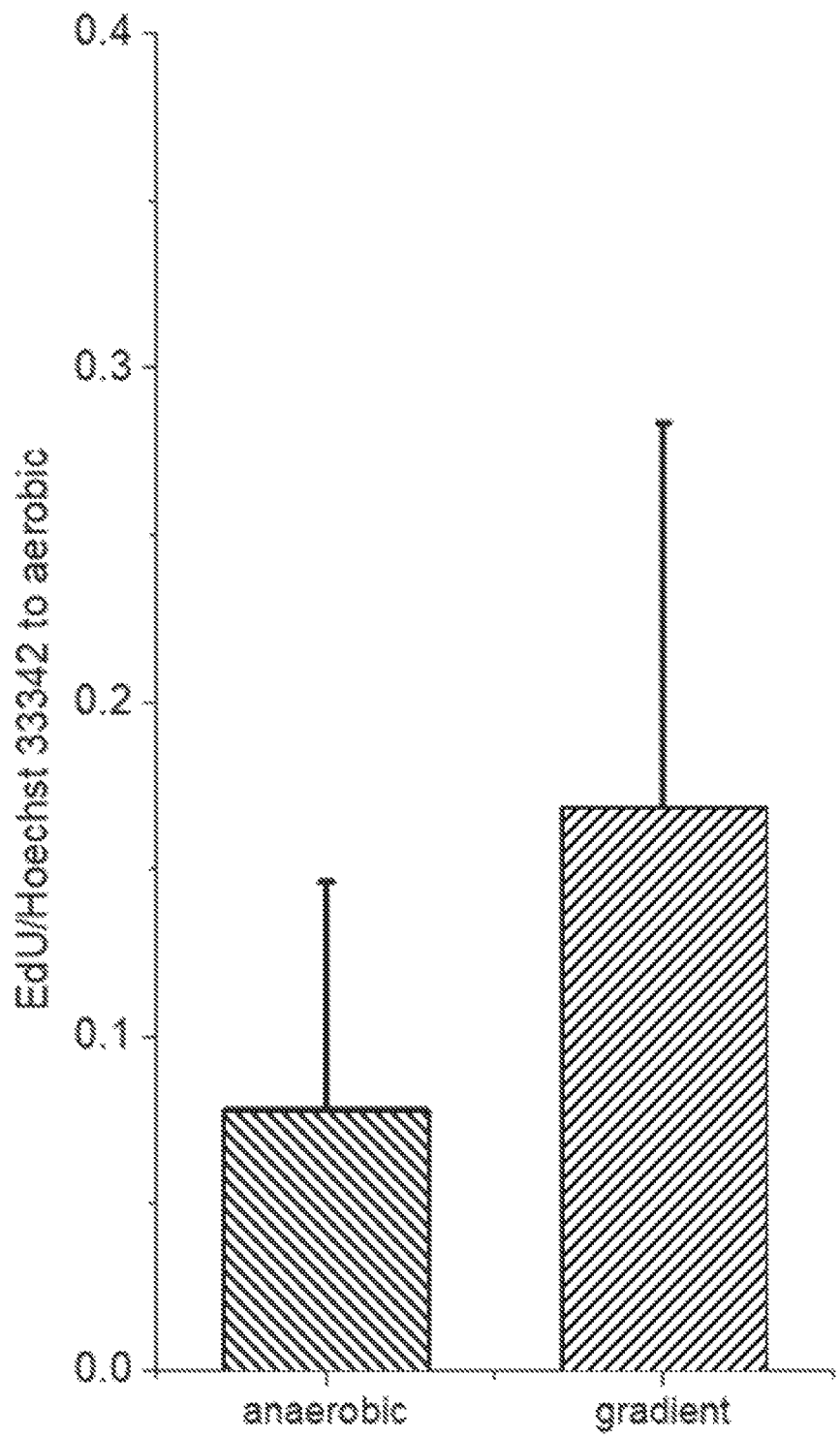
Figure 10C:
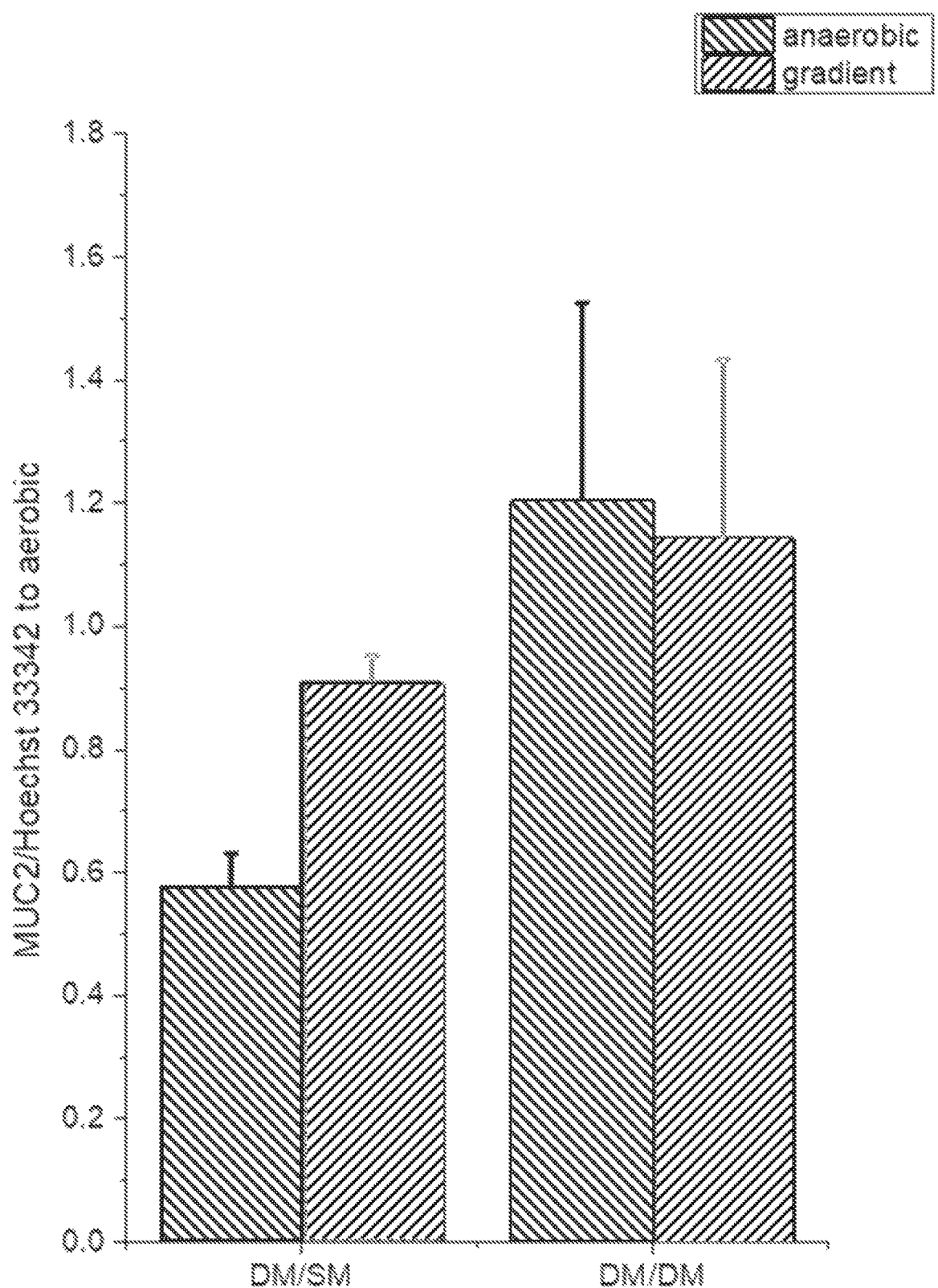

FIGS. 10A through 10C show the proliferation and goblet cell differentiation in cells exposed to different oxygen environments. The cells were cultured aerobically for 10 days as described herein and then on day 10 exposed to aerobic, anaerobic and the oxygen gradient. FIG. 10A (top panel) shows proliferative cells labeled by EdU pulse (24 h) in aerobic, anaerobic, and under the oxygen gradient for 2 days in the presence of the growth factors in the basal side. FIG. 10A (bottom panel) shows MUC2 detected by immunofluorescence in the cells exposed to aerobic, anaerobic, and the oxygen gradient for 2 days in the presence and absence of the growth factors. FIG. 10B shows the portion of EdU positive proliferative cells in aerobic, anaerobic and the oxygen gradient condition in respect to the aerobic sample (n=9). FIG. 10C shows the portions of MUC2 positive goblet cell populations in aerobic, anaerobic and the oxygen gradient conditions in the presence (DM/SM) or absence (DM/DM) of the growth factors in the basal media compared to the aerobic samples (n=3).

Figure 11A:
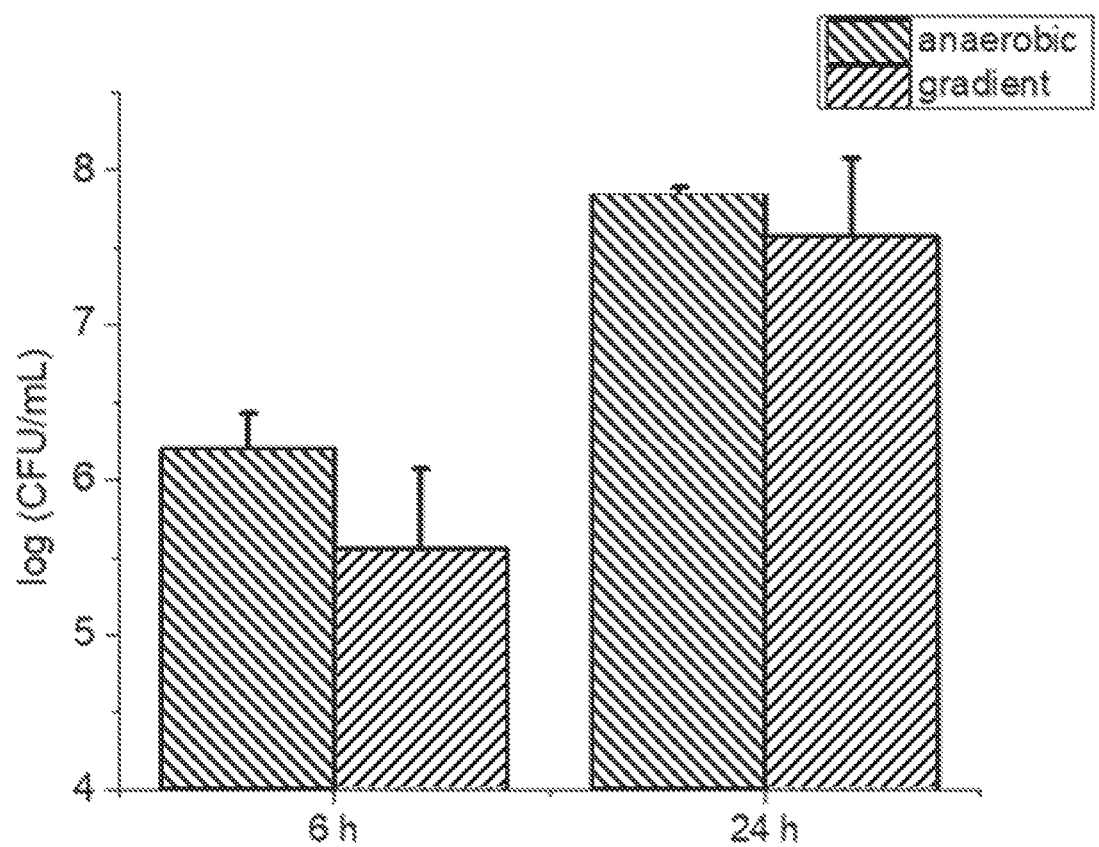
Figure 11B:
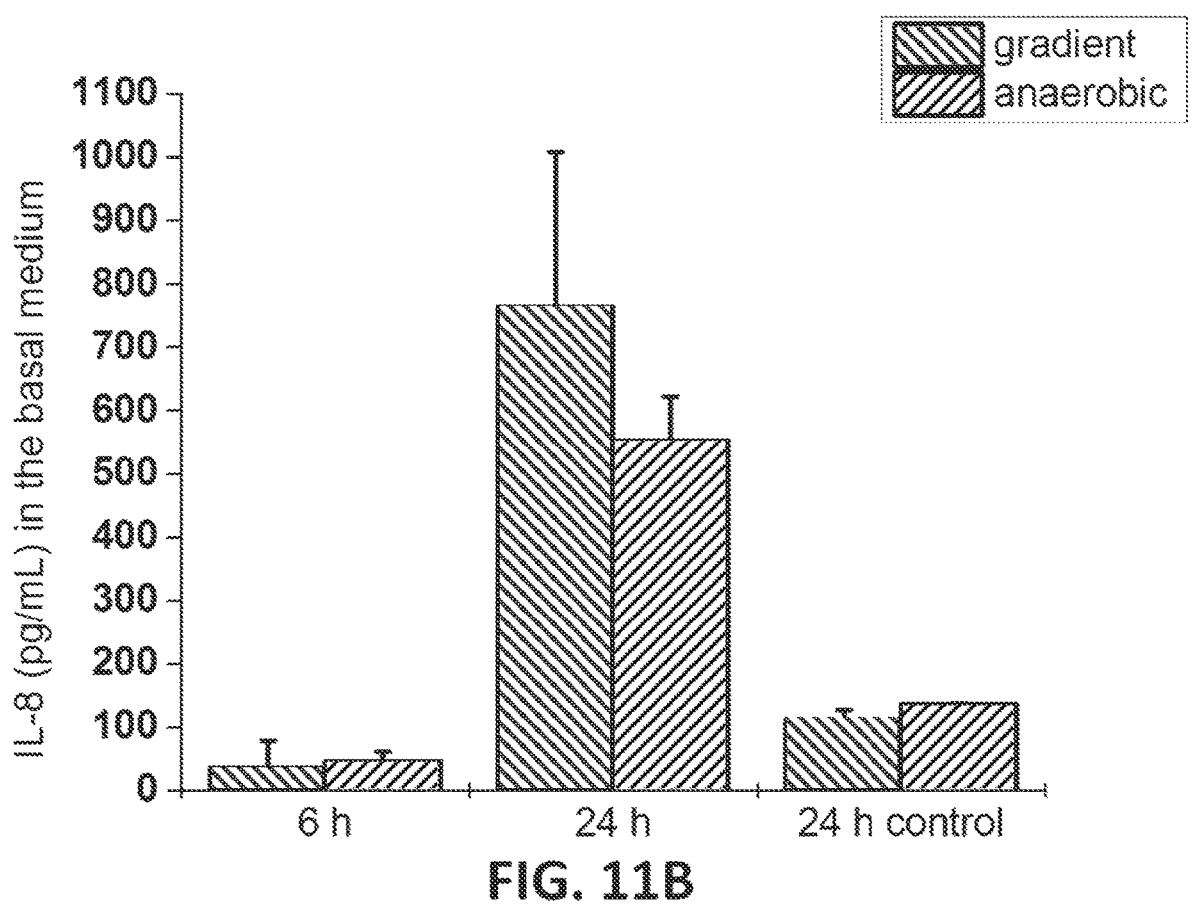
Figure 11C:
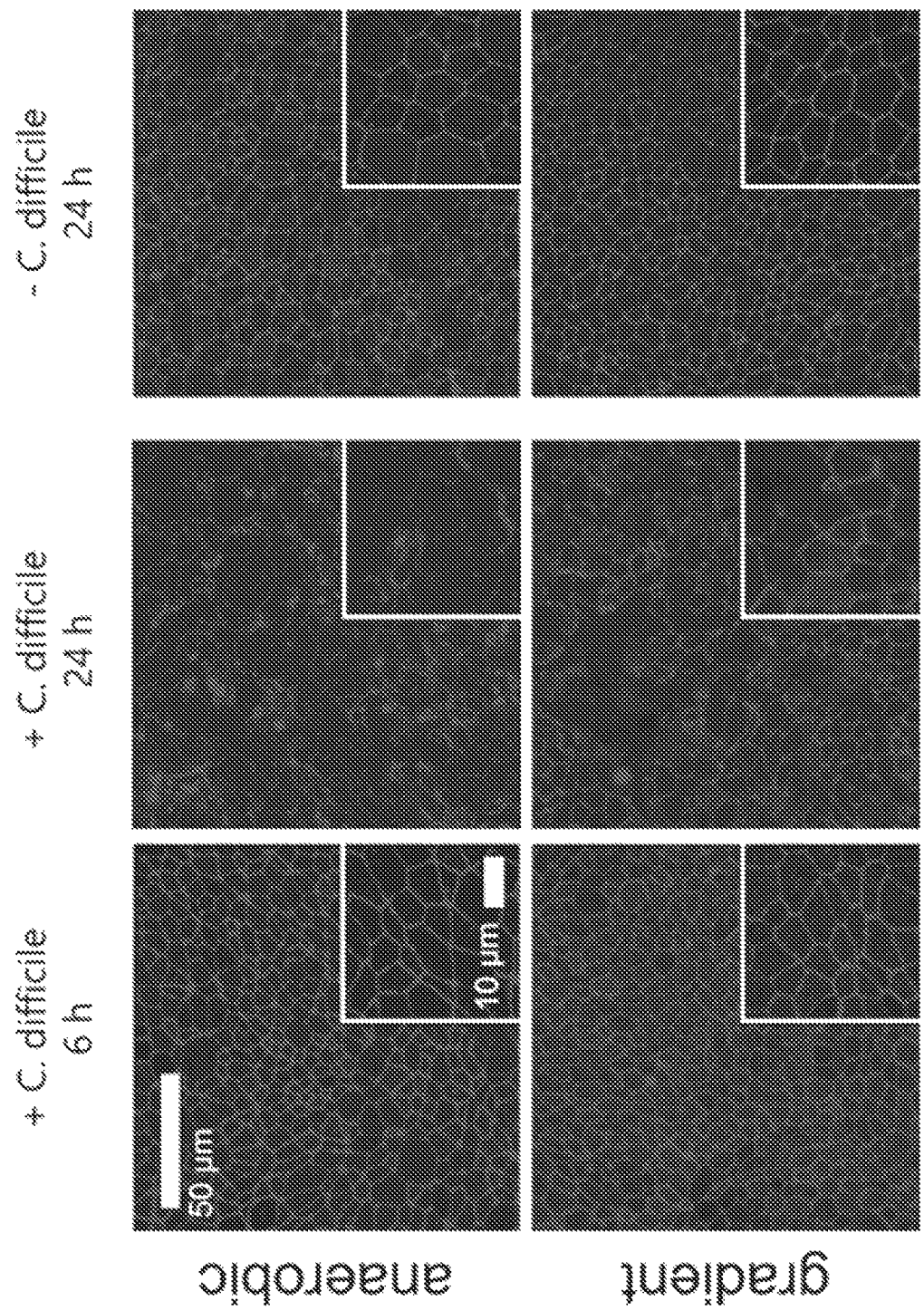
Figure 11D:
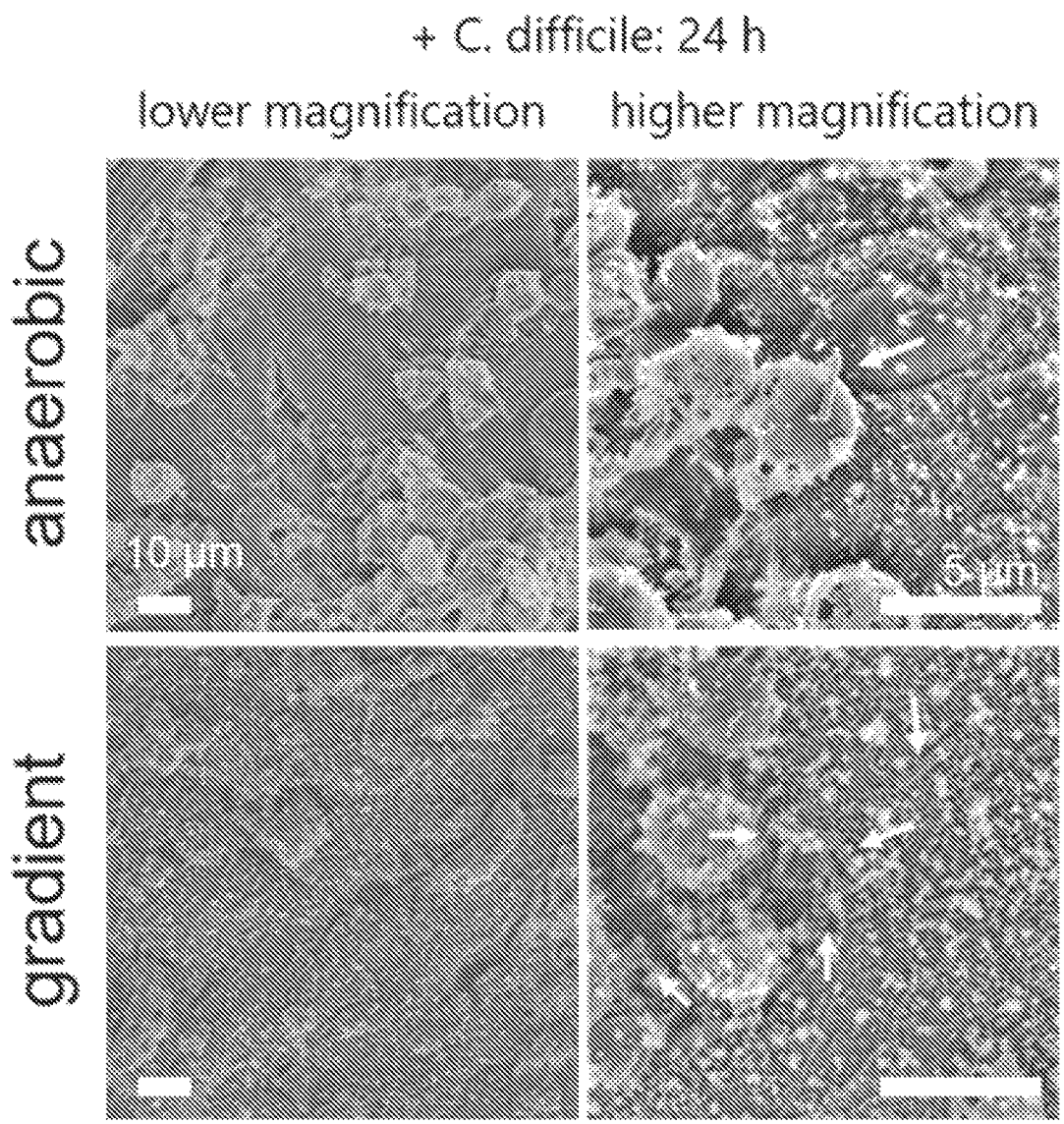

FIGS. 11A through 11D show *C. difficile* coculture in different oxygen conditions. FIG. 11A shows vegetative *C. difficile* after 6 h and 24 h coculture in anaerobic conditions and under the oxygen gradient (n=3). FIG. 11B shows IL-8 concentration of the basal media after *C. difficile* cocultures in different oxygen conditions (n=3) for 6 h and 24 h coculture samples (n=2) for 24 h control without *C. difficile*. FIG. 11C shows immunofluorescence for ZO-1 in the human colonic epithelial cells after *C. difficile* coculture (duration indicated above) and without bacteria exposure in the anaerobic and oxygen gradient conditions. FIG. 11D shows SEM images of the human colonic epithelial cells with and without *C. difficile* cocultured for 24 h anaerobically and under the oxygen gradient.

Figure 12A:
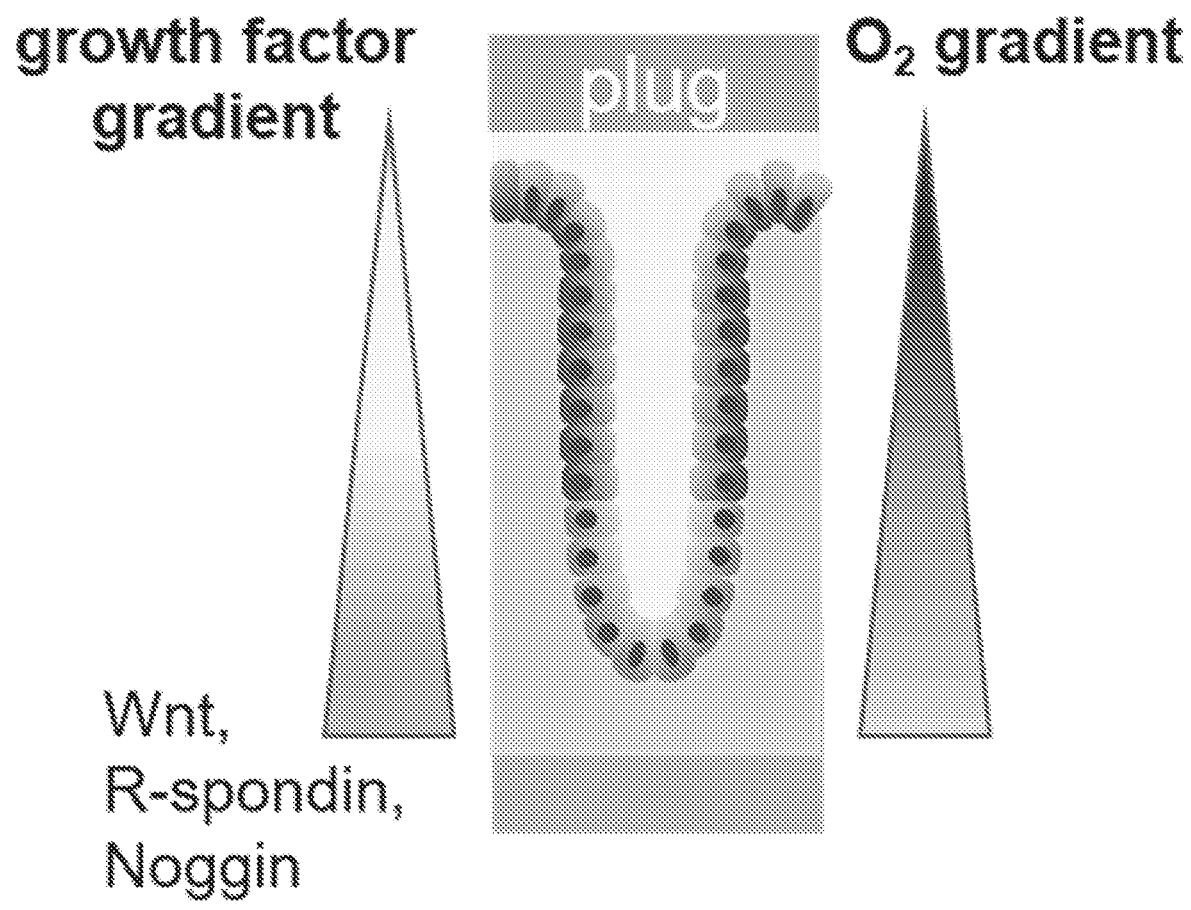
Figure 12B:
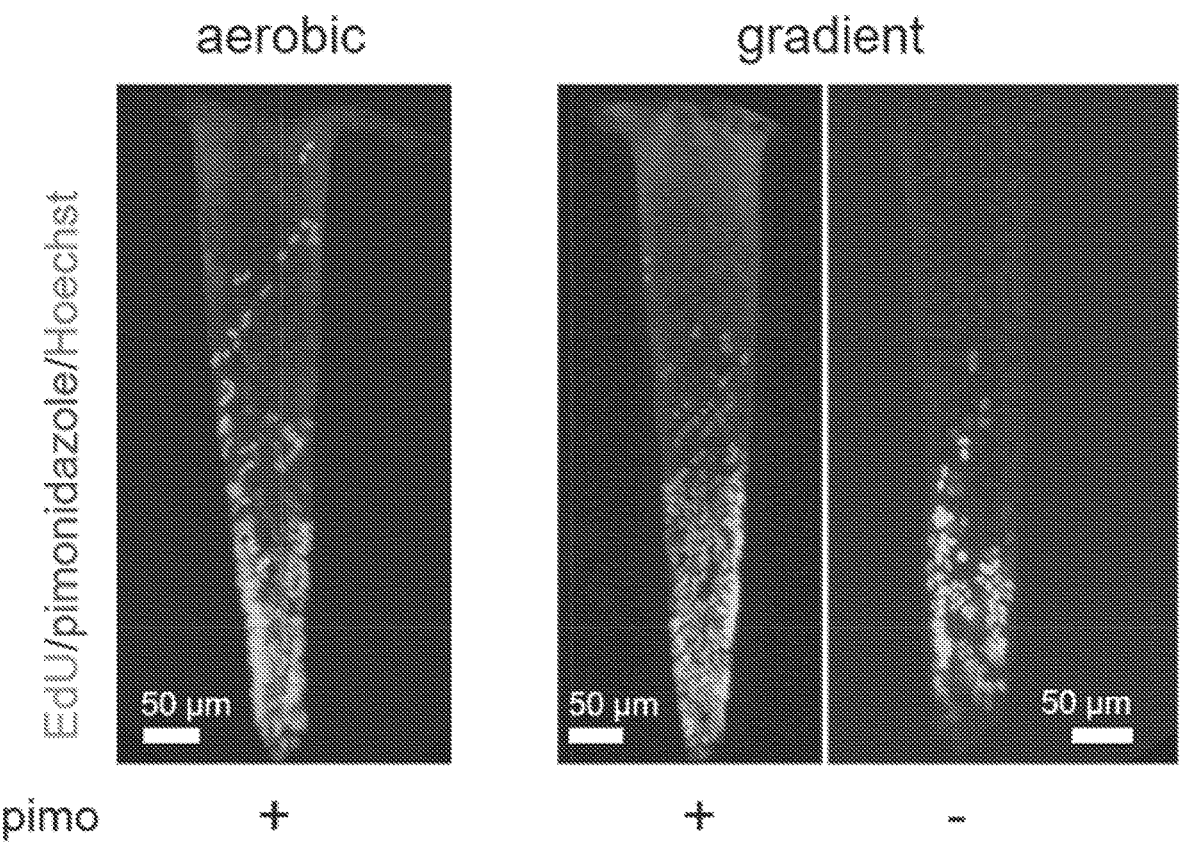
Figure 12C:
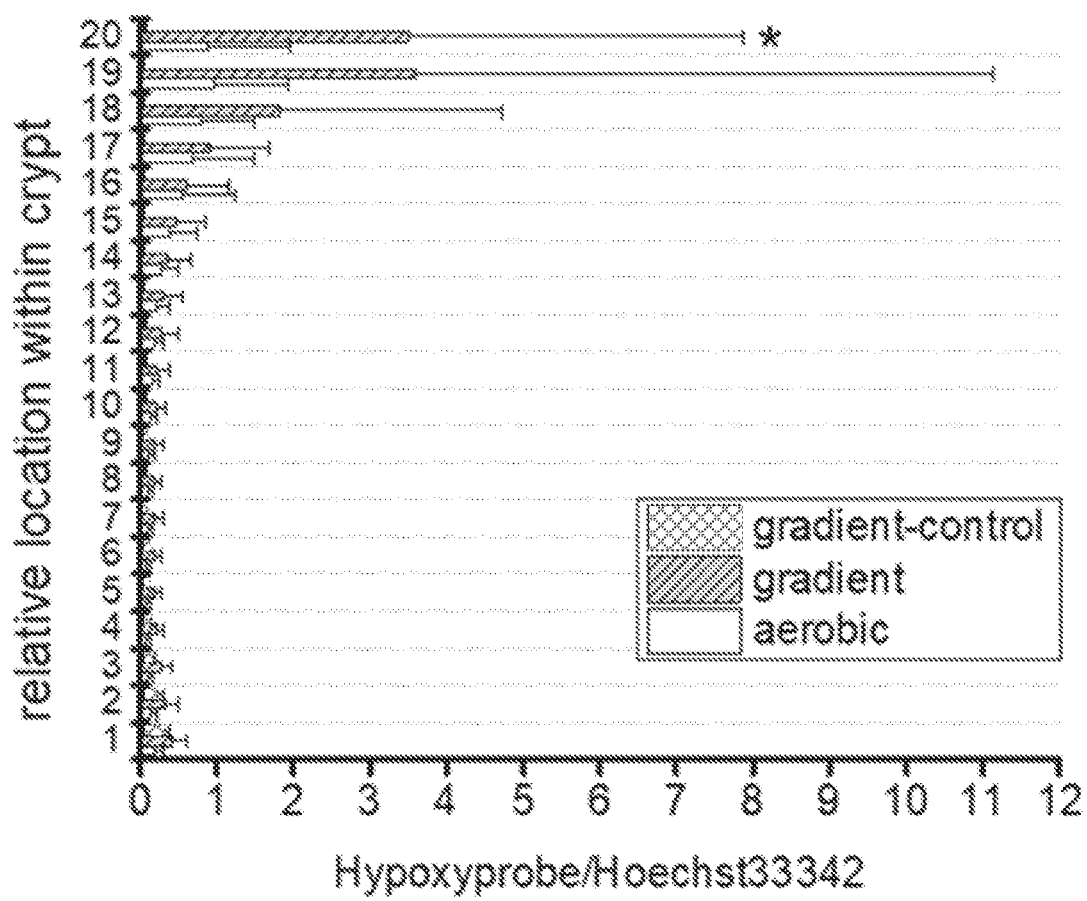
Figure 12D:
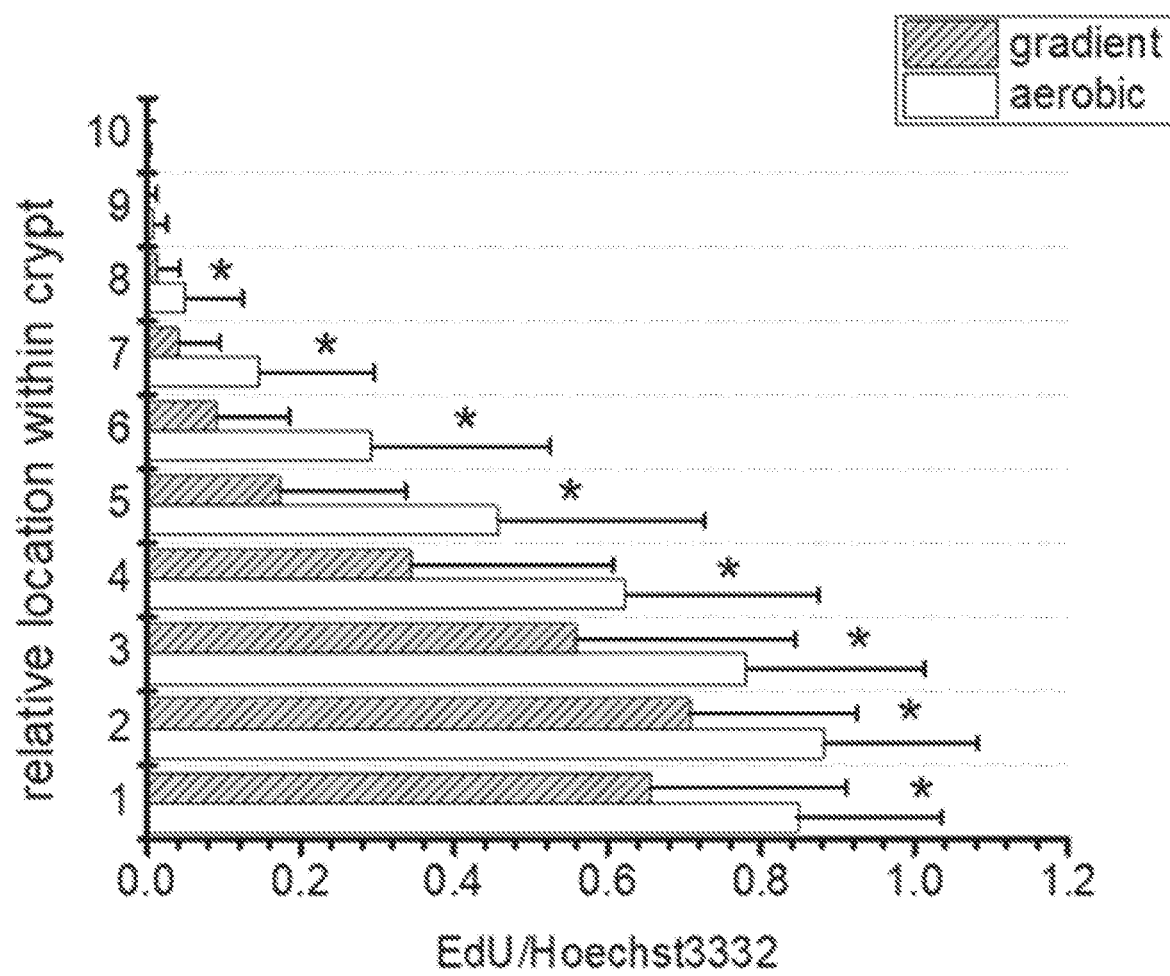
Figure 12E:
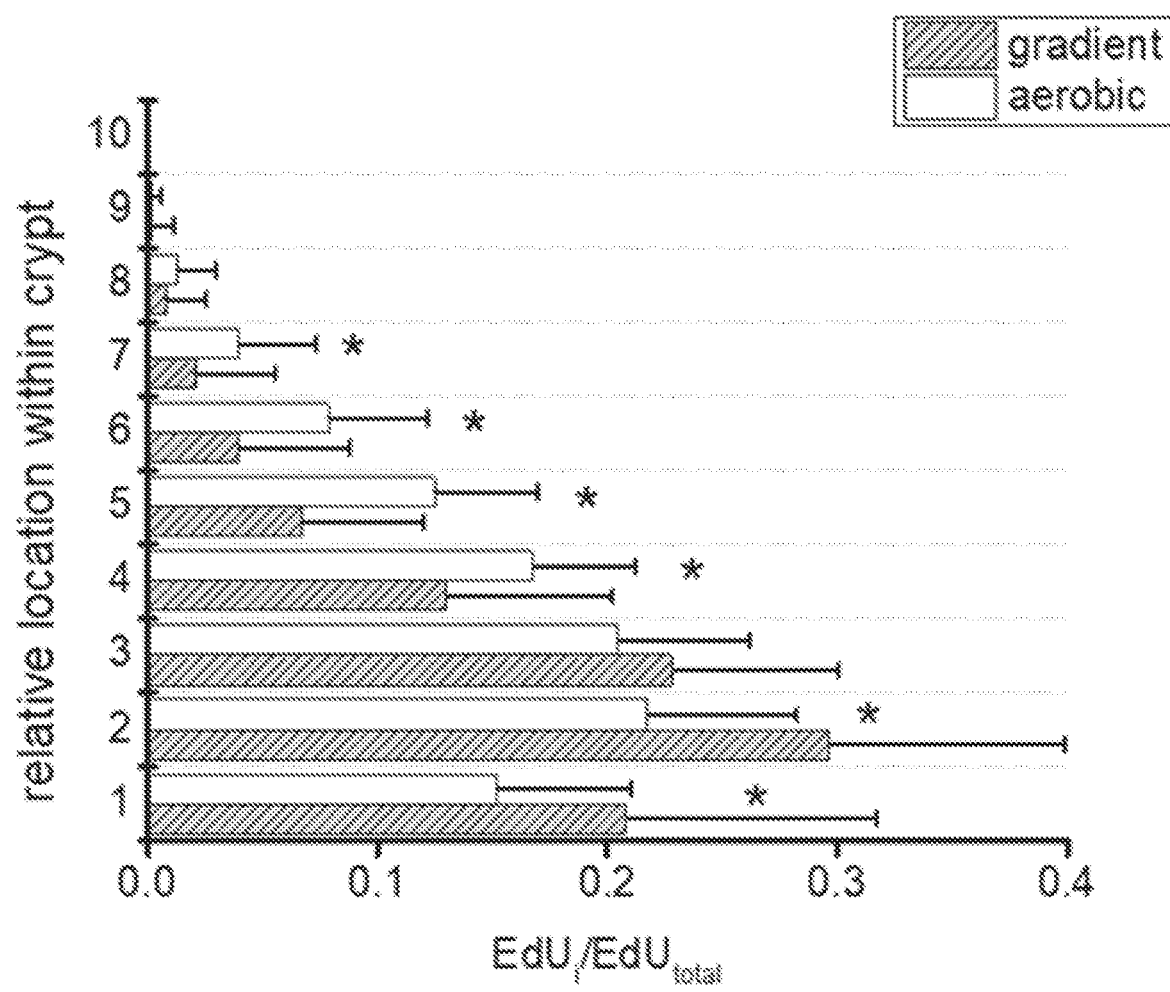
Figure 12F:
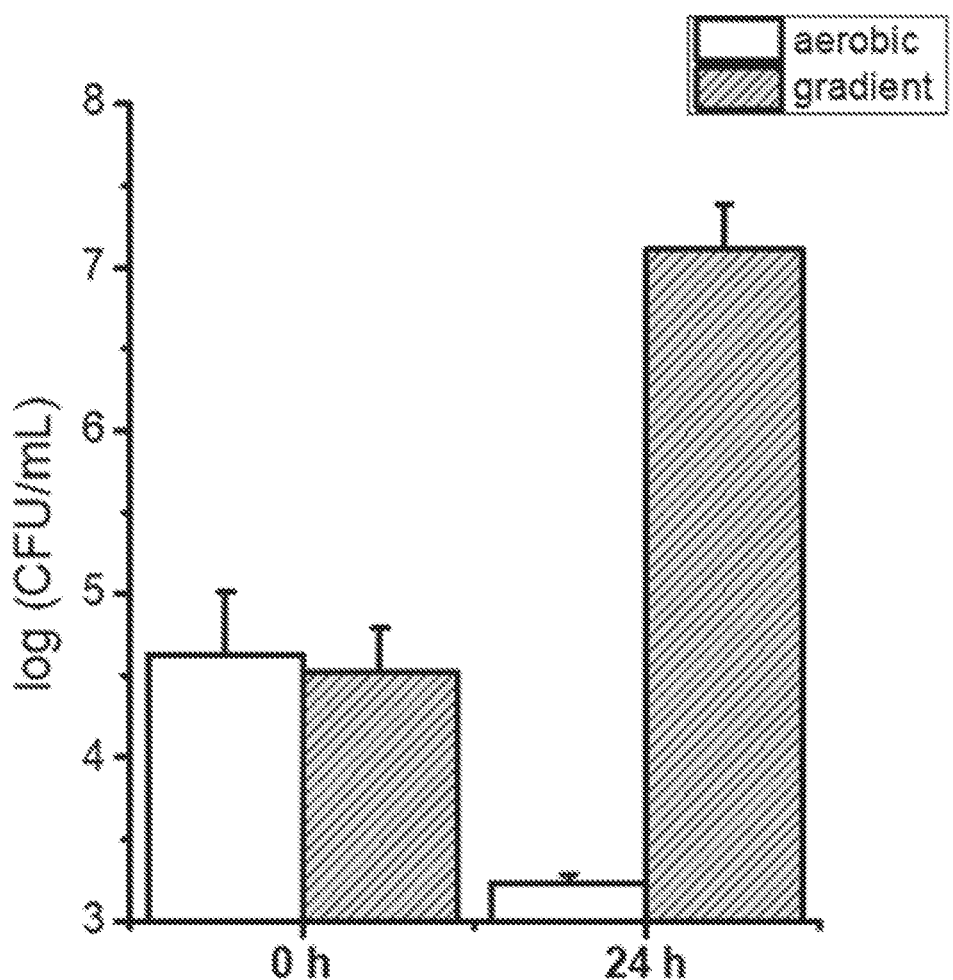

FIG. 12A schematic diagram of a culture condition in the three-dimensional crypt shaped model. FIG. 12B shows cells in a three-dimensional in vitro crypts in fully oxygenated condition (left) and in the oxygen gradient (right two). The cells were pulsed with EdU (24 hours) and pimonidazole (2 hours) to label the proliferative cells and visualize the relative extent of oxygen depletion, respectively. In the negative control for pimonidazole staining (right) pimonidazole pulse was omitted. FIG. 12C shows the relative fluorescence intensity of pimonidazole detected by immunofluorescence. Confocal images of individual crypt were divided into 20 sections and the fluorescence intensity of pimonidazole detecting antibody was normalized with the fluorescence intensity of Hoechst 33342 within each section (*indicates p<0.05). FIG. 12D shows the portion of EdU labeled cells within individual crypt. The area of EdU labeled cells was normalized by the area of Hoechst 33342 within each section (*indicates p<0.05). FIG. 12E shows the relative distribution of the EdU labeled cells within the crypt. The area of EdU labeled cells within each section was normalized by the area of the entire EdU labeled cells within the crypt (*indicates p<0.05). FIG. 12F shows growth of *B. adolescentis* in 24 hour coculture in fully oxygenated condition and in the oxygen gradient.

FIG. 13A is a schematic illustration of a system according to a first example embodiment thereof, the system comprising a plurality of fluidically connected apparatuses according to any of FIGS. 1A-1K.

Figure 13B:
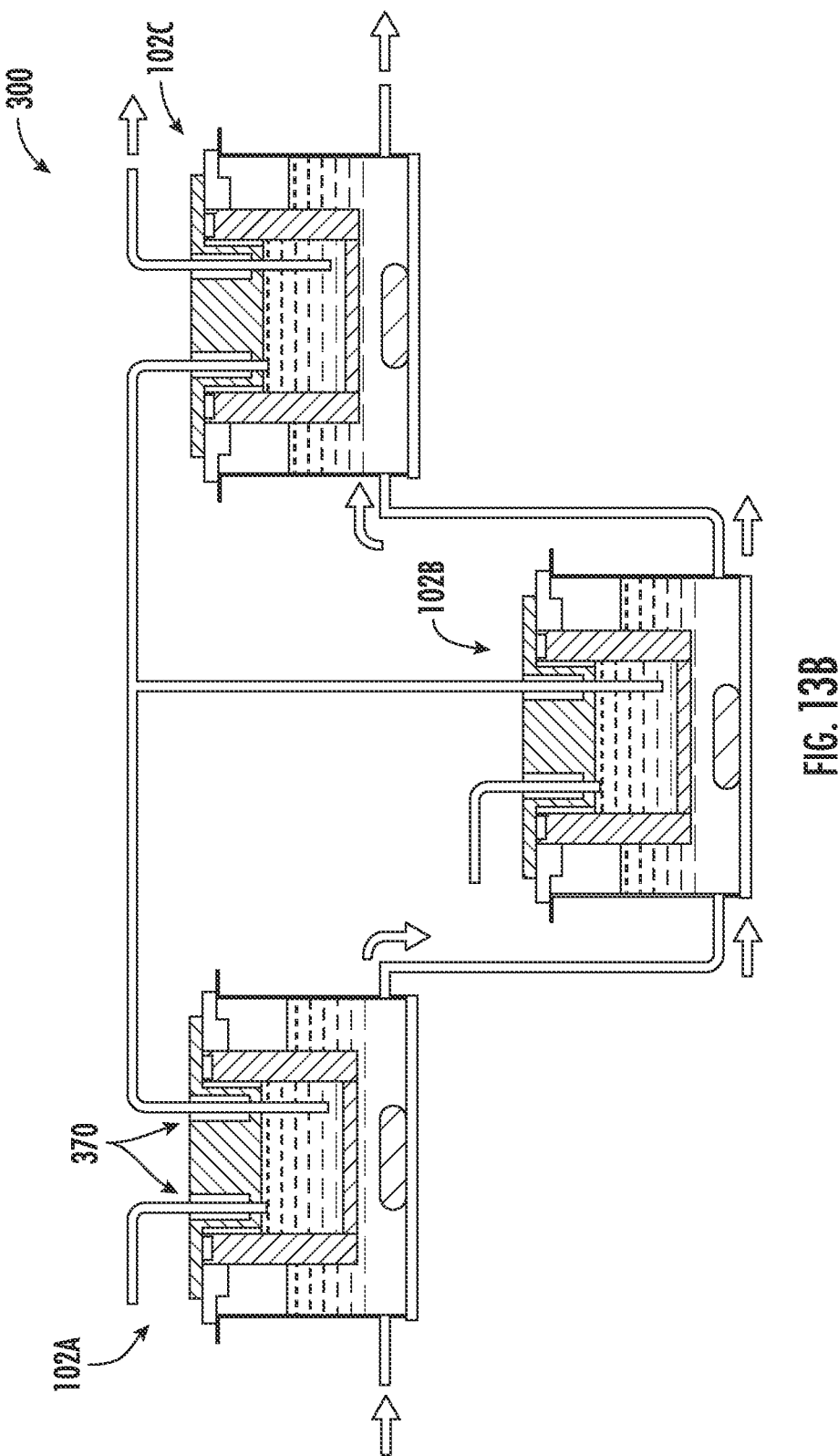

FIG. 13B is a schematic illustration of a system according to a second example embodiment thereof, the system comprising a plurality of fluidically connected apparatuses according to any of FIGS. 1A-1K.

Figure 14A:
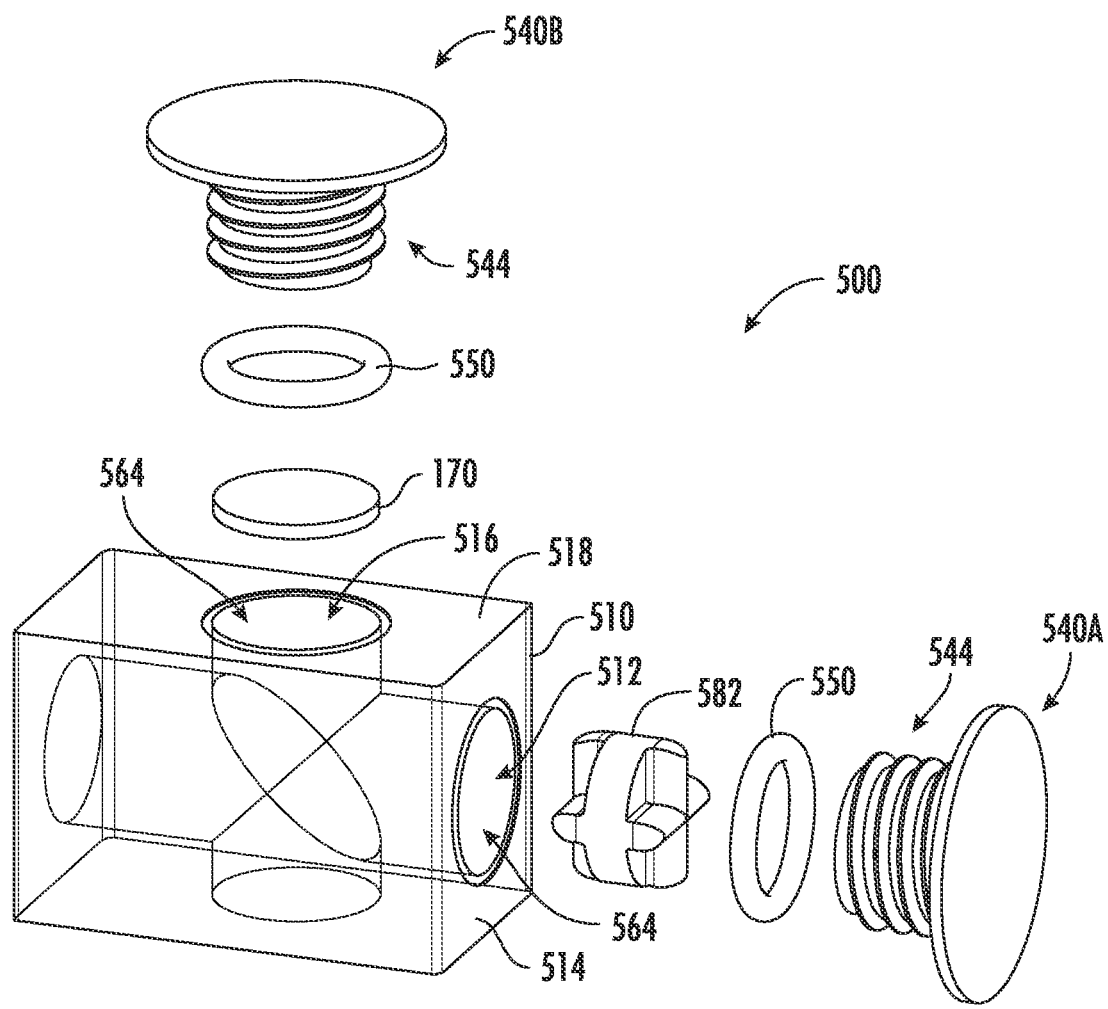

FIG. 14A is a schematic exploded view of a device for measuring an oxygen consumption rate (OCR) of a tissue sample contained therein.

Figure 14B:
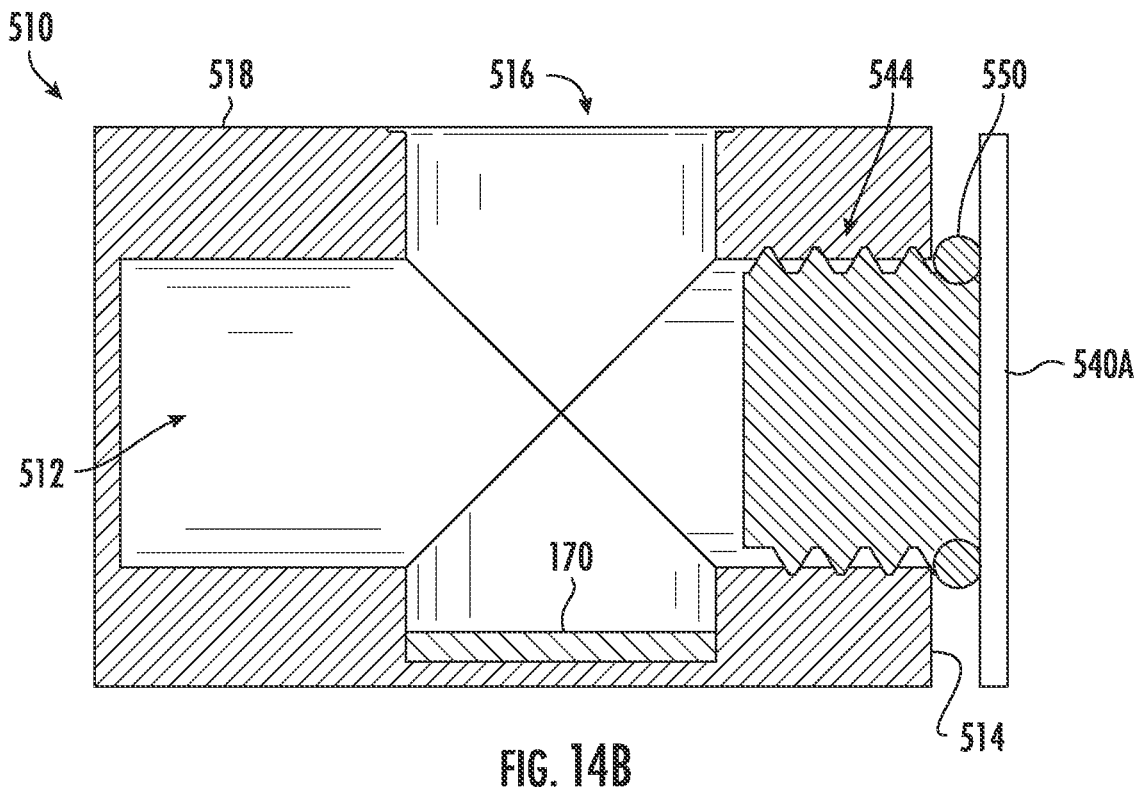

FIG. 14B is a partially assembled schematic cross-sectional view of the device of FIG. 14A.

Figure 14C:
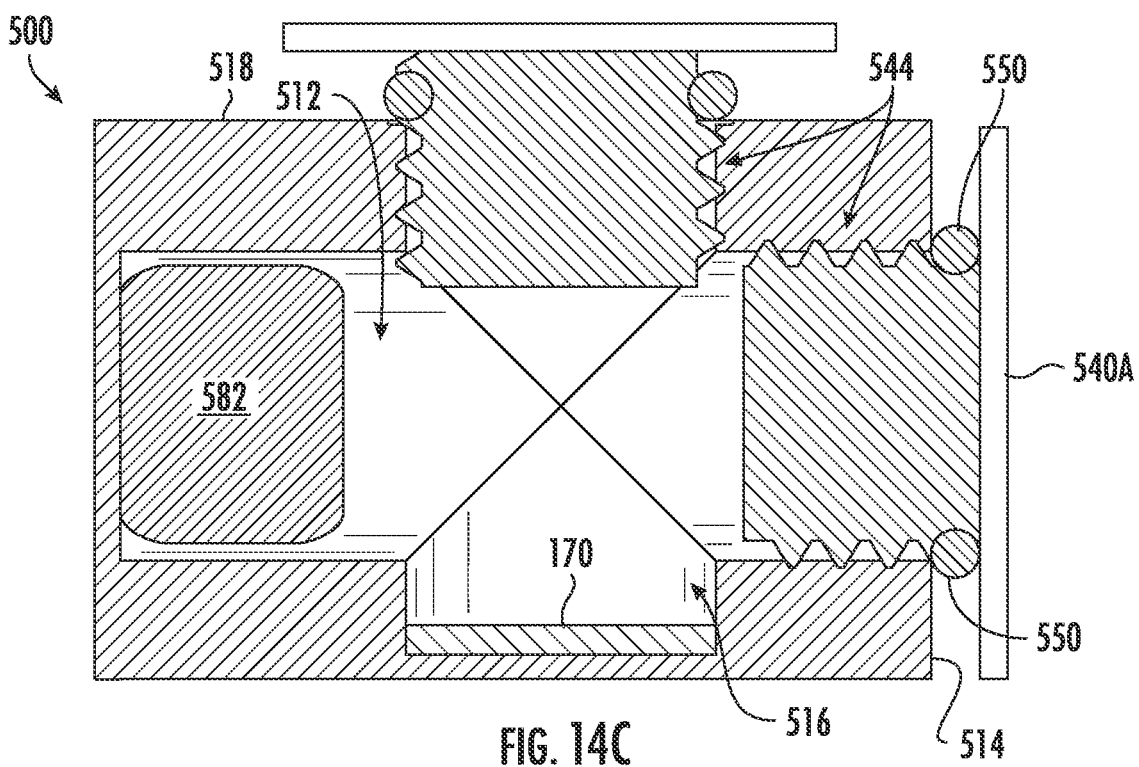

FIG. 14C is a schematic cross-sectional view of the device of FIG. 14A.

DETAILED DESCRIPTION

The presently disclosed subject matter now will be described more fully hereinafter, in which some, but not all embodiments of the presently disclosed subject matter are described. Indeed, the disclosed subject matter can be embodied in many different forms and should not be construed as limited to the embodiments set forth herein; rather, these embodiments are provided so that this disclosure will satisfy applicable legal requirements.

Definitions

The terminology used herein is for the purpose of describing particular embodiments only and is not intended to be limiting of the presently disclosed subject matter.

While the following terms are believed to be well understood by one of ordinary skill in the art, the following definitions are set forth to facilitate explanation of the presently disclosed subject matter.

All technical and scientific terms used herein, unless otherwise defined below, are intended to have the same meaning as commonly understood by one of ordinary skill in the art. References to techniques employed herein are intended to refer to the techniques as commonly understood in the art, including variations on those techniques or substitutions of equivalent techniques that would be apparent to one skilled in the art. While the following terms are believed to be well understood by one of ordinary skill in the art, the following definitions are set forth to facilitate explanation of the presently disclosed subject matter.

In describing the presently disclosed subject matter, it will be understood that a number of techniques and steps are disclosed. Each of these has individual benefit and each can also be used in conjunction with one or more, or in some cases all, of the other disclosed techniques.

Accordingly, for the sake of clarity, this description will refrain from repeating every possible combination of the individual steps in an unnecessary fashion. Nevertheless, the specification and claims should be read with the understanding that such combinations are entirely within the scope of the present disclosure and the claims.

All publications, patent applications, patents and other references cited herein are incorporated by reference in their entireties for the teachings relevant to the sentence and/or paragraph in which the reference is presented.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, reaction conditions, and so forth used in the specification and claims are to be understood as being modified in all instances by the term "about". Accordingly, unless indicated to the contrary, the numerical parameters set forth in this specification and attached claims are approximations that can vary depending upon the desired properties sought to be obtained by the presently disclosed subject matter.

As used herein, the term "about," when referring to a value or to an amount of a composition, mass, weight, temperature, time, volume, concentration, percentage, etc., is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

The term "comprising", which is synonymous with "including" "containing" or "characterized by" is inclusive or open-ended and does not exclude additional, unrecited elements or method steps. "Comprising" is a term of art used in claim language which means that the named elements are essential, but other elements can be added and still form a construct within the scope of the claim.

As used herein, the phrase "consisting of" excludes any element, step, or ingredient not specified in the claim. When the phrase "consists of" appears in a clause of the body of a claim, rather than immediately following the preamble, it limits only the element set forth in that clause; other elements are not excluded from the claim as a whole.

As used herein, the phrase "consisting essentially of" limits the scope of a claim to the specified materials or steps, plus those that do not materially affect the basic and novel characteristic(s) of the claimed subject matter.

With respect to the terms "comprising", "consisting of", and "consisting essentially of", where one of these three terms is used herein, the presently disclosed and claimed subject matter can include the use of either of the other two terms.

As used herein, the term "and/or" when used in the context of a listing of entities, refers to the entities being present singly or in combination. Thus, for example, the phrase "A, B, C, and/or D" includes A, B, C, and D individually, but also includes any and all combinations and subcombinations of A, B, C, and D.

As used herein, the term "substantially," when referring to a value, an activity, or to an amount of a composition, mass, weight, temperature, time, volume, concentration, percentage, etc., is meant to encompass variations of in some embodiments ±40%, in some embodiments ±30%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed apparatuses and devices. For example, a media or environment is "substantially hypoxic" when it is at least 60%, or at least 75%, or at least 80%, or at least 85%, or at least 90%, or at least 95%, and, in certain cases, at least 99%.

The term "basal medium", as used herein, refers to a minimum essential type of medium, such as Dulbecco's Modified Eagle's Medium, Ham's F12, Eagle's Medium, RPMI, AR8, etc., to which other ingredients can be added. The term does not exclude media which have been prepared or are intended for specific uses, but which upon modification can be used for other cell types, etc.

A "compound," as used herein, refers to any type of substance or agent that is commonly considered a drug, therapeutic, pharmaceutical, small molecule, or a candidate for use as the same, as well as combinations and mixtures of the above.

The use of the word "detect" and its grammatical variants is meant to refer to measurement of the species without quantification, whereas use of the word "determine" or "measure" with their grammatical variants are meant to refer to measurement of the species with quantification. The terms "detect" and "identify" are used interchangeably herein.

The term "growth factor" as used herein means a bioactive molecule that promotes the proliferation of a cell or tissue. Growth factors useful in the present disclosure include, but are not limited to, transforming growth factor-alpha (TGF-α), transforming growth factor-beta (TGF-β), platelet-derived growth factors including the AA, AB and BB isoforms (PDGF), fibroblast growth factors (FGF), including FGF acidic isoforms 1 and 2, FGF basic form 2, and FGF 4, 8, 9 and 10, nerve growth factors (NGF) including NGF 2.5s, NGF 7.0s and beta NGF and neurotrophins, brain derived neurotrophic factor, cartilage derived factor, bone growth factors (BGF), basic fibroblast growth factor, insulin-like growth factor (IGF), vascular endothelial growth factor (VEGF), EG-VEGF, VEGF-related protein, Bv8, VEGF-E, granulocyte colony stimulating factor (G-CSF), insulin like growth factor (IGF) I and II, hepatocyte growth factor, glial neurotrophic growth factor, stem cell factor (SCF), keratinocyte growth factor (KGF), skeletal growth factor, bone matrix derived growth factors, and bone derived growth factors and mixtures thereof. Some growth factors can also promote differentiation of a cell or tissue. TGF, for example, can promote growth and/or differentiation of a cell or tissue.

The term "ingredient" refers to any compound, whether of chemical or biological origin, that can be used in cell culture media to maintain or promote the proliferation, survival, or differentiation of cells. The terms "component," "nutrient", "supplement", and ingredient" can be used interchangeably and are all meant to refer to such compounds. Typical non-limiting ingredients that are used in cell culture media include amino acids, salts, metals, sugars, lipids, nucleic acids, hormones, vitamins, fatty acids, proteins and the like. Other ingredients that promote or maintain cultivation of cells ex vivo can be selected by those of skill in the art, in accordance with the particular need.

The term "inhibit," as used herein, refers to the ability of a compound, agent, or method to reduce or impede a described function, level, activity, rate, etc., based on the context in which the term "inhibit" is used. Preferably, inhibition is by at least 10%, more preferably by at least 25%, even more preferably by at least 50%, and most preferably, the function is inhibited by at least 75%. The term "inhibit" is used interchangeably with "reduce" and "block."

The term "material", as used herein, refers to synthetic and natural materials such as matrix components. The term "materials and compounds" as used herein, refers to, inter alia, materials, compounds, cells, peptides, nucleic acids, drugs, matrix components, and imaging agents.

The term "modulate", as used herein, refers to changing the level of an activity, function, or process. The term "modulate" encompasses both inhibiting and stimulating an activity, function, or process. The term "modulate" is used interchangeably with the term "regulate" herein.

The term "prevent," as used herein, means to stop something from happening, or taking advance measures against something possible or probable from happening. In the context of medicine, "prevention" generally refers to action taken to decrease the chance of getting a disease or condition.

The term "regulate" refers to either stimulating or inhibiting a function or activity of interest.

A "sample," as used herein, refers to a biological sample from a subject, including, but not limited to, normal tissue samples, diseased tissue samples, biopsies, blood, saliva, feces, semen, tears, and urine. A sample can also be any other source of material obtained from a subject which contains cells, tissues, or fluid of interest.

As used herein, "scaffold" refers to a supporting framework, such as one for cell or tissue growth, either in vivo or in vitro.

The terms "solid support", "surface" and "substrate" are used interchangeably and refer to a structural unit of any size, where said structural unit or substrate has a surface suitable for immobilization of molecular structure or modification of said structure and said substrate is made of a material such as, but not limited to, metal, metal films, glass, fused silica, synthetic polymers, and membranes.

The term "stimulate" as used herein, means to induce or increase an activity or function level such that it is higher relative to a control value. The stimulation can be via direct or indirect mechanisms. In one aspect, the activity or function is stimulated by at least 10% compared to a control value, more preferably by at least 25%, and even more preferably by at least 50%. The term "stimulator" as used herein, refers to any composition, compound or agent, the application of which results in the stimulation of a process or function of interest, including, but not limited to, wound healing, angiogenesis, bone healing, osteoblast production and function, and osteoclast production, differentiation, and activity.

"Tissue" means (1) a group of similar cells united to perform a specific function; (2) a part of an organism consisting of an aggregate of cells having a similar structure and function; and/or (3) a grouping of cells that are similarly characterized by their structure and function, such as muscle or nerve tissue.

General Considerations

The intestinal epithelium is one of the largest cell barriers separating the host from the external environment. Nutrients, electrolytes and water from the diet are absorbed by the intestinal epithelium. The intestinal epithelium consists of multiple cell types including stem cells, absorptive cells, and secretory cells (enterocytes, enteroendocrine cells, goblet cells, Paneth cells, Tuft cells). Intestinal stem cells reside in the base of epithelial invaginations or crypts and produce transient amplifying progenitors which rapidly proliferate, migrate upward along the crypts and differentiate into the various differentiated cell types. The proliferation and differentiation of these epithelial cells is regulated by the microenvironment including signaling molecules from other cells such as mesenchymal cells (e.g. Wnt, Noggin, BMP)[1,2], fibroblasts, ingested molecules (contained in food) and bacterial metabolites (such as short chain fatty acids and indole) or bacterial components such as lipopolysaccharides.[3,4]

Fast renewal of the differentiated cells, continuous protein secretion and nutrient absorption in the intestinal epithelium require considerable quantities of oxygen.[5] Oxygen is delivered via the bloodstream to meet this oxygen demand. An extensive vascular network in the laminapropria on the basal aspect of the epithelium ensures that all crypt stem cells receive oxygen. Meanwhile, oxygen saturation within the intestinal lumen falls into the hypoxic range (around 5% oxygen) in the small intestine and even anoxic (below 2% oxygen) in the large intestine.[6] In turn there is a steep gradient of oxygen across the intestinal epithelium between the lumen and the lamina propria of the intestine.[7] In the colon in particular the anoxic lumen provides a suitable and critical environment for commensal and beneficial microbes which include facultative anaerobes, obligate anaerobes, and extremely oxygen sensitive (EOS) members of the obligate anaerobe family.

The mammalian lower gastrointestinal tract hosts various commensal microbes. In human intestine, the number of bacterial cells is estimated to be about $10^{14}$, which outnumbers the total number of the host's cells.[8] Symbiosis between the mammalian host and the gut microbiota influences differentiation, metabolism, microvascularization and host immune system.[8] Over 99% of the commensal microbes in the healthy gut are anaerobes. Among them some anaerobes produce metabolites that are beneficial to the host such as vitamins[9], neurotransmitters[10] and short chain fatty acids and protect the host from pathogenic infection.[11] Moreover, growing evidence has shown that characteristic mixtures of microbes are associated with healthy and various disease states of the host,[12,13] suggesting that microbiota are excellent targets for drug screening and therapeutic alteration.[14] However, the biological and physiological complexity of the microbial community and the intestinal tissue has posed obstacles to revealing the underlying mechanisms of gut microbe influence on various disease states.[15] In addition, the current microbe collection procedure (from fecal samples) allows only a subset of microbes to be retrieved. With current technology, the microbes that are bound to the intestinal epithelium cannot be collected without sacrificing the subject, which is not generally possible for humans. To enhance the understanding of how microbiota interact with the host epithelial cells, in vitro co-culture systems that recapitulate the intestinal ecosystem are an attractive and desirable alternative to in vivo animal models. Further these in vitro model culture systems might include other mammalian cell types (immune cells, fibroblasts, muscle, macrophages, neurons, glial cells, among others) cultured with the epithelial cells so that the interactions of the intestinal bacteria with these other cell types can also be explored.

Development of in vitro intestinal culture systems such as intestinal organoid cultures,[16,17] intestinal self-renewing monolayers,[18] and gut-on-a-chip type devices[19-21] offer useful in vitro platforms with advantages over the use of in vivo animal models. Organoid culture has been in the spotlight recently since it enables long term primary cell culture with proper physiologic responses to biochemical cues. Organoids have also been used as disease models and for transplantation into animals after gut damage. However, the enclosed lumen of an organoid limits access to the lumen as well as manipulation of the luminal environment. Gut-on-a-chip devices have demonstrated some physiological aspects of the in vivo intestine, for example, the impact of rhythmic mechanical motions[19,20] the application of various gas compositions to the epithelium[21] and the influence of bacterial co-culture[20-22]. Oxygen gradient in the intestine was recreated in several in vitro model systems by flowing deoxygenated medium into the luminal compartments[22,23,24]. See, also US20170306278A1. An oxygen gradient was also implemented in microfluidic based chips[21]. However, these systems require intricate fabrication and assembly procedures, complex fluidic handling during operation, and are extremely difficult to scale to increase assay throughput. These systems can also require that external anaerobic gas sources be connected to the system, which is an enormous barrier to broader usage of these devices especially by biologists or medical and drug researchers. Notably, with regard to the intestinal environment, frequently these devices are not compatible with the culture of primary intestinal epithelial cells (undifferentiated and/or differentiated primary cells) and therefore employ model tumor cell lines which do not recapitulate the features of normal intestinal epithelial cells. So far, in vitro platforms have either failed to replicate the unique oxygen distribution or gradient found in the intestine or require application of external anaerobic gas mixtures.[25,26]

Typically hypoxic conditions are achieved by mixing oxygen-free gas (premixed anaerobic gas or nitrogen gas) with controlled amounts of oxygen to achieve a target oxygen saturation (0-10%).[27] Alternatively, a cell incubator can be placed in a hypoxic glove box or working station. These hypoxic cell culture environments have been routinely used in hypoxia research especially, for study of hypoxic tumors. However, these environments require continuous purging to maintain the low oxygen environment. Recently, hypoxic chambers that are used in a normoxic tissue culture incubator have been developed. In this type of chamber, hypoxic conditions are created by flowing hypoxic gas into the chamber with the tissue culture vessels. Once the gas inside the chamber is completely exchanged, the chamber is sealed and placed in a normoxic tissue culture incubator. This type of hypoxic chamber is economical and occupies significantly less space than a designated hypoxic incubator, but still requires an initial anaerobic gas purge for usage. Anaerobic gas generating sachet can create anaerobic and $CO_2$ rich gas environment which is required for strict anaerobic bacterial culture in a closed plastic container or a sealable plastic bag without external gas. However, these devices do not form gradients of gas within the chambers as would be found along the luminal-to-basal axis of the intestine.

The present disclosure provides methods and devices that create hypoxic conditions and gas gradients (e.g., oxygen gradient) that can be readily implemented and paired with conventional tissue culture methods. Some embodiments utilize the cells themselves to consume available oxygen while spatially limiting the oxygen influx into the system. Depending on the need, hypoxia can be created within the entire reservoir or on one side (luminal side) of the cell layer. In the latter case, the oxygen necessary for cell survival is provided via the basal medium permitting the dissolved oxygen from air to diffuse through the basal media to the cells. This strategy creates a self-sustainable hypoxic environment in one of the compartments in a system with two or more compartments or the entire chamber when only one compartment exists in the system without the need for an external anaerobic gas, an oxygen scavenger (chemical or enzymatic), or an oxygen purge mechanisms. This strategy also yields a steep oxygen drop across, for example, an epithelial cell layer along the luminal to basal axis as exists in vivo in the colon.

One aspect of the present disclosure relates to a method of generating a gas gradient across a cell support structure, the method comprising: providing a luminal container comprising a bottom wall, at least one sidewall extending upwardly from the bottom wall, and a top opening defined by the at least one sidewall, wherein the bottom wall of the luminal container comprises a gas permeable membrane; positioning a cell support structure above the bottom wall; positioning one or more cells and/or tissues on the cell support structure; installing a cover on the luminal container to close the open top, wherein a luminal reservoir is defined between a bottom surface of the cover and the cell support structure and/or the one or more cells and/or tissue; generating a gas gradient (higher to lower or lower to higher) between the bottom wall across the cell support structure and into the luminal reservoir.

A second aspect of the present disclosure relates to a method of culturing one or more cells and/or tissue under hypoxic conditions, the method comprising: providing a luminal container comprising a bottom wall, at least one sidewall extending upwardly from the bottom wall, and a top opening defined by the at least one sidewall; positioning a cell support structure on the bottom wall; positioning one or more cells and/or tissues on the cell support structure; installing a cover on the luminal container to close the open top, wherein a luminal reservoir is defined between a bottom surface of the cover and the cell support structure and/or the one or more cells; and generating hypoxic conditions in the luminal reservoir, wherein the hypoxic conditions are generated by the one or more cells and/or tissue on the cell support structure in the luminal container.

A third aspect of the present disclosure relates to an apparatus to produce hypoxic conditions for in vitro and/or ex vivo cell culture and/or to generate gas and/or non-gaseous gradients, the apparatus comprising: a luminal container comprising a bottom wall, at least one sidewall extending upwardly from the bottom wall, and an open top defined by the at least one sidewall; a cell support structure on the bottom wall; and a cover that is configured to engage the luminal container and close the open top in an installed position, wherein a luminal reservoir is defined between a bottom surface of the cover and the cell support structure with the cover in the installed position, and wherein the apparatus is configured to generate a hypoxic condition in the luminal reservoir with the cover in the installed position.

The methods and devices of the present disclosure offer easy access to the luminal side of the epithelium for assay of metabolites, bacterial co-culture, and addition of compounds, growth factors, food stuffs or drugs. The luminal surface is also available for application of a shear force or other mechanical perturbation. The luminal reservoir can be accessed by removal of the gas barrier from the luminal reservoir or by integrating ports, channels and or tubing within the gas barrier.

Oxygen partial pressure in many healthy tissues is lower than the atmospheric oxygen level with a range of 1-14% oxygen depending on the tissue. For example, oxygen concentrations measured in the healthy brain are typically around 4.6%, in the eye between 1-5%, in the kidney from 2 to 9.5%, and in the bone marrow ranging from 0 to 4%.[40] Considering the broad impact of oxygen on signaling, gene expression, metabolism and immune response[41-43], employing physiologically hypoxic oxygen levels in tissue culture in vitro can be necessary for the understanding of both diseased and normal tissue physiology and development as well as creation of effective therapeutic strategies. The instant disclosure provides methods and apparatuses to create a physiologically relevant oxygen concentration within a cell/tissue reservoir or oxygen gradient across cells/tissues (over time and/or space).

The devices, apparatuses and method of the present disclosure can also implement ports, channels, or tubing for adding test drugs, test microbes, or exchanging medium. In addition, the ports allow for the use of sensors for monitoring of a cell/tissue culture system.

Additional compartments or reservoirs with cell support structures can be added to the device to facilitate the study of multiple organ systems and/or cell types. Such organs can include the gastrointestinal tract, liver, kidney, heart, skin, reproductive tract, lungs, bile ducts, gall bladder, muscle, bone, cartilage, and brain.

The devices and apparatuses of the present disclosure can be a subcomponent of a microfluidic device. The microfluidic device can be integrated with other organ systems or it can act as a standalone device for a single tissue. This can involve redesign of the presented features in the figures but the essential compartments would be retained albeit in a different geometry.

Accordingly, in some embodiments, a method of generating a gas gradient across a cell support structure (e.g., perpendicularly through one or more cells and or tissue positioned on the cell support structure) is provided, the method comprising: providing a luminal container comprising a bottom wall, at least one sidewall extending upwardly from the bottom wall, and a top opening defined by the at least one sidewall, wherein the bottom wall of the luminal container comprises a gas permeable membrane; positioning a cell support structure above the bottom wall; positioning one or more cells and/or tissue on the cell support structure; installing a cover on the luminal container to close the open top, wherein a luminal reservoir is defined between a bottom surface of the cover and the cell support structure and/or the one or more cells and/or tissue; generating a gas gradient (higher to lower or lower to higher) between the bottom wall through the one or more cells and/or tissue across the cell support structure and into the luminal reservoir.

In some embodiments, the present disclosure further provides a method of culturing one or more cells and/or tissue under hypoxic conditions, the method comprising: providing a luminal container comprising a bottom wall, at least one sidewall extending upwardly from the bottom wall, and a top opening defined by the at least one sidewall; positioning a cell support structure above the bottom wall; positioning one or more cells and/or tissue on the cell support structure; installing a cover on the luminal container to close the open top, wherein a luminal reservoir is defined between a bottom surface of the cover and the cell support structure and/or the one or more cells; and generating hypoxic conditions in the luminal reservoir, wherein the hypoxic conditions are generated by the one or more cells and/or tissue on the cell support structure in the luminal container. In some embodiments, the bottom wall of the luminal container used for culturing one or more cells and/or tissue under hypoxic conditions comprises a gas impermeable membrane. In some embodiments, the bottom wall of the luminal container used for culturing one or more cells and/or tissue under hypoxic conditions comprises a gas permeable membrane. The method of culturing one or more cells and/or tissue under hypoxic conditions can further provide a gas gradient across the cell support structure (high concentration to low concentration or low concentration to high concentration). In some embodiments, the gradient can be an oxygen gradient, wherein the oxygen concentration is lower on the luminal side of the one or more cells and higher on the cell support side of the cells. In some embodiments, the gradient can be an oxygen gradient, wherein the oxygen concentration is higher on the luminal side of the one or more cells and lower on the cell support side of the cells. In some embodiments, the method of culturing one or more cells and/or tissue under hypoxic conditions can further comprise generating a non-gaseous chemical gradient across the cell support structure.

As used herein, "positioned above the bottom wall" can include "positioned on the bottom wall." In some embodiments, the bottom wall can comprise a cell support structure.

As used herein, a cell support structure can be any structure upon which the one or more cells and/or tissue can be positioned including, for example, any porous or mesh membrane. A "cell support structure" can include, but is not limited to, a membrane, ECM (extracellular matrix), hydrogel, natural or synthetic polymers, and/or a two- or three-dimensional scaffold and/or any combination thereof. In some embodiments, for example, the bottom wall of a luminal reservoir can be a cell support structure (e.g., a membrane). In some embodiments, a cell support structure can comprise microstructures (e.g., features having a size of less than about 1 mm; e.g., a microwell, a post, and/or a groove). In some embodiments, a cell support structure can be comprised of, for example, polytetrafluoroethylene (PTFE), polyethylene terephthalate (PET), polycarbonate (PC), polyvinylidiene fluoride (PVDF), polyethersulfone (PES), cellulose acetate, regenerated cellulose, cellulose nitride, nylon, carbon grid, graphene films, glass, Bioglass (e.g., 4555 Bioglass), hydroxyapatite, calcium phosphate, silicon, silicon oxide, silicon nitride, titanium oxide, aluminum oxide, gold, nickel, and/or stainless steel, or any combination thereof.

In some embodiments, a material useful as a cell support structure of this disclosure that is not naturally porous, can be made porous by methods that include, but are not limited to, sintering, etching, leaching, lithography, laser micromachining, etc. For example, a porous mesh of silicon and gold can be fabricated by lithography/etching. In some embodiments, photoreactive polymers such as photoresist that are fabricated into a film with micro or nanopores or micro or nanomesh by photolithography can be used for a cell support structure. In some embodiments, elastomeric films such as polydimethylsiloxane (PDMS) or EcoFlex that are fabricated into porous film or micro/nanomesh by soft lithography or molding can also be used as cell support structure. In some embodiments, a cell support structure can also be a dehydrated or flexible yet strong matrix such as a collagen or fibrin film or a composite.

Cells and or tissues can be placed on a cell support structure or scaffold with or without additional adhesion proteins or extracellular matrices. In some embodiments, a scaffold can comprise extracellular matrix (ECM) materials including, but not limited to, collagen, gelatin, laminin, elastin, fbronectin, vitronectin, heparin sulfate, chondroitin sulfate, keratin sulfate, hyaluronic acid, gelatinous protein mixture secreted by Engelbreth-Holm-Swarm mouse sarcoma cells (e.g. MATRIGEL®, GELTREX®, MaxGel™, etc.), and/or commercially available cell substrates (e.g., CELLstart™ CTS™) and any combination thereof (e.g., a collagen/Matrigel mixture). In some embodiments, hydrogel from natural polymers, synthetic polymers and hybrid hydrogel can be used to build a scaffold in two dimensions or three dimensions. Examples of natural polymers and synthetic polymers include, but are not limited to, chitosan, agarose, alginate (e.g., ALGIMATRIX®), fibrin, silk, polyvinyl alcohol, sodium polyacrylate, acrylate polymers, polyethylene glycol (PEG), synthetic peptides, poly N-isopropylacrylamide, and/or polyacrylamide, and/or any combination thereof. In some embodiments, the surface of a scaffold can be engineered to promote cell adhesion with any one or a combination of ECM molecules, natural or synthetic polymers or synthetic peptides including, but not limited to, poly-l-lysine, RGD-peptide and other integrin recognizing peptide segments. In some embodiments, a cell support structure useful with this present disclosure can be mixed with cellular materials (immune cells or other cell types, tissues, blood), or non-cellular materials (drugs, polymer beads, magnetic particles, etc.). In some embodiments, a cell support structure can comprise a two or three dimensional micropatterns or microstructures.

In some embodiments, the one or more cells can comprise one or more cell types (e.g., 1, 2, 3, 4, 5, 6, 7, 8, 9, 10, or more). A "cell type" as used herein refers to morphologically or phenotypically distinct cell forms within a species.

In some embodiments, the one or more cells can be from a eukaryotic cell line. In some embodiments, the one or more cells can be primary cells. In some embodiments, the one or more cells can be mammalian cells, optionally human cells.

In some embodiments, the one or more cells positioned on a cell support structure can include, but are not limited to, cells from a digestive tract, a reproductive tract, a respiratory tract, an eye, a nose, an ear, a kidney, a brain, skin, a bone, a tendon, a ligament, a cartilage, bone marrow, a liver, a pancreas, a gall bladder, a connective tissue, a lymphatic system, blood, a nerve system. Thus, in some embodiments, the one or more cells positioned on the cell support structure can include, but are not limited to, fibroblasts, myofibroblasts, endothelial cells, adipocytes, muscle cells, bone cells, nervous cells, immune cells, stem cells (e.g., embryonic, induced pluripotent stem cells, mesenchymal stem cells, hematopoietic stem cells), digestive tract cells, reproductive tract cells, eye cells, kidney cells, brain cells, bone marrow cells, intestinal cells, and/or epithelium cells (e.g., human primary colon epithelial cells). In some embodiments, the one or more cells can be cells from any type of cancer. In some embodiments, the one or more cells positioned on the cell support structure can be microbial cells. In some embodiments, the one or more cells can be gastrointestinal cells. In some embodiments, the one or more cells can be primary colon epithelial cells, optionally human primary colon epithelial cells.

In some embodiments, the one or more cells can be in a two dimensional form (e.g., a monolayer) or a three dimensional form (e.g., a spheroid, or an organoid, crypt or crypt-villi like structures). In some embodiments, the one or more cells and/or tissue can be in a three dimensional culture format of an in vitro culture, an ex vivo culture, an entire organism, an entire organ, a partial organ, and/or an ex vivo tissue section. In some embodiments, an in vitro culture or an ex vivo culture can be embedded in a natural or artificial hydrogel.

In some embodiments, the cells positioned on a cell support structure can be from healthy, inflamed, or diseased human or animal tissue.

In some embodiments, the one or more tissues can be one or more types of tissue (e.g., 1, 2, 3, 4, 5, 6, 7, 8, 9, 10 or more). In some embodiments, the one or more tissues can be comprised of the one or more cells as described herein. In some embodiments, the one or more tissues can be an entire organism, an entire organ, a part of an organ, an in vitro culture, an ex vivo culture, and/or an ex vivo tissue section. In some embodiments, an organ can include, but is not limited to, a liver, a kidney, a heart, skin, a reproductive tract (e.g., ovary, testes, etc.), a lung, a bile duct, a gall bladder, a muscle, a bone, cartilage, and/or a brain. In some embodiments, the one or more cell or tissues can comprise cells and/or tissues of a gastrointestinal tract including, but not limited to, a mouth, a salivary gland, an esophagus, a stomach, a small intestine, a large intestine and/or a rectum.

In some embodiments, the one or more cells and/or one or more tissues can be an in vitro colonic epithelial crypt, the crypt comprising a luminal side and a basal side above the cell support structure. In some embodiments, an in vitro colonic epithelium crypt can be a human in vitro colonic epithelium crypt. In some embodiments, at least one microorganism can be added to a luminal reservoir comprising an in vitro colonic epithelial crypt, thereby providing the microorganism access to the luminal side of the crypt and/or the cell support side of the crypt.

In some embodiments, a gas can be provided to the one or more cells and/or tissues through a gas permeable membrane of a bottom wall of a luminal container, thereby generating a gas gradient across a cell support structure between the gas permeable membrane of the bottom wall of the luminal container (higher gas concentration) through the one or more cells and/or tissues and into the luminal reservoir (lower gas concentration). In some embodiments, the gas can be provided passively from the atmosphere through a permeable membrane (e.g., the atmosphere in which the luminal container is maintained or held).

In some embodiments, the method of generating a gas gradient across a cell support structure can further comprise providing a basal container comprising a bottom wall and at least one sidewall extending upwardly from the bottom wall, wherein the bottom wall and the at least one sidewall define a well, and wherein: the luminal container is held within the well of the basal container; the bottom wall of the basal container is spaced apart from the bottom wall of the luminal container; a basal reservoir is defined between the bottom wall of the basal container and the bottom wall of the luminal container and/or between the at least one sidewall of the basal container and the at least one sidewall of the luminal container; and a basal medium positioned in the basal reservoir, wherein the basal medium provides the gas to the one or more cells and/or tissue through the gas permeable membrane of the bottom wall, thereby generating a gas gradient between the basal medium and the luminal reservoir (higher concentration to lower concentration perpendicularly through the one or more cells and/or tissue from the basal medium to the luminal reservoir).

A gas gradient generated using the methods and devices of the present disclosure can be across a cell support structure (e.g., perpendicularly across the one or more cells or tissues) in either direction. Thus, in some embodiments, a gas gradient that is generated can have a higher concentration of the gas in the basal reservoir and/or container and a lower concentration of the gas in the luminal reservoir and/or container or a gas gradient that is generated can have a lower concentration of the gas in the basal reservoir and/or container and a higher concentration of the gas in the luminal reservoir and/or container. In some embodiments, when more than one gas gradient is generated, the gradient for each gas can be across a cell support structure in the same direction or in a different direction.

In some embodiments, a gas gradient can be generated by the consumption of the gas by the one or more cells and/or tissues positioned on the cell support structure (e.g., as a sink) upon installing of the cover. In some embodiments, a gas gradient can be generated by the production of the gas by the one or more cells and/or tissue (e.g., as a source) upon installing of the cover. In some embodiments, generation of a gas gradient can be assisted by the use of one or more secondary cells, tissues or organisms that are introduced into a luminal or basal container or reservoir.

A gas useful with the present disclosure, for which a gas gradient can be generated (e.g., which can be introduced, generated or consumed by the one or more cells and/or tissues, or by secondary cells, tissues, or organisms), can include, but is not limited to, oxygen, nitrogen, carbon dioxide, carbon monoxide, hydrogen, methane, hydrogen sulphide, skatole (a by-product of meat digestion), indole (a by-product of meat digestion), methanethiol (a sulfur compound), dimethyl sulfide (a sulfur compound), volatile amines, volatile sulfur compounds (VSC), methyl mercaptan (MM; also known as methanethiol, MT), dimethyl disulfide (DMDS) and dimethyl trisulfide (DMTS), volatile fatty acids, and/or or nitric oxide. In some embodiments, a gradient of any of these or other gases of interest can be generated in parallel with or independent of any other gas gradient. For example, an oxygen gradient can be established across a cell support structure that is parallel with any other gas of interest or the oxygen gradient can be established across a cell support structure independent of any other gas of interest. In some embodiments, to establish a gradient, a luminal medium or a basal medium can comprise a dissolved gas of interest or can be pre-saturated with the gas of interest and/or ports or tubing can be used for intermittent or continuous purging of a gas of interest or introducing of a gas of interest. Alternatively, a cell, tissue, or organism that produces or consumes a gas of interest can be introduced into a luminal and/or basal container/reservoir to act as a gas source (supply) or sink.

In some embodiments, the at least one gas that is produced and/or consumed can be oxygen and the oxygen concentration in the luminal reservoir can recapitulate conditions of a hypoxic environment. Thus, in some embodiments, oxygen concentration can be the less than about 21%. In some embodiments, oxygen concentration can be about 0% to about 14%, about 0% to about 10%, about 0% to about 8%, or about 0% to about 5%. In some embodiments, hypoxic conditions in a luminal reservoir can be stable (e.g., stable hypoxia) or substantially stable. In some embodiments, stable hypoxia in a luminal reservoir can generate an oxygen gradient between a luminal reservoir and a basal reservoir.

"Stable hypoxia" as used herein means that once a state of hypoxia is achieved it is stable or substantially stable over time. "Substantially stable hypoxia" is stable or constant hypoxia with some minor variability, e.g. a slight increase or decrease of about 1%, 2%, 3%, 4%, 5% or more, but not more than 15% variability. Once stable hypoxia is achieved, small perturbations, including addition of new media and other substances to the basal and luminal reservoirs, or an agitation can affect the hypoxic state but for only brief periods after which the system quickly returns to a stable or substantially stable hypoxic state.

In some embodiments, a luminal container can be divided into at least two compartments by a second gas permeable membrane and a gas gradient can be generated between the at least two compartments.

In some embodiments, a luminal container can comprise at least two luminal containers, including a first luminal container comprising a bottom wall, at least one sidewall extending upwardly from the bottom wall, and a top opening defined by the at least one sidewall, wherein the bottom wall of the first luminal container comprises a gas permeable membrane, and a second luminal container comprising a bottom wall, at least one sidewall extending upwardly from the bottom wall, and a top opening defined by the at least one sidewall, wherein the bottom wall of the second luminal container comprises a gas permeable membrane, wherein the first luminal container is held within the second luminal container; and a gas gradient is generated between the at least two luminal containers. In some embodiments, one of the at least two luminal containers can be inserted inside the other of the at least two luminal containers (that is, for example, the first luminal container is smaller than the second luminal container and the first luminal container is inserted into the reservoir of the second luminal container).

As used herein, "a gas permeable membrane" refers to a membrane that is permeable to dissolved gas and other molecules while supporting cells and not allowing cells to pass through. Exclusion can be based on pore size, porosity, tortuosity, hydrophobicity, etc. of the material. In some embodiments, a gas permeable membrane can be an oxygen permeable membrane. In some embodiments, a gas permeable membrane can be permeable to non-gaseous chemicals.

In some embodiments, a gas permeable membrane can be, but is not limited to, an extracellular matrix (ECM), a hydrogel, a natural or synthetic polymer, a micro/nanomesh, polydimethylsiloxane (PDMS), polyurethane, high Dk contact lens material (oxygen permeability greater than 31) (e.g., paflufocon polymer (e.g., Fluoroperm™ polymer)), and/or combinations thereof.

In some embodiments, a gas permeable membrane can be comprised of the same material as a cell support structure, for example, any porous or mesh membrane, as described herein.

In some embodiments, a material suitable for a gas permeable membrane can include, but is not limited to, polytetrafluoroethylene (PTFE), polyethylene terephthalate (PET), polycarbonate (PC), polyvinylidiene fluoride (PVDF), polyethersulfone (PES), cellulose acetate, regenerated cellulose, cellulose nitride, nylon, carbon grid, graphene films, glass, Bioglass (e.g., 45S5 Bioglass), hydroxyapatite, calcium phosphate, silicon, silicon oxide, silicon nitride, titanium oxide, aluminum oxide, gold, nickel, and/or stainless steel, or any combination thereof.

In some embodiments, a material useful for a gas permeable membrane that is not naturally porous, can be made porous by methods that include, but are not limited to, sintering, etching, leaching, lithography, laser micromachining, etc. For example, a porous mesh of silicon and gold can be fabricated by lithography/etching. In some embodiments, photoreactive polymers such as photoresist that are fabricated into film with micro or nanopores or micro or nanomesh by photolithography can be used for a gas permeable membrane. In some embodiments, elastomeric films such as polydimethylsiloxane (PDMS) or EcoFlex that are fabricated into porous film or micro/nanomesh by soft lithography or molding can also be used as a gas permeable membrane. In some embodiments, a gas permeable membrane can also be a dehydrated or flexible yet strong matrix such as a collagen or fibrin film or a composite.

In some embodiments, a luminal and/or basal container can comprise ports or channels into which substances can be introduced or extracted. In some embodiments, the ports or channels can be comprised in a cover, a side wall or a bottom wall of the basal and/or luminal containers. Thus, in some embodiments, a cover useful for this present disclosure can comprise at least one port or channel (e.g., about 1, 2, 3, 4, 5, or more) extending from a top or a side surface of the cover to a bottom surface of the cover of the luminal container. In some embodiments, a luminal container can comprise at least one port or channel (e.g., about 1, 2, 3, 4, 5, or more) in a side wall or bottom wall. In some embodiments, a basal container can comprise at least one port or channel (e.g., about 1, 2, 3, 4, 5, or more) in a side wall or bottom wall.

In some embodiments, the method of the present disclosure can further comprise inserting at least one sensor and/or tubing (e.g., glass, rubber, etc.) into the at least one port or channel of the cover and/or the basal container. In some embodiments, the at least one sensor can be, but is not limited to, a gas sensor, a pH sensor, pressure sensor, flow sensor, temperature sensor, and/or a chemical/biological sensor. In some embodiments, the at least one sensor can be, but is not limited to, a needle probe, a microelectrode, a microchip sensor, a membrane sensor, and/or microtip sensor. In some embodiments, the needle probe can be a fiber optic needle probe.

In some embodiments, the method of the present disclosure can further comprise sealing the at least one port or channel (to create a gas barrier and prevent gas exchange outside of the luminal container and/or basal container). In some embodiments, a port or channel can be sealed by inserting a sensor into the port or channel. In some embodiments, tubing that is inserted into a port or channel can be sealed. In some embodiments, sealing of the tubing can be similar to sealing of a port or a channel as described herein. In some embodiments, a seal can be formed between the tubing and/or sensors and an inside wall of the port or channels into which the tubing or sensor is inserted.

In some embodiments, the method further comprises resealing an opened sealed port, channel and/or tubing. In some embodiments, "sealing" and/or "resealing" can comprise the use of a "seal" or a "gas barrier" that includes, but is not limited to, a plug, a cap, a lid, a bung, a coupling, a compression fitting, a gasket, threads, a press fit, induction sealing, an adhesive sealant, a bonded seal, a diaphragm seal, a vacuum seal, a magnet, a heat seal, a glass-to-metal seal, a hermetic seal, a hydrostatic seal, a hydrodynamic seal, an inflatable seal, a labyrinth seal, an end face mechanical seal, a face seal, and/or a wiper seal. In some embodiments, "seal" or a "gas barrier" can be mechanically joined to the luminal reservoir and/or luminal container by gluing, taping, cementing, brazing, soldering, welding, crimping, magnetic force, vacuum force and/or friction force. In some embodiments, fasteners including, but not limited to, screws, clips, clamps, weights, locks, springs, hinges, rivets, buckles, pins, flanges, grommets, hook-and-eye fasteners, hook-and-loop fasteners, latches, nails, pegs, retaining rings, threaded fasteners, bands, snap fasteners, staples, stitches, straps, ties, zippers, and/or toggle bolts can be used to join the "seal" or to create a "gas barrier" to the luminal container and/or luminal reservoir.

In some embodiments, substances can be introduced into or extracted (e.g., purged or drawn) from the luminal reservoir and/or the basal reservoir through the at least one port and/or channel. In some embodiments, a substance that can be introduced into the luminal reservoir or the basal reservoir can include, but is not limited to, a gas, a non-gaseous chemical, a luminal medium, a basal medium, a cell (e.g., a secondary cell), a tissue (e.g., a secondary tissue), an organism, a growth factor, a growth factor receptor, a protein (e.g., an extracellular matrix (ECM) protein), a fatty acid, a hormone, a test compound (e.g., a test drug), an inflammatory mediator, a metabolite (e.g., a microbial metabolite), a neurotransmitter, a nanoparticle, a microparticle, mucous, a carbohydrate, a fiber, an amino acid, a hydrogel or an ion (e.g., proton, chloride, bicarbonate), and the like.

Any substance useful for the growth/maintenance of a cell and/or tissue or for studying the effects of the substance on the cell or tissue can be introduced into a basal reservoir or luminal reservoir. In some embodiments, a substance can include, but is not limited to, fibronectin; laminin; epidermal growth factor (EGF); R-spondin; noggin; cytokines (e.g., interleukin (e.g., IL-6, IL-17, IL-22), tumor necrosis factor (TNF)); ephrin receptors (e.g., EphrinB, EphBs); bone morphogenetic proteins (BMPs, BMP-2, BMP-7); Wnt (wingless-related integration site) (e.g., Wnt3, Wnt3A, and other Wnts); notch signaling factors (notch receptors); Dll1/4; Noggin; Grem1; Grem2; acetate; butyrate; proprionate, desaminotyrosine, catecholamine (e.g., dopamine, norepinephrine) cytokines, and/or short chain fatty acids.

In some embodiments, a gas can be introduced, produced, extracted or consumed in a luminal container, a luminal reservoir, a basal reservoir and/or a basal container. In embodiments in which a gas can be introduced, extracted, produced or consumed, the gas can include, but is not limited to, oxygen, nitrogen, carbon dioxide, carbon monoxide, hydrogen, methane, hydrogen sulphide, skatole (a by-product of meat digestion), indole (a by-product of meat digestion), methanethiol (a sulfur compound), dimethyl sulfide (a sulfur compound), volatile amines, volatile sulfur compounds (VSC), methyl mercaptan, MM (also known as methanethiol, MT), dimethyl disulfide (DMDS) and dimethyl trisulfide (DMTS), volatile fatty acids, and/or nitric oxide.

In some embodiments, a port or channel can be used to extract/purge the atmosphere of a luminal reservoir (or of a basal reservoir) to remove undesired gases produced through, for example, the metabolism of the cells, tissues or organisms. In some embodiments, the purging can be intermittent (e.g., occasionally, as needed, or periodic, e.g., every 30 min., every hour, every 12 hours, every 24 hours, every other day, weekly and the like). In some embodiments, purging can be continuous (for example, once the cells are positions and the cover installed; or once the gradient is steady state or at any designated/desired time). Example gases for which purging can be desirable include, but are not limited to, gases produced via metabolism such as nitrogen, methane and carbon dioxide.

In some embodiments, a luminal medium and/or a basal medium can comprise a dissolved gas. In some embodiments, a luminal medium and/or a basal medium can be saturated (pre-saturated) with a gas. In some embodiments, a gas can be provided by a gas generating material. In some embodiments, when the gas to be provided is oxygen, a basal medium can comprise an oxygen generating material including, but not limited to, $CaO_2$, calcium peroxide, urea peroxide, oxygen containing beads, and/or artificial blood.

In some embodiments, providing at least one gas to a luminal reservoir through at least one port or channel of the cover can assist in generating a gas gradient across a cell support structure. In some embodiments, providing at least one gas to a basal reservoir through at least one port or channel of a basal container can assist in generating a gas gradient across the cell support structure.

In some embodiments, at least one gas can be provided by a gas generating cell, tissue, or organism or at least one gas can be consumed by a gas consuming cell, tissue or organism, thereby assisting with generating and stabilizing a gas gradient. A cell or tissue useful for providing or consuming a gas can be the same cell or tissue as the one or more cells or tissues positioned on a cell support structure or the cell or tissue can be a secondary cell or tissue that can be of the same type or a different type from the one more cells or tissues positioned on a cell support structure. In some embodiments, gas generating or gas consuming cells can be used for faster development of a hypoxic condition, for faster development of a gradient, and/or for generation of a steeper gradient. Secondary cells/tissues or organisms can be positioned in a luminal compartment in contact with the primary cells or can be separated from the primary cells by porous support or the secondary cells/tissues or organisms can be positioned in the basal compartment.

In some embodiments, at least one non-gaseous chemical can be provided by a non-gaseous chemical generating cell, tissue, or organism or at least one non-gaseous chemical can be consumed by a non-gaseous chemical consuming cell, tissue or organism, thereby assisting with setting up and stabilizing a non-gaseous chemical gradient. A cell or tissue useful for providing or consuming a non-gaseous chemical can be the same cell or tissue as the one or more cells or tissues positioned on a cell support structure or the cell or tissue can be a secondary cell or tissue that can be of the same type or a different type from the one more cells or tissues positioned on a cell support structure. In some embodiments, non-gaseous chemical generating or non-gaseous chemical consuming cells can be used for faster development of a gradient, and/or for generation of a steeper gradient. Secondary cells/tissues or organisms can be positioned in a luminal compartment in contact with the primary cells or can be separated from the primary cells by porous support or the secondary cells/tissues or organisms can be positioned in the basal compartment.

In some embodiments, secondary cells, tissues or organisms can also introduced for studying the effects of the secondary cells, tissues or organisms on the one or more cells or tissues of interest positioned on the cell support. In some embodiments, secondary cells, tissues or organisms can also be introduced for studying the effects of the one or more cells or tissues of interest on the secondary cells, tissues or organisms.

A secondary cell or tissue can be the same or a different type of cell or tissue as the one or more cells or tissues positioned on the cell support structure. In some embodiments, a secondary cell can be one type of cell or can be multiple different types of cells. A secondary cell can be, but not is not limited to, any eukaryotic cell lines or primary cells including fibroblasts, myofibroblasts, endothelial cells, adipocytes, muscle cells, bone cells, nervous cells, immune cells, stem cells (embryonic, induced pluripotent stem cells, mesenchymal stem cells, hematopoietic stem cells), cancerous cells and microbes, or a combination of any of these as a monolayer, spheroid, or organoid. In some embodiments, secondary cells can be from healthy, inflamed, or diseased human or animal tissue. In some embodiments, a secondary cell or tissue can be in a culture format of a patch or monolayer. In some embodiments, a secondary cell or tissue can be in a culture format including, but not limited to, a three dimensional (3D) system that includes, but is not limited to, in vitro or ex vivo culture (with or without embedding in a natural or artificial hydrogel), an entire organism, entire or partial organ, or ex vivo tissue section.

An organism useful with this present disclosure for consuming or producing a gas or a non-gaseous chemical, for studying the effects of secondary cells, tissues or organisms on the one or more cells or tissues of interest, or for studying the effects of the one or more cells or tissues of interest on the secondary cells, tissues or organisms can include, but is not limited to a microorganism (e.g., bacterium, fungus, virus), an amoeba, a helminth (e.g., tapeworms, pin worms, hook worms, whipworms, etc.), virus and/or a protozoan (e.g., giardia, etc.) and can include benign/commensal organisms and/or infectious/pathogenic organisms.

A microorganism useful with this present disclosure can include any bacterium (gram negative and gram positive), fungus (unicellular or multicellular), and/or archaeon that is now known or later identified as a consumer or generator of a gas or a non-gaseous chemical of interest.

In some embodiments, a bacterium useful with the present disclosure can be a type found in ordinary or healthy gut flora (or "microbiome") of a mammal (e.g., a human, a dog, a horse, a cow, a cat, a sheep, and the like). Such bacteria are well-known, see, e.g., US Patent Application Publication No. US 2014/0093478, which describes human gut bacteria that can be useful with this present disclosure. In some embodiments, a microorganism useful with this present disclosure can be a pathogenic bacterium, including, but not limited to, *Clostridium, Cholera, Salmonella*, and/or *Shigella*. Accordingly, in some embodiments, a bacterium useful with this present disclosure can include, but is not limited to, *Acinetobacter baumannii, Actinomyces israelii, Bacillus anthracis, Bacteroides fragilis, Bartonella henselae, Bordetella pertussis, Borrelia burgdorferi, Borrelia garinii, Borrelia afzelil, Borrelia recurrentis, Brucella abortus, Brucella canis, Brucella melitensis, Brucella suis, Burkholderia pseudomallei, Campylobacter jejuni, Chlamydia pneumoniae, Chlamydia trachomatis, Chlamydophila psittaci, Clostridium botulinum, Clostridium difficile, Clostridium perfringens, Clostridium tetani, Corynebacterium amycolatum, Corynebacterium diphtheriae, Coxiella burnetii, Ehrlichia canis, Ehrlichia chaffeensis, Enterococcus faecalis, Enterococcus faecium, Escherichia coli*, Enterotoxigenic *Escherichia coli*, Enteropathogenic *Escherichia coli*, Enteroinvasive *Escherichia coli*, enterohemorrhagic *Escherichia coli, Francisella tularensis, Haemophilus influenzae, Helicobacter pylori, Klebsiella pneumoniae, Legionella pneumophila, Leptospira species, Listeria monocytogenes, Mycobacterium leprae, Mycobacterium tuberculosis, Mycoplasma pneumoniae, Neisseria gonorrhoeae, Neisseria meningitidis, Parachlamydia, Pseudomonas aeruginosa, Nocardia asteroides, Rickettsia rickettsii, Salmonella, Shigella, Staphylococcus aureus, Staphylococcus epidermidis, Staphylococcus saprophyticus, Streptococcus agalactiae, Streptococcus pneumoniae Streptococcus pyogenes, Streptococcus viridans, Treponema pallidum, Vibrio cholerae, Vibrio vulnificus, Vibrio parahaemolyticus*, and/or *Yersinia*, or any combination thereof.

In some embodiments, an organism useful with this present disclosure can be a virus including, but not limited to, a Simplexvirus, Varicellovirus, Cytomegalovirus, Roseolovirus, Lymphocryptovirus, Rhadinovirus, Mastadenovirus, Alphapapillomavirus, Betapapillomavirus, Gammapapillomavirus, Mupapillomavirus, Nupapillomavirus, Polyomavirus, Molluscipoxvirus, Orthopoxvirus, Parapoxvirus, Alphatorquevirus, Betatorquevirus, Gammatorquevirus, Gemycircularviruses, Erythrovirus, Dependovirus, Bocavirus, Coltivirus, Rotavirus, Seadornavirus, Hepevirus, Alphacoronavirus, Betacoronavirus, Torovirus, Mamastrovirus, Norovirus, Sapovirus, Flavivirus, Hepacivirus, Pegivirus, Cardiovirus, Cosavirus, Enterovirus, Hepatovirus, Kobuvirus, Parechovirus, Rosavirus, Salivirus, Alphavirus, Rubivirus, Deltavirus, Lyssavirus, Vesiculovirus, Filoviridae, Ebolavirus, Marburgvirus, Paramyxoviridae, Henipavirus, Morbilivirus, Respirovirus, Rubulavirus, Metapneumovirus, Pneumovirus, Arenavirus, Peribunyaviridae, Orthobunyavirus, Hantavirus, Nairovirus, Phenuiviridae, Phlebovirus, Influenzavirus A Influenzavirus B, Influenzavirus C, Thogotovirus, Gammaretrovirus Deltaretrovirus, Lentivirus, Spumavirus, and/or Orthohepadnavirus, or any combination thereof.

In some embodiments, an organism useful with the present disclosure can be a fungus that is now known or later identified as a consumer or generator of a gas or a non-gaseous chemical of interest. Fungi that interact with the one or more cells or tissues of interest naturally as commensal or pathogenic organisms are also useful with this present disclosure. In some embodiments, a fungus useful with the present disclosure can be unicellular. In some embodiments, a fungus useful with the present disclosure can be multicellular (mycelial). In some embodiments, a fungus can include, but is not limited to, a fungus from the genus *Aspergillus, Blastomyces, Candida, Coccidioides, Cryptococcus neoformans, Cryptococcus* (e.g., *Cryptococcus gattii*), *Histoplasma, Rhizopus, Mucor, Lichtheimia, Pneumocystis* (e.g., *Pneumocystis jirovecii*), *Sporothrix*.

In some embodiments, an organism useful with the present disclosure can be a protozoan including, but not limited to, *Entamoeba histolytica, Cryptosporidium parvum, Cryptosporidium hominis, Cyclospora cayetanensis*, and/or *Giardia lamblia*.

In some embodiments, a gas can be provided and/or consumed using more than one method. Thus, for example, a gas can be provided directly, provided by a gas generating material, and/or provided by a gas generating cell, tissue and/or organism; consumed by gas consuming materials, and/or by a gas consuming cell, tissue and/or organism, and the like.

In some embodiments, at least one gas generating/consuming organism can be present in the basal medium and can provide the gas to the one or more cells and/or tissue through a gas permeable membrane of the bottom wall, thereby generating a gradient across the cell support structure between the basal medium and the luminal reservoir.

In some embodiments, the at least one gas generating/consuming organism can be in a luminal medium positioned in a luminal reservoir and in direct contact with the one or more cells positioned on the cell support structure, thereby providing gas directly to the one or more cells and/or tissue and generating a gradient across the cell support structure between the luminal medium and the basal reservoir, or consuming a gas in the luminal reservoir, thereby generating a gradient across the cell support structure between the luminal medium and the basal reservoir.

In some embodiments, the methods of the present disclosure provide a gas generating/consuming organism in the same luminal container as the one or more cells and/or tissue, the method comprising: providing a luminal container comprising a bottom wall, at least one sidewall extending upwardly from the bottom wall, and a top opening defined by the at least one sidewall; positioning a first cell support structure on the bottom wall; positioning a second cell support structure above the first cell support structure; positioning a one or more cells and/or tissue on the second cell support structure; positioning a gas generating organism on the first cell support structure; installing a cover on the luminal container to close the open top, wherein a luminal reservoir is defined between a bottom surface of the cover and the second cell support structure and/or the one or more cells and/or tissue; and generating a gas gradient (higher to lower) between the gas generating organism on the first cell support structure and through the one or more cells and/or tissue into the luminal reservoir (the gradient generated perpendicularly through the one or more cells and/or tissue).

In some embodiments, a non-gaseous chemical gradient can be generated using the methods and devices of the present disclosure. In some embodiments, the one or more cells or tissues positioned on the cell support structure can be a generator or a consumer of a gas/or a non-gaseous chemical, thereby generating a gradient of a non-gaseous chemical across a cell support structure (perpendicularly through the one or more cells and/or tissue). A non-gaseous chemical gradient can be across a cell support structure in either direction. Thus, in some embodiments, a non-gaseous chemical gradient that is generated can have a higher concentration of the non-gaseous chemical in the basal reservoir and/or container and a lower concentration of the non-gaseous chemical in the luminal reservoir and/or container or a non-gaseous chemical gradient that is generated can have a lower concentration of the non-gaseous chemical in the basal reservoir and/or container and a higher concentration of the non-gaseous chemical in the luminal reservoir and/or container. In some embodiments, when more than one non-gaseous chemical gradient is generated, the gradient for each non-gaseous chemical can be across a cell support structure in the same direction or in a different direction.

In some embodiments, a non-gaseous chemical producing or consuming cell, tissue or organism can be introduced into a basal medium or luminal medium, thereby generating the gradient across a cell support structure (perpendicularly through the one or more cells and/or tissue). In some embodiments, an introduced non-gaseous chemical producing or consuming cell, tissue or organism can be non-adherent and suspended in the medium. The non-gaseous chemical producing or consuming cell, tissue or organism can also be adherent and grown side by side with cells/tissues of interest (e.g., one or more cells or tissues positioned on a cell support structure) or they can be adhered on a separate cell support structure within a luminal chamber or a basal chamber. A non-gaseous chemical producing or consuming cell, tissue or organism can be the same as or different from the gas producing/consuming cells, tissues or organisms as described herein (e.g., different or the same as a secondary cell, tissue, or organism) and/or can be different from or the same as the one or more cells/tissue positioned on the cell support structure.

In some embodiments, a non-gaseous chemical producing or consuming cell, tissue or organism can also be positioned on the other side of a cell support structure from the one or more cells/tissues of interest. For example, a non-gaseous chemical producing cell, tissue or organism can be located on the bottom of a cell support structure so that the non-gaseous chemical producing cell, tissue or organism is exposed to the basal side but the chemical produced by the non-gaseous chemical producing cell, tissue or organism can diffuse through the cell support structure to the one or more cells/tissues of interest located on the support structure in the luminal side of the support structure.

In some embodiments, a non-gaseous chemical can be introduced directly into a basal medium or into a luminal medium, thereby generating a gradient of the non-gaseous chemical across a cell support structure (perpendicularly through the one or more cells and/or tissue) from the luminal medium to the basal medium or from the basal medium to the luminal medium.

In some embodiments, a non-gaseous chemical can include, but is not limited to, a protein, a fatty acid, a growth factor, a hormone, a metabolite, an ion, a carbohydrate (e.g., sugar), a peptide, a lipopeptide, an amino acid, a test drug, an extracellular matrix (ECM) protein, a growth factor and/or receptor(s), and/or an inflammatory mediator. In some embodiments, a non-gaseous chemical can include, but is not limited to, fibronectin, laminin, epidermal growth factor (EGF), R-spondin; noggin; cytokines (e.g., interleukin (e.g., IL-6, IL-17, IL-22), tumor necrosis factor (TNF)), ephrin receptors (e.g., EphrinB, EphBs), bone morphogenetic proteins (BMPs, BMP-2, BMP-7), Wnt (wingless-related integration site) (e.g., Wnt3, Wnt3A, other Wnts), notch signaling factors (notch receptors), Dll1/4, Noggin, Grem1, Grem2, acetate; butyrate; proprionate, desaminotyrosine, and/or catecholamine (e.g., dopamine, norepinephrine). In some embodiments, the non-gaseous chemical can be butyrate; proprionate, desaminotyrosine, catecholamine as provided by a microorganism.

In some embodiments, a gas gradient that is generated can be stable in about 30 minutes to about six hours, in some embodiments, in about 30 minutes, about an hour, about two hours, about three hours, about four hours, about five hours or about six hours.

In some embodiments, a gas gradient can be self-sustaining. As used herein, "self-sustaining" refers to a gas gradient that is maintained in a stable state by the consumption or production of the gas by the one or more cells and tissue positioned on a cell support structure in a closed system for at least about four hours to about one month or more (e.g., indefinitely, for as long as the cells are living), or in some embodiments about 4, 8, 12, 24, 36, or 48 hours or more, or in some embodiments about 1, 2, 3, 4, 5, 6, 7, 8, 9, 10, 15, 20, 25, 30 days or more. A self-sustaining gas gradient returns to its stable profile following disruptions such as media changes (each compartment within +/−1% of the target concentration). This stable profile is distinct from that attainable without the walls, and/or permeable membrane, and/or luminal lid.

In some embodiments, a gas gradient can be modulated by mixing of the basal medium. Mixing of the basal medium can generate a steeper gradient more quickly than without mixing and a stable gradient can be achieved more quickly with mixing. Mixing can be implemented in one compartment or an entire system in order to obtain uniform or proper oxygen saturation within a compartment(s). In some embodiments, mixing can be provided by a magnetic stirrer, a shaker plate, an orbital shaker, a vortexer, a rocker, gas induced turbulence, surface acoustic waves, or any combination thereof. In some embodiments, mixing can further include, but is not limited to, a mechanical agitator (e.g., a bead and/or other particle). In some embodiments, mixing can be accomplished by gas-induced turbulence provided by, for example, electrodes within the apparatus. For steeper oxygen gradients, oxygen transfer from the air to the medium can be facilitated by mixing, or using oxygen permeable material in the bottom of the medium reservoir such as PDMS, polyurethane, or high Dk contact lens material including Fluoroperm polymers or paflufocon polymers. Oxygen generating materials including, for example, $CaO_2$, calcium peroxide, urea peroxide, oxygen containing beads, or artificial blood, can be added to the basal medium to increase the oxygen saturation and/or to apply oxygen gradients across the cells. In some embodiments, a basal compartment can contain a vasculature or vasculature mimicking channels that can deliver liquids, micro/nanoparticles, and/or microbes to supply or deplete oxygen or other gas(es).

In some embodiments, a gradient can be modulated by providing a second permeable membrane in the luminal container. In some embodiments, the second permeable membrane can be placed above a first permeable membrane. In some embodiments, the first permeable membrane can be the bottom wall of the luminal container. In some embodiments, the bottom wall of the luminal container comprises an impermeable membrane and the first permeable membrane can be above the bottom wall. In some embodiments, a second permeable membrane can be provided by inserting a first luminal container inside a second luminal container. In some embodiments, a second permeable membrane can modulate a gradient by steepening the gradient. In some embodiments, a second permeable membrane can provide a stable gradient more quickly.

In some embodiments, a gradient can be modulated by selection of the cells or tissue positioned on the cell support structure or the secondary cells, tissues or organisms that are introduced. Cells or tissues can be selected, for example, for their rate of gas consumption, rate of gas production, their rate of non-gaseous chemical consumption, rate of non-gaseous chemical production, ability to tolerate hypoxic/normoxic conditions, ability to produce/eliminate other gases and/or non-gaseous chemicals, or any combination thereof.

Final oxygen levels and time to reach desired oxygen levels can be manipulated by, for example, adjusting oxygen permeability of the materials (Table 1), the thickness of the materials, the volume of the (luminal and basal) medium, or the volume of the gas inside the cell reservoir or using more than one material for each compartment or within one compartment. For example, the luminal reservoir and gas barrier can be made out of materials with low oxygen permeability, while the basal reservoir can be made wholly or partially out of relatively thin material and/or materials with high oxygen permeability.

TABLE 1

Oxygen permeability of elastomers and polymers

| Material | $O_2$ Permeability $(m^2 \cdot s^{-1} \cdot Pa^{-1})$ |
|---|---|
| Fluorinated ethylene propylene | $1.3 \times 10^{-12}$ |
| Polydimethyl siloxane | $6 \times 10^{-14}$ |
| Polystyrene | $2.0 \times 10^{-17}$ |
| Polycarbonate | $1.1 \times 10^{-17}$ |
| Polypropylene | $6.8 \times 10^{-18}$ |
| Polyethylene terephthalate | $4.1 \times 10^{-19}$ |

TABLE 1-continued

Oxygen permeability of elastomers and polymers

| Material | $O_2$ Permeability $(m^2 \cdot s^{-1} \cdot Pa^{-1})$ |
|---|---|
| Acrylonitrile | $4.5 \times 10^{-20}$ |
| Ethylene vinyl alcohol | $7.7 \times 10^{-22}$ |

Accordingly, in some embodiments, a gas gradient can be modulated by modifying the volume of the luminal reservoir, the volume of the basal reservoir, the gas permeability of the cell support structure, the gas permeability of the side wall of the luminal container, the gas permeability of the bottom wall of the luminal container, and/or the gas permeability of the cover, or any combination thereof. In some embodiments, the gas permeability of the side wall of the luminal container, the bottom wall of the luminal container, the cover, the side wall of the basal container, and/or the bottom wall of the basal container can be modulated by selecting materials for construction based on gas permeability and thicknesses.

In some embodiments, a gas gradient can be modulated by modifying the volume of the basal medium, the gas permeability of the side wall of the basal container, and/or the gas permeability of the bottom wall of the basal container, or any combination thereof.

In some embodiments, the materials for construction of a container of this present disclosure and parts thereof (e.g., luminal container/reservoir, the basal container/reservoir, cover, and parts thereof (e.g., plug, seal, cap, etc.)) can include, but are not limited to, plastic, polyester, natural rubber, synthetic rubber, elastomers, glass and/or metal. In some embodiments, the materials for construction of the containers of this present disclosure, and parts thereof, can include, but are not limited to, polystyrene (PS), polyethylene (PE), polypropylene (PP), polyvinylchloride (PVC), polymethylmethacrylate (PMMA), acrylonitrile butadiene styrene (ABS), acryl styrene acrylonitrile (ASA), styrene acrylonitrile (SAN), nylon, polycarbonate (PC), polyethylene terephthalate (PET), polyphenylene oxide, ethylene-vinyl acetate (EVA), cycloolefin copolymer (COC), polytetrafluoroethylene (PTFE), polyether ether ketone (PEEK), acetal polymer, acrylic resin, epoxy, thermosetting polyester resin, polyurethanes, furan, polydimethylsiloxane (PDMS), silicone rubbers, VITON™, polychloroprene, nitrile rubber, polyurethane rubber, natural rubber, ethylene propylene diene monomer (EPDM), fluorocarbon rubber, borosilicate, sodalime, quartz, aluminum, steel, stainless steel, or any combination thereof.

Apparatuses, Devices and Systems

The present disclosure further provides for an apparatus useful in the method(s) of producing a hypoxic condition or for generating a gas gradient across a cell support structure. Thus, in some embodiments, an apparatus for producing hypoxic conditions in in vitro and/or ex vivo cell culture and/or for generating a gas gradient across a cell support structure can comprise: a luminal container comprising a bottom wall, at least one sidewall extending upwardly from the bottom wall, and an open top having a cross-sectional opening that is defined by the at least one sidewall; a cell support structure on the bottom wall; and a cover that is configured to engage within and/or against the luminal container and close the open top in an installed position, wherein a luminal reservoir is defined between a bottom surface of the cover and the cell support structure when the cover is in the installed position, and wherein the apparatus is configured to generate a hypoxic condition in the luminal reservoir when the cover is in the installed position (see, e.g., FIGS. 1A-1K). In some embodiments, one or more cells and/or tissue can be positioned on the cell support structure.

In some embodiments, hypoxic conditions that are produced using the devices of the present disclosure are self-sustaining.

In a first example embodiment, illustrated in FIGS. 1A-1C, an apparatus, generally designated 100, comprises a basal reservoir, generally designated 120, in which a luminal reservoir, generally designated 140, is at least partially arranged. As shown, a cover 160 is removably (e.g., threadably) inserted and secured within an open end of the luminal reservoir such that, when the cover 160 is in an installed position, the luminal reservoir 140 and the cover 160 are substantially sealed together in a gas-tight arrangement, thereby allowing for the creation of a hypoxic environment within the luminal reservoir 140. In the embodiment shown, the luminal basin has, on a side that is distal from the basal reservoir 120, one or more threads, generally designated 144, formed on an inner surface thereof. The cover has, on an outer surface thereof, one or more corresponding threads, generally designated 164, that interlock (e.g., threadably engage with) with threads 144 to form the gas-tight seal within the luminal reservoir 140 when the cover is in the installed position within the luminal reservoir 140. Cover 160 further comprises, in the embodiment shown, a cover flange 162 that rests against a luminal reservoir flange 152 to provide an enhanced seal about the luminal reservoir 140. In some embodiments, a gasket can be positioned on, and/or in a slot formed in, the cover flange 162 and/or the luminal reservoir flange 152. In the embodiment shown, the cover 160 is substantially solid, however, the cover 160 may also be hollow or of any suitable construction type capable of creating and maintaining a hypoxic environment within the luminal reservoir 140 when the cover 160 is installed thereon.

As can be seen FIGS. 1A-1C, which illustrate a first example embodiment of the apparatus 100, the basal reservoir 120 has a generally cylindrical shape, one end of which is enclosed by a bottom wall 122 and a height of which is defined by the dimensions of the cylindrically-shaped sidewall 124. The end of the basal reservoir 120 opposite the bottom wall 122 is substantially open (e.g., unobstructed) and a basal flange 126 is attached to at or adjacent to the open end of the basal reservoir 120 and extends radially away therefrom. As shown in FIG. 1C, the flange 126 can be used to support the apparatus 100 within a plurality of holes formed within an array formed, for example, as part of a microtiter plate, generally designated 10. Stated somewhat differently, a microtiter plate 10 can comprise a basal reservoir 120 comprising a plurality of wells or a shared basal well and a plurality of luminal reservoirs 140, wherein each of the luminal reservoirs 140 is held in one of the basal wells or the shared basal well.

The luminal reservoir 140 shown in this embodiment has a generally cylindrical shape, such that the luminal reservoir will fit concentrically within, yet radially spaced apart from, the basal reservoir 140. The bottom surface of the luminal reservoir 140 that rests within the basal reservoir 120 during operation comprises a bottom wall 170, which can be in the form of a porous membrane, over which a collagen scaffold 172 can be deposited, arranged, and the like. The luminal reservoir has a wall 142 that extends away from the bottom wall 170 in a substantially vertical direction. At least two support arms 156 extend radially outwardly from the wall 142 of the luminal reservoir in a position that will contact the flange 126 of the basal reservoir 120 to support the luminal reservoir 140 within the basal reservoir 120. One or more of the support arms 156 can have keyed features (e.g., steps) formed therein that will ensure adequate spacing of the luminal reservoir 140 within the basal reservoir 120. One or more of the support arms 156 may have a slot formed circumferentially therein to allow for the circulation of ambient air, oxygen, or a combination thereof through the slot formed in the support arms 156, into the space between the basal reservoir 120 and the luminal reservoir 140, when the luminal reservoir 140 is installed within the cavity of the basal reservoir 120.

The wall 142 of the luminal reservoir 140 is shorter than the sidewall 124 of the basal reservoir 120, such that, when the support arms 156 are in contact with the flange 126 of the basal reservoir, bottom wall 170 is spaced apart from the inner surface of the bottom wall 122 of the basal reservoir 120. This space between the bottom wall 170 and the inner surface of the bottom wall 122 of the basal reservoir 120 defines a basal fluid region, generally designated 180. Similarly, a luminal fluid region, generally designated 182, is contained within the luminal reservoir 140, on an opposite side of the bottom wall 170 from the basal fluid region 180 and substantially sealed within the luminal reservoir 140 when the cover 160 is engaged with the luminal reservoir 140 in the installed position. The end of the luminal reservoir 120 distal from the bottom wall 170 is substantially open to allow for the cover 160 to be inserted and secured therein.

While basal reservoir 120 and luminal reservoir 140 each have a substantially cylindrical shape, one or both of the basal reservoir 120 and the luminal reservoir 140 can have a non-cylindrical shape. In fact, while it is generally true that the luminal reservoir 140 must be sufficiently smaller than the basal reservoir 120 to fit at least a portion thereof necessary for proper operation of the apparatus, basal reservoir 120 and luminal reservoir 140 can have any shape, including those that are both complementary or non-complementary to each other.

In some embodiments, the cover 160 engages the luminal reservoir 140 in the installed position (see, e.g., FIGS. 1A-1C). In some embodiments, each of an inner surface of the at least one wall 142 of the luminal reservoir 140 and an outer surface of the cover 160 comprise threads 144, 164, respectively, and the cover 160 is configured for threadable engagement with the luminal reservoir 140 when in the installed position.

In some embodiments, the basal reservoir 120 comprises a bottom wall and at least one sidewall 124 extending upwardly from the bottom wall. The bottom wall 122 and the at least one sidewall 124 define a well. The luminal reservoir 140 is held within the well of the basal reservoir 120. The bottom wall of the basal reservoir 120 is spaced apart from the bottom wall of the luminal reservoir 140. A basal fluid region 180 is defined between the bottom wall of the basal reservoir 120 and the bottom wall 170 of the luminal reservoir 140 and/or between the at least one sidewall 124 of the basal reservoir 120 and the at least one sidewall 142 of the luminal reservoir 140. In some embodiments, the bottom wall 170 of the luminal reservoir 140 comprises a porous membrane, a semipermeable membrane, a low permeability membrane, or an impermeable membrane. In some embodiments, the bottom wall 170 of the luminal reservoir 140 comprises an oxygen-permeable membrane.

In some embodiments, apparatus 100 further comprises a basal medium in the basal fluid region 180 within the basal reservoir 120. In some embodiments, the basal medium can be configured to provide a gas or non-gaseous chemical to be adjacent to the bottom wall 170. In some embodiments, the basal medium can be configured to provide, for example, oxygen to the one or more cells and/or tissue of the collagen scaffold 172 arranged on or adjacent to the bottom wall 170 within the luminal fluid region 182 within the luminal reservoir 140.

FIGS. 1D-1F show a second example embodiment of the apparatus, generally designated 101. In the illustrations of this embodiment, features that are the same as, or substantially similar to, the features described elsewhere herein regarding the first embodiment of apparatus 100 use like reference numerals. In apparatus 101, the basal reservoir 120 and the luminal reservoir 140 are substantially similar to those used and described in apparatus 100 of FIGS. 1A-IC. However, a mixer 182, which can be, for example, a magnetically driven stir bar, is disposed within the basal fluid region 180. In this embodiment, the cover 260 comprises a release port 266 formed through an entire thickness of the cover 260, such that release port extends from the upper surface of the cover 260 to be adjacent to, and in fluidic communication with, the luminal fluid region 182 within the luminal reservoir 140. As such, the release port 266 allows for fluid to be extracted from, introduced to, and/or circulated through luminal fluid region 182. A release port plug 268 is provided, in this embodiment, in a position such that the release port plug 268 is removably inserted into the release port 266 to prevent fluid exchange to and/or from the luminal fluid region via the release port 266 when the release port plug is installed. In some embodiments, the release port 266 can be inclined, relative to a vertical direction, or a non-linear shape, including shapes that have angles of substantially 90° or more formed therein.

In the embodiment shown in FIGS. 1D-1F, the release port 266 is in a form of a channel extending from a top surface of the cover 160 to a bottom surface of the cover 160 that is within the luminal reservoir 140 when in the installed position. In some embodiments, the release port plug 268 can be removed, temporarily or permanently, and a sensor can be installed through the length of the release port 266, passing through the entire thickness of the cover 160 to be adjacent to, and/or disposed at least partially in, the luminal fluid within the luminal fluid region 182. In some embodiments, such a sensor can be configured to extend through the release port 266 and into the luminal reservoir 140 to measure an oxygen saturation level therein. As shown in FIG. 1F, the flange can be used to support the apparatus 100 within a plurality of holes formed within an array formed, for example, as part of a microtiter plate, generally designated 10.

As discussed hereinabove, the release port 266 can be sealed to create a gas barrier and prevent gas exchange outside of the luminal reservoir 140 and/or basal reservoir 120. In some embodiments, the release port 266 can be sealed around a sensor at the top surface of the cover 260. In some embodiments, the release port 266 can be sealed by inserting a sensor therein. In some embodiments, tubing that is inserted into the release port 266 can be sealed. In some embodiments, sealing of the release port 266 can be similar to the sealing of a port or a channel, as described herein. In some embodiments, a seal can be formed between the tubing and/or sensors and an inside wall of the release port 266 into which the tubing or sensor is inserted. In some embodiments, the apparatus 101 can comprise an annular gasket extending along at least a portion of a length of the release port 266, wherein the gasket can be configured to receive a sensor therethrough and seal the release port 266.

As shown in FIGS. 1D-1F, apparatus 101 can further comprise a stirring device 184 configured to stir the basal medium within the basal fluid region 180 within the basal reservoir 120. In some embodiments, the stirring device 184 can comprise a magnetic stirrer (e.g., a magnetic stir bar), a shaker plate, an orbital shaker, a vortexer, a rocker, gas-induced turbulence, surface acoustic waves, or any combination(s) thereof. In some embodiments, the stirring device 184 can further include, but is not limited to, a mechanical agitator (e.g., a bead and/or other particle). In some embodiments, the stirring device 184 comprises gas-induced turbulence provided by, for example, electrodes within the apparatus 101.

FIGS. 1G and 1H show a third example embodiment of the apparatus, generally designated 102. In the illustrations of this embodiment, features that are the same as, or substantially similar to, the features described elsewhere herein regarding the first and/or second embodiments of apparatus 100,101 use like reference numerals. In apparatus 102, the luminal reservoir, generally designated 340, comprises a different configuration for the support arms 156, having three support arms 156 with "keyed" alignment features formed on the underside thereof to maintain adequate circumferential spacing between the wall 124 of the basal reservoir 120 and the wall 142 of the luminal reservoir 340. This circumferential spacing can generally be in the form of a hollow cylindrical prism to allow oxygen to come into contact with the basal fluid within the basal fluid region 182.

Apparatus 102 further comprises a cover, generally designated 360, that comprises a plurality of through-holes, generally designated 370, formed through the entire thickness of the cover 360. Through-holes 370 are configured such that one or more sensors 372, such as, for example, a temperature sensor, can extend therethrough to be adjacent to, or immersed in, the luminal fluid within the luminal fluid region 182. In the embodiment shown, a plurality of inlet/outlet ports are provided through a respective one of the through-holes 370. Regardless of whether a sensor 372 or an inlet/outlet port 374A, 374B is arranged within the through-holes 370, it is advantageous to provide a seal in the form of an elastic (e.g., rubber or any suitable elastomeric material) annular gasket 371 along a portion (e.g., all) of the length of the through-holes 370 to maintain the desired atmospheric conditions (e.g., hypoxic) within the luminal fluid region 182.

Unlike the threaded engagement of the first and second example embodiments, which could also be implemented in the embodiment shown in FIGS. 1G and 1H, the cover 360 comprises a plurality of keyed protrusion features (e.g., tabs 364) that extends radially outward from the portion of the cover 360 that extends into the luminal reservoir 340 when in the installed position. The walls 142 of luminal reservoir 340 comprise, on an inner surface thereof, notches that extend circumferentially around the luminal reservoir 140 and has a depth less than a thickness of the wall 142 of the luminal reservoir 340. This slot formed in the wall 142 of the luminal reservoir 340 is defined, on a top side thereof, by a circumferentially protruding ring 344, which has gaps formed radially therein to allow the tabs 364 to pass therethrough and be retained within the slot after the cover 360 is rotated so that the tabs 364 are no longer aligned with the gaps formed in the ring 344. The tabs 344 are dimensioned to have a height that is smaller than the height of the slot defined by the ring 344, such that a gasket 354, which is in the form of an O-ring in this embodiment, can be sealingly arranged between the cover 360 and the lower surface of the slot formed in the luminal reservoir 340. In some embodiments, In some embodiments, the sensor 372 can be a gas sensor, a pH sensor, a pressure sensor, a flow sensor, a temperature sensor, and/or a chemical/biological sensor. In some embodiments, the sensor 372 can be, but is not limited to, a needle probe, a microelectrode, a microchip sensor, a membrane sensor, and/or a microtip sensor. In some embodiments, such a needle probe can be a fiber optic needle probe. In some embodiments, the sensor 372 can be an oxygen sensor, a nitrogen sensor, a hydrogen sensor, a methane sensor, a carbon dioxide sensor, a carbon monoxide sensor, a sulphide sensor, a skatole sensor, an indole sensor, a methanethiol sensor, a dimethyl sulfide sensor, a volatile amine sensor, a volatile sulfur compounds (VSC), a methyl mercaptan or methanethiol sensor, a dimethyl disulfide (DMDS) sensor, a dimethyl trisulfide (DMTS) sensor, a volatile fatty acid sensor, and/or a nitric oxide sensor.

As discussed hereinabove, the through-holes 370 can be sealed to create a gas barrier and prevent gas exchange outside of the luminal reservoir 340 and/or basal reservoir 120. In some embodiments, one or more of the through-holes 370 can be sealed around a sensor at the top surface of the cover 360. In some embodiments, the one or more of the through-holes 370 can be sealed by inserting a sensor therein. In some embodiments, tubing that is inserted into one or more of the through-holes 370 can be sealed. In some embodiments, sealing of one or more of the through-holes 370 can be similar to the sealing of a port or a channel, as described herein. In some embodiments, a seal can be formed between the tubing and/or sensors and an inside wall of one or more of the through-holes 370 into which the tubing or sensor is inserted. In some embodiments, the apparatus 102 can comprise an annular gasket 371 extending along at least a portion of a length of one or more of the through-holes 370, wherein the gasket can be configured to receive a sensor therethrough and seal a corresponding one of the through-holes 370.

In the embodiments shown in FIGS. 1G-1K, a through-hole 370, 470 (or channel) extending from a top surface of the cover 160 to the bottom surface of the cover 160 can be a first through-hole 370; and at least one second through-hole 370 extends from the top surface of the cover 160 to the bottom surface of the cover 160. In some such embodiments, the at least one second through-hole 370 can be used for introducing substances into, or extracting substances from, the luminal reservoir 340. For example, the at least one second through-hole 370 can be used for adding test drugs, adding test microbes, and/or exchanging medium in the luminal reservoir 340. In some such embodiments, at least one second through-hole 370 can be configured to receive a sensor 372 therethrough. In some embodiments, at least one second through-hole 370 can be configured to receive any useful sensor, as described herein. In some such embodiments, at least one second through-hole 370 can be configured to receive a sensor 372 therethrough. In some embodiments, the at least one second through-hole 370 can be configured to receive any useful sensor, as described herein. In some embodiments, at least one second through-hole 370 can be configured to receive a pH sensor and/or a chemical sensor therethrough. In some embodiments, the apparatus 102 can comprise at least one annular gasket 371 extending along at least a portion of a length of the at least one second through-hole 370, wherein the at least one annular gasket 371 can be configured to receive the sensor 372 therethrough and seal the at least one second through-hole 370. In some embodiments, the at least one second through-hole 370 can be sealable (e.g., at the top surface of the plug).

In some embodiments, the cover 160, 260, 360, 460 can have the same diameter as the inner diameter of the luminal reservoir 140, 340, 440. In some embodiments, an annular gasket 354 (e.g., an o-ring) can be disposed between the cover 360 and the luminal reservoir 340 when the cover 360 is in the installed position. In some embodiments, the apparatus 102 comprises a seat (e.g., opposite ring 344) that can be defined in the at least one sidewall of the luminal reservoir 340 and a gasket 354 can rest on the. In the embodiment shown, the luminal reservoir 340 and the cover 360 comprise a locking mechanism configured to lockingly engage the luminal reservoir 340 and the cover 360 together. In this embodiment, the cover 360 comprises a locking fin (e.g., tab 364) and the wall 142 of the luminal reservoir 340 comprises a recess (e.g., a slot) formed circumferentially about an inner surface thereof, which is configured to receive the locking fin when the cover 360 is in the installed position.

In the embodiment shown in FIGS. 1J and 1K, a fourth example apparatus, generally designated 103, is shown. In the illustrations of this embodiment, features that are the same as, or substantially similar to, the features described elsewhere herein regarding the first and/or second embodiments of apparatus 100, 101, 102 use like reference numerals. In apparatus 103, the luminal reservoir, generally designated 440, has a slot formed on an upper surface 152 thereof, such that the open end of the slot is adjacent to the cover 460 when the cover 460 is in the installed position. A ring-shaped gasket 454 is provided within the slot of the luminal reservoir 440 such that the cover 460 can be sealingly pressed thereagainst when in the installed position. In some embodiments, the gasket 454 can rest on an upper surface 152 of the at least one sidewall of the luminal reservoir 440. The cover 460 comprises, as was shown in apparatus 102, a plurality of through-holes 470, which can advantageously be sealed with annular gaskets 471 extending part or all of the length of the through-holes 470. Through-holes 470 are formed through the entire thickness of the cover 460. Through-holes 470 are configured such that one or more sensors 472, 474, 476, such as, for example, a pH sensor 474, an oxygen sensor 472, and a glucose sensor 476, can extend through a corresponding one of the through-holes 470 to be adjacent to, or immersed in, the luminal fluid within the luminal fluid region 182. In the embodiment shown, the cover 160 is advantageously weighted (e.g., with a material having a large mass embedded therein) to press the flange 162 of the cover 460 against the gasket 454 to form a seal thereagainst. The luminal reservoir 440 is spaced circumferentially spaced apart (e.g., within) the basal reservoir 120 by keyed features formed in support arms 156, thereby forming an annular passage to allow oxygen to come into contact with the basal fluid within the basal fluid region 182.

FIG. 2A illustrates computational results of oxygen saturation in an apparatus such as that disclosed herein and illustrated in FIGS. 1A-1K.

In some embodiments, a seal can include, but is not limited to, a plug, a cap, a lid, a bung, a coupling, a compression fitting, a gasket, threads, a press fit, an induction sealing, an adhesive sealant, a bonded seal, a diaphragm seal, a vacuum seal, a magnet, a heat seal, a glass-to-metal seal, a hermetic seal, a hydrostatic seal, a hydrodynamic seal, an inflatable seal, a labyrinth seal, an end face mechanical seal, a face seal, and/or a wiper seal. In some embodiments, a "seal" or a "gas barrier" can be mechanically joined to a luminal reservoir and/or luminal container by gluing, taping, cementing, brazing, soldering, welding, crimping, magnetic force, vacuum force and/or friction force. In some embodiments, fasteners, including, but not limited to, such as screws, clips, clamps, weights, locks, springs, hinges, rivets, buckles, pins, flanges, grommets, hook-and-eye fasteners, hook-and-loop fasteners, latches, nails, pegs, retaining rings, threaded fasteners, bands, snap fasteners, staples, stitches, straps, ties, zippers, and/or toggle bolts can be used to join a "seal" or a "gas barrier" to a luminal container and/or luminal reservoir.

Referring now to FIG. 13A, in some embodiments, a system 200 is provided. System 200 comprises a first apparatus 102A, which comprises a luminal reservoir that can be a first luminal reservoir, a basal reservoir that can be a first basal reservoir, a cover that can be a first cover, a luminal fluid region that can be a first luminal fluid region, and a basal fluid region that can be a first basal fluid region. The system 200 further comprises a second apparatus 102B, which comprises a second luminal reservoir and a second cover that define a second luminal fluid region when the second cover is in the installed position, and a second basal reservoir having the second luminal reservoir received therein to define a second basal fluid region. A first tissue and/or one or more cells (e.g., in the form of collagen scaffold 172, see FIGS. 1A-1K) is received in the first luminal reservoir. A second tissue and/or one or more cells (e.g., in the form of collagen scaffold 172, see FIGS. 1A-1K) is received in the second luminal reservoir. The first and second luminal fluid regions are fluidically connected to one another and the first and second basal fluid regions are fluidically connected to one another.

Referring now to FIG. 13B, in some embodiments, a system 300 is provided. System 300 comprises, in addition to the first apparatus 102A and the second apparatus 102B, described hereinabove regarding FIG. 13A, a third apparatus 102C. Third apparatus 102C comprises a third luminal reservoir and a third cover that define a third luminal fluid region when the third cover is in the installed position. The third apparatus 102C further comprises a third basal reservoir having the third luminal reservoir received therein to define a third basal fluid region. A third tissue and/or one or more cells (e.g., in the form of collagen scaffold 172, see FIGS. 1A-1K) is received in the third luminal reservoir. The luminal fluid regions of the first, second, and third apparatuses 102A, 102B, 102C are fluidically connected to one another. The basal fluid regions of the first, second, and third apparatuses 102A, 102B, 102C are fluidically connected to one another.

In some embodiments, a bottom wall of the luminal reservoir 140, 340, 440 can comprise an oxygen-impermeable member or low-permeability member. In such embodiments, the oxygen impermeable member can comprise plastics including polystyrene (PS), polyethylene (PE), polypropylene (PP), polyvinylchloride (PVC), polymethylmethacrylate (PMMA), acrylonitrile butadiene styrene (ABS), acryl styrene acrylonitrile (ASA), styrene acrylonitrile (SAN), nylon, polycarbonate (PC), polyester including polyethylene terephthalate (PET), polyphenylene oxide, ethylene-vinyl acetate (EVA), cycloolefin copolymer (COC), polytetrafluoroethylene (PTFE), polyether ether ketone (PEEK), acetal polymer, acrylic resin, epoxy, thermosetting polyester resin, polyurethanes, furan, rubbers and elastomers such as Vitron, polychloroprene, nitrile rubber, polyurethane rubber, natural rubber, ethylene propylene diene monomer (EPDM), fluorocarbon rubber, glass such as borosilicate, sodalime, quartz, or metal including aluminum, steel, and stainless steel. In some such embodiments, the oxygen-impermeable member can comprise glass (e.g., a glass coverslip).

In some embodiments, the cover 160, 260, 360, 460 can comprise a lid comprising a top wall and at least one sidewall extending downwardly from the top wall and that engages the at least one sidewall of the luminal reservoir 140, 340, 440 when in the installed position. In some embodiments, each outer surface of at least one sidewall of the luminal reservoir 140, 340, 440 and an inner surface of at least one sidewall of a cover 160, 260 comprises threads 164, and the cover 160, 260 is threadably engaged with the reservoir 140, 340 when the cover 160, 260 is in the installed position. In some embodiments, a bottom wall of the luminal reservoir 140, 340, 440 comprises an oxygen-permeable material (e.g., an oxygen-permeable membrane).

In some embodiments, a luminal reservoir 140, 340, 440 of an apparatus 100, 101, 102, 103 disclosed herein can be, for example, a petri dish, a cell culture dish, a vessel, or a substrate. In some embodiments, a luminal reservoir 140, 340, 440 of an apparatus 100, 101, 102, 103 disclosed herein can be a commercially available cell culture dish, vessel, or substrate.

In some embodiments, an apparatus 100, 101, 102, 103 disclosed herein (e.g., a luminal reservoir 140, 340, 440, a basal reservoir 120, and parts thereof (e.g., cover, plug, cap, seal, gasket, etc.)) can be comprised of any material suitable for the purpose of generating a gas (or a non-gaseous chemical) gradient or hypoxic conditions including, but not limited to, plastic, polyester, natural rubber, synthetic rubber, elastomers, glass and/or metal. In some embodiments, the materials for construction of an apparatus 100, 101, 102, 103 disclosed herein, and parts thereof, can include, but is not limited to, polystyrene (PS), polyethylene (PE), polypropylene (PP), polyvinylchloride (PVC), polymethylmethacrylate (PMMA), acrylonitrile butadiene styrene (ABS), acryl styrene acrylonitrile (ASA), styrene acrylonitrile (SAN), nylon, polycarbonate (PC), polyethylene terephthalate (PET), polyphenylene oxide, ethylene-vinyl acetate (EVA), cycloolefin copolymer (COC), polytetrafluoroethylene (PTFE), polyether ether ketone (PEEK), acetal polymer, acrylic resin, epoxy, thermosetting polyester resin, polyurethanes, furan, polydimethylsiloxane (PDMS), silicone rubbers, VITON™, polychloroprene, nitrile rubber, polyurethane rubber, natural rubber, ethylene propylene diene monomer (EPDM), fluorocarbon rubber, borosilicate, sodalime, quartz, aluminum, steel, stainless steel, or any combination thereof. In some embodiments, a plug (e.g., release port plug 268) can comprise, for example, polydimethylsiloxane (PDMS).

In some embodiments, the collagen scaffold, which can be any suitable cell support structure or scaffold, of the can comprise extracellular matrix (ECM) materials including, but not limited to, collagen, gelatin, laminin, elastin, fibronectin, vitronectin, heparin sulfate, chondroitin sulfate, keratin sulfate, hyaluronic acid, gelatinous protein mixture secreted by Engelbreth-Holm-Swarm mouse sarcoma cells (e.g. Matrigel®, Geltrex®, MaxGel™, etc.), and/or commercially available cell substrates (e.g., CELLstart™ CTS™) and any combination thereof (e.g., a collagen/Matrigel mixture). In some embodiments, hydrogels from natural polymers, synthetic polymers and hybrid hydrogel can be used to build a scaffold in two dimensions or three dimensions. Examples of natural polymers and synthetic polymers include, but are not limited to, chitosan, agarose, alginate (e.g., AlgiMatrix®), fibrin, silk, polyvinyl alcohol, sodium polyacrylate, acrylate polymers, polyethylene glycol (PEG), synthetic peptides, poly N-isopropylacrylamide, and/or polyacrylamide, and/or any combination thereof. In some embodiments, the surface of a scaffold can be engineered to promote cell adhesion with any one or a combination of ECM molecules, natural or synthetic polymers or synthetic peptides including, but not limited to, poly-l-lysine, RGD-peptide and other integrin recognizing peptide segments. In some embodiments, a cell support structure useful with this present disclosure can be mixed with cellular materials (immune cells or other cell types, tissues, blood), or non-cellular materials (drugs, polymer beads, magnetic particles, etc.). In some embodiments, a cell support structure of the apparatus 100, 101, 102,103 can comprise a two or three dimensional micropatterns or microstructures.

In some embodiments, an apparatus 100, 101, 102, 103 disclosed herein can be a subcomponent of a microfluidic device that can be integrated with other organ systems or can act as a standalone device for a single tissue.

FIGS. 14A-14C illustrate a device, generally designated 500, which is configured to measure the oxygen consumption rate (OCR) in media (Table 2) by cells, for example, colon cells. The device 500 comprises a housing 510. The device comprises a first passage 516 which is formed in a top side 518 of the device 500. The device further comprises a second passage 512, which is formed in a side 514 of the device 500. First passage and second passage 512 extend axially through the housing 510 and intersect each other internal to the housing 510. It is advantageous for the first and second passages 516, 512 to extend beyond the intersection point a sufficient distance to allow the cells 170 and the stir bar 582 to be spaced sufficiently apart. In some embodiments, the terminal ends of the first and second passages 516, 512 terminate adjacent to, but not coincident with, an outer surface of the housing 510, such that they extend through substantially an entire thickness of the housing 510 without extending through the entire thickness thereof. First and second covers 540A, 540B are provided to sealingly engage with gaskets 550 at the inlets to the first and second passages 516, 512.

The cells 170 are inserted within the first passage and can, in some embodiments, be allowed to settle therein according to the direction of gravity. It is advantageous to allow the cells to be cultured within the device 500 under normoxic conditions with expansion media (EM) for 6 days. The cells may then, in some embodiments, be cultured within the device 500 in differentiation media (DM) for a further 4 days. The device 500 is then rotated 90 degrees and a stir bar 582, which can be any suitable agitation device, as described elsewhere herein, inserted within the second passage of the housing 510. The device 500 can be sealed with an oxygen sensor extending through cover 540B and placed on a stir plate to uniformly mix the media within the first and second passages 516, 512 within the housing 510. In some embodiments, the oxygen sensor is a fiber optic oxygen sensor. The oxygen concentration is advantageously measured for 24 hours within the housing 510 by the oxygen sensor.

In some embodiments, the present disclosure provides a method of making a live cell and/or tissue construct under hypoxic conditions, the method comprising: providing an apparatus disclosed herein and culturing the one or more cells and/or tissue positioned on the cell support structure, thereby producing hypoxic conditions under which the cells/tissues are grown. The hypoxic conditions are generated by oxygen consumption of the one or more cells and/or tissue on the cell support structure in the luminal reservoir when the cover is in the installed position.

In some embodiments, the present disclosure provides a method of culturing one or more cells and/or tissue under hypoxic conditions, the method comprising: providing an apparatus disclosed herein and culturing the one or more cells and/or tissue positioned on the cell support structure, thereby producing hypoxic conditions under which the cells/tissues are grown, wherein the hypoxic conditions are generated by the one or more cells and/or tissue on the cell support structure in the luminal reservoir when the cover is in the installed position.

In some embodiments, the present disclosure provides a method of generating a gas gradient across a cell support structure (e.g., perpendicularly through the one or more cells and or tissue positioned on the cell support structure), the method comprising: providing an apparatus disclosed herein and culturing the one or more cells and/or tissue positioned on the cell support structure, and generating a gas gradient (e.g., higher to lower or lower to higher) across the cell support structure.

The apparatuses, devices, systems and methods of the present disclosure are versatile and readily implemented for a plurality of different uses including, for example, but not limited to:

1) in vitro model for physiological studies (transport of macromolecules, ions and water across the cells, enzymatic functions, interaction with bacteria);
2) screening of drugs, biologics, dietary compounds, toxins, mutagens, carcinogens, pathogens, viruses, microbiota, etc.;
3) disease models by using stem and/or primary cells derived from a translational animal models or human;
4) pharmacological, pharmacokinetic and pharmacodynamic models for screening including comprehensive dose-response profiles for drugs, dietary compounds, etc.;
5) in vitro models to study metabolism;
6) in vitro models for wound healing of epithelial tissue to maintain and repair barrier function;
7) in vitro models for study microbe-host interaction;
8) tissue engineering for implantation to repair damaged epithelium;
9) personalized medicine by studies performed on cells from individual patients with specific genetic backgrounds;
10) functional assays such as absorption and transport of water and electrolytes (sodium, chloride, bicarbonate, proton, potassium, calcium), microbe-derived metabolites such as short chain fatty acids, and salvage of unabsorbed nutrients;
11) mucus production, flow, movement and disease related impact on mucus such as in cystic fibrosis;
12) assays of antidiarrheal agents and treatments for constipation, for example, laxatives
13) assays of synbiotics, prebiotics and probiotics;
14) assays of and testing radiopaque and scintigraphic markers and their impact on epithelium;
15) impact of immune cells and their products (antibodies and cytokines) on epithelium;
16) impact of enteric nerve cells and their products on epithelium;
17) impact of muscle cells, their contraction and relaxation and their metabolic products on epithelium;
18) assay of soluble and insoluble fibers and its impact on the epithelium;
19) understanding repair of epithelium in response to injury of any type;

20) investigation of bacteria leading to pseudomembrane formation, for example, *Clostridium difficile;*
21) screening for biowarfare compounds;
22) studies to understand side effect of drugs and therapeutics such as NSAID treatment, chemotherapy and radiotherapy;
23) studies of the role of the innate and adaptive immune system on epithelial integrity, function and disease (e.g. inflammatory bowel diseases, enteropathies, cancer, etc.);
24) assays for radio- and chemotherapeutics and agents that ameliorate off-target effects;
25) tumor models to mimic hypoxia or oxygen gradient in time and/or space including liquid cancers such as leukemia, or myeloma, and/or solid cancers such as melanoma, carcinoma, sarcoma, lymphoma, germ cell tumor, and/or mixed cancer;
26) assays of antibacterial, antiviral, and/or antifungal agents;
27) studies to understand the effect of bacteriophage on commensal and pathogenic bacteria and their interaction with host cells;
28) in vitro model systems for gram positive and/or gram negative bacterial infection including Gram negative bacteria, gram positive bacteria including, but not limited to, *Acinetobacter baumannii, Actinomyces israelii, Bacillus anthracis, Bacteroides fragilis, Bartonella henselae, Bordetella pertussis, Borrelia burgdorferi, Borrelia garinii, Borrelia afzelil, Borrelia recurrentis, Brucella abortus, Brucella canis, Brucella melitensis, Brucella suis, Burkholderia pseudomallei, Campylobacter jejuni, Chlamydia pneumoniae, Chlamydia trachomatis, Chlamydophila psittaci, Clostridium botulinum, Clostridium difficile, Clostridium perfringens, Clostridium tetani, Corynebacterium amycolatum, Corynebacterium diphtheriae, Coxiella burnetii, Ehrlichia canis, Ehrlichia chaffeensis, Enterococcus faecalis, Enterococcus faecium, Escherichia coli,* Enterotoxigenic *Escherichia coli,* Enteropathogenic *Escherichia coli,* Enteroinvasive *Escherichia coli,* enterohemorrhagic *Escherichia coli, Francisella tularensis, Haemophilus influenzae, Helicobacter pylori, Klebsiella pneumoniae, Legionella pneumophila, Leptospira species, Listeria monocytogenes, Mycobacterium leprae, Mycobacterium tuberculosis, Mycoplasma pneumoniae, Neisseria gonorrhoeae, Neisseria meningitidus, Parachlamydia, Pseudomonas aeruginosa, Nocardia asteroides, Rickettsia rickettsii, Salmonella, Shigella, Staphylococcus aureus, Staphylococcus epidermidis, Staphylococcus saprophyticus, Streptococcus agalactiae, Streptococcus pneumoniae Streptococcus pyogenes, Streptococcus viridans, Treponema pallidum, Vibrio cholerae, Vibrio vulnificus,* and/or *Yersinia;*
29) in vitro culture system for understanding infection by virus including double strand DNA viruses, single strand DNA viruses, double strand RNA viruses, positive strand RNA viruses, negative strand RNA viruses, circular single strand RNA viruses, RNA reverse transcribing viruses, DNA reverse transcribing viruses such as Simplexvirus, Varicellovirus, Cytomegalovirus, Roseolovirus, Lymphocryptovirus, Rhadinovirus, Mastadenovirus, Alphapapillomavirus, Betapapillomavirus, Gammapapillomavirus, Mupapillomavirus, Nupapillomavirus, Polyomavirus, Molluscipoxvirus, Orthopoxvirus, Parapoxvirus, Alphatorquevirus, Betatorquevirus, Gammatorquevirus, Gemycircularviruses, Erythrovirus, Dependovirus, Bocavirus, Coltivirus, Rotavirus, Seadornavirus, Hepevirus, Alphacoronavirus, Betacoronavirus, Torovirus, Mamastrovirus, Norovirus, Sapovirus, Flavivirus, Hepacivirus, Pegivirus, Cardiovirus, Cosavirus, Enterovirus, Hepatovirus, Kobuvirus, Parechovirus, Rosavirus, Salivirus, Alphavirus, Rubivirus, Deltavirus, Lyssavirus, Vesiculovirus, Filoviridae, Ebolavirus, Marburgvirus, Paramyxoviridae, Henipavirus, Morbilivirus, Respirovirus, Rubulavirus, Metapneumovirus, Pneumovirus, Arenavirus, Peribunyaviridae, Orthobunyavirus, Hantavirus, Nairovirus, Phenuiviridae, Phlebovirus, Influenzavirus A Influenzavirus B, Influenzavirus C, Thogotovirus, Gammaretrovirus Deltaretrovirus, Lentivirus, Spumavirus, and/or Orthohepadnavirus);
30) in vitro culture systems for producing vaccine that requires hypoxic condition;
31) in vitro culture system for protozoan infection including *Entamoeba histolytica, Cryptosporidium parvum, Cryptosporidium hominis, Cyclospora cayetanensis,* and/or *Giardia lamblia;*
32) in vitro culture system for unicellular and/or multicellular fungal infection *Aspergillus, Blastomyces, Candida, Coccidioides, Cryptococcus neoformans, Cryptococcus gatti, Histoplasma, Rhizopus, Mucor, Lichtheimia, Pneumocystis jirovecii,* and/or *Sporothrix;*
33) a model for biofilm formation, development, dispersal and/or disruption by antibiofilm agents; and/or
34) a model system or combination of the systems that requires oxygen gradient (in space or time) or hypoxia, such as a hair follicle niche, brain hypoxia post stroke, cyanide poisoning, scar in a dish systems, fibrosis and wound healing, retinopathy, corneal hypoxia and vascularization, periodontitis, upper and lower airway models, bronchiolitis, bronchitis, chronic obstructive pulmonary disease (COPD), pneumonia (bacterial, viral, mycoplasma infection), interstitial lung disease, pulmonary edema, hypoxic pulmonary vasoconstriction models, liver tissue models, liver regeneration, liver fibrosis, viral hepatitis, fatty liver disease, nephropathy, nephritis, bone development and regeneration, cartilage regeneration, bone marrow, fracture healing model, thrombosis, hematopoietic stem cell niche, anemia including sickle cell disease, muscles in exercise models, reproductive tract models, endometriosis, placenta development models including intrauterine hypoxia, embryo development models, ischemia (cardiac, bowel, brain, limb, cutaneous) and ischemia-reperfusion injury models, anesthesia and/or obesity models.

EXAMPLES

The present disclosure will now be described with reference to the following examples. It should be appreciated that these examples are not intended to limit the scope of the claims to the present disclosure, but are rather intended to be exemplary of certain embodiments. Any variations in the exemplified methods that occur to the skilled artisan are intended to fall within the scope of the present disclosure.

Materials and Methods for Examples 1-9

Fabrication of the threaded chamber and the plug. The cell chamber cassettes and the plug were fabricated by milling polycarbonate slab using a computer numerical control (CNC) milling machine. The cell chamber was designed to have the same cell growth area as commercial 12-well TRANSWELL® (Corning, Inc., Corning, N.Y., United States of America) culture inserts. The cell chamber and the plug were threaded (M12×1.75) for efficient sealing of the luminal side. The cell chambers and the plug were plasma treated for 5 minutes. Then porous membrane (BGCM00010; Millipore, Burlington, Mass., United States of America) was attached to the bottom of the cell chamber cassette using 3M double-side medical tape (#1504XL, 3M, Maplewood, Minn., United States of America).

Prior to culturing cells in the cell chamber, collagen scaffold was prepared in the device prior to cell seeding as previously reported[54] with slight modification. First, the devices were placed onto 12 well plates and collagen gel (250 μL) was formed by mixing rat tail collagen I with neutralization buffer at final concentration of 1 mg/mL and then incubating at 37° C. for 1 hour. Then the collagen gel was crosslinked from the bottom side by adding 0.5 mL PBS in the luminal side (device) and 1.5 mL of EDC:NHS:MES buffer (0.6 M EDC in water, 0.15 M NHS in water, 0.1 M MES in water, pH5, 1:1:1 volume ratio) in the basal side (the well plate) and incubating for 1 hour at 25° C. Residual EDC and NHS in the collagen gel were removed by soaking in water at least for 16 hour at 25° C. The resulting, partially crosslinked collagen in the chamber was sterilized with 70% ethanol (at least 5 min) and washed thoroughly with PBS prior to cell seeding.

The plug was placed when the cells were ready as described herein. The luminal media was added (0.4 mL) and then the plug was placed by rotating. While rotating, the air trapped between the plug and the media was released through the hole in the plug. Then the hole was sealed with an EPDM rubber cap (outside diameter 0.020 inch).

Power analysis. Power analysis[55] was performed using G*Power applet[56] (version 3.1.9.2) to calculate minimum sample size required for distinguishing the cell behaviors in aerobic condition from those in anaerobic conditions, assuming that the cell behaviors in the oxygen gradient would be combination of those two. As a preliminary data for this analysis, proliferative cell populations of human colonic epithelial cells grown on neutralized collagen in 24-well plate and exposed to either aerobic or anaerobic conditions were used. The cells were grown aerobically in extracellular matrix (EM) for 4 days with medium exchange every 2 days then on day 4 the cells were either grown aerobically or anaerobically for 2 more days in EM. To label proliferative cells, 5-ethynyl-2'-deoxyuridine (EdU) was pulsed on day 5 either aerobically or anaerobically. On day 6, the cells were fixed with 4% PFA and stained for EdU and Hoechst 33342 as described below. Then the cells were imaged using a NIKON® Eclipse TE300 inverted epifluorescence microscope (Nikon, Inc., Melville, N.Y., United States of America) with Cy5 filter for EdU and DAPI filter for Hoechst 33342. The mean of the EDU positive cell portion in aerobic and anaerobic condition was 0.55 and 0.06, respectively, and the standard deviation 0.044 and 0.029, respectively, resulting the sample size of 2 ($\alpha$=0.05, power (1-$\beta$)=0.95).

In all graphs the bars and the error bars indicate the mean values and the standard deviations. One way ANOVA analysis was used for all the statistical analyses in this study.

Human colonic epithelial cell culture. Human primary colon epithelial cells from two different sources were used in this study (one was obtained from biopsy specimen and the other was from a cadaveric donor). The colonic crypts were isolated and expanded in expansion media on collagen gel in 6-well plate as described previously.[57] The cells were subcultured every 5-7 days up to 16 passaging by digesting collagen using collagenase and then dissociating the cells using 0.5 mM EDTA. Karaotyping of the cells at passage 7 and 15 confirmed that the chromosomes of the cells were normal.

All human cells were cultured in a $CO_2$ incubator at 37° C. The human colon cells were grown in expansion medium (0.5 mL/2.5 mL) for 6 days with medium change every other day to form confluent monolayer. On day 6, the media were removed and then the luminal medium was switched to DM and the basal medium was switched to SM for DM/SM (0.4 mL/3 mL) condition to preserve proliferative cell population, and DM for DM/DM (0.4 mL/3 mL) to model further differentiated cells. Then the cells were further incubated for 4 days with medium replaced every other day. On day 10, the plug was placed in the chamber to induce luminal hypoxia and the cells were further incubated for 2 more days and assayed on day 12 as described below. Aerobic culture samples were prepared the same except that the plug was not used, and the luminal media were exposed to the air. For anaerobic control, the same media were deoxygenated so that the oxygen level decreased below 1% prior to anaerobic culture. The media were replaced in anaerobic environment with less than 1% oxygen either in a plastic environmental chamber by purging nitrogen gas for 30 min or in an anaerobic chamber filled with 5% $CO_2$ and 95% $N_2$ and then the cells were placed in a glasslock container that contained 50 mL water for hydration and filled with anaerobic gas mix (5% $CO_2$, 10% $H_2$, 85% $N_2$). After 2 days of culture in each condition, transepithelial electrical resistance (TEER) was measured using a voltohmmeter (EVOM2, World Precision Instruments, Florida, United States of America) and a chopstick electrode.

Oxygen sensing. The oxygen level was measured using Microx4 oxygen sensor (PreSens Precision Sensing GmBH, Regensburg, Germany) with a needle type oxygen probe (NTH-PSt7, PreSens Precision Sensing GmBH) according to the manufacturer's instruction. For profiling the oxygen level in the luminal medium upon luminal hypoxia induced by placing the plug, the sensor was located at the center of the plug through the hole and the 1 mm below the plug. For the oxygen measurement of the basal media, a basal container that contains the same size of well as a commercial 12-TRANSWELL® was fabricated by milling polycarbonate slab and then a hole was drilled in the wall 7 mm above the bottom so that the needle type oxygen probe can be installed for the oxygen measurement. The measurement was taken every 5 min for at least 16 h with temperature manually setup as 37° C.

Viability. 2 μM of Propidium iodide and 12.5 M Hoechst 33342 in 0.5 mL of PBS were added in the luminal side and incubated for 30 min. The labeled cells were punched with a biopsy punch (5 mm in diameter), transferred onto glass slides and the entire punched area were imaged with an Olympus FLUOVIEW® FV3000® confocal microscope (10× lens; Olympus Corporation, Tokyo, Japan) with 561 nm and 405 nm lasers for exciting propidium iodide and Hoechst 33342, respectively.

Hypoxyprobe staining. The cells exposed to each oxygen condition were incubated with 200 μM of pimonidazole (HYPOXYPROBE®, HP1-100Kit; Hypoxyprobe, Inc., Burlington, Mass., United States of America) added in the basal medium for 2 hours. Then the cells were fixed with 3% glyoxal in PBS (pH 5) for 20 min at −20° C. and 10 min at 25° C., permeabilized with 0.5% Triton X-100 in PBS for 20 min at 25° C. and then blocked with 3% BSA in PBS for 1 h at 25° C. Mouse antibody against pimonidazole (HYPOXYPROBE®, HP1-100Kit) diluted in 3% BSA (1:50) in PBS was incubated at 4° C. for at least 15 h. And the cells were washed with 3% BSA in PBS for 3 times and then incubated with anti-mouse antibody conjugated with Alexa Fluor 647 (1:500, 715-605-150, Jackson ImmunoResearch Laboratories, Inc., West Grove, Pa., United States of America) diluted in 3% BSA (1:500) for 1 h at 25° C. Finally, the cells were washed with 3% BSA in PBS for 2 times and then with PBS. For imaging, the cells and the collagen gels were picked up with forceps and transferred onto glass slides and imaged using Olympus FLUOVIEW® FV3000® confocal microscope (Olympus Corporation, Tokyo, Japan) with a 640 nm laser for excitation.

Immunofluorescence and EdU staining. The cells were fixed with glyoxal solution for ZO-1 staining and with 4% paraformaldehyde for 15-20 min for staining other targets and cryosectioning. Then the fixed samples were permeabilized with 0.5% Triton X-100 in PBS for 20 min, blocked with 3% BSA in PBS for 1 hour at 25° C. and then incubated with primary antibody at 4° C. for at least 15 hours. Primary antibodies for MUC2 (SC-515032, Santa Cruz Biotechnology, Inc., Dallas, Tex., United States of America), ZO-1 (21733-1-AP, Proteintech Group, Inc., Rosemont, Ill., United States of America), ezrin (PA5-17518, Thermo Fisher Scientific, Waltham, Mass., United States of America) were diluted in 3% BSA at 1:200 and incubated at 4° C. overnight. Then the cells were washed with 3% BSA in PBS for three times and then incubated with secondary antibody conjugated with fluorophores (Alexa Fluor 488 donkey anti-mouse (Jackson ImmunoResearch, 715-545-150) for MUC2, Alexa Fluor 594 donkey anti-rabbit ReadyProbes (Thermo Fisher Scientific, R37119) at 1:100 dilution in 3% BSA in PBS for 1 hour at 25° C. When necessary, Hoechst 33342 (2 M at final concentration) was added with the secondary antibody for nuclear staining. Finally, the cells were washed with 3% BSA twice and then PBS.

To label proliferative cells, 5-ethynyl-2'-deoxyuridine (EdU) was pulsed for 24 hours and stained following manufacturer's protocol (Click-iT® EdU Alexa Fluor® 647 Imaging kit, C10340, Thermo Fisher Scientific, Inc., Waltham, Mass., United States of America). The cells were incubated for 24 hours in the presence of EdU (10 μM) in the basal medium. The cells were fixed with 4% paraformaldehyde for 15 minutes at 25° C., permeabilized for 20 minutes with 0.5% Triton X-100 in PBS. The EdU incorporated into the cellular DNA was stained with Cy5 conjugated azide following the manufacturer's protocol for 1 hour at 25° C. For imaging, the samples were either punched with a biopsy punch (5 mm) or picked up with forceps and then transferred on glass slides and imaged using an Olympus Fluoview FV3000 confocal microscope with 405 nm, 488 nm, 561 nm, 640 nm lasers for exciting Hoechst 33342, Alexa Fluor 488, Alexa Fluor 594, Cy5, respectively.

Bacteria coculture. For $C.$ $difficile$ coculture, the human colonic epithelial cells were grown for 10 days as the samples for LGG coculture. Then on day 10, the media were replaced prior to inoculation. Here, for the oxygen gradient samples, DM preequilibrated in anaerobic gas (<1% $O_2$) was added in the luminal side and the plug was placed in anaerobic chamber. $C.$ $difficile$ overnight culture started from a single colony in brain heart infusion salt (BHIS) broth was diluted in BHIS at 1:100 and then 4 μL was inoculated in an anaerobic chamber onto the luminal side of the human colonic epithelial cells for all oxygen conditions. The inoculation resulted in about $1\times10^4$ CFU/mL. Then the aerobic and oxygen gradient samples were taken out from the anaerobic chamber and incubated aerobically in a $CO_2$ incubator at 37° C. Anaerobic samples were incubated in the anaerobic chamber at 37° C. in a glasslock container with 50 mL water to prevent media evaporation. After 6 hours and 24 hours coculture, the supernatant and the collagen gel with the human cells were collected in a microcentrifuge tube and then the collagen gel was digested with collagenase for 15 minutes at 37° C. Then the solution was vortexed vigorously 3 times and the plated on BHIS agar plates.

Scanning electron microscopy. The coculture samples were fixed with 4% paraformaldehyde for 40 minutes, washed with PBS, then dehydrated by washing with gradually increased ethanol:water solution and eventually 100% ethanol. Then the samples were dried with a critical point dryer, coated with 15 nm of platinum using a sputter coater (Cressington Scientific Instruments UK, Watford, United Kingdom) and observed with SEM (Hitachi S-4700, Hitachi High Technologies America, Inc., Shaumburg, Ill., United States of America).

Example 1

Establishing Hypoxic Conditions in a Cassette Containing a Porous Support Structure This example describes a method to establish hypoxic conditions in a cassette containing a porous support structure (e.g. TRANSWELL® insert, Corning, Inc., Corning, N.Y., United States of America) using a PDMS plug. FIG. 2A illustrates computational results of oxygen saturation in a device as disclosed herein. To confirm this modeling, a cylindrical plug was fabricated by molding polydimethylsiloxane (PDMS) in a cylindrical polycarbonate (PC) mold that has the same inner diameter as the top of a commercially available 12-well TRANSWELL® insert (Falcon). PDMS (Sylgard 184 Silicone Elastomer) mix was added into the mold and cured at 95° C. for 20 minutes (plug 1 in FIG. 2B) or 70° C. for 2 hours (plug 2 in FIG. 2B). The cured PDMS plug was separated from the mold and disinfected with 70% ethanol prior to use. The resulting PDMS plug was 15-20 mm long and fit tightly into the TRANSWELL® insert.

Before plating the cells, collagen gel was formed as a scaffold in 12-well TRANSWELL® inserts by adding 200 μL of neutralized rat tail collagen I solution (1 mg/mL) per insert and incubating for 1 hour at 37° C. Then the neutralized collagen gel in the inserts was chemically crosslinked by adding a mixture of EDC and NHS in MES buffer (0.6 M of EDC:0.15 M of NHS:0.1 M MES buffer=1:1:1 volume ratio) in the well plate and PBS into the inserts. This creates a gradient of crosslinking density where crosslinking density is at maximum at the bottom of the collagen gel and decreases toward the top (See, International Patent Application No. PCT/US2017/043601, published as International Patent Application Publication No. WO2018/022548). This gradient of crosslinking density facilitates growth of human primary colon cells as a monolayer. Alternatively, a thin coating of collagen I, collagen IV, or Matrigel can be used to promote cell adhesion.

Human primary colon cells were grown as a monolayer on the collagen gel with a gradient of crosslinking density in expansion medium which contains essential components (Wnt, R-spondin, noggin, EGF) for self-renewal until confluent. Once a complete monolayer was formed, the cells were then differentiated in differentiation medium lacking the growth promoting components. At day 2 in differentiation medium, the plug was placed to seal the insert and oxygen level of the luminal side (inside the insert) was measured over time.

A needle type optical oxygen probe (PreSens) was located approximately 1 mm above the cells for the measurement. Without the plug, oxygen level inside the insert fluctuated but did not decrease below 10% oxygen. When there were no cells to consume oxygen, the oxygen saturation remained above 16%. However, when the PDMS plug (20 mm in height) that was cured at 95° C. was placed (plug 1 in FIG. 2B), the oxygen saturation decreased within 2 hours to <1% oxygen near the cells and remained low for 2 days without loss of cell viability. This confirms that oxygen consumption by cells depletes oxygen to such a degree that hypoxic conditions are created within the insert.

When a shorter PDMS plug (15 mm) that was cured at 70° C. was used (plug 2 in FIG. 2B), the oxygen saturation near the cells fell into hypoxia within 2 hours but final oxygen saturation dropped to 2.5% and remained at this level. This shows that final oxygen saturation can be targeted by changing the dimensions and material properties of the plug. While the luminal side of the cells is hypoxic, the media in the basolateral side is open to air so that oxygen can diffuse into the media to insure cell survival and function. Although the PDMS plug is gas permeable, the height of the PDMS plug was such that the cells consumed oxygen faster than oxygen could diffuse through the very tall plug. However other designs modifying the height of the PDMS plug to balance the rate of oxygen consumed by cells against that diffusing into the chamber can provide any level of oxygen saturation between 0 and >16% oxygen saturation. Additionally, the oxygen permeability of PDMS can be modulated by plasma treatment[44], changing the ratio of PDMS monomer and crosslinker[45], coating with parylene[29], depositing a silicon oxide layer, or adding oxygen scavenging or reacting particles in the PDMS so that oxygen saturation values below 1% can be attained. Other silicone elastomers such as polyvinylmethyl siloxane or other rubber materials Vitron, polychloroprene, nitrile rubber, polyurethane rubber, natural rubber, ethylene propylene diene monomer (EPDM), fluorocarbon rubber can be also used as a plug.

Example 2

Generating a Self-Sustaining Hypoxic Environment

This example describes a method to create a self-sustaining hypoxic condition using an internally threaded insert and a corresponding externally threaded plug. A threaded insert body and a threaded plug were fabricated by milling polycarbonate slabs. A hole (1-2 mm in diameter) was drilled for insertion of a needle-type oxygen probe to measure oxygen saturation in the luminal compartment (See FIGS. 3B-3D). The hole was sealed around the needle probe using PDMS, epoxy or other glues/sealants. The inner diameter and height of the insert was designed to be the same size as that of a commercially available TRANSWELL® insert for a 12-well plate (Corning, Inc.). A porous PET membrane (pore size 0.4 μm, Corning, used when a thin coating of collagen was employed) or a PTFE membrane (pore size 0.4 μm, used when a collagen scaffold was employed) was attached to the bottom of the luminal chamber body to support the collagen and cell monolayer.

Prior to cell culture, collagen layer was prepared on the porous membrane in two different ways. The porous membrane was sterilized with 70% ethanol for 5 minute, air dried and then coated with 10 μg/mL of rat tail collagen I in PBS for 1 hour at 37° C. Alternatively, about 250 μm thick neutralized collagen gel was prepared on PTFE membrane and crosslinked in the luminal compartment as described in Example 1. The collagen coated porous membrane was washed twice with PBS and then human primary colon epithelial cells were seeded onto the collagen scaffold within the insert and grown in expansion media containing key components for intestinal stem cell proliferation (Wnt, R-spondin, noggin, EGF) until fully confluent. At day 6, the medium in the luminal chamber and the well plate were switched to differentiation medium which does not contain the growth promoting components to initiate cellular differentiation. On day 7 or 8, the threaded plug was placed to seal the insert and block oxygen influx from the outside. Cellular oxygen consumption should then result in a decrease of the oxygen saturation in the luminal side of the epithelium. The oxygen saturation of the luminal medium was measured with a needle type oxygen probe (PreSens) over time. The probe was located about 8 mm above the cells. FIG. 3A shows the oxygen level changes of the luminal media with the cells on thin collagen coating and thick collagen scaffold over 40 hours.

Hypoxic conditions were established within 6 hours throughout the volume of the luminal medium above the epithelium and maintained over 2 days without visually detectable loss of cell viability. Moreover, the scaffold underneath the cells significantly altered the rate of establishing hypoxic condition in the luminal medium and the final oxygen saturation. It is in part due to the difference in cell number on the scaffolds since cell density on the collagen gel (FIG. 3F) is higher than that on the thin collagen coating (FIG. 3E) when prepared on porous membrane. These data show that final oxygen saturation can be modulated by changing the cell population or height of the plug.

Mouse primary colon cells were grown on collagen scaffold prepared in the same method in the insert with the same dimension as above in the presence of the necessary growth factors (EGF, Noggin, R-spondin, Wnt, namely ENRW medium) in the luminal and basal compartments for 4 days. On day 4, the medium was removed and replaced with ENR medium that contain EGF, Noggin and R-spondin but not Wnt in the luminal compartment and ENRW in the basal compartment creating Wnt gradient across the cell layer and incubated for a day. On day 5, the luminal and basal media were switched to the fresh media (ENR as luminal medium and ENRW as basal medium) and a threaded plug was introduced to create luminal hypoxia as described above. A corresponding aerobic control sample without a plug was also prepared in parallel.

FIG. 4A shows that the oxygen saturation decreased and reached to physical hypoxia (2-9%)[46] in 4 hours and stayed within the range for over 12 hours. After 2 days of luminal hypoxia, the luminal media of the cells exposed to luminal hypoxia and corresponding aerobic control were collected to compare the amount of secreted mucin-2 into the luminal media and the cells were fixed and stained for alkaline phosphatase (ALP) activity (an absorptive colonocyte marker), mucin-2 (a goblet cell marker) and nuclear DNA (for labeling all cells). The amounts of secreted mucin-2 were not significantly different (FIG. 4B). The abundance of cell bound mucin-2 was not different while the ALP activity of the luminal hypoxia exposed cells was higher than that of the aerobic control. These data show that this platform can be used to create luminal hypoxia in mouse cells as well as human cells and to observe and understand how physiological hypoxia affect cell behavior such as cell differentiation, expression of proteins, or enzyme activities.

Final oxygen saturation of the luminal reservoir and the time to reach hypoxia can be manipulated by changing the volume of the luminal reservoir or changing the cell metabolism. The oxygen saturation of the smaller luminal compartment (0.5 mL in luminal volume) that was measured about 2 mm above the human primary colon epithelial cells in the same differentiation medium in both luminal compartment and bottom well (FIG. 5A, condition 1, bottom curve) decreased faster than that measured in longer luminal reservoir, showing that the oxygen saturation level can be manipulated by changing the dimensions of the compartment. When the growth factors for the proliferation of intestinal epithelial cells were added in the luminal reservoir (FIG. 5A, condition 3, middle curve) or both luminal and basal reservoirs (FIG. 5A, condition 2, top curve) the oxygen level decreased slower and final oxygen saturation was higher. These data clearly show that the luminal oxygen saturation can be modulated by changing media composition that leads to changes in metabolic activity.

In this device configuration, oxygen underneath the cell layer started dropping approximately when the luminal oxygen was rapidly depleted, about in 1 hour but soon reached to steady state where the oxygen diffusing through the medium and the oxygen being consumed by cells are balanced. As a result, the cells experience oxygen gradient across the cell layer. Confocal fluorescence microscopic imaging (not shown) was conducted on human primary colon epithelial cells that were exposed to DM in both luminal and basal reservoirs (DM/DM condition in FIG. 5A) in the aerobic control without a plug and in the luminal hypoxia with a plug. The human primary colon epithelial cells expressed less mucin-2 and showed less ALP activity under this oxygen gradient than aerobic control while tight junctions were maintained throughout the cell layer in both samples. Basal oxygen saturation and in turn oxygen gradient across the cell layer can be modulated by mixing the basal medium. As shown in FIG. 5B, stirring the basal medium increased the oxygen level of the basal medium below the luminal chamber from 12% to 19%. This data demonstrates that the basal oxygen level and the oxygen gradient across the cell layer can be modulated. Final oxygen saturation or rate of establishing hypoxia can be also targeted by adjusting initial oxygen level of the medium (e.g. deoxygenated medium or oxygen saturated medium), controlling the volume or composition of the air in the insert, or manipulating material properties (oxygen permeability) of the plug. To reduce oxygen permeability, parylene coating or silicon oxide deposition can be applied to the surface of the plug.

The same threaded insert and matching plug were used to establish luminal hypoxia during culture of an in vitro colon crypt. The in vitro human colonic epithelium crypt was fabricated by culturing human primary colon epithelial cells on crypt-shaped array of collagen scaffold molded with a PDMS stamp 47. After 7 days in culture in expansion medium, the cells of the in vitro crypt were induced to polarize by maintaining proliferation promoting compounds in the basal medium and differentiation medium in the luminal compartment. The threaded plug was placed at day 8 and the oxygen level of the luminal medium was measured with a needle type oxygen probe inserted through the central hole in the plug. The oxygen saturation decreased to <5% within 3 hours and decreased further to 1.5% oxygen saturation without any visually detectable loss in cell viability (FIG. 6A). To verify whether the cells experienced hypoxia, on day 10 pimonidazole, a compound that binds to thiols of cellular proteins only when oxygen level is less than 10 mmHg (1.3% oxygen saturation)[48] was introduced in the basal medium and incubated for 1 hour at 37° C. Then the cells were fixed with 4% paraformaldehyde. The retained pimonidazole was detected by an anti-pimonidazole mouse monoclonal antibody followed by staining with an anti-mouse secondary antibody conjugated with Alexa Fluor 647. The nuclei were stained with Hoechst 33342. The resulting microscopic image (FIG. 6B) showed a clear staining pattern of pimonidazole at the luminal surface and weaker staining at the bottom of the crypt. The nuclei staining confirmed that crypt structure was well preserved without cell loss despite the hypoxic lumen.

Example 3

Generating Hypoxic Conditions in a Closed Cell Reservoir

This example describes a method to create hypoxic conditions in a closed cell reservoir. An internally threaded cell culture well and an externally threaded plug were fabricated by milling polycarbonate slabs. At the center of the plug, a hole (1-2 mm in diameter) was drilled for insertion of a needle-type oxygen probe. A cell reservoir was prepared by attaching a circular glass coverslip (18 mm in diameter), which is oxygen impermeable, to the bottom of the threaded cell culture well with medical tape (3M). To facilitate intestinal cell growth, collagen gel (rat tail collagen I) was overlaid onto the coverslip forming the base of the cell reservoir. Human primary colon cells were cultured on the collagen gel until confluent in the expansion medium which contains necessary growth factors for proliferation. Once the cells formed a complete monolayer, the medium was switched to differentiation medium which lacked proliferation promoting compounds.

After 2 days of culture, the medium was changed to fresh differentiation medium and the cell reservoir was sealed with the externally threaded plug. The oxygen level of the cell reservoir was measured at the mid-point of the cell reservoir with the inserted needle type oxygen probe. During the measurement, the cell reservoir with the plug and the oxygen probe was placed on an orbital shaker in an incubator. Oxygen saturation decreased below 5% within 6 hours throughout the cell reservoir and remained <2% thereafter (FIG. 7). Oxygen influx into the medium is minimized by using an oxygen impermeable glass bottom and low oxygen permeating polycarbonate body of the cell reservoir. Final oxygen can be targeted by changing the materials and oxygen permeability of the plug, cell reservoir, and the bottom, adjusting the height of the plug, and medium and air volume in the cell reservoir.

Example 4

Establishing a Vertical Oxygen Gradient

This example describes a method to establish a vertical oxygen gradient in a device/system as disclosed herein, including an externally threaded petri dish and a corresponding internally threaded lid. The bottom of the petri dish is made of oxygen permeable material such as a silicone polymer, for example, PDMS, polyurethane, parflufocon or ceramic membranes to facilitate diffusion of oxygen to the cells. Extracellular matrix proteins such as fibronectin, collagen, laminin, Matrigel or synthetic polymer such as poly-l-lysine can be coated to promote the cell adhesion. Or 3D cell culture or organoids can be prepared by mixing the cells with extracellular matrix and placed in the dish. By placing the threaded lid oxygen influx from the top is efficiently blocked while cells obtain oxygen from the bottom through oxygen permeable material. The oxygen gradient can be modulated by changing the volume of the medium and the air in the dish, and oxygen permeability of the bottom of the dish.

Example 5

Design of an in Vitro System to Establish an Oxygen Gradient

The goal of this effort was to design a simple oxygen gradient cassette that was readily accessible to the biomedical research community and which could support a primary intestinal cell monolayer growing on a thick collagen scaffold. In some instances, the thick collagen scaffold was preferred over a simple porous membrane since when properly shaped, the collagen scaffold supports formation of a fully polarized in vitro crypt. Further the formed oxygen gradient should enable culture of obligate anaerobes within the luminal cassette compartment yet maintain an oxygenated basal reservoir. The designed cassette possessed dimensions similar to that of a commercial TRANSWELL® and was comprised of a luminal plug, a cassette insert supporting the cells on their scaffold and forming the luminal reservoir, and the basal reservoir. This format was utilized due to its familiarity to the biomedical research community, its ease of use, and the accessibility of the basal and luminal reservoirs for sampling or reagent addition. A gas impermeable plug inserted into the luminal reservoir was designed to block oxygen influx from above the cell monolayer. The threaded plug was fabricated from polycarbonate due to its low oxygen permeability and ease of fabrication by milling. A port in the plug enabled gas release during sealing, sampling of the luminal contents, addition of reagents or bacteria, and measurement of oxygen saturation. During cell culture, the port was sealed with a rubber cap. A thin porous membrane formed the base of the polycarbonate cassette insert. A collagen-based hydrogel scaffold (about 1 mm thick) was formed on the porous membrane to support the epithelial cell monolayer. The wells of a 12-well microtiter plate formed basal reservoir. The system was designed to create an anaerobic luminal compartment by minimizing the influx of oxygen into the luminal reservoir and by utilizing cell respiration to scavenge oxygen molecules existing or entering the luminal reservoir. The basal compartment below the monolayer was supplied with oxygen by leaving the fluid in this reservoir in contact with the atmosphere. These two opposing processes, cell oxygen consumption and oxygen through the luminal reservoir were then predicted to initiate a self-sustaining oxygen gradient over time.

To model oxygen concentrations over time within the device in the presence of cells, a COMSOL® simulation was developed (Comsol, Inc., Stockholm, Sweden). Critical to model precision was accurate values for the diffusion of oxygen within the collagen hydrogel as well as for the cell respiration rate. For this reason, the oxygen diffusion coefficient was experimentally measured in collagen as well as the rate of oxygen consumption by primary intestinal epithelial cells. Deoxygenated thick collagen gel (0.5% $O_2$) was placed in contact with fully oxygenated medium to allow oxygen diffusion at 37° C. The oxygen level of the thick collagen gel was measured and fitted into the equation derived from Fick's second law of diffusion. The resulting oxygen diffusion coefficient in the collagen gel was $1.2 \pm 0.1 \times 10^{-9}$ $m^2/s$ which is significantly lower than previously reported oxygen diffusion coefficient in water ($3 \times 10^{-9}$ $m^2/s$).[49] For the cellular oxygen consumption rate measurement of the human primary colon epithelial cells on collagen gel in the culture medium, the oxygen level of the culture medium was measured in the presence of the cell monolayer in an oxygen impermeable reservoir which allows complete sealing and complete mixing of the medium without mechanically damaging the cells. The measured oxygen level was fitted into integrated Michaelis-Menten kinetic equation to obtain the Michaelis-Menten parameters OCRmax ($1.7 \pm 0.3 \times 10^{-8}$ mol/$m^3$·s·cell) and Km ($1.3 \pm 0.5 \times 10^{-4}$ mol/$m^3$·cell). The measured oxygen consumption rate at 37° C. in conventional aerobic condition is at least an order of magnitude higher than previously reported values measured with various cell types.[50] The mitochondrial respiration rates of undifferentiated[51] and semidifferentiated.[51] Caco-2 cells reported previously are about 7-15 times less than the oxygen consumption rate measured here. The difference in cell type (cancer cell line vs. primary cells) and the culture medium may result in the difference in metabolism or oxygen consumption rate. Moreover, mitochondrial respiration rate measures oxidative phosphorylation in specially designed medium intentionally to exclude other oxygen consumption process such as aerobic glycolysis. The oxygen consumption rate result reflects all oxygen consumption processes that occur in the cell monolayer on the collagen gel in the cell culture medium, which would be more accurate and useful for simulation.

Oxygen consumption rate (OCR) in media (Table 2) by cells was measured using a device described and disclosed herein, and illustrated in FIGS. 14A-14C. Previous studies have shown that oxygen consumption rate in cells can be modeled using Michaelis-Menten kinetics.[52, 53, 54] An integral of the Michaelis-Menten kinetics equation was used to fit the measured data.[55,56]

$$C_{O_2} = K_m \cdot W\left(\frac{C_0}{K_m} \cdot \exp\left(\frac{C_0 + OCR_{max} \cdot t}{K_m}\right)\right) + C_{min}$$

In this equation, W is the Lambert W function, $K_m$ is the Michaelis constant, $OCR_{max}$ is the maximum rate achieved, $C_0$ is the initial oxygen concentration, $C_{min}$ is the minimum oxygen concentration that the cells were consuming oxygen, and t is time. $C_{O_2}$ is the oxygen concentration in mol·$m^{-3}$·cell$^{-1}$ and can be related to the measured oxygen concentration by the following equation:

$$C_{O_2} = \frac{[O_2] \cdot V_{Ch}}{V_c \cdot n_c}$$

In this equation, $[O_2]$ is the concentration of oxygen in the chamber in mol·$m^{-3}$, $V_{Ch}$ is the volume of the chamber, $V_c$ is the volume of the cells, and $n_c$ is the number of cells. To determine the number of cells within the chamber, the cell density was measured at 10 different locations (640×640 μm each). The density was then multiplied by the total surface area to calculate the number of total cells.

The fit was used to calculate the $OCR_{max}$ ($-1.7 \pm 0.3 \times 10^{-8}$ mol·$m^{-3}$·$s^{-1}$·cell$^{-1}$) and $K_m$ ($1.3 \pm 0.5 \times 10^{-4}$ mol·$m^{-3}$·cell$^{-1}$) for the colon cells, which in turn was used to calculate the OCR as a function of oxygen concentration for the oxygen gradient device:

$$OCR = n_c \cdot \frac{OCR_{max} \cdot ([O_2] - [O_2]_{min})}{[O_2] - [O_2]_{min} + K_m} \cdot \delta([O_2] > [O_2]_{min})$$

In this equation, $[O_2]$ is the oxygen concentration within the gradient device, $[O_2]_{min}$ is the minimum oxygen concentration measured in the device over a 24 hour period, and δ is a step function.

TABLE 2

Composition of the media used in this study

| Component | EM Concentration | SM Concentration | DM Concentration |
|---|---|---|---|
| Advanced DMEM/F12 (Thermo Fisher) | 50% (v/v) | 50% (v/v) | 50% (v/v) |
| L-WRN | 50% (v/v) | 50% (v/v) | — |
| FBS (Atlanta Biologicals) | — | — | 10% (v/v) |
| GlutaMAX (Thermo Fisher) | 0.5X | 0.5X | 1X |
| HEPES (Thermo Fisher) | 10 mM | 10 mM | 10 mM |
| Murine EGF (Peprotech) | 50 ng/mL | 50 ng/mL | 50 ng/mL |
| B27 (Thermo Fisher) | 1X | 1X | — |
| N-Acetyl cysteine (MP Bio) | 1.25 mM | 1 mM | 1.25 mM |
| Gastrin (Anaspec) | 10 nM | 10 nM | — |
| Y-27632 (ApexBio) | 10 μM | 10 μM | — |
| 50A83-01 (Sigma Aldrich) | 500 nM | — | 500 nM |
| PGE2 (Cayman chemicals) | 10 nM | — | — |
| Nicotinamide (Sigma) | 10 mM | — | — |
| SB202190 (Selleckchem) | 3 μM | — | — |
| Primocin (InvivoGen) Not used for antibiotic free formulation | 50 μg/mL | 50 μg/mL | 50 μg/mL |

Efforts were also taken to measure the diffusion coefficient of $O_2$ in the collagen gel. The diffusion coefficient of $O_2$ through water was taken to be $3\times10^{-9}$ m$^2$/s at 37° C. as other groups have done.[52] The diffusion coefficient of $O_2$ through cross-linked collagen was determined experimentally by measuring the oxygen concentration with a needle-type fiber optic oxygen probe within the devices and systems as shown herein.

The basal reservoir containing a stir bar and media that was in contact with atmospheric oxygen acted as an infinite source of $O_2$. The luminal reservoir was completely filled with cross-linked collagen and deoxygenated by nitrogen purging. The luminal reservoir was sealed with an oxygen sensor. The luminal reservoir was placed within the basal reservoir containing a stir bar and normoxic media (Table 2) that was in contact with atmospheric oxygen, which acted as an infinite source of $O_2$. Oxygen measurements were taken within the cross-linked collagen every 5 seconds for a 1-hour period. The resultant measurements were fit to the following equation, which was derived from Fick's second law of diffusion.[57]

$$f(t) = (C_b - C_l)\left(\text{erfc}\left(\frac{z}{2\sqrt{D \cdot t}}\right) + \text{erfc}\left(\frac{-z + 2W}{2\sqrt{D \cdot t}}\right)\right) + C_l$$

where $C_b$ and $C_l$ are the starting $O_2$ concentration within the basal media (Table 2) and luminal collagen plug, respectively. z is the distance from the luminal/basal interface the $O_2$ measurements were taken and W is the height of the collagen plug. W and z were set to 4.5 mm and 2.5 mm, respectively. t is the time the oxygen measurement was taken, and D is the diffusion coefficient. A resultant fit had an $R^2$ of 0.999 and gave a diffusion coefficient (D) of $1.4\times10^{-9}$ m$^2$/s. The diffusion coefficient of oxygen through cross-linked collagen was $1.2\pm0.1\times10^{-1}$ m$^2$/s (n=3) at 37° C.

Then to validate whether oxygen gradient can be generated without anaerobic gas or perfusion of anaerobic medium, the oxygen level change over time was simulated in a device/apparatus disclosed herein and using the measured values of oxygen diffusion coefficient through collagen and the oxygen consumption rate of the human primary colon epithelial cells on collagen gel. The wall of the cell culture insert, plug and the well plate were assumed to be $O^2$ impermeable and the porous membrane to readily permeate oxygen. The simulation result indicated that luminal hypoxia could be created within a few hours after the plug was inserted in the cassette. The oxygen level underneath the collagen gel decreased over time but was maintained at about 10%. In this simulation, an oxygen gradient across the cell layer and collagen gel (1 mm thick) was formed and sustained stably (FIG. 1B) demonstrating the feasibility of oxygen gradient formation without additional oxygen depleting procedures.

Example 6

Establishing Oxygen Gradient for an in Vitro Intestinal Epithelial Model System

Additional experiments were conducted to experimentally validate whether luminal hypoxia can be achieved and maintained in the device by cellular oxygen consumption and minimizing oxygen influx, the cells were grown into confluent monolayer throughout the porous membrane. On day 10, the medium was replaced to fresh medium and the threaded plug was placed in the threaded insert and then the oxygen level of the luminal and basal medium was measured. FIG. 8A shows that the oxygen profiles over time from three independent measurements using a needle type oxygen probe show that luminal oxygen level decreased below 2% within 3 h and maintained lower than 1% over 24 h while the oxygen level in the basal medium was maintained at around 10%. These data clearly demonstrate that an oxygen gradient can be established across the epithelial cell layer in a way that the luminal side is hypoxic while basal side is oxygenated, exactly mimicking, or at least substantially mimicking, the oxygen gradient of colonic epithelium shown in vivo. When deoxygenated medium is filled in the luminal side, an oxygen gradient can be established (FIG. 8A), which can be more practical for coculturing with obligate anaerobic bacteria where inoculation should be done anaerobically. Other than the initial inoculation, any other deoxygenating procedure is not required to maintain the oxygen gradient.

The intracellular oxygen level was then examined in different oxygen conditions using Hypoxyprobe. Hypoxyprobe (pimonidazole hydrochloride) is a chemical that is retained inside the cells when oxygen partial pressure is below 10 mmHg[58] by binding to thiol containing proteins.[59] Using an antibody recognizing Hypoxyprobe, the extent of oxygen depletion in the cells can be visualized and qualitatively compared by immunofluorescence. Hypoxyprobe was added in the basal media of the cells incubated aerobically, anaerobically and under the oxygen gradient for two days allowing diffusion to the cells for 2 hours and then the cells were fixed. The retained Hypoxyprobe was detected by immunofluorescence using antibody against it. The immunofluoresence images (FIG. 8C) exhibited that the cells in the anaerobic conditions indeed exhibited 80% more intense fluorescence (FIG. 8B) indicating the higher retention of Hypoxyprobe by low intracellular oxygen level. The retention of Hypoxyprobe in the cells under the oxygen gradient was significantly lower than that in the cells in the anaerobic condition and slightly higher than the aerobic samples but not statistically distinguishable. These data suggest that the cells under the oxygen gradient experience similar intracellular oxygen level as the cells in conventional aerobic setting and significantly higher oxygen level than the cells in anaerobic gas.

In summary, these results computationally and experimentally show that an oxygen gradient can be created and maintained across the human intestinal epithelial cells by limiting oxygen influx from the luminal side and utilizing cellular oxygen consumption.

Example 7

Cell Behaviors in Different Oxygen Conditions

Next, various cell behaviors were examined under the oxygen gradient formed in the device and compared with those in normoxic and complete hypoxic conditions. The human colonic epithelial cells were grown for 6 days in expansion medium (EM) with the growth promoting factors both in the luminal and basal sides and cultured for 4 more days with the growth promoting factors only in the basal side (DM/SM) to preserve proliferative cell population, or without them from both luminal and basal sides (DM/DM) to model fully differentiated cells. Up to this point, all cells were cultured aerobically. On day 10, the cells were exposed to conventional aerobic, anaerobic, and the oxygen gradient with luminal hypoxia for 2 days.

First, cell viability was assayed using propidium iodide (PI) that stains DNAs of necrotic cells and Hoechst 33342 that stains all DNA (FIGS. 9A and 9C). In all conditions, more than 90% of the cells were viable (excluded from propidium iodide stain). The portion of PI positive cells were not statistically different among the samples with different oxygen conditions in the same media conditions. This is consistent with the previous reports that intestinal epithelial cells can tolerate oxygen depletion in vitro.[60] PI positive cells were slightly higher when the growth factors were completely withdrawn in anaerobic conditions but still most of the cells were viable.

Next, experiments were conducted to determine whether the cells under the oxygen gradient exhibit proper intestinal epithelial cell behaviors. Intestinal epithelial cells in vivo are highly polarized into apical and basolateral surfaces and this polarization can be important for proper function.[61] To verify whether the cells are properly polarized, the cells exposed to aerobic, anaerobic and under the oxygen gradient for last two days were fixed, cryosectioned and then subjected to immunofluorescence for ezrin, a brush border marker that locates in the cytoplasmic side of the microvilli on the cryosectioned cell layers. The confocal microscopic images shown in FIG. 9D indicate that the cells in all conditions formed monolayers and polarized properly based on the location of ezrin in the apical surfaces in both DM/SM and DM/DM. The microvilli were also clearly visible in the SEM images.

The epithelial integrity was also assessed by immunofluorescence staining for a tight junction marker, ZO-1 and measuring transepithelial electrical resistance (TEER). In all conditions, regardless of whether the growth factors were present or absent in the basal media, the cells formed tight junctions (FIGS. 9B and 9C). Also, TEER values measured after 2 days of exposure to different oxygen conditions were statistically indistinguishable (FIG. 9B). These data indicate that the oxygen gradient as well as anaerobic condition did not impair tight junction, which is consistent with the previous report that 2 days of hypoxia on T84 intestinal epithelial cells did not alter epithelial barrier functions.[60]

Then the influence of oxygen depletion on the proliferation and differentiation of the intestinal epithelial cells was evaluated. Although the significance of oxygen depletion in the intestinal lumen has been well perceived, its influence on the primary intestinal epithelial cells in vitro has not been experimentally investigated even though primary intestinal epithelial cell culture is now routinely performed. To investigate how oxygen level affects cell proliferation of human intestinal epithelial cells, a thymidine analog EdU was pulsed from the basal side for 24 hours in the presence of the growth promoting factors in the basal side so that the proliferative cells could incorporate EdU in their DNAs. FIG. 10A show the representative images of the EdU labeled cells in the different oxygen conditions. Exposure to anaerobic environment for 2 days significantly reduced the portion of the EdU+ proliferative cells (by 92%, FIG. 10B) compared to the cells in conventional aerobic culture condition. It is consistent with decreased proliferation in many different cells under hypoxia.[62,63] Interestingly, the cells under the oxygen gradient also showed reduced proliferation compared to the cells in conventional normoxic conditions by 83% (FIG. 10B) even though the intracellular oxygen levels estimated by Hypoxyprobe staining were similar. Under the oxygen gradient slightly more proliferative cells were present than anaerobic condition but the difference was not statistically significant (p=0.064). It suggests that the physiological hypoxia in vivo may have a protective role by suppressing hyperproliferation or neoplasia of intestinal epithelium.

Finally, mucus producing goblet cell populations under the different oxygen conditions were assessed by detecting a goblet cell marker MUC2 protein. When the growth factors were present in the basal media, the portion of MUC2+ area in the cells under the oxygen gradient was similar to the cells in the conventional aerobic condition (FIG. 10A (bottom panel) and FIG. 10C). However, MUC2 expression decreased by 40% in hypoxic condition compared to conventional aerobic condition (FIG. 10A (bottom panel) and FIG. 10C). This decrease of MUC2 positive population did not occur when the cells were let differentiated prior to exposure to different oxygen conditions, indicating that oxygen depletion, from the basal side in particular, affects cell lineage decision. These data demonstrate that proper oxygenation of intestinal tissue is crucial for epithelial barrier function through mucus production.

In summary, the data herein demonstrate that the cells under the oxygen gradient in the platform are viable, polarized properly and possess intact barrier function. Also, this data shows that oxygen condition can alter the intestinal epithelial behaviors such as proliferation and differentiation.

Example 8

Anaerobic Bacterial Coculture

To verify whether the luminal hypoxia established in the disclosed devices and systems can support anaerobic bacteria growth, obligate anaerobic bacteria were cocultured with the human colonic epithelial cells under the oxygen gradient and compared with the aerobic and anaerobic coculture samples. *C. difficile* is a spore forming, Gram positive obligate anaerobe. *C. difficile* infection occurs when the homeostasis of the gut microbiota is disrupted by prolonged antibiotic treatment and causes diarrhea and pseudomembranous colitis typically in colon.[64] Hospitalization incidences and mortality from *C. difficile* infection is increasing worldwide[65,66] necessitating comprehensive understanding and inexpensive and reliable test platform.

To examine whether the disclosed devices and systems can support growth of obligate anaerobes, *C. difficile* was cocultured under the oxygen gradient and anaerobically for comparison. Colony forming units (CFU) of *C. difficile* (630Δerm) was inoculated anaerobically in the luminal side of the human colonic epithelial cells and cocultured in anaerobic condition and under the oxygen gradient as described herein. At 6 hours and 24 hours postinoculation, both *C. difficile* that were bound and unbound to the human cells in the coculture were collected and vegetative *C. difficile* CFUs in the cocultures were estimated by culturing on BHIS plate. The estimated numbers of vegetative *C. difficile* after 6 hour and 24 hour cocultures are shown in FIG. 11A. The vegetative *C. difficile* were statically indistinguishable in anaerobic and oxygen gradient coculture samples at both 6 hours and 24 hours postinoculation. *C. difficile* coculture for 24 hours increased the inflammatory cytokine IL-8 secretion more than 3 times in the oxygen gradient cocultures and more than 10 times in anaerobic coculture (FIG. 11B).

*C. difficile* impairs epithelial barrier functions by disrupting cytoskeletal organization through their toxins.[67] To investigate whether different oxygen conditions influence *C. difficile* virulence on the human cells, tight junctions were visualized by immunofluorescence on the cells cocultured and the cell morphology was observed using scanning electron microscopy. At 6 hours postinoculation, no visible changes in tight junctions was observed in either condition (FIG. 11C). At 24 hours postinoculation, a significant difference in the organization of tight junctions and cell morphologies was observed in the cells exposed to anaerobic environment and the oxygen gradient, despite the similar CFU of the vegetative *C. difficile* (FIG. 11C). In the anaerobic coculture, the polygonal cell outline was severely distorted and ZO-1 fluorescence intensity at the cell outlines was largely decreased while irregular hotspots were also observed. Under the oxygen gradient, loss of cell-cell contacts was observed but the remaining cells maintained the polygonal cell outlines that were labeled with ZO-1.

To further investigate the differences in human cell morphology after 24 hours of *C. difficile* coculture, the cells cocultured with *C. difficile* anaerobically and under the oxygen gradient were observed using scanning electron microscopy (SEM). FIG. 11D shows the representative SEM images of the cells cocultured with *C. difficile* and without *C. difficile* exposure. When anaerobically cocultured, the polygonal outlines of the cells that are clearly visible in the cells without *C. difficile* exposure were severely distorted and cell-cell contacts were broken exposing collagen fibers underneath, which is consistent with the result of ZO-1 immunofluorescence in FIG. 11C. The cells cocultured under the oxygen gradient also possessed necrotic cells but significant portion of the cells retained the epithelial morphology. These cells exhibited loss of cell-cell contact but to much less extent compared to the cells cocultured anaerobically. Interestingly, it was found that more *C. difficile* bound to the epithelial cells in the cells cocultured under the oxygen gradient than the cells anaerobically cocultured. The mechanistic explanation on these differences of the cell morphology and tight junctions is beyond the scope of this paper. However, these data clearly show that oxygen environment significantly influences the interaction of the host epithelial cells and the microbes in vitro, emphasizing the importance and significance of properly recapitulating the oxygen environment in vivo.

Example 9

Application of an Oxygen Gradient Across an in Vitro Crypt

Finally, the oxygen gradient was applied to three-dimensional crypt shaped epithelial model to more closely recapitulate the human colon crypts in vivo. A method to fabricate the in vitro colon crypt array that possesses the same three-dimensional structure as the human colon crypt in vivo was previously reported.[68] Chemical gradients along the crypt axis induce polarization of the crypt into proliferative regions at the base and differentiated cells at the surface of the crypt. To evaluate the influence of the oxygen gradient on the crypt polarization, the oxygen gradient was applied to the three-dimensional in vitro crypt with the growth factor gradient and compared with the crypt grown in the growth factor gradient in fully oxygenated condition.

First, it was assessed whether the cells in the in vitro crypt experienced the oxygen gradient along the crypt axis by measuring pimonidazole adduct formation. The fluorescence intensity of the pimonidazole binding antibody was the highest at the surface of the crypt and decreased toward the base, indicating the cells at the crypt surface experienced oxygen depletion while the cells at the crypt base were oxygenated. Without pimonidazole the fluorescence was weak regardless the location which excludes the possibility of imaging artifact or nonspecific binding. This pimonidazole staining pattern is consistent with that in the crypts in vivo.[69] Interestingly, the chemical gradient in fully oxygenated condition also induced less intense but similar pimonidazole adduct formation pattern in the three-dimensional in vitro crypt. This indicates that the oxygen level inside the differentiated cells at the crypt surface is lower than the proliferative cells at the crypt base which is determined by cellular oxygen consumption as well as oxygen in the medium. The difference of oxygen consumption between proliferative and differentiated cells has been suggested in other stem cells and the intestinal epithelial cells may have similar difference in metabolism depending on their fate.

Earlier in this work, it was showed that the oxygen gradient decreases the proliferative cell population in the cell monolayer. To assess if the oxygen gradient influences the proliferative cell population and, in turn, the polarization in the three-dimensional crypt, the proliferative cells were labeled by pulsing EdU for 24 hours in the oxygen gradient and in fully oxygenated condition. While the EdU labeled proliferative cells were located toward the base of the crypt in both oxygen conditions, the portion of EdU labeled cells to the total cells labeled with Hoechst33342 decreased in the oxygen gradient compared to the fully oxygenated condition, more evidently toward the crypt surface (>3 times in the top half vs. 1.2-1.4 within bottom 3/10 of the crypt). Moreover, 73% of the EdU labeled cells were located within bottom 3/10 of the crypt in the oxygen gradient condition while only 57% in the fully oxygenated condition. This suggests that the luminal oxygen depletion facilitate polarization of the crypt in vitro by confining the proliferative cells toward the base of the crypt.

Finally, to test whether the luminal oxygen depletion support the growth of colon bacteria, the growth of anaerobic bacteria in the oxygen gradient condition was assessed and compared with the fully oxygenated condition. *Bifidobacterium adolescentis* is a Gram-positive, obligate anaerobe[70] and one of common probiotic strains. *B. adolescentis* was inoculated and cocultured for 24 hours in the luminal side of the three-dimensional in vitro crypt under the oxygen gradient and also in fully oxygenated condition. The number of viable *B. adolescentis* increased more than 100 times after 24 hour coculture in the oxygen gradient while significantly decreased in the fully oxygenated condition. This demonstrates the coculture ability of the oxygen gradient with obligate anaerobic bacteria. See FIGS. 12A-12F.

Discussion of Examples 1-9

These data and experimental results demonstrate the effectiveness of the disclosed devices, systems and apparatuses in recapitulating, in an in vitro setting, the oxygen gradient across the epithelium in vivo. In the disclosed systems, devices and apparatuses oxygen gradient is established in a few hours when normoxic medium was used and instantaneously when deoxygenated medium in the luminal side without continuous deoxygenation. In parallel, oxygen is supplied through the basal medium that is exposed to the atmospheric air. These studies confirm that the intestinal epithelial cells consume significant amount of oxygen. As such, in some embodiments cellular oxygen consumption was leveraged to create and/or maintain oxygen gradient. The simulated and the experimental data clearly demonstrate that establishing and maintaining oxygen gradient is feasible without external anaerobic purging or preequilibration. The Hypoxyprobe staining showed that under the oxygen gradient in the disclosed devices, apparatuses and systems, oxygen supply from the basal side oxygenated the cells. This approach enables the establishment and maintenance of an oxygen gradient in the conventional normoxic setting without continuous perfusion as long as the intestinal epithelial cells consume oxygen. This minimal or no requirement of anaerobic environment and perfusion makes the systems and apparatuses disclosed herein attractive and accessible for broader usage.

The human primary colonic epithelial cell behaviors under the oxygen gradient were characterized and compared to those in conventional aerobic culture setting and complete anaerobic condition. Oxygen depletion, whether only in the luminal side or in both sides, did not impair viability, polarization, epithelial integrity assessed by tight junctions and TEER. It is consistent with the previous observation on T84 cells that anaerobic culture did not disrupt intestinal epithelial barrier properties.[60] However, oxygen depletion decreased proliferation of the intestinal epithelial cells. The portion of proliferative cells was slightly higher in the cells under the oxygen gradient than the cells in completely anaerobic conditions, but they were not statistically different. It explains why oxygen level is higher at the base of the crypt where proliferative cells reside than at the surface of the crypt with differentiated cells.[71] Oxygen depletion decreased MUC2 positive goblet cell populations but only when both luminal and basal sides were depleted of oxygen in the presence of Wnt, R-spondin and Noggin in the basal side. This is consistent with the reduced goblet cell population in ulcerative colitis[72] where inflammatory hypoxia is thought to occur as implicated as hypoxemia[73] and also shown in TNBS induced colitis model. This inhibitory effect of oxygen depletion was negligible when the cells were differentiated. These data suggest that the presence (or depletion) of oxygen involves cell fate decision and regulates barrier functions through mucus producing goblet cells but its influence on the differentiated cells is minimal.

The data and results herein show that the luminal hypoxia achieved in the disclosed apparatuses, systems and devices can support anaerobic bacteria growth using *C. difficile*. Earlier studies of *C. difficile* cocultures with human colon cancer cell lines or other animal cells did not implement proper oxygen gradient that mimics the in vivo oxygen environment (either aerobically or anaerobically cocultured).[74-76] These studies show that the stable oxygen gradient with anaerobic luminal medium support *C. difficile* growth as anaerobic environment. These studies further show that oxygenation status has remarkable influence on the interaction of the human cells and microbes.

The oxygen gradient was implemented into three dimensional crypt shaped epithelial cell layer. The growth factor gradient induced oxygen depleted crypt surface in fully oxygenated condition but the oxygen gradient augmented the oxygen depletion pattern along the crypt. The oxygen gradient in the three dimensional crypt regulated the polarization of the crypt by inhibiting proliferation near the crypt surface. The oxygen gradient established in the crypt supported the growth of obligate anerobic bacteria *B. adolescentis*, clearly demonstrating that anaerobic bacterial coculture is feasible.

In conclusion, disclosed herein are systems, devices, apparatuses and methods that recapitulate oxygen gradient across the intestinal epithelial cells in vivo by limiting oxygen influx into the luminal side and utilizing cellular oxygen consumption for luminal hypoxia and atmospheric air for basal oxygenation. This method does not require continuous perfusion of liquid or gas. The cell behaviors under the oxygen gradient were characterized and compared with those in the conventional aerobic and anaerobic setting. The cells under the oxygen gradient were as viable, polarized, and tightly bound themselves as the cells in the aerobic and anaerobic conditions whether the growth factors were present in or absent from the basal media. Compared to the conventional aerobic culture, the oxygen gradient decreased the proliferative cell population to the similar extent as anaerobic condition, while maintained MUC2 positive goblet cells as opposed to the anaerobic culture setting. These data and results demonstrate that the disclosed apparatuses, devices and systems can be used to coculture anaerobes using anaerobic bacteria *C. difficile*. These bacteria grew in the luminal compartment of the device under the oxygen gradient. The human cells under the oxygen gradient behaved differently from the conventional aerobic culture or anaerobic culture setting, suggesting the significance of implementing correct oxygen gradient in an in vitro system to model in vivo intestinal tissue. With ready access to the both luminal and basal sides, the disclosed apparatuses, systems and methods offer an in vitro system that more closely mimic and model the intestinal tissue in vivo.

REFERENCES

All references listed herein including but not limited to all patents, patent applications and publications thereof, scientific journal articles, and database entries are incorporated herein by reference in their entireties to the extent that they supplement, explain, provide a background for, or teach methodology, techniques, and/or compositions employed herein.

1 Crosnier, C., Stamataki, D. & Lewis, J. Organizing cell renewal in the intestine: stem cells, signals and combinatorial control. *Nature Reviews Genetics* 7, 349-359 (2006).
2 Schuijers, J. & Clevers, H. Adult mammalian stem cells: the role of Wnt, Lgr5 and R-spondins. *The EMBO journal* 31, 2685-2696 (2012).
3 Blouin, J. M. et al. Butyrate elicits a metabolic switch in human colon cancer cells by targeting the pyruvate dehydrogenase complex. *International journal of cancer* 128, 2591-2601 (2011).
4 Leonel, A. J. & Alvarez-Leite, J. I. Butyrate: implications for intestinal function. *Current Opinion in Clinical Nutrition & Metabolic Care* 15, 474-479 (2012).
5 Ward, J. B., Keely, S. J. & Keely, S. J. Oxygen in the regulation of intestinal epithelial transport. *The Journal of physiology* 592, 2473-2489 (2014).
6 Zheng, L., Kelly, C. J. & Colgan, S. P. Physiologic hypoxia and oxygen homeostasis in the healthy intestine. A review in the theme: cellular responses to hypoxia. *American Journal of Physiology-Cell Physiology* 309, C350-C360 (2015).
7 Zeitouni, N. E., Chotikatum, S., von Kockritz-Blickwede, M. & Naim, H. Y. The impact of hypoxia on intestinal epithelial cell functions: consequences for invasion by bacterial pathogens. *Molecular and cellular pediatrics* 3, 14 (2016).
8 Kaiko, G. E. & Stappenbeck, T. S. Host-microbe interactions shaping the gastrointestinal environment. *Trends in immunology* 35, 538-548 (2014).
9 LeBlanc, J. G. et al. Bacteria as vitamin suppliers to their host: a gut microbiota perspective. *Current opinion in biotechnology* 24, 160-168 (2013).
10 Galland, L. The gut microbiome and the brain. *Journal of medicinal food* 17, 1261-1272 (2014).
11 Kim, Y.-G. et al. Neonatal acquisition of *Clostridia* species protects against colonization by bacterial pathogens. *Science* 356, 315-319, doi:10.1126/science.aag2029 (2017).
12 Sampson, T. R. et al. Gut microbiota regulate motor deficits and neuroinflammation in a model of Parkinson's disease. *Cell* 167, 1469-1480. e1412 (2016).
13 Goldszmid, R. S. & Trinchieri, G. The price of immunity. *Nature immunology* 13, 932-938 (2012).
14 Nagpal, R., Yadav, H. & Marotta, F. Gut microbiota: the next-gen frontier in preventive and therapeutic medicine? *Frontiers in medicine* 1 (2014).
15 Cani, P. D. Gut microbiota [mdash] at the intersection of everything? *Nature Reviews Gastroenterology & Hepatology* 14, 321-322 (2017).
16 Sato, T. et al. Single Lgr5 stem cells build crypt-villus structures in vitro without a mesenchymal niche. *Nature* 459, 262 (2009).
17 Sato, T. et al. Long-term expansion of epithelial organoids from human colon, adenoma, adenocarcinoma, and Barrett's epithelium. *Gastroenterology* 141, 1762-1772 (2011).
18 Wang, Y. et al. Self-renewing monolayer of primary colonic or rectal epithelial cells. *Cellular and Molecular Gastroenterology and Hepatology* (2017).
19 Kim, H. J., Huh, D., Hamilton, G. & Ingber, D. E. Human gut-on-a-chip inhabited by microbial flora that experiences intestinal peristalsis-like motions and flow. *Lab on a Chip* 12, 2165-2174 (2012).
20 Kim, H. J., Li, H., Collins, J. J. & Ingber, D. E. Contributions of microbiome and mechanical deformation to intestinal bacterial overgrowth and inflammation in a human gut-on-a-chip. *Proceedings of the National Academy of Sciences* 113, E7-E15 (2016).
21 Shah, P. et al. A microfluidics-based in vitro model of the gastrointestinal human-microbe interface. *Nature communications* 7 (2016).
22 Anonye, B. O. et al. Probing host-anaerobe interactions in innovative human gut cellular models. *bioRxiv*, doi: 10.1101/269035 (2018).
23 Chen, Y. et al. Robust bioengineered 3D functional human intestinal epithelium. *Scientific reports* 5, 13708 (2015).
24 Zhou, W. et al. Multifunctional bioreactor system for human intestine tissues. *ACS biomaterials science & engineering* 4, 231-239 (2017).
25 Ulluwishewa, D. et al. Live *Faecalibacterium prausnitzii* in an apical anaerobic model of the intestinal epithelial barrier. *Cellular microbiology* 17, 226-240 (2015).
26 Marzorati, M. et al. The HMI™ module: a new tool to study the Host-Microbiota Interaction in the human gastrointestinal tract in vitro. *BMC microbiology* 14, 133 (2014).
27 Byrne, M. B., Leslie, M. T., Gaskins, H. R. & Kenis, P. J. Methods to study the tumor microenvironment under controlled oxygen conditions. *Trends in biotechnology* 32, 556-563 (2014).
28 Oppegard, S. C., Nam, K.-H., Carr, J. R., Skaalure, S. C. & Eddington, D. T. Modulating temporal and spatial oxygenation over adherent cellular cultures. *PloS one* 4, e6891 (2009).
29 Oppegard, S. C., Blake, A. J., Williams, J. C. & Eddington, D. T. Precise control over the oxygen conditions within the Boyden chamber using a microfabricated insert. *Lab on a chip* 10, 2366-2373 (2010).
30 Oppegard, S. C. & Eddington, D. T. A microfabricated platform for establishing oxygen gradients in 3-D constructs. *Biomedical microdevices* 15, 407-414 (2013).
31 UCHIDA, H., SATO, A., MIYAYAMA, A. & TSUKADA, K. Generation of an oxygen gradient in a microfluidic device and cellular analysis in hypoxia. *Advanced Biomedical Engineering* 2, 143-149 (2013).
32 Rexius-Hall, M. L., Mauleon, G., Malik, A. B., Rehman, J. & Eddington, D. T. Microfluidic platform generates oxygen landscapes for localized hypoxic activation. *Lab on a chip* 14, 4688-4695 (2014).
33 Brennan, M. D., Rexius-Hall, M. L. & Eddington, D. T. A 3D-printed oxygen control insert for a 24-well plate. *PloS one* 10, e0137631 (2015).
34 Anonye, B. O. et al. Probing host-anaerobe interactions in innovative human gut cellular models. *bioRxiv,* 269035 (2018).
35 Walsh III, D. I. et al. Emulation of Colonic Oxygen Gradients in a Microdevice. *SLAS TECHNOLOGY: Translating Life Sciences Innovation*, 2472630317743425 (2017).
36 Skolimowski, M. et al. Microfluidic dissolved oxygen gradient generator biochip as a useful tool in bacterial biofilm studies. *Lab on a Chip* 10, 2162-2169 (2010).
37 Takano, A., Tanaka, M. & Futai, N. in *Engineering in Medicine and Biology Society (EMBC), 2013 35th Annual International Conference of the IEEE.* 4474-4477 (IEEE).
38 Chen, Y.-A. et al. Generation of oxygen gradients in microfluidic devices for cell culture using spatially confined chemical reactions. *Lab on a Chip* 11, 3626-3633 (2011).

39 Huang, Y., Zitta, K., Bein, B., Steinfath, M. & Albrecht, M. An insert-based enzymatic cell culture system to rapidly and reversibly induce hypoxia: investigations of hypoxia-induced cell damage, protein expression and phosphorylation in neuronal IMR-32 cells. *Disease models & mechanisms* 6, 1507-1514 (2013).

40 Ivanovic, Z. Hypoxia or in situ normoxia: The stem cell paradigm. *Journal of cellular physiology* 219, 271-275 (2009).

41 Bertout, J. A., Patel, S. A. & Simon, M. C. The impact of O2 availability on human cancer. *Nature reviews. Cancer* 8, 967 (2008).

42 Colgan, S. P. & Taylor, C. T. Hypoxia: an alarm signal during intestinal inflammation. *Nature Reviews Gastroenterology and Hepatology* 7, 281-287 (2010).

43 Simon, M. C. & Keith, B. The role of oxygen availability in embryonic development and stem cell function. *Nature reviews. Molecular cell biology* 9, 285 (2008).

44 Markov, D. A., Lillie, E. M., Garbett, S. P. & McCawley, L. J. Variation in diffusion of gases through PDMS due to plasma surface treatment and storage conditions. *Biomedical microdevices* 16, 91-96 (2014).

45 Lamberti, A., Marasso, S. L. & Cocuzza, M. PDMS membranes with tunable gas permeability for microfluidic applications. *Rsc Advances* 4, 61415-61419 (2014).

46 Koh, M. Y. & Powis, G. Passing the baton: the HIF switch. *Trends in biochemical sciences* 37, 364-372 (2012).

47 Wang, Y. et al. A microengineered collagen scaffold for generating a polarized crypt-villus architecture of human small intestinal epithelium. *Biomaterials* 128, 44-55 (2017).

48 Gross, M. W., Karbach, U., Groebe, K., Franko, A. J. & Mueller-Klieser, W. Calibration of misonidazole labeling by simultaneous measurement of oxygen tension and labeling density in multicellular spheroids. *International journal of cancer* 61, 567-573 (1995).

49 Buchwald, P. FEM-based oxygen consumption and cell viability models for avascular pancreatic islets. *Theoretical Biology and Medical Modelling* 6, 5 (2009).

50 Wagner, B. A., Venkataraman, S. & Buettner, G. R. The rate of oxygen utilization by cells. *Free radical biology & medicine* 51, 700-712 (2011).

51 JanssenDuijghuijsen, L. M. et al. Mitochondrial ATP Depletion Disrupts Caco-2 Monolayer Integrity and Internalizes Claudin 7. *Frontiers in Physiology* 8 (2017).

52 Buchwald, P. FEM-based oxygen consumption and cell viability models for avascular pancreatic islets. *Theoretical Biology and Medical Modelling* 6, 5 (2009).

53 Lynch, S. V. & Pedersen, O. The Human Intestinal Microbiome in Health and Disease. *N Engl J Med* 375, 2369-2379 (2016).

54 Sommer, F., Anderson, J. M., Bharti, R., Raes, J. & Rosenstiel, P. The resilience of the intestinal microbiota influences health and disease. *Nat Rev Microbiol* 15, 630-638 (2017).

55 Ward, J. B., Keely, S. J. & Keely, S. J. Oxygen in the regulation of intestinal epithelial transport. *The Journal of physiology* 592, 2473-2489 (2014).

56 Wang, Y. et al. Bioengineered Systems and Designer Matrices That Recapitulate the Intestinal Stem Cell Niche. *Cell Mol Gastroenterol Hepatol* 5, 440-453 e441 (2018).

57 Crank, J. & Crank, E. P. J. The Mathematics of Diffusion. (Clarendon Press, 1979).

58 Gross, M. W., Karbach, U., Groebe, K., Franko, A. J. & Mueller-Klieser, W. Calibration of misonidazole labeling by simultaneous measurement of oxygen tension and labeling density in multicellular spheroids. *International journal of cancer* 61, 567-573 (1995)

59 Varia, M. A. et al. Pimonidazole: a novel hypoxia marker for complementary study of tumor hypoxia and cell proliferation in cervical carcinoma. *Gynecologic oncology* 71, 270-277 (1998).

60 Colgan, S. P., Dzus, A. L. & Parkos, C. A. Epithelial exposure to hypoxia modulates neutrophil transepithelial migration. *Journal of Experimental Medicine* 184, 1003-1015 (1996).

61 Schneeberger, K., Roth, S., Nieuwenhuis, E. E. & Middendorp, S. Intestinal epithelial cell polarity defects in disease: lessons from microvillus inclusion disease. *Disease models & mechanisms* 11, dmm031088 (2018).

62 Hubbi, M. E. & Semenza, G. L. Regulation of cell proliferation by hypoxia-inducible factors. *American Journal of Physiology-Cell Physiology* 309, C775-C782 (2015).

63 Kaidi, A., Williams, A. C. & Paraskeva, C. Interaction between β-catenin and HIF-1 promotes cellular adaptation to hypoxia. *Nature cell biology* 9, 210-217 (2007).

64 Leffler, D. A. & Lamont, J. T. *Clostridium difficile* Infection. *New England Journal of Medicine* 372, 1539-1548 (2015).

65 Wiegand, P. N. et al. Clinical and economic burden of *Clostridium difficile* infection in Europe: a systematic review of healthcare-facility-acquired infection. *Journal of Hospital Infection* 81, 1-14 (2012).

66 Peery, A. F. et al. Burden of gastrointestinal disease in the United States: 2012 update. *Gastroenterology* 143, 1179-1187. e1173 (2012).

67 Aktories, K., Schwan, C. & Jank, T. *Clostridium difficile* Toxin Biology. *Annual Review of Microbiology* 71, 281-307 (2017).

68 Wang, Y. et al. Formation of Human Colonic Crypt Array by Application of Chemical Gradients Across a Shaped Epithelial Monolayer. *Cellular and Molecular Gastroenterology and Hepatology* 5, 113-130 (2018).

69 Kelly, C. J. et al. Fundamental role for HIF-1a in constitutive expression of human β defensin-1. *Mucosal Immunology* 6, 1110 (2013).

70 Shimamura, S. et al. Relationship Between Oxygen Sensitivity and Oxygen Metabolism of *Bifidobacterium* Species. *Journal of Dairy Science* 75, 3296-3306 (1992).

71 Zheng, L., Kelly, C. J. & Colgan, S. P. Physiologic hypoxia and oxygen homeostasis in the healthy intestine. A review in the theme: cellular responses to hypoxia. *American Journal of Physiology-Cell Physiology* 309, C350-C360 (2015).

72 Gersemann, M. et al. Differences in goblet cell differentiation between Crohn's disease and ulcerative colitis. *Differentiation* 77, 84-94 (2009).

73 Tsujij, M. et al. Colonic mucosal hemodynamics and tissue oxygenation in patients with ulcerative colitis: Investigation by organ reflectance spectrophotometry. *Journal of Gastroenterology* 30, 183-188 (1995).

74 Waligora, A. J., Barc, M. C., Bourlioux, P., Collignon, A. & Karjalainen, T. *Clostridium difficile* cell attachment is modified by environmental factors. *Applied and environmental microbiology* 65, 4234-4238 (1999).

75 Janvilisri, T., Scaria, J. & Chang, Y.-F. Transcriptional profiling of *Clostridium difficile* and Caco-2 cells during infection. *The Journal of infectious diseases* 202, 282-290 (2010).

76 Eveillard, M. et al. Identification and characterization of adhesive factors of *Clostridium difficile* involved in adhesion to human colonic enterocyte-like Caco-2 and mucus-secreting HT29 cells in culture. *Molecular microbiology* 7, 371-381 (1993).

It will be understood that various details of the presently disclosed subject matter can be changed without departing from the scope of the presently disclosed subject matter. Furthermore, the foregoing description is for the purpose of illustration only, and not for the purpose of limitation.

What is claimed is:

1. A method of generating a gas gradient across a cell support structure, the method comprising:
   providing a luminal container comprising a bottom wall, at least one sidewall extending upwardly from the bottom wall, and a top opening defined by the at least one sidewall, wherein the bottom wall of the luminal container comprises a gas permeable membrane;
   positioning the cell support structure above the bottom wall;
   positioning one or more cells and/or tissues on the cell support structure;
   installing a cover on the luminal container to close the top opening, wherein a luminal reservoir is defined between a bottom surface of the cover and the cell support structure and/or the one or more cells and/or tissues; and
   generating the gas gradient between the bottom wall, across the cell support structure, across the one or more cells and/or tissues and into the luminal reservoir, wherein one or more cells and/or tissues produce and/or consume a gas, thereby generating the gas gradient, wherein the gas gradient is stable in about 30 minutes to about six hours, and wherein the gas gradient is self-sustaining.

2. The method of claim 1, further comprising:
   providing the gas to the one or more cells and/or tissues through the gas permeable membrane of the bottom wall of the luminal container, and
   generating the gas gradient between the gas permeable membrane of the bottom wall of the luminal container through the one or more cells and/or tissues and into the luminal reservoir.

3. The method of claim 1, further comprising
   providing a basal container comprising a bottom wall and at least one sidewall extending upwardly from the bottom wall, wherein the bottom wall and the at least one sidewall define a well, and wherein:
   the luminal container is held within the well of the basal container;
   the bottom wall of the basal container is spaced apart from the bottom wall of the luminal container;
   a basal reservoir is defined between the bottom wall of the basal container and the bottom wall of the luminal container and/or between the at least one sidewall of the basal container and the at least one sidewall of the luminal container; and
   a basal medium positioned in the basal reservoir, wherein the basal medium provides the gas to the one or more cells and/or tissues through the gas permeable membrane of the bottom wall, thereby generating the gas gradient between the basal medium and the luminal reservoir.

4. The method of claim 3, wherein the cover comprises at least one port or channel extending through a top or a side surface of the cover.

5. The method of claim 4, further comprising inserting at least one sensor and/or tubing into the at least one port or channel of the cover.

6. The method of claim 4, further comprising providing at least one gas to the luminal reservoir or to the basal reservoir through the at least one port or channel, wherein the one or more cells and/or tissues produce and/or consume the at least one gas, thereby generating the gas gradient across the cell support structure.

7. The method of claim 3, comprising providing the gas or consuming the gas in the luminal container, luminal reservoir, basal reservoir and/or basal container.

8. The method of claim 1, wherein the at least one gas is oxygen and the luminal reservoir has a concentration of oxygen that is less than about 21%.

9. The method of claim 1, further comprising generating a gradient of a non-gaseous chemical across the cell support structure, wherein the one or more cells and/or tissues positioned on the cell support structure produce and/or consume the non-gaseous chemical, thereby generating the gradient across the cell support structure.

10. The method of claim 1, wherein the one or more cells are primary mammalian cells.

11. The method of claim 1, wherein the one or more cells and/or tissues are in a three dimensional culture format of an in vitro culture, an ex vivo culture, an entire organism, an entire organ, a partial organ, and/or an ex vivo tissue section.

* * * * *